United States Patent [19]

Goodman et al.

[11] Patent Number: 4,928,692

[45] Date of Patent: * May 29, 1990

[54] METHOD AND APPARATUS FOR DETECTING OPTICAL PULSES

[76] Inventors: David E. Goodman, 454 Roosevelt Way, San Francisco, Calif. 94114; James E. Corenman, 1095 Sherman Ave., Menlo Park, Calif. 94025

[*] Notice: The portion of the term of this patent subsequent to Feb. 7, 2006 has been disclaimed.

[21] Appl. No.: 275,727

[22] Filed: Nov. 23, 1988

Related U.S. Application Data

[63] Continuation of Ser. No. 742,720, Jun. 5, 1985, Pat. No. 4,802,486, which is a continuation of Ser. No. 718,525, Apr. 1, 1985, abandoned.

[51] Int. Cl.$^5$ ................................................ A61B 5/02
[52] U.S. Cl. ..................................... 128/633; 128/666; 128/687; 128/700
[58] Field of Search .............................. 128/632—633, 128/637, 668, 670, 687–690, 696, 700, 706, 708, 664–667

[56] References Cited

U.S. PATENT DOCUMENTS

| | | | |
|---|---|---|---|
| Re. 27,042 | 1/1971 | Jorgensen et al. | 128/700 |
| 2,827,040 | 3/1958 | Gilford. | |
| 2,933,081 | 4/1960 | Passanante. | |
| 3,318,303 | 5/1967 | Hammacher | 128/687 X |
| 3,412,729 | 11/1968 | Smith, Jr. | |
| 3,520,295 | 7/1970 | Kelly | 128/708 |
| 3,590,811 | 7/1971 | Harris. | |
| 3,608,545 | 9/1971 | Novack et al. | 128/700 |
| 3,618,592 | 11/1971 | Stewart. | |
| 3,651,806 | 3/1972 | Hirshberg. | |
| 3,658,060 | 4/1972 | Eklof. | |
| 3,704,706 | 12/1972 | Herczfeld et al. | |
| 3,734,086 | 5/1973 | Phelps, Sr. | |

(List continued on next page.)

FOREIGN PATENT DOCUMENTS

| | | |
|---|---|---|
| 0102816 | 3/1984 | European Pat. Off. . |
| 0104771 | 4/1984 | European Pat. Off. . |
| 0104772 | 4/1984 | European Pat. Off. . |
| 2089999 | 6/1982 | United Kingdom . |

OTHER PUBLICATIONS

Schotz et al.; "The Ear Oximeter as a Circulating Monitor"; *Anesthesiology*, vol. 19, p. 386 (1958).

Cohen et al; "Self-Balancing System For Medical and Physiological Instrumentation", *IEEE Trans. Bio-Med Eng.*, vol. BME-18, p. 66 (1971).

Goodlin; "Interpartum Fetal Heart Rate Responses and Plethysmographic Pulse"; *Amer. J. Obstet. Cynec.*, vol. 110, p. 210 (1971).

Goodlin et al; "Systolic Time Intervals in the Fetus and Neonate"; *Obstetrics and Gynecology*, vol. 34, p. 295 (2-1972).

Goodlin; *Care for the Fetus;* p. 101 (Masson, 1979).

Huch et al; "Continuous PO$_2$ and Heart Rate Recording in the Human Newborn"; *Advances in Experimental Medicine and Biology;* pp. 737–745 (1975).

*Primary Examiner*—Angela D. Sykes

[57] ABSTRACT

A method and apparatus for measuring and correlating a patient's heart activity with optical detection of the patient's blood flow. The method and apparatus permit more accurate determination of blood flow characteristics such as oxygen saturation and pulse rate. In a preferred embodiment, the heart activity is detected by monitoring the patient's EKG waveform, and the blood flow is detected by a non-invasive pulse oximeter. The occurrence of the R wave portion of the EKG signal is detected and the time delay by which an arterial pulse follows the R wave is determined to establish a time window in which an arterial is to be expected. The established time window provides the oximeter with a parameter enabling the oximeter to analyze the blood flow only when it is likely to present an arterial blood pulse for waveform analysis. The invention also includes adjusting the polarity of the detected EKG signal to have a preselected uniform upgoing or downgoing polarity.

13 Claims, 15 Drawing Sheets

U.S. PATENT DOCUMENTS

| | | | |
|---|---|---|---|
| 3,742,938 | 7/1973 | Stern | 128/687 |
| 3,773,033 | 11/1973 | Rodbard et al. | |
| 3,948,248 | 4/1976 | Zuckerman et al. | |
| 3,994,284 | 11/1976 | Voelker | |
| 3,994,285 | 11/1976 | Doll | |
| 3,998,550 | 12/1976 | Konishi et al. | 356/39 |
| 4,000,461 | 12/1976 | Barber et al. | 324/102 |
| 4,023,563 | 5/1977 | Reynolds et al. | |
| 4,023,564 | 5/1977 | Valiguette et al. | |
| 4,030,485 | 6/1977 | Warner | |
| 4,036,211 | 7/1977 | Veth et al. | |
| 4,053,911 | 10/1977 | Hudspeth et al. | 364/415 |
| 4,063,551 | 12/1977 | Sweeney | |
| 4,086,915 | 5/1978 | Kofsky | |
| 4,154,230 | 5/1979 | Lee | |
| 4,181,134 | 1/1980 | Mason et al. | 128/689 |
| 4,216,779 | 8/1980 | Squires et al. | 128/682 |
| 4,266,554 | 5/1981 | Hamaguri | 128/633 |
| 4,325,384 | 4/1982 | Blaser et al. | 128/696 |
| 4,353,998 | 12/1982 | Sawa | 128/633 |
| 4,402,325 | 6/1983 | Sawa | 128/666 |
| 4,406,658 | 9/1983 | Lattin et al. | 128/802 X |
| 4,407,290 | 10/1983 | Wilber | 128/633 |
| 4,422,458 | 12/1983 | Kravath | 128/671 |
| 4,425,921 | 1/1984 | Fujisaki et al. | 128/700 |
| 4,425,922 | 1/1984 | Conti et al. | 128/691 |
| 4,440,176 | 4/1984 | Miodownik | 128/708 |
| 4,446,868 | 5/1984 | Aronson | 128/708 |
| 4,450,838 | 5/1984 | Miodownick | 128/204.23 |
| 4,545,387 | 10/1985 | Balique | 128/666 X |
| 4,573,478 | 3/1986 | Arnold et al. | 128/670 |
| 4,577,639 | 3/1986 | Simon et al. | 128/709 |
| 4,586,513 | 5/1986 | Hamaguri | 128/633 |
| 4,589,420 | 6/1986 | Adams et al. | 128/702 |
| 4,617,937 | 10/1986 | Peel et al. | 128/686 |

Fig. 3.
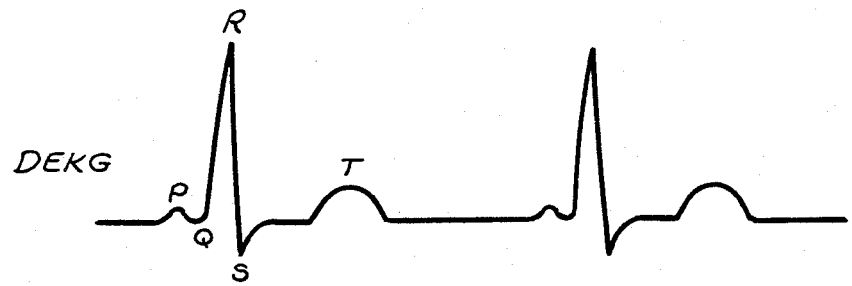
DIAGNOSTIC EKG WAVEFORM
BANDPASS FILTERED EKG WAVEFORM
R-WAVE DETECTOR Fig. 5B.
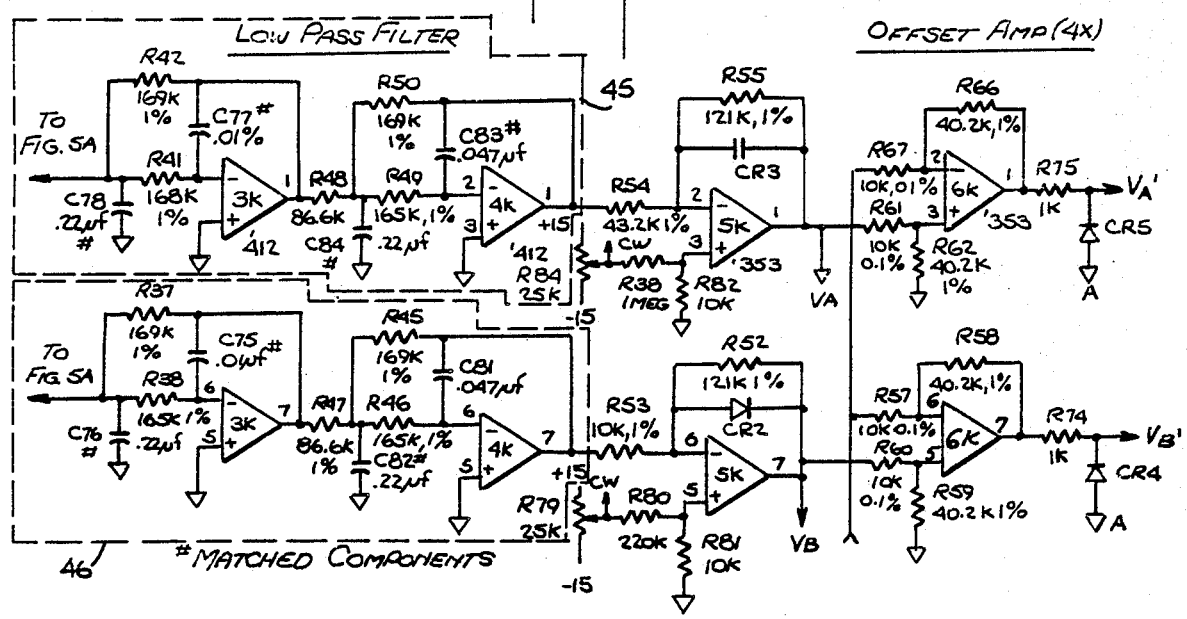
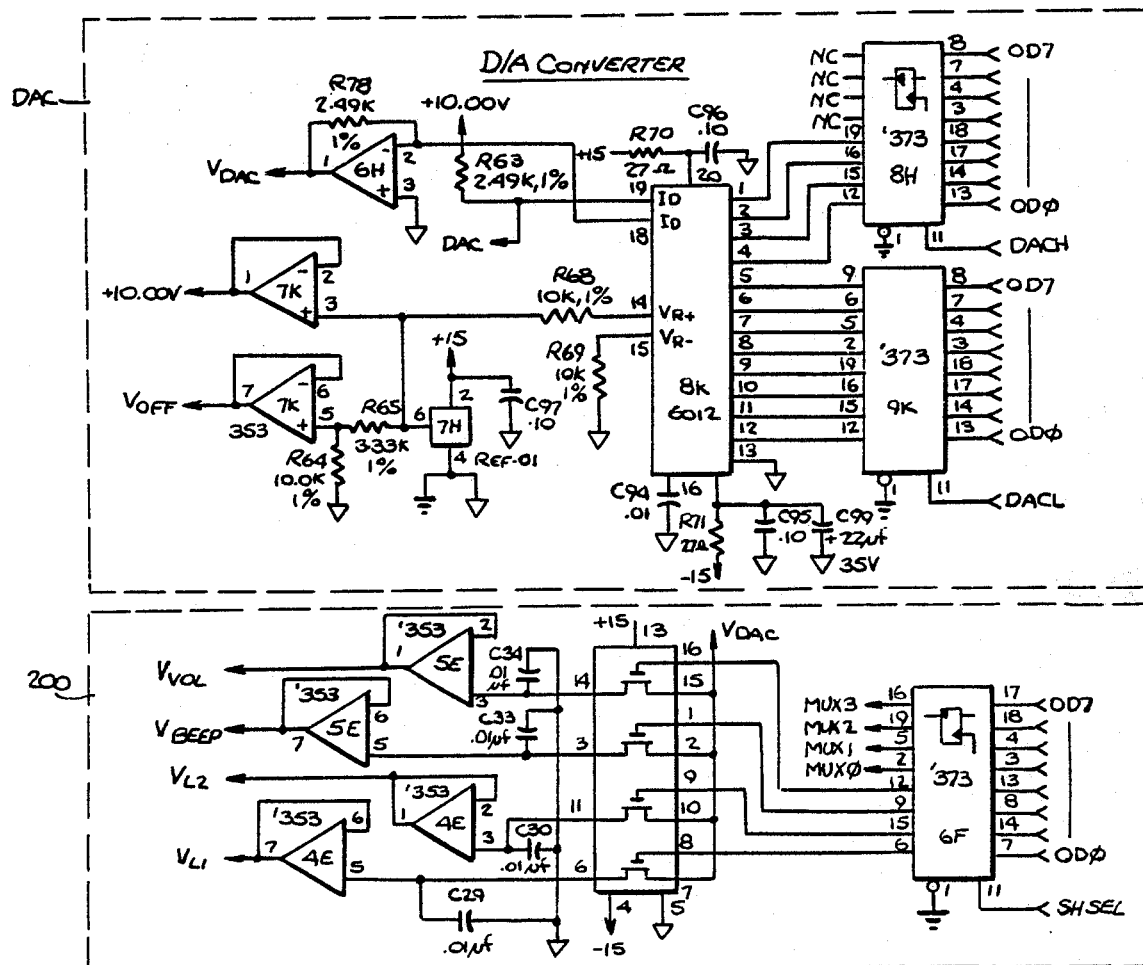

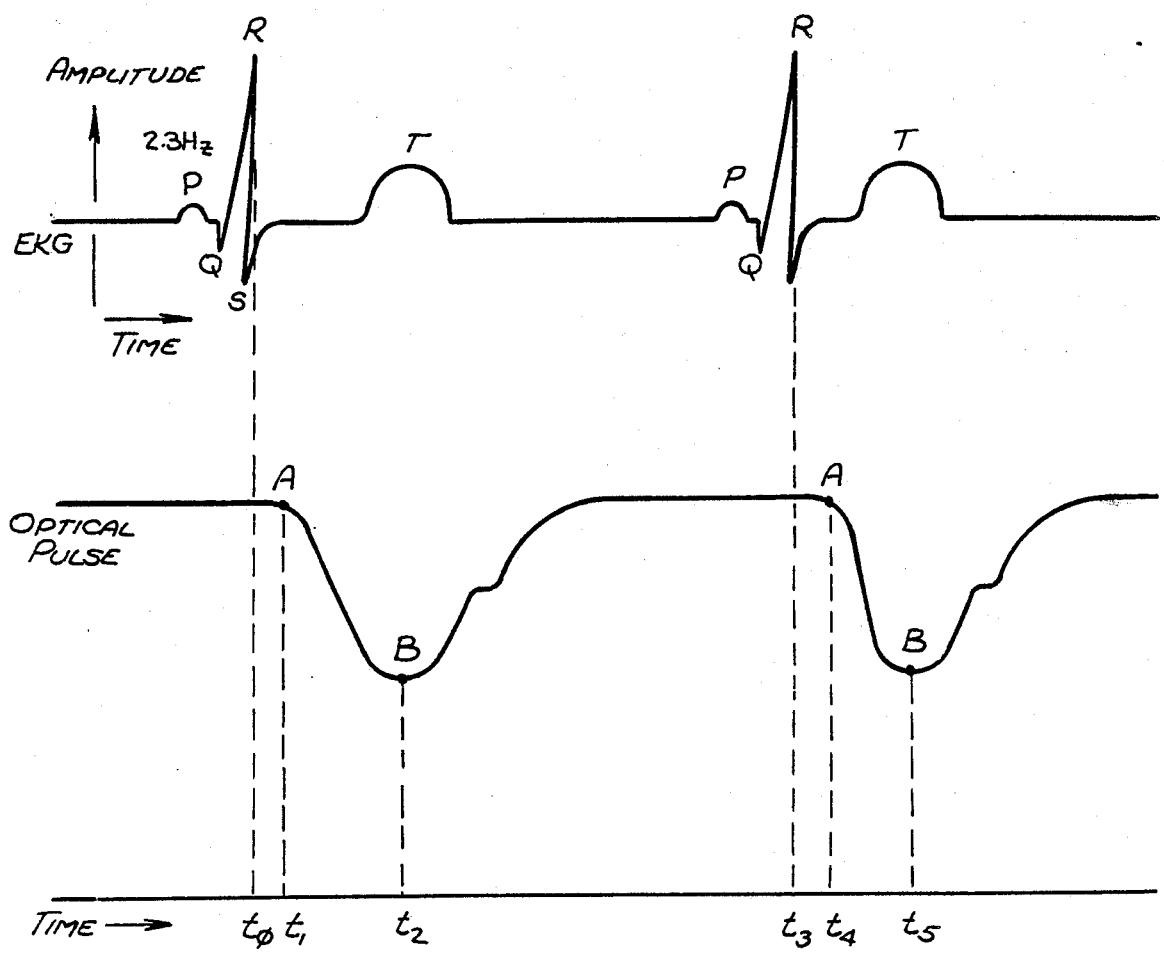

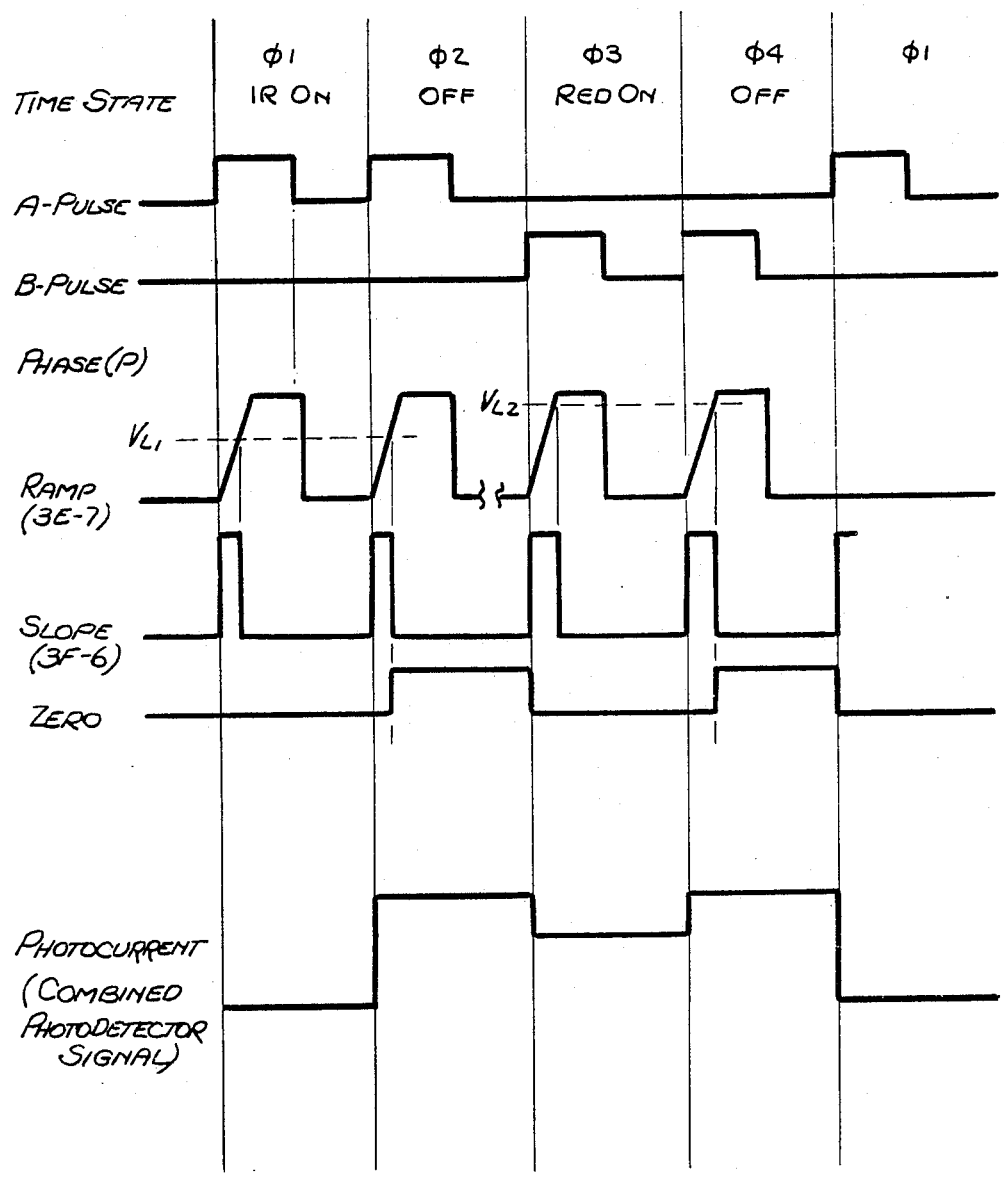

METHOD AND APPARATUS FOR DETECTING OPTICAL PULSES

CROSS REFERENCE TO RELATED APPLICATIONS

This application is a continuation of application Ser. No. 742,720 filed June 5, 1985 by David E. Goodman and James E. Corenman entitled Improved Method And Apparatus For Detecting Optical Pulses now issued as U.S. Pat. No. 4,802,486 which is a continuation application of copending and commonly assigned application Ser. No. 718,525 filed Apr. 1, 1985 by David E. Goodman and James E. Corenman entitled IMPROVED METHOD AND APPARATUS FOR DETECTING OPTICAL PULSES now abandoned.

This invention relates to non-invasive pulse oximetry and specifically to an improved method and apparatus for photoelectric determination of blood constituents. A 123 page computer program is appended as a part of this application.

BACKGROUND OF THE INVENTION

Non-invasive photoelectric pulse oximetry has been previously described in U.S. Pat. Nos. 4,407,290, 4,266,554, 4,085,915, 3,998,550, 3,704,706, European Patent Application No. 102,816 published Mar. 13, 1984, European Patent Application No. 104,772 published Apr. 4, 1984, and European Patent Application No. 104,771 published Apr. 4, 1984. Pulse oximeters are commercially available for Nellcor Incorporated, Hayward, Calif., and are known as, for example, Pulse Oximeter Model N-100.

Pulse oximeters typically measure and display various blood flow characteristics including but not limited to blood oxygen saturation of hemoglobin in arterial blood, volume of individual blood pulsations supplying the flesh, and the rate of blood pulsations corresponding to each heartbeat of the patient. The oximeters pass light through human or animal body tissue where blood perfuses the tissue such as a finger, an ear, the nasal septum or the scalp, and photoelectrically sense the absorption of light in the tissue. The amount of light absorbed is then used to calculate the amount of blood constituent being measured.

The light passed through the tissue is selected to be of one or more wavelengths that is absorbed by the blood in an amount representative of the amount of the blood constituent present in the through the tissue will vary in accordance with the changing amount of blood constituent in the tissue and the related light absorptio. For example, the Nellcor N-100 Pulse Oximeter measures oxygen saturation of hemoglobin using two light emitting diodes ("LED's"), one having a discrete frequency of about 660 nanometers in the red light range and the other having a discrete frequency of about 925 nanometers in the infrared range. The two LED's are illuminated. alternately with a four-state clock so that the incident light will pass through a fingertip and the detected or transmitted light will be detected by a single photodetector. The clock uses a high strobing rate, e.g., two thousand cycles per second, to be easily distinguished from other light sources. The photodetector current changes in response to both red and infrared transmitted light, in sequence, and is then amplified and separated by a two-channel synchronous detector—one channel for processing the red light waveform and the other channel for processing the infrared light waveform. The separated signals are filtered to remove the strobing frequency, electrical noise, and ambient noise and then digitized by an analog to digital converter ("ADC"). As used herein, incident light or transmitted light refers to light generated by the LED or other light source, as distinguished from ambient or environmental light.

The light source intensity may be adjusted to accomodate variations among patients' skin color, flesh thickness, hair, blood, and other variants. The light transmitted is thus modulated by the variants, particularly the arterial blood pulse or pulsatile component, and is referred to as the optical signal. The digital representation of the optical signal is referred to as the digital optical signal. The portion of the digital optical signal that refers to the pulsatile component is labeled the optical pulse.

The digital optical signal is processed by the microprocessor of the Nellcor N-100 Pulse Oximeter in order to identify individual optical pulses and to compute the oxygen saturation from the ratio of maximum and minimum pulse levels as seen by the red wavelength compared to the pulse seen by the infrared wavelength.

Several alternate methods of processing and interpreting optical signal data have been disclosed in the patents and references cited above.

A problem with non-invasive pulse oximeters is that the optically derived pulse rate may be subject to irregular variants that interfere with the detection of the blood flow characteristics including but not limited to motion artifact. Motion artifact is caused by the patient's muscle movement proximate to the oximeter sensor, for example, the patient's finger, ear or other body part to which the oximeter sensor is attached, and may cause spurious pulses that are similar to pulses caused by arterial blood flow. These spurious pulses, in turn, may cause the oximeter to process the artifact waveform and provide erroneous data. This problem is particularly significant with infants, fetuses, or patients that do not remain still during monitoring.

A second problem exists in circumstances where the patient is in poor condition and the pulse strength is very weak. In continuously processing the optical data, it can be difficult to separate the true pulsatile component from artifact pulses and noise because of a low signal to noise ratio. Inability to reliably detect the pulsatile component in the optical signal may result in a lack of the information needed to calculate blood constituents.

It is well known that electrical heart activity occurs simultaneously with the heartbeat and can be monitored externally and characterized by the electrocardiogram ("EKG") waveform. The EKG waveform, as is known to one skilled in the art, comprises a complex waveform having several components that correspond to electrical heart activity. The QRS component relates to ventricular heart contraction. The R wave portion of the QRS component is typically the steepest wave therein, having the largest amplitude and slope, and may be used for indicating the onset of cardiovascular activity. The arterial blood pulse flows mechanically and its appearance in any part of the body typically follows the R wave of the electrical heart activity by a determinable period of time. See, e.g., Goodlin et al., "Systolic Time Intervals in the Fetus and Neonate", *Obstetrics and Gynecology*, Vol. 39, No. 2, February 1972, where it is shown that the scalp pulse of fetuses lag behind the EKG "R" wave by 0.03–0.04 second, and U.S. Pat. No. 3,734,086.

It is therefore an object of this invention to provide an improved method and apparatus for detecting the pulsatile component of the optical signal and measuring the amount of blood constituent and the pulse rate by incorporating the patient's heart activity, preferably detected electrically in the form of an EKG waveform, into the oximeter operation and thereby solve problems caused by motion artifact and low signal to noise ratio, as well as simplify and improve the operation of oximeters.

Another object of this invention is to have the oximeter analyze only those digital optical signals occurring during a period of time when the optical pulses are expected to be found and use information from that portion of the signal to calculate the amount of blood constituent. This increases the likelihood that the oximeter will process only optical waveforms that contain the pulsatile component of arterial blood, and will not process spurious pulses.

Another object of the invention is to provide for using pulse oximeters to monitor patients having irregular heartbeats by using the EKG information, particularly the R wave component, to determine when an arterial pulse is likely to occur and processing the digital optical signal waveform during that time period to make the desired measurement.

A further object of this invention is to cross correlate the pulse rate information determined by the oximeter from the digital signal with the heart rate determined from the EKG. The cross correlation function will allow measurement of the time relationship between the EKG and the optical pulse and is particularly advantageous when the optical signal may be weak and in the delivery room where fetal heart rate is an important and commonly monitored vital sign.

A further object of this invention is to provide for redundant measurement of the heart rate from both the optical signal and the EKG to continuously monitor the patient even if one of the signals were to be lost.

A further object of this invention is to provide a polarity compensation circuit for use with EKG detection so that the polarity of the EKG waveform can be made uniform, upgoing or downgoing, without having to adjust the leads.

SUMMARY OF THE INVENTION

This invention increases the accuracy and reliability of pulse oximeters used during surgery, life threatening medical situations, and childbirth, by measuring the patient's blood flow to more accurately calculate and measure vital information such as oxygen saturation and pulse rate. In one embodiment the correlation comprises using auto- and cross correlation techniques to enhance periodic information contained in each individual waveform as well as determine the time relationship of one waveform to another. In the preferred embodiment, the method comprises correlating the occurrence of cardiovascular activity with the detection of arterial pulses by measuring an EKG signal, detecting the occurrence of the R wave portion of the EKG signal, determining the time delay by which an optical pulse follows the R wave, and using the determined time delay between an R wave and the following optical blood pulse so as to evaluate arterial blood flow only when it is likely to present a true blood pulse for waveform analysis. The method also includes determining the heart rate of the patient based on the EKG signal, the optical pulse, or both.

In a preferred embodiment, the method and apparatus comprise an improvement in the use of a Model N-100 Pulse Oximeter (herein "N-100 oximeter") manufactured and sold by Nellcor Incorporated, Hayward, Calif. The improved method provides an oximeter with an additional parameter enabling the oximeter to better analyze the digital optical signal waveform of the patient. The apparatus comprises a heart activity detection device, the pulse oximeter functions of a Nellcor N-100 Pulse Oximeter, and a microprocessor system incorporating software and memory for controlling and processing the oximeter and heart activity information. Additional inputs to a multiplexer and a digital status input latch of the oximeter are provided to receive the inputs from the heat activity detection electronics. The improved oximeter processes the detected heart activity waveforms simultaneously with and independent of the optical signals, both waveforms having been converted to digital signals for signal processing by the signal processing components of the N-100 oximeter.

The heart activity parameter may be provided by conventional and nonconventional methods capable of detecting heart activity independent of peripheral arterial pulses, including but not limited to EKG signals, ultrasound, ballistocardiogram, accelerometers, nuclear magnetic resonators, electrical impedance techniques, and the like. The primary requirement of the heart activity parameter and the related circuitry is that it provide an identifiable and detectable signal in response to each heartbeat for use by the signal processing of the oximeter.

In the preferred embodiment, heart activity parameter is detected by electronic heart detection circuitry in the form of an EKG signal which is passed through an instrumentation amplifier electrically isolated from the oximeter, and system electronics to generate a variety of waveforms derived from the EKG signal. The amplifier differentially amplifies the raw EKG data, inverts and returns the common mode signal to the patient to null the patient's common mode voltage, amplifies and AC couples the signal to eliminate any DC (offset) voltage component, filters the signal to eliminate unwanted frequencies such as, for example, frequencies below 0.05 Hz, buffers, and then couples the EKG signal to the system electronics. Coupling may be effected, for example, by amplitude modulation of a carrier signal across a transformer having the appropriate circuitry, or by an optically coupled isolation barrier.

The system electronics demodulates the coupled signal, where necessary, amplifies the signal and passes it to an automatic gain control ("AGC") amplifier to maintain the EKG signal output within a desired range even though the actual EKG signal strength may vary from patient to patient or from lead location to lead location.

In the preferred embodiment, the output of the AGC amplifier is routed through a polarity compensation circuit that changes the polarity of the waveform to have a preselected upgoing or downgoing polarity, without having to switch the leads or manipulate the patient. This is advantageous in critical life threatening situations where an incorrect connection of EKG leads otherwise might not permit proper detection of a heart rate and correlation with an optical pulse, and with fetal patients where it is not desirable to apply and reapply leads.

The resultant signal, referred to as the diagnostic EKG, is an analog representation of the electrical heart activity and can be displayed on an analog device such as a cathode ray tube or a chart recorder. The diagnostic EKG is filtered to select for the R wave of the EKG waveform and AC coupled to remove the DC component. The resulting signal is the filtered EKG signal.

The filtered EKG is processed to detect when an R wave occurs so that a digital pulse may be generated and sent to the oximeter to indicate that an R wave has occurred.

The oximeter functions remain essentially unchanged, except as specified herein. The microprocessor provides a bipolar drive current for the two LED's so that a positive current pulse drives the infrared LED and a negative current pulse drives the red LED. The magnitude of the current is adjusted by the microprocessor to help account for the variants of the patient's tissue. The light emitted by the LED's is detected by a single photodetector, preferably a photodiode, which generates a current proportional to the amount of transmitted light detected. The photocurrent may be amplified by a current to voltage converter. The resulting voltage is processed by the system electronics under the control of the microprocessor, to analyze and detect arterial pulses and to develop a history as to pulse periodicity, pulse shape, and oxygen saturation. The oximeter decides whether or not to accept a detected pulse as corresponding to an arterial pulse by comparing the detected pulse against the pulse history. To be accepted, a detected pulse must meet certain predetermined criteria in accordance with a desired degree of confidence. The blood constituent measurement is then made on the basis of accepted pulses.

According to the improved method and apparatus, the EKG signals from the electronic heart detection circuitry are processed using the analog to digital conversion and digital processing circuitry of the N-100 Pulse Oximeter to determine polarity, rhythmicity, and amplitude of the EKG signals. During this determination, the microprocessor converts the diagnostic EKG, the filtered EKG signal, or both, into digital EKG signals, analyzes the digital EKG signals, determines the amplitude and the polarity of the EKG, and adjusts the AGC amplifier and the polarity compensation circuit accordingly.

In the preferred embodiment the microprocessor operates in an integrated mode in which it develops and compares information from an EKG waveform and the optical pulse signal. The microprocessor first separately measures the time period by which an optical pulse follows an R wave, averages it over several pulses, independently calculates the pulse rate for each waveform, and compares the optical and EKG pulse rates. This insures reliability of both the electrical heart and arterial blood flow waveform analyses.

Predetermined criteria for optical pulse signal may include, for example, the expected size of the pulse, when the pulse is expected to occur, and the expected ratio of the red light to infrared light of the detected optical pulse. The predetermined criteria may be preselected or established by creating a pulse history. The pulse history may comprise a number of most recent pulses, e.g., four, in a push-down stack memory which may automatically store the data for the last four accepted detected optical pulses.

The improved oximeter uses the measured time delay between an R wave and an optical pulse to determine a time window when, following the occurrence of an R wave, the probability of finding an optical pulse corresponding to a true arterial pulse is high. The time window provides an additional criterion to be used in accepting or rejecting a detected pulse as an optical pulse. Any pulses detected that do not fall within the time window are rejected and not used to calculate the amount of blood constituent. Similarly these rejected pulses normally do not become a part of the pulse history. However, if there have been no acceptable pulses within the time window for approximately 3 pulse periods, pulses within the time window that normally would be rejected will be accepted. This may be accomplished, as discussed below, by changing the predetermined optical pulse criteria.

Adjustments may be made to the microprocessor so that, when the optical signals are of high quality and easily detected a relatively high correlation between a detected pulse and the pulse history can be required before a detected pulse is accepted as an optical pulse. This would provide measurements having a high confidence level. When the optical signals are of low quality, the degree of correlation necessary can be lessened, providing measurements having a lower confidence level. This confidence factor may be adjusted in accordance with the bear to bear variability of the optical signals or the relative strength of the optical pulse signal.

If, even with degraded criteria no acceptable optical pulse is detected within the window for a specified period, e.g., 10 seconds, the microprocessor will revert to the initialization procedure and re-establish a relationship between EKG R waves and acceptable optical pulses.

In its integrated mode, the improved oximeter can calculate the blood constituent amount from the digital optical signal detected only during the determined time window. The time window thus can be used to reduce the processing of any spurious pulses caused by motion artifact or noise so that integrating the EKG information establishes reliable measurement of oxygen saturation.

One advantage to the integrated measurement of heart activity and optical signals is that it indicates that the oximeter is detecting an optical pulse when it is expected to occur. One advantage to using EKG signals is the determinable relationship between an R wave and an arterial pulse, which can confirm the regularity or irregularity of the heart beat, and ensure, for example, that the oxygen saturation measurements are based on the pulsatile component of the blood flow and are accurate.

Another advantage is that if one of the EKG or optical signals were to fail, the oximeter can revert to a non-integrated mode, allowing independent processing of the EKG and optical signals. The non-failing signal would continue to provide certain vital information and, more importantly, indicate that the failure of the signal was not due to the patient's loss of bodily function, e.g., cardiac arrest. Thus, the improved oximeter provides for redundant measuring of the heart rate of the patient, and indicates that one of the EKG or optical signal detection devices is not working properly. In the event that the missing signal is restored, integrated operations would resume as described above.

A further advantage of the improved method and apparatus is that patients who do not have a regularly occurring heartbeat can now be reliably monitored.

The improved oximeter of this invention has improved capability to deal with arrhythmias and can detect and analyze the period of time by which an optical pulse follows an R wave and determine an appropriate time window. Then, on the occurrence of successive R waves, including irregularly occurring R waves, the determined time window is used so that the oximeter digitally processes the digital optical signal detected during the time window, develops an optical pulse history, and calculates the amount of blood constituent present. A patient having an irregular heartbeat also can be monitored, and an amount of blood constituent measured based on the actual blood pulse.

BRIEF DESCRIPTION OF THE DRAWINGS

FIG. 3 is a graphical representation of the outputs of FIG. 2.

FIGS. 5a and 5b are a detailed schematic of the microprocessor analog multiplexors and digital to analog converter of FIG. 1.

FIGS. 6a, 6b, and 6c are flow charts for the EKG and optical pulse related microprocessor operation of this invention.

FIG. 7 is a graphical representation of the outputs of FIG. 1.

DETAILED DESCRIPTION OF THE INVENTION

Figure 1:
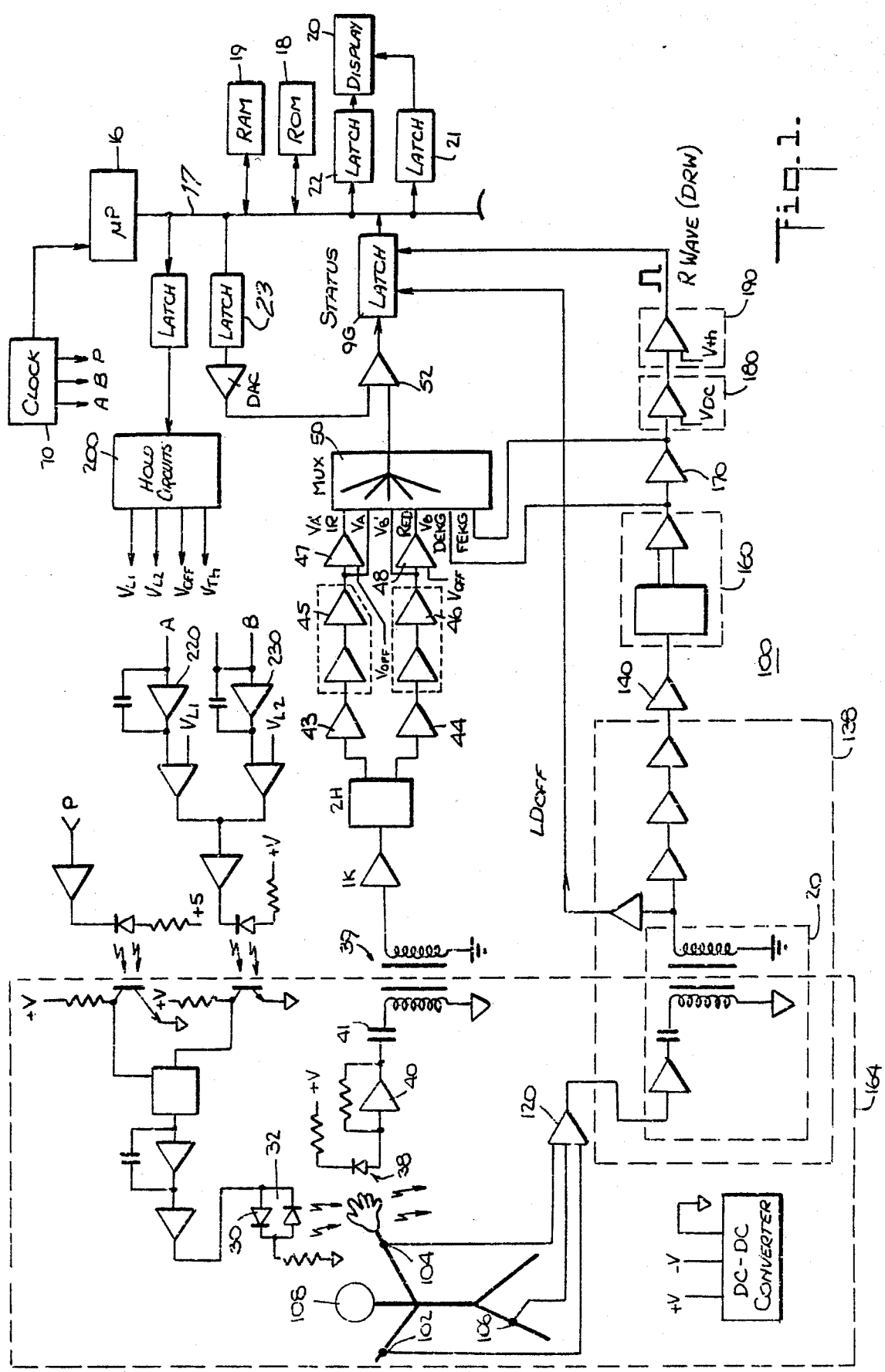
FIG. 1 is a block diagram of the improved method and apparatus of this invention.

As shown in FIG. 1, an embodiment of this invention comprise EKG detection means 100 and pulse oximeter 200. EKG detection means 100 has positive lead 102, negative lead 104, and reference lead 106, each electrically connected to patient 108. Typically, positive lead 102 is connected to the right arm, negative lead 104 is connected to the left arm and reference lead 106 is connected to the right leg. When the patient is a fetus, positive lead 102 is connected to the fetus, negative lead 104 is connected to the maternal vaginal canal, and reference lead 106 is connected to the maternal right leg. An alternate perinatal oximeter probe combining optical detecting means and EKG detecting leads is described in co-pending and commonly assigned U.S. patent application Ser. No. 644,051, filed Aug. 24, 1984, which disclosure is incorporated herein by reference.

EKG detection means 100 also includes preamplifier 120, coupling circuit 138, automatic gain control ("AGC") amplifier 140, polarity switch 160, bandpass filter 170, DC level shifter 180, and R wave detector 190. In operation, EKG detector means 100 produces three outputs, diagnostic EKG waveform DEKG, filtered EKG waveform FEKG, and detected R wave DRW. These outputs are shown in FIG. 3.

Figure 2A:
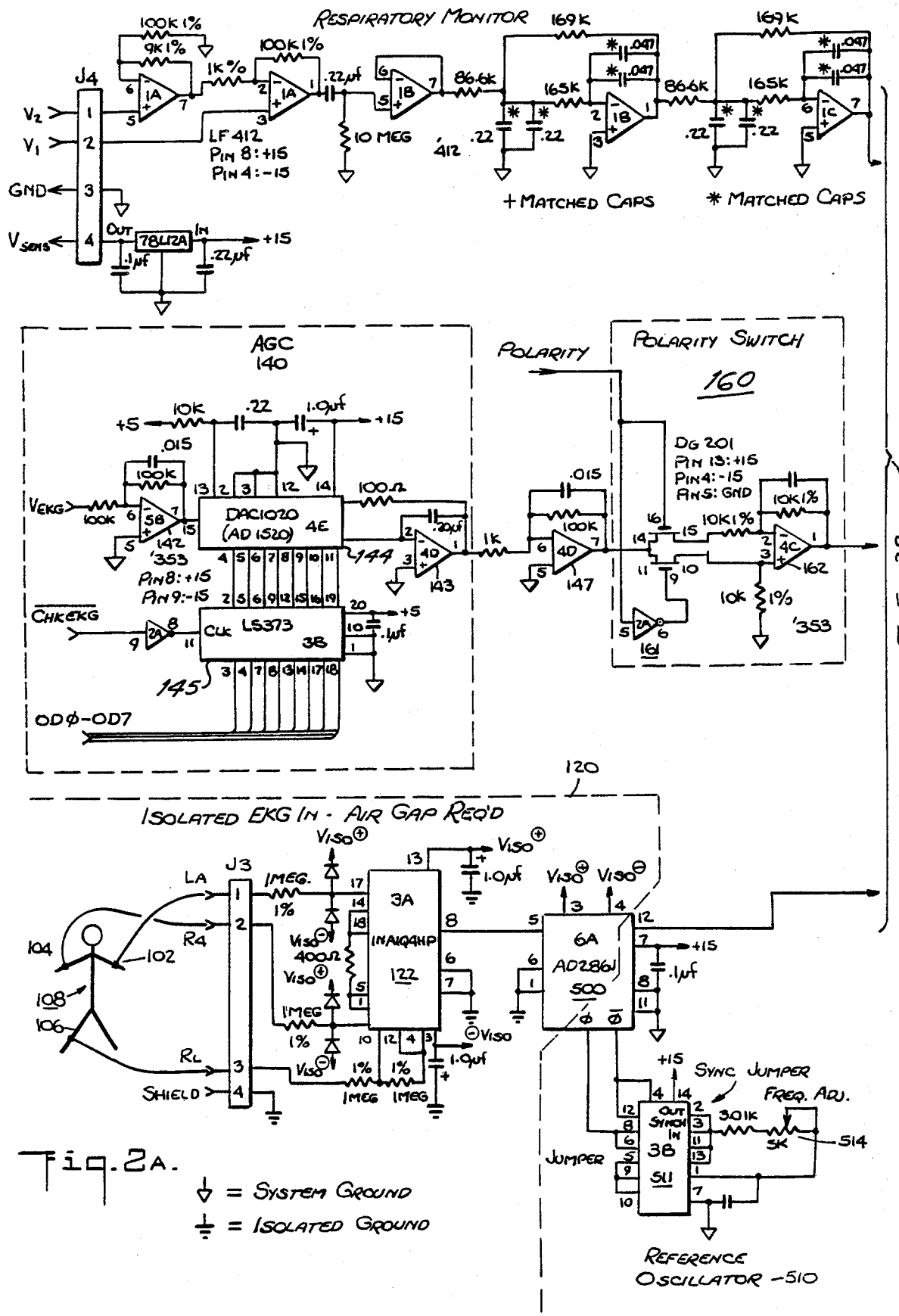
FIGS. 2a and 2b are a circuit schematic of the EKG detection circuitry and the system electronics of this invention.
Figure 2B:
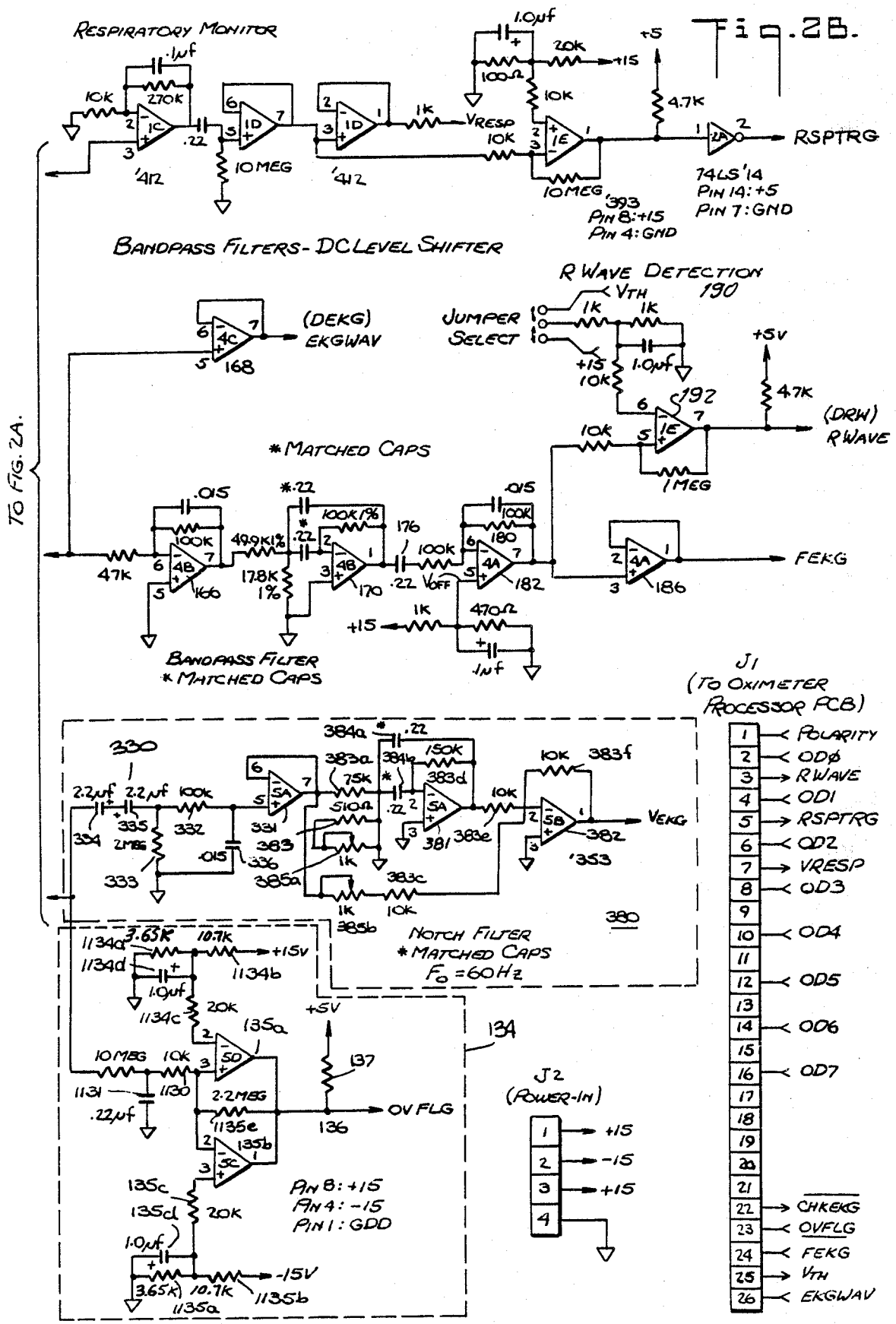

Referring to FIGS. 2a and 2b preamplifier 120 is mounted on the EKG front end printed circuit board 164 ("board 164") which is electrically isolated to protect patient 108 from strong electrical signals used to analyze and process the EKG and the optical signal waveforms. Preamplifier 120 comprises instrumentation amplifier 122, preferably a Burr-Brown INA104HP Very High Accuracy Instrumentation Amplifier, protected against high voltage inputs by diodes 124 and isolation voltages $\pm V_{iso}$. It is designed to have a gain factor of about 100.

The signal generated at negative lead 104 is input to pin 17, the signal generated at positive lead 102 is input to pin 2, common mode signal CMS is returned to the patient by reference lead 106 thus lowering the null common mode voltage of the patient, increasing rejection of common mode signals. The other pins are connected as indicated in FIGS. 2a and 2b, as known to one skilled in the art. For ease of understanding and distinguishing what input or output of the particular solid state element is being discussed, the electronic circuit drawings may be referred to herein as element "A101-16", meaning element A101 at pin 16.

The output of instrumentation amplifier 122 is passed to isolation amplifier 500, preferably model 286J, manufactured by Analog Devices, Inc. Isolation amplifier 500 provides transformer coupling of the EKG signal from isolated preamplifier 120 to the system electronics. Isolation amplifier 500 also provides isolated power for instrumentation amplifier 122. Oscillator circuit 510 consists of hex Schmitt inverter 511, resistor 512, capacitor 513, and variable resistor 514. This circuit provides a 100 kHz signal for proper operation of isolation amplifier 500.

The EKG signal, once coupled to the system electronics, travels to two different circuits. The first circuit is LDOFF detector circuit 134. LDOFF circuit 134 indicates when the EKG leads have become disconnected or inoperative and comprises parallel comparators 135a and 135b arranged in a window comparator configuration so that when the output of isolated preamplifier 120 is within + or −3.8 volts, the voltage at node 136 will be at +5 volts, realized from the pullup resistor 137. Comparator 135a has a resistor-divider network with a filter capacitor connected to the inverting input of comparator 135a consisting of resistors 1134a, b and capacitor 1134d, and is provided with a +15 volt reference voltage. This voltage is divided down to +3.8 volts and is presented to the inverting input across resistor 1134c. Similarly, comparator 135b has resistor-divider network with a filter capacitor connected to the noninverting input of comparator 135b consisting of resistors 1135a, b and capacitor 1135d and is provided a −15 volt reference voltage. This reference voltage is divided down to −3.8 volts which is presented to the non-inverting input of comparator 135b across resistor 1135c. Comparator 135a has feedback resistor 1135e connected to the non-inverting input from the output to provide hysteresis.

The output from isolated preamplifier 120 is fed to both the inverting input of comparator 135b and the non-inverting input of comparator 135a across filter capacitor 1131 and resistor 1130. The voltage at node 136 will be at +5 volts when the leads 102 and 104 are properly connected to patient 108. If either lead 102 or 104 becomes disconnected or inoperative, the voltage at node 136 will be at 0 volts. This is the digital OVFLG which is presented to status latch 9G-13.

The EKG signal is also fed to the second circuit, a bandpass filter circuit 330 consisting of buffer amplifier 331, resistors 332–333 and capacitors 334–336 designed to selectively filter out frequencies below about 0.05 Hz and frequencies above about 100 Hz. The signal is then passed through notch filter 380 to eliminate selected signal components for example, 60 Hz or 50 Hz, primarily designed to eliminate any interference from noise sources such as from the power line. Notch filter 380 consists of amplifiers 381 and 382, resistors 383a–f, capacitors 384a–b, and variable resistors 385a and b, for tuning the filter to 60 Hz. The output of notch filter 380 is substantially identical in waveform to the output of instrumentation amplifier 122.

The output of notch filter 380, the EKG signal, is input to bandwidth limited inverting amplifier 142, and to AGC amplifier 140 which receives the bandwidth limited signal at pin 15, and an analog input, of digital to analog converter ("DAC") 144, located in the feedback loop of inverting amplifier 143. DAC 144 also receives digital input from latch 145. The digital word fed to DAC 144 is entered into latch 145 by microprocessor 16 of the oximeter. By changing the digital word fed to latch 145 in response to the amplitude of diagnostic EKG signal DEKG, microprocessor 16 can adjust the gain of AGC amplifier 140—DAC 144 is utilized as a variable resistor in the feedback loop.

Amplifier 147 provides a second level of gain to the signal, which is then fed to polarity switch 160. Polarity switch 160, preferably a DG201 Analog Switch, manufactured by Siliconix, is designed to maintain uniform polarity of the EKG signal as it is being processed by appropriately gating the signal to one of either an inverting or noninverting input of amplifier 162. Microprocessor 16 processes the filtered EKG waveform, detects polarity, and generates a voltage signal, for example, +5 volts, which is also inverted by inverter 161 to form a second voltage signal, e.g., 0.0 volts, which together to form a logical word (polarity, polarity). The voltage values of the logical word causes polarity switch 160 to gate the EKG signal being processed to the appropriate input of amplifier 162 accordingly. The output of amplifier 162 is diagnostic EKG signal DEKG which is buffered by amplifier 168 and sent to the analog to digital converter ("ADC") of the pulse oximeter for conversion by microprocessor 16.

The output of amplifier 162 is amplified by amplifier 166 and also fed to bandpass filter 170, for selectively passing frequencies from about 15 to about 40 Hz having a center frequency of about 20 Hz. The filtered signal is passed through capacitor 176 for eliminating any DC voltage components that may have been introduced during prior amplifications, and is then inputted to DC level-shifter 180. DC level-shifter 180 comprises an offset voltage $V_{off}$, preferably +5 volts, being fed to the noninverting input of amplifier 182 and the filtered signal being fed to the inverting input of amplifier 182. $V_{off}$ is adjusted so that the output of amplifier 182 will be within the detectable range of the ADC of the pulse oximeter. In the preferred mode, the ADC of the pulse oximeter can only detect positive voltages, necessitating DC level-shifter 180. In circumstances where the ADC of the pulse oximeter can detect a bipolar signal having positive negative voltages, a DC level-shifter may not be required.

The output signal of amplifier 182 is filtered EKG signal FEKG, which is buffered by amplifier 186 and sent to the ADC of the pulse oximeter for waveform analysis. Output FEKG is also fed to R wave detector 190 comprising comparator 192, threshold voltage $V_{th}$, preferably +5.5 volts, and digital pulse voltage $V_{CL2}$, preferably a pull up voltage of +5 volts. When the amplitude of filtered EKG signal FEKG rises above the value of threshold voltage $V_{th}$ input to the inverting input of the comparator 192, comparator 192 generates as its output a digital pulse representing a logical 1, having an amplitude equal to $V_{CL2}$, e.g., +5 volts. At all other times, comparator 192 has an output that is a logical 0, e.g., about 0 volts. $V_{th}$ may be adjustable by the operator of the pulse oximeter so that if no R wave pulses are generated, the threshold voltage (and the confidence level) can be reduced until R wave pulses occur. Alternately, $V_{th}$ can be adjusted by the microprocessor if no R wave pulses are detected and the LDOFF signal indicates there should be R wave pulses. The output signal of R wave detector 190 is detected R wave DRW, and each pulse (+5 volts) represents the occurrence of R waves (logical 1's) in the patients" EKG waveform, as shown in FIG. 3.

Figure 4A:
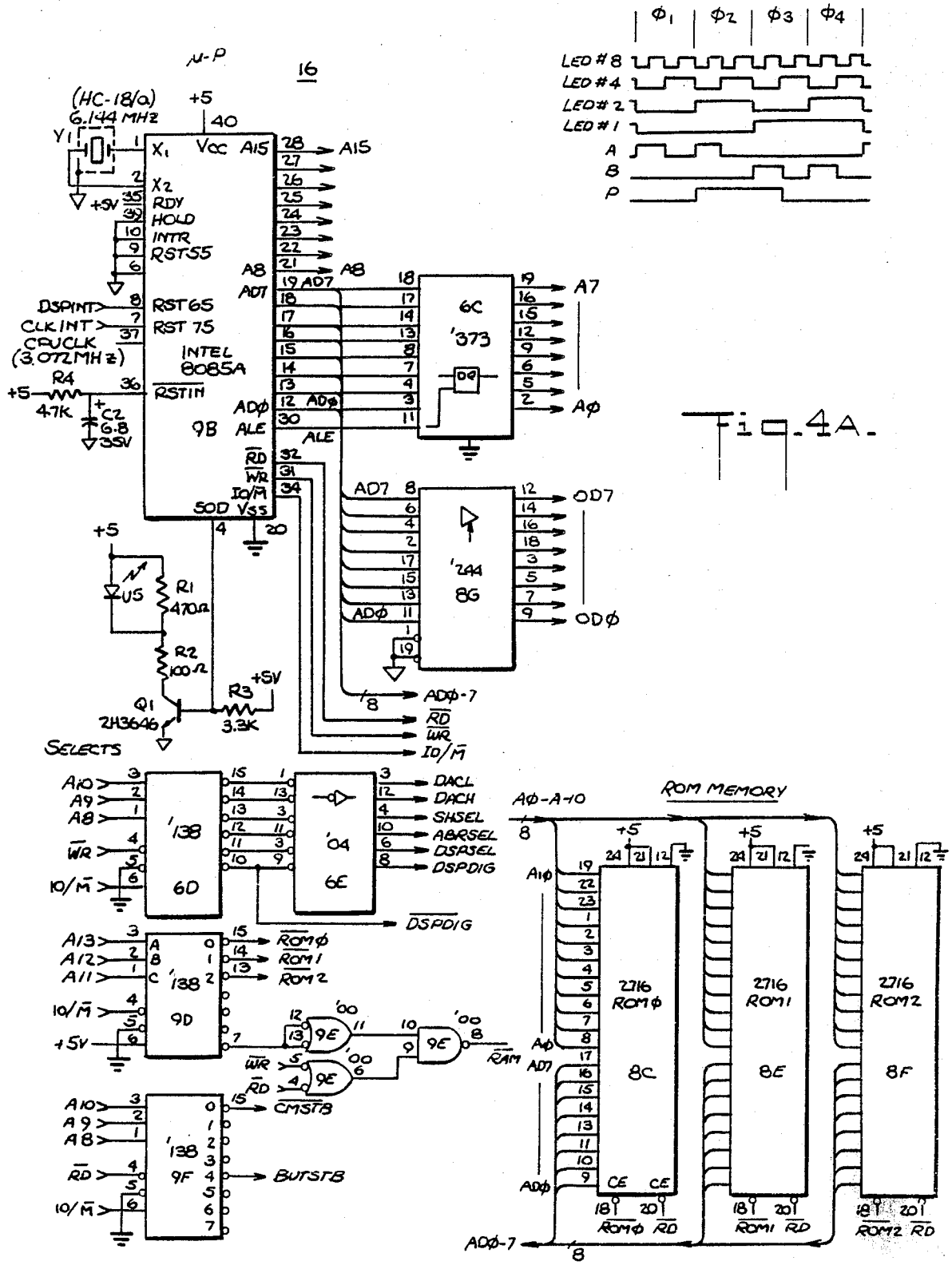
FIGS. 4a and 4b are a detailed circuit schematic of the microprocessor status input of FIG. 1.
Figure 4B:
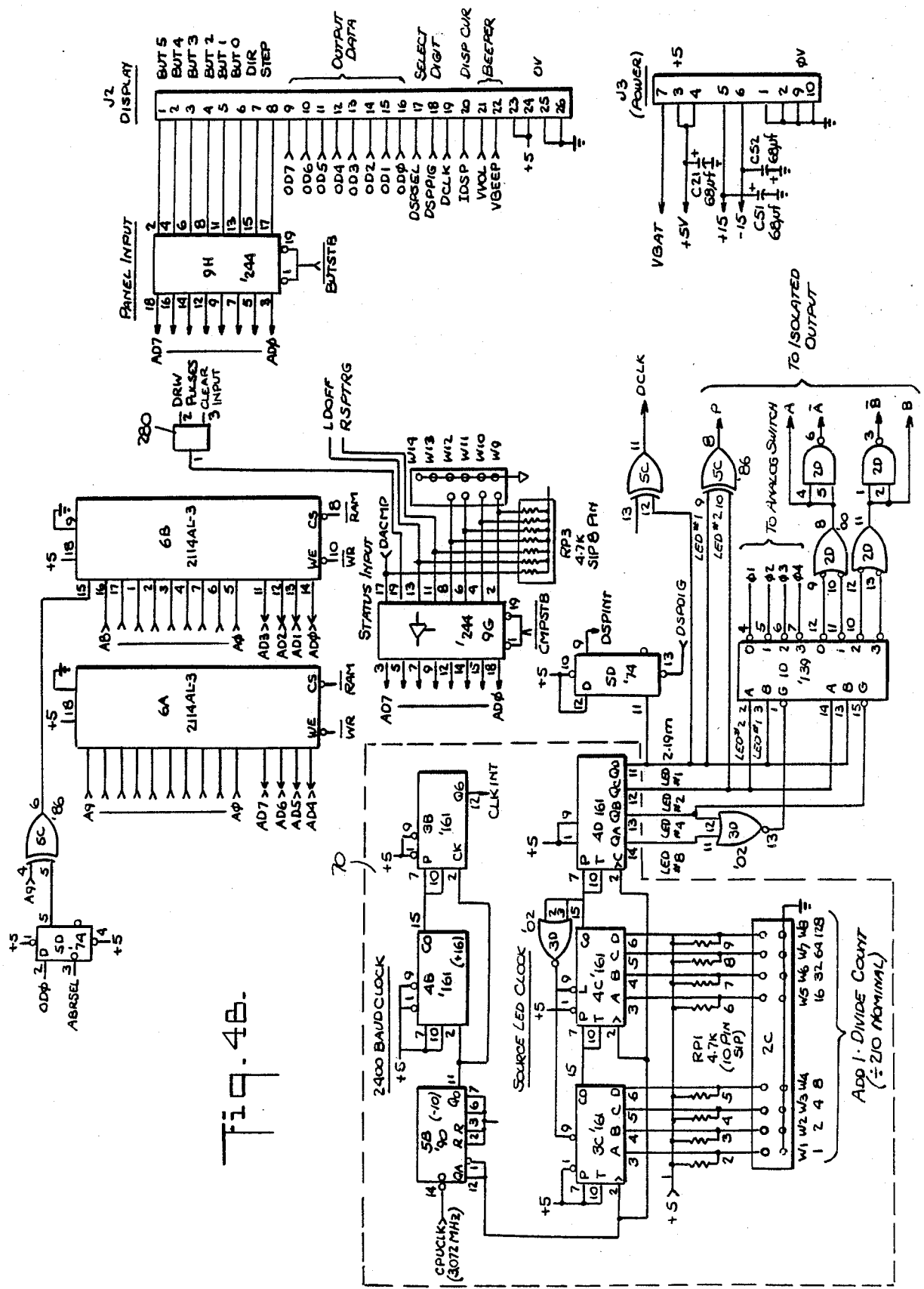

Referring to FIGS. 4a and 4b, detected R wave DRW is then fed to input 280-2 of flipflop 280. Flipflop 280 changes logical conditions from a logical 0 to a logical 1 output at output 280-1 when it detects the rising edge of an R wave pulse as the voltage of signal DRW rises from about 0 to $V_{CL2}$, and will maintain a logical 1 output until cleared by microprocessor 16 at clear input 280-3. When cleared, flipflop 280 has a logical 0 at output 280-1. The output of flipflop 280 is fed to status input latch 9G-19, where it is stored as a logical 1, representing an R wave flag. In this manner, the presence of an R wave pulse is indicated even though the instantaneous R wave signal DRW voltage has returned to logical 0.

Microprocessor 16 frequently checks the condition of each input of status input latch 9G for information relating to signal processing sequence control. As indicated in FIGS. 6(a–c), the presence of an R wave flag causes microprocessor 16 to (1) reset output 280-1 of flipflop 280 to a logical zero output, thereby clearing the R wave flag at status input latch 9G-19 so that flipflop 280 will return to a logical 1 output when it next detects an R wave pulse, and (2) either initiate non-integrated EKG waveform analysis to determine frequency and regularity of R waves to establish the period of delay between an R wave and an optical pulse (see FIG. 7) or initiate integrated searching for an optical pulse waveform during the established time period to analyze vital signs such as oxygen saturation, pulse flow, and pulse rate.

As shown in FIG. 3, diagnostic EKG waveform DEKG comprises an analog wave train of signals having components labeled P, Q, R, S, and T. The QRS portion is representative of ventricular contraction of the heart, the occurrence of the heartbeat. For normal patients, each heartbeat generates a similar PQRST pattern. Filtered EKG waveform FEKG is also an analog signal but contains substantially only the R portion of the diagnostic waveform as the other components are filtered out. The R portion is more distinctive than the other components having a significantly greater slope and amplitude. The R wave of filtered EKG waveform FEKG corresponds to the R wave portion of diagnostic EKG waveform DEKG, and detected R wave DRW contains a step or digital R pulse waveform that corresponds to the R wave portion of diagnostic EKG waveform DEKG.

The arterial blood pulse detection circuitry is the same as that found in the N-100 Pulse Oximeter manufactured and sold by Nellcor Incorporated, Hayward, Calif.

Referring to FIGS. 1, 4a, 4b, and 8, pulse oximetry occurs as follows. Clock 70 has a duty cycle of four segments $\phi 1$, $\phi 2$, $\phi 3$, $\phi 4$ that are sequential. Clock 70 is connected to microprocessor 16. Segment $\phi 1$ turns on LED 30, segment $\phi 2$ turns off LED 30, segment $\phi 3$ turns on LED 32 and segment $\phi 4$ turns off LED 32. The LED's are strobed in sequence so that only one LED is transmitting at a time. The LED's are turned off to allow the photoelectric detector to return to a quiescent condition to being measure ambient environmental light levels. As clock 70 operates through its duty cycle, the light transmitted through the tissue of patient 108 is received by photodetector 38. Clock 70 has three signal outputs A, B and P. Outputs A and B are input to a conventional pulse width modulation circuit to couple the pulse widths from the system electronics to board 164, and to establish the desired LED intensities for the LEDs 30 and 32. The reference intensities are established by microprocessor 16 which generates intensity voltage $V_{L1}$ for infrared LED 30 and intensity voltage $V_{L2}$ for red LED 32. These reference voltages are adjusted as described elsewhere herein, and form a part of the output of hold circuit 200.

Figure 5A:
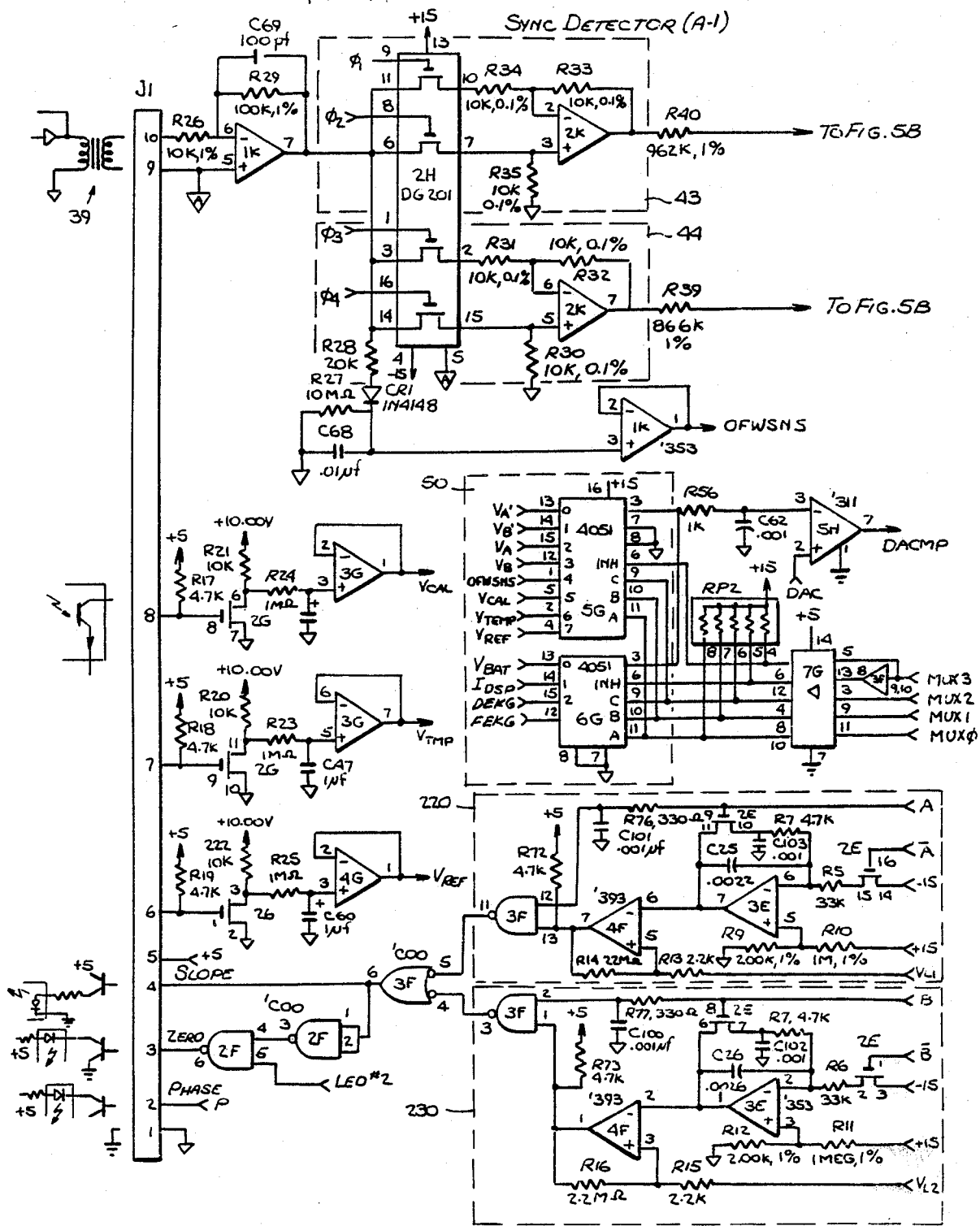
Figure 8B:
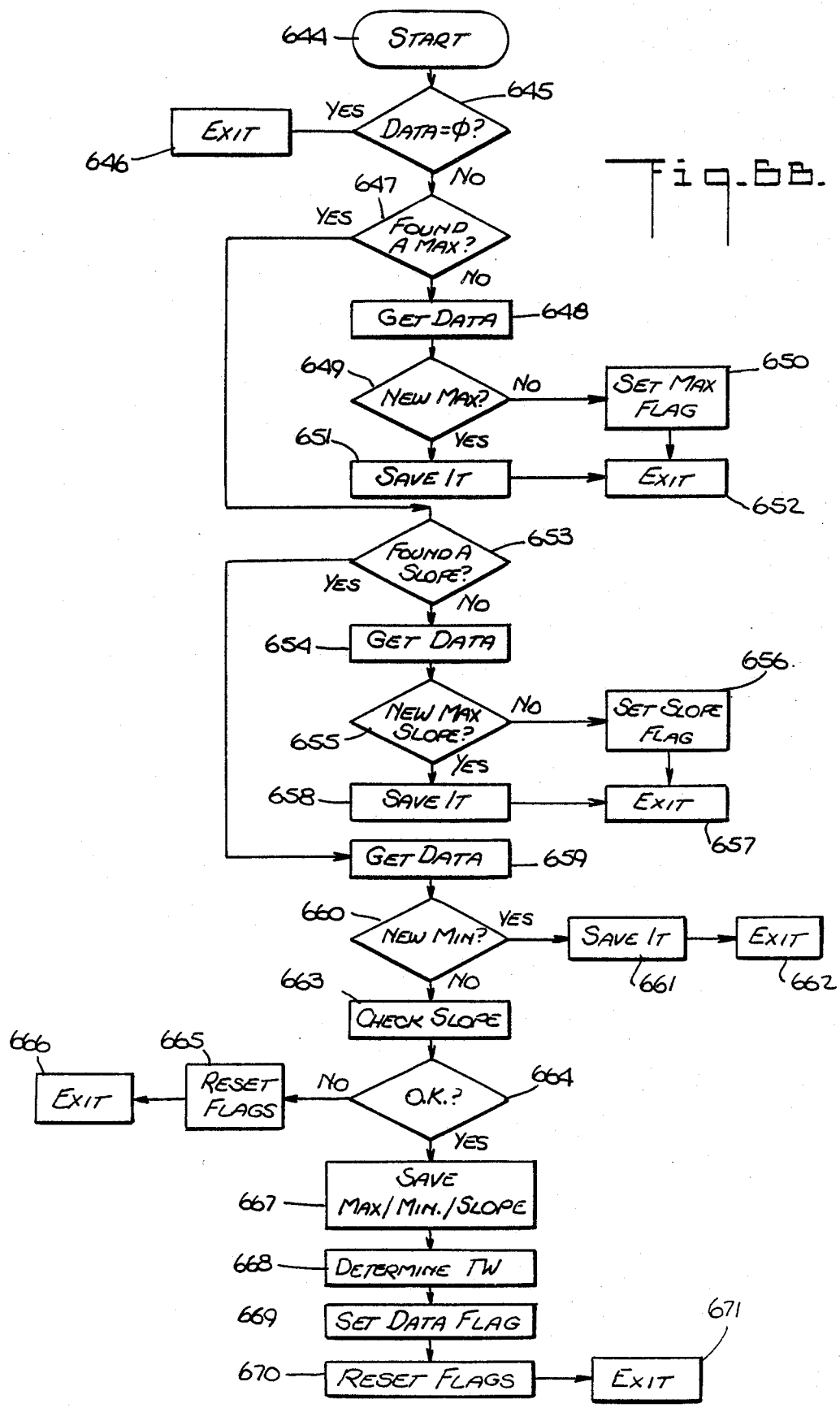
FIG. 8 is a graphical representation of the oximeter timing diagram.

Referring to FIG. 1 and FIGS. 5a and 5b parallel pulse width modulation circuits 220 and 230 are shown. Circuit 220 has as inputs A, $\overline{A}$, $-15$ volts, $+15$ volts, and $V_{L1}$. Matching amplifiers 3E are used with the same resistor, gates, and capacitor networks shown as ramping generators to provide the waveform labeled "ramp" in FIG. 8. When A is a logical 1, gate 2E will open circuit, the $-15$ volt supply, otherwise connected to inverting input 3E-6 and the feedback loop comprising resistors R5 and R7 and capacitors C25 and C103, will be made conductive by the closing of gate 2E-9. This condition will cause the amplifier output to ramp from 0 volts to $+15$ volts as shown in FIG. 8 labeled ramp. When A is a logical 0, or at about 0 volts, gate 2E-16 is closed and a $-15$ volt supply is input to amplifier 3E at E3-6, and feedback loop resistor R7 is open circuited by gate 2E-9 so that output 3E-8 will be and maintained at about 0 volts. During the time A is a logical 1, signal B is a logical 0. Because pulse width modulation circuit 230 works the same as circuit 220, ramping output 3E-1 will be at about 0 volts, except when signal B is a logical high when it will ramp from about 0 to $+15$ volts.

Outputs 3E-7 and 3E-1 are inputted to comparators 4F-6 and 4F-2, respectively. Intensity voltage inputs $V_{L1}$ and $V_{L2}$ are fed to comparator inputs 4F-5 and 4F-3, respectively, so that when a ramping voltage exists it is compared to its respective intensity voltage. Thus, comparator output 4F-7 will reflect a logical 1 condition, about $+5$ volts from pull up voltage at resistor R72, for the time period when ramping voltage at 3E-7 is less than intensity voltage $V_{L1}$. When ramping voltage is greater than $V_{L1}$, output 4F-7 will change to a logical 0, creating a pulse having a width responsive to the intensity level. Similarly, comparator output 4F-1 will be a logical 1, about $+5$ volts, during the time period when ramp voltage 3E-1 is less than intensity voltage $V_{L2}$ from pull up voltage $+5$ volts across resistor R73. Thus, the outputs of 4F-7 and 4F-1 are pulses having a width representing the desired voltage intensity for $V_{L1}$ and $V_{L2}$, respectively.

The outputs of comparators 4F-7 and 4F-1 are input to NAND gate inputs 3F-13 and 3F-1, respectively. Signal A is input to NAND gate input 3F-12 and signal B is input to NAND gate input 3F-2. The outputs of NAND gates 3F-11 and 3F-3 are input to NAND gate 3F-5 and 3F-4 respectively, where the signals are effectively combined so that output 3F-6 is a digital waveform Slope shown in FIG. 8.

Output 3F-6 is also input to both inputs 2F-1 and 2F-2 of NAND gate 2F, and output 2F-3 is input to NAND gate input 2F-4. Signal LED*2 is input to NAND gate input 2F-5, and output 2F-6 is digital waveform zero, shown in FIG. 8.

Figure 9A:
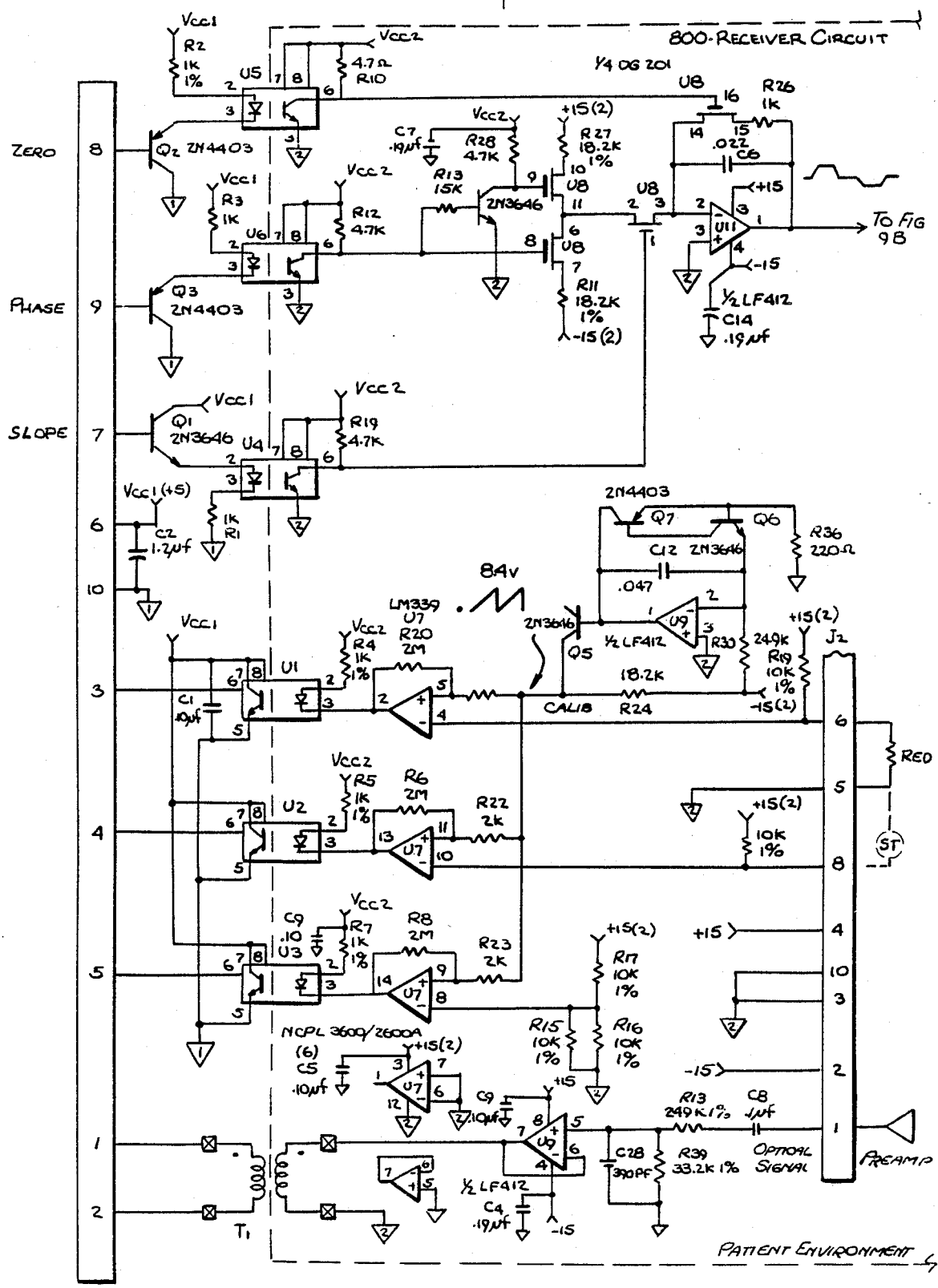
FIGS. 9a and 9b are a detailed circuit schematic of the isolated front end printed circuit board of FIG. 1.
Figure 9B:
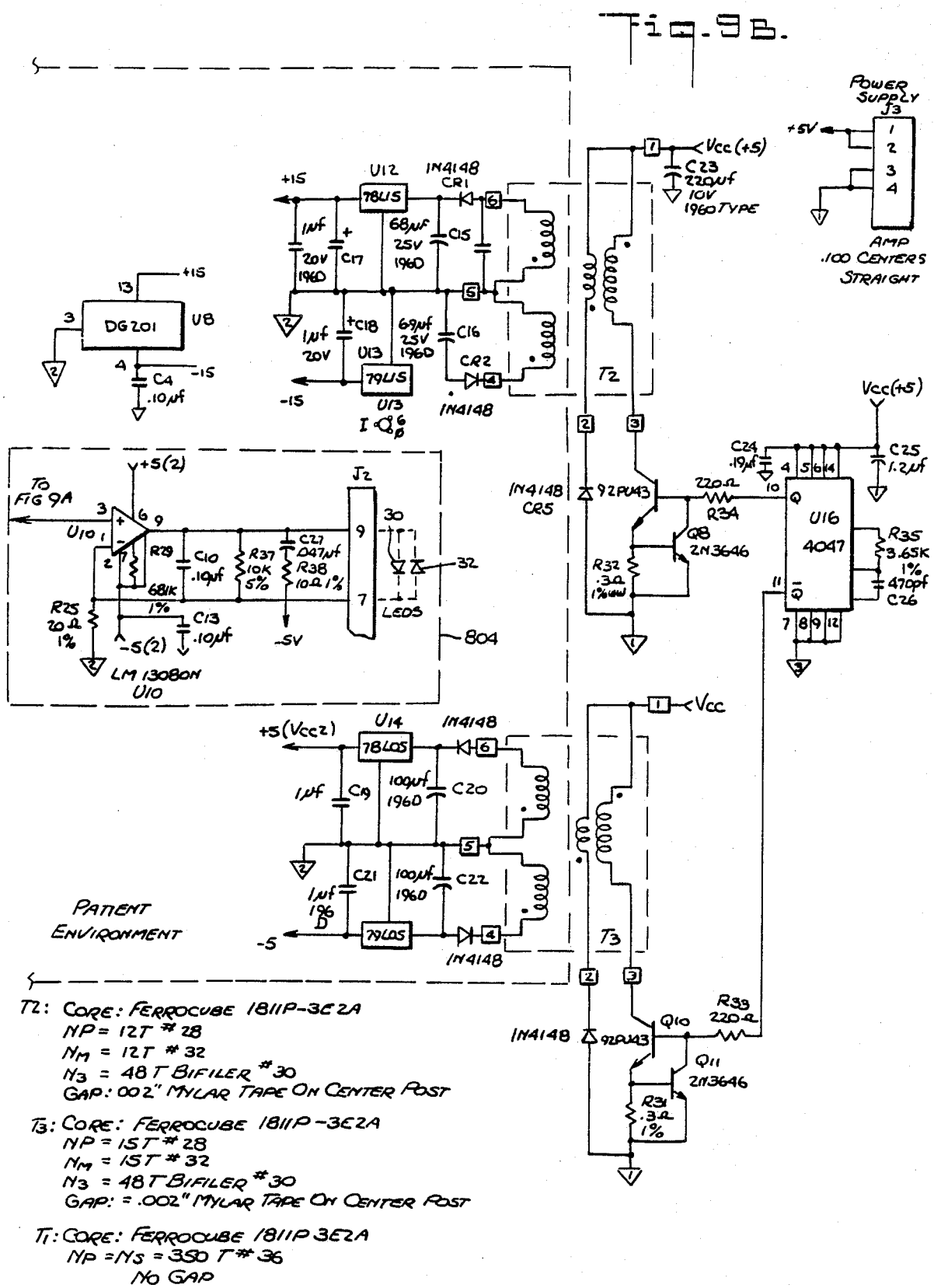

Signals "Slope", "Zero", and "Phase", the latter being generated by clock 70 and shown in FIG. 8, are coupled to board 164 by optical couplers U4, U5, and U6, respectively (shown in FIGS. 9a and 9b). The signals are input to receiver circuit 800 for decoding of the pulse width information contained in signals Slope, Zero, and Phase and for generating voltages to be used for driving infrared LED 30 and red LED 32 in accordance with the stated duty cycle.

Referring to FIGS. 8, 9a and 9b, signal Zero controls switching gate U8-16 which alters the gain of amplifier U11. Signal Slope controls gate U8-1 which controls whether there is input to integrator amplifier U11 and associated capacitor C6. The magnitude of output U11-1 is dependent upon the width of signal Slope. The greater the width is, the longer gate U8-1 will be closed. This directly relates to how long amplifier U11 and capacitor C6 will integrate the input signal, or the peak value at output U11-1. This in turn relates to a proportional current level is amplifier circuit 804 through the selected LED resulting in the selected intensity of emitted light. Signal Zero acts to turn off the gain of amplifier U11 at selected intervals so that the voltage will decay to about zero and the current in amplifier circuit 804 will decay to about zero, thus turning off whichever LED was on and allowing it to return to its quiescent state. Signal Zero also prevents leakage current from causing a progressive error in integrator amplifier U11 and associated capacitor C6. Signal Phase controls gates U8-8 and U8-9 which selects which voltage supply, $+15$ volts or $-15$ volts will be input to gate U8-2 for throughput to integrator amplifier U11 when gate U8-1 is closed by signal Slope.

The signal at amplifier output U11-1 thus provides the waveform (shown in FIG. 8) that controls LEDs 30 and 32. LEDs 30 and 32 are connected in parallel, anode to cathode and cathode to anode at the output ports J2-9 and J2-7 of amplifier circuit 804. Amplifier circuit 804 converts the voltage output U11-1 to the LED drive current using power amplifier U10 and current sensing resistor R25. Therefore, as output U11-1 varies from positive to negative, as converted to current by circuit 804, a positive current at port J2-9 turns on LED 30, LED 32 remaining off and open circuited by the current bias, and a negative current turns on LED 32 and open circuits LED 30. Between the positive and negative currents, the LED drive current has been turned off, turning off LEDs 30 and 32, due to the effect of signal Zero.

The light emitted by LEDs 30 and 32 is passed through tissue of patient 108, preferably through a finger. Alternate preferred tissue locations include the ear lobe, nasal septum, reflected light off the forehead and the like. In situations where reflected light is used, it is preferred to place an optical barrier (not shown) between the emitting LEDs and the detecting photodetector to prevent distortion of the light content transmitted through the tissue.

Referring to FIG. 1, photodetector 38 receives all light transmitted through the tissue of patient 108 so that photodetector 38 receives infrared plus ambient light and noise during clock output $\phi1$, ambient light and noise during clock output $\phi2$, red plus ambient light and noise during clock output $\phi3$ and ambient light and noise during clock output $\phi4$. This signal ("DLS") is passed through preamplifier 40, which converts the photodetected current into a voltage at a rate of about one volt per microamp, capacitor 41, and is then coupled by transformer 39 from electrically isolated board 164 to the system electronics. After coupling to system electronics, which may itself be electrically isolated, the signal is processed by parallel circuitry for separating the red and infrared signals, in order to adjust for the different gains required to process red and infrared signals. Clock 70 outputs $\phi1$–$\phi4$ control the synchronization detector gates 2H to divide composite signals DLS into infrared light signal IRLS and red light signal RLS and direct signals IRLS and RLS to parallel amplifiers 43 and 44. Parallel synchronous detector gates 2H and parallel amplifier 43 an 44 also act to invert the pure ambient light and noise signals and, using a slow time constant filter, add them to the adjacent LED light plus ambient light and noise signals to subtract out the ambient light and noise signal components. These filtered signals then pass through parallel low pass filters 45 and 46 to eliminate the switching frequencies and noise. Signal outputs $V_a$ and $V_b$ are sent to the ADC of the oximeter for digitization, and also sent through parallel offset amplifiers 47 and 48 for subtracting out a portion of the DC bias and amplifying the remaining voltage signals. Offset amplifiers 47, 48 increase the resolution of the AC voltage signal component for digital conversion. Outputs $V_{a'}$ and $V_{b'}$ are also sent to the ADC of the oximeter for analog to digital conversion.

Referring to FIGS. 5a and 5b, the system electronics for processing signal DLS is described in more detail. Signal DLS is coupled through transformer 39 on front end printed circuit board 164 and enters the system electronics at pin 10 of connecting strip J1. Signal DLS consists of the time-sequenced response of photodetector 38 to infrared LED 30 and red LED 32 as shown in the timing diagram (see FIG. 8 under the label "Photocurrent"). Signal DLS is amplified by one-half of dual amplifier 1K.

The output of amplifier 1K is connected to four analog switches forming switching element 2H of parallel two-channel synchronous detectors 43 and 44 which separate the pulses of infrared and red light detected by photodetector 38 and eliminate low frequency noise and DC offset voltages. As clock 70 goes through its duty cycle, during state $\phi1$ first analog switch 2H-10 closes, coupling preamplified signal DLS through detector channel 43 and amplifier 2K-1 having a gain of about $-1$ formed by resistors R33 and R34. During state $\phi2$, first switch 2H-10 opens and second switch 2H-7 closes so that amplifier 2K-1 has a gain of about $+1$ wherein it acts essentially as a voltage follower with resistors R34 open circuited and resistor R33 forming the feedback loop. During states $\phi3$ and $\phi4$ red LED 32 turns on and off and a similar switching occurs for second detector channel 44 and amplifier 2K-7. The output of detector amplifiers 2K-1 and 2K-7 will thus be active with a duty cycle of 50 percent, half of that inverting and half non-inverting. Any DC or low-frequency voltage should be cancelled by the two adjacent pulses of opposite polarity, while photodetector signal DLS, which is present in only one of the two time states, will be amplified with an effective gain of about 0.25.

The outputs of amplifiers 2K-1 and 2K-7, signals IRLS and RLS, respectively, are fed to matched low-pass filters 45 and 46 for passing only frequencies below about 10.0 Hz, having amplifiers 3K-1 and 4K-1, and 3K-7 and 4K-7, for providing a respective gain of about 4 to signals IRLS and RLS. These filters remove the switching component which is about 2 kilohertz and filter out any high frequency noise.

The signal processing means for processing the EKG signals and the optical signals includes a programmed microprocessor such as the Intel 8085 A. The basic functions of the equipment will be described for comprehension, while the improvements forming a part of this invention will be described in detail.

Referring to FIG. 1, the signal processing means comprises microprocessor 16, data bus 17, RAM 19, ROM 18, latch 23, comparator 52, analog multiplexor 50, hold circuits 200, gate 24, latch select 21, latch digit 22, and display 20, each connected to bus 17 and thereby under the control of microprocessor 16. Data bus 17 shunts digital information into and out of microprocessor 16 and each of the components. Latch select 21, latch digit 22, and display 20 all relate to a preferred numerical display of the amount of blood constiuent measured, e.g., optical pulse rate and oxygen saturation.

The function of the signal processing means is to convert the analog signals from the optical signal detector and from the EKG detector, independently, to digital signals, for subsequent waveform analysis. The waveform analysis is controlled by microprocessor 16, ROM 18, and RAM 19.

FIGS. 6(a–c) and the 123 page software appendix relate to the software used by the oximeter to control the signal processing of the optical signals and the EKG detection system. The microprocessor of the oximeter evaluates the optical signal to determine the oxygen saturation and pulse rate according to the following method.

A preferred embodiment of this invention incorporates into microprocessor 16 the means for processing the EKG signals and displaying the calculated EKG pulse rate, converting the analog diagnostic EKG signal DEKG and filtered EKG signal FEKG to digital EKG signals using the same analog to digital conversion circuits used for processing the optical signals. Referring to FIGS. 5a and 5b, analog multiplexer 50 is the input to the ADC of the pulse oximeter, and comprises two analog multiplexors 6G and 6G. Optical pulse signals $V_{a'}$, $V_{b'}$, $V_a$, and $V_b$ are connected to pins 13, 14, 15 and 12 of multiplexer 5G. According to the improved apparatus, diagnostic EKG signal DEKG is connected to pin 15 of multiplexer 6G and filtered EKG signal FEKG is connected to pin 12 of multiplexor 6G.

In order to convert any of the analog inputs to digital signals, microprocessor 16 must address the proper channel of one of analog multiplexers 5G and 6G by inputting a three bit word through bus 17 to pins 9, 10, and 11 of both multiplexers 5G, 6G. The microprocessor program is configured to allow for analog to digital conversion of the EKG signals KEKG, FEKG in addition to $V_a$, $V_b$, $V_{a'}$, and $V_{b'}$, and appropriate storage of the digital signals in RAM 19.

Referring to FIGS. 4a, 4b, 5a and 5b, microprocesser 16 converts analog signals to digital signals by selecting which input is to be converted and loading a digital word into latches 8G and 9K. Latches 8H and 9K store the digital word presented to the inputs of digital to analog converter ("DAC") 8K, which converts the digital word to analog signal DAC. Signal DAC is fed to pin 2 of comparator 5H. The other input to comparator 5H, at pin 3, is the analog signal from multiplexer 50 selected by microprocessor 16 for conversion. When the analog signal provided by DAC 8K exceeds the analog value presented by multiplexer 50, output DACMP of comparator 5H is at logical 1. The digital word which generates the analog voltage from DAC 8K that is less than the analog voltage present at multiplexer 50 will cause output DACMP of comparator 5H to change to logical 0. Output DACMP is inputted to status latch 9G-17 shown in FIG. 4b which is sampled by microprocessor 16 at a rate of about 57 cycles per second. When the microprocessor detects a logical 0, the word stored in latches 8H and 9K of FIG. 6 represents the digital value of the analog signal and is stored by microprocessor 16 into the accessed address of RAM 19 for later processing.

In connection with EKG signal processing, as shown in the software appendix, microprocessor 16 analyzes the stored digital words and calculates an amplitude for the EKG waveform. This amplitude is used to control AGC amplifier 140 by changing the digital word fed to DAC 144 so that outputs DEKG and FEKG will fall within and be compatible with the voltage range limits of the electronic circuitry used to process the signals, without losing any of the significant information contained therein. The start or non-integrated condition includes independent and continuous signal processing of the optical pulse to calculate and display oxygen saturation and pulse rate, and simultaneously, continuously processing EKG waveforms DEKG, FEKG, and DRW. When certain conditions exist, flags are raised at status input latch 9G and internally within microprocessor 16, indicating what operation is to follow.

Referring to FIGS. 4a, 4b, 5a and 5b, microprocessor 16 regularly searches status input latch 9G at a rate of about 57 cycles per second. According to this invention, output DRW is also input to status latch 9G through flipflop 280. Thus when detected R wave DRW is a logical 1, the microprocessor detects the 1 status and based upon that status selects the next operation. That operation can be one of the following events which occur in sequence. At startup conditions, upon detecting an R wave, microprocessor 16 clears output 280-1 of flipflop 280 to logical 0, clearing status input latch at input 9G-19 relating to EKG output DRW. At this first level, microprocessor 16 begins counting time intervals, using clock 70, from the detection of an R wave pulse DRW until the occurrence of the next logical 1 at status input latch 9G. Based upon this time interval, the improved pulse oximeter displays the pulse rate. After averaging several time intervals and establishing a regular EKG pulse rate, microprocessor 16 will change to the second level of processing.

With the detection of an R wave pulse, microprocessor 16 will begin to correlate the period of time by which an optical pulse, as separately determined by microprocessor 16 analyzing the digital optical signal, follows the detected R wave pulse to establish the time window during which the optical pulse is likely to occur. During this second level, the pulse oximeter is still calculating and displaying the time period or pulse rate between detected R wave DRW pulses.

The third level of processing is reached after a time window has been established. On detecting an R wave pulse, microprocessor 16 activates the time window so that only optical signals detected within the time window, following the occurrence of a R wave pulse, will be evaluated for acceptance or rejection for use in calculating and displaying vital measurements such as oxygen saturation, pulse flow, and pulse rate. The evaluation of a detected pulse is made in conjunction with a preselected confidence factor that is associated with the quality of the optical signals. The higher the optical signal quality, the better the correlation between the recorded pulse history and a detected pulse, and the higher the confidence level. The confidence level may be set automatically by the microprocessor, or it may be adjusted by the operator of the improved oximeter. Microprocessor 16 will reject any detected pulses occurring outside a time window. A typical time window for an adult male having a fingertip oximeter probe may be about 50 milliseconds, plus or minus 10 milliseconds, after the occurrence of an R wave.

The oximeter will also reject any additional pulses detected after an optical pulse is detected within the same time window, even though the time window has not expired.

However, if an optical pulse is not found within an opened time window, microprocessor 16 will continue to search for optical pulses using the degraded criteria during the time window period for a limited number of successive detected R wave DRW pulses, e.g., 3, after which it continues to search with degraded criteria. After a specific interval, e.g., 10 seconds, without detection of an optical pulse, microprocessor 16 will revert to independent or non-integrated processing of the optical signal and the EKG signals, returning the pulse oximeter to the start up condition. Therefore, if the oximeter cannot establish or maintain a reliable correlation between the R wave and the optical pulse, the waveforms will be processed independently. Preferably there is a display to indicate that the oximeter is integrating the EKG and optical signal data and so calculating the blood constituent amount. After attaining the third level of processing, losing either the EKG or optical pulse signals will activate an alarm and return the program to the start up condition.

Figure 6A:
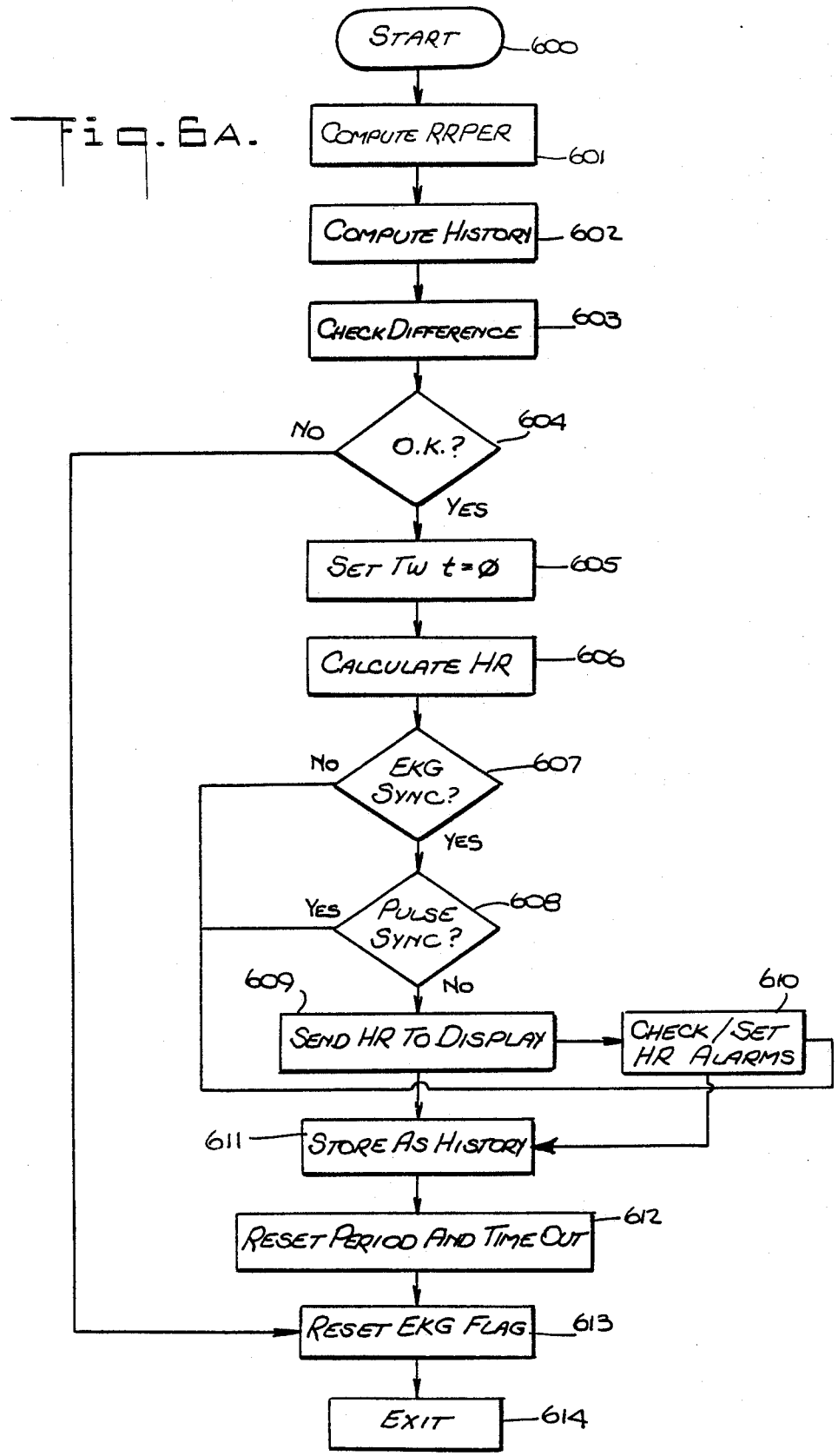
Figure 6C:
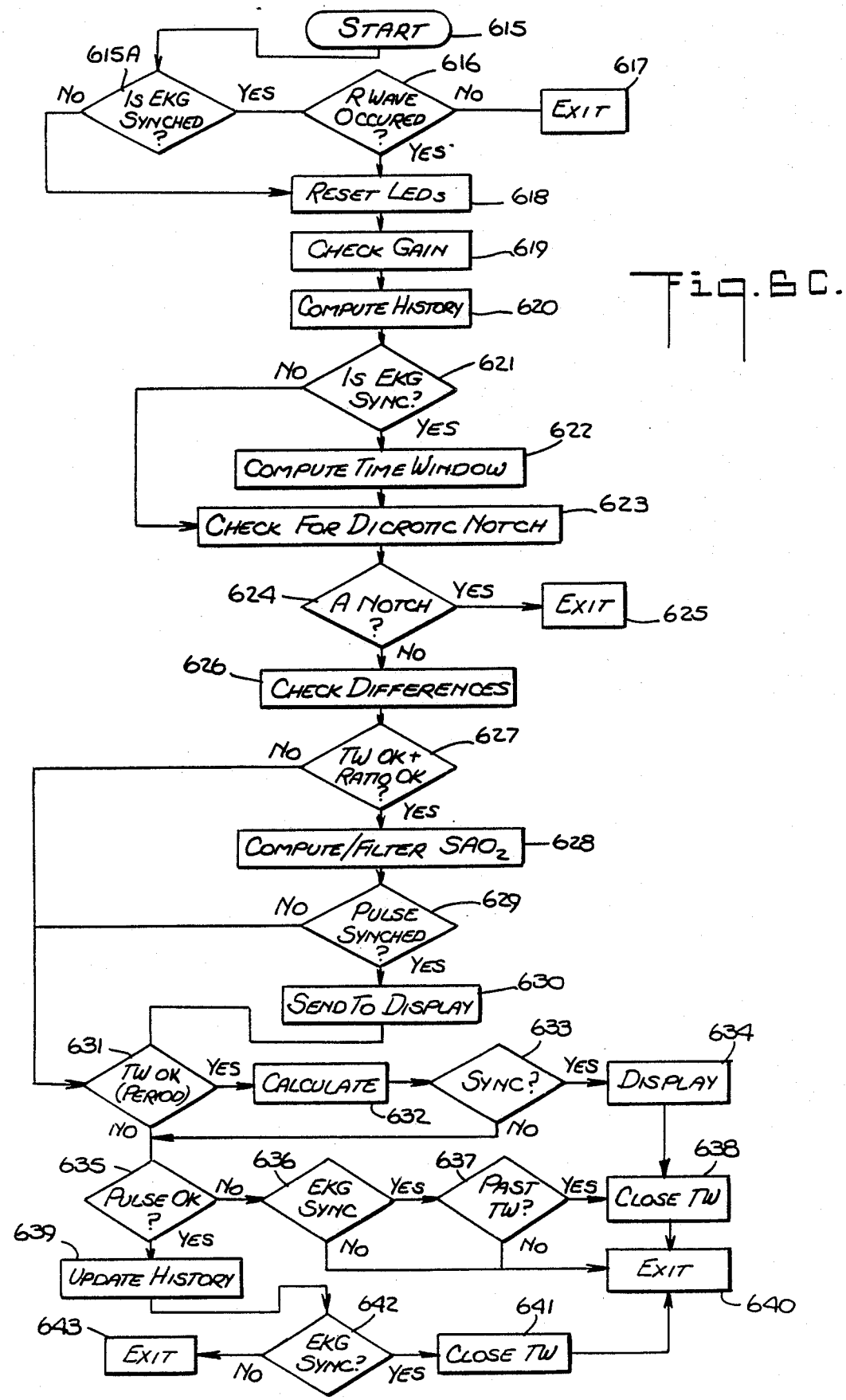

Having described the overall operation, referring to FIGS. 6a, 6b, and 6c the flow chart for the software calculations is shown and described. In FIG. 6a, the R wave determination routine begins at 600 with electrical signals received from the EKG leads and calculating the period RRPER between the last detected R wave and the presented R wave at 601. The average period HISTORY from previous R waves and the present R wave is calculated at 602 and the determined period RRPER from 601 is compared to the average period HISTORY at 603. If RRPER does not correspond to HISTORY at 605, then the routine jumps to 613 where the R wave (or EKG flag) at flip flop 280 is reset and the routine is exited to await another R wave. If RRPER does correspond to HISTORY at 604, the a timer is activated at 605 to measure the interval from the occurrence of the R wave to the occurrence of the topical pulse. At 606, output HR (EKG heart rate) is calculated based on successive R waves. At 607, the system inquires whether a series of R-R periods have been synchronized (EKG synchronization). If not synchronized, then the system checks for alarms by comparing output HR at 609, to a preselected heart rate and generating an alarm if output HR is too low. If the EKG is synchronized but the optical pulse to optical pulse series is not synchronized at 608, then output HR is sent to display at 609 and then checked for alarms at 610.

However, if the optical pulse is synchronized at 608, then the system just checks for alarms at 610. Only if the EKG is synchronized and the optical pulse is not synchronized, and if the R wave looks like a value R wave by comparison with HISTORY, then HISTORY is updated using the new R wave at 611. After updating HISTORY, the system itself is updated (TIME OUT) to maintain synchronization at 612. If TIME OUT is not updated for a period of five seconds, then EKG synchronization is lost and must begin building a new history.

Referring to FIG. 6b the system routine for processing digital optical pulse information for optical pulses to send to LEVEL 3 (shown in FIG. 6c) is flow charted. The system begins by continuously evaluating the data from the detected digital optical signal at 644. The data is first evaluated for compatibility with the signal processing at 645. If the data is over or undervalued electronically, i.e., beyond the voltage range of the circuitry, then the system exits the routine at 646, and the LED intensities are adjusted to correct the electrical values accordingly. When the data is compatible, it is next evaluated for a maximum signal. A relative maximum is determined and saved at 651. The next value is compared to the saved value, and if it is a new maximum it is saved at 651 instead. When the value found is not a new max, then a MAX FLAG is set at 650. Thereafter, the system evaluates the following data received, bypassing the maximum value section 648-652, to find the maximum slope at 653, again by successive comparisons. When the largest slope value is found it is saved at 658 and the SLOPE FLAG is raised at 656. Thereafter the following data is evaluated, bypassing the maximum and slope calculations, to find the minimum value corresponding to the end of the pulse at 659-662. When the smallest minimum is found, it is saved at 661 and the slope value saved at 658 is compared to a pre-established minimum threshold to determine whether it is large enough to be a possible optical pulse at 663. If it is not large enough, then the pulse is rejected at 664, the FLAGs raised at 659 and 656 are reset at 665 and the routine begins processing the next possible pulse at 644. If the slope is large enough then the pulse parameters, maximum, minimum, and slope, are saved in memory at 667 for use by LEVEL 3 processing in evaluating the possible pulse. Then, the time delay from the R wave to the possible pulse is calculated. Thereafter, the DATA FLAG is set at 669, indicating to LEVEL 3 that there is a possible pulse to be evaluated, the MAX and SLOPE FLAGs are reset at 670, and the routine begins again to process the following data, looking for new maximum values corresponding to possible pulses.

Referring to FIG. 6c, LEVEL 3 of software for computing the saturation measurements is shown. The system starts by inputting a potential optical pulse at 615 after a DATA FLAG has been raised and inquiring whether there is EKG synchronization i.e., a regular EKG period has been established. If a DATA FLAG has not been raised, then the system exits the routine at 617. If there has not been EKG synchronization, then the microprocessor processes the optical pulse signals independent of the EKG, as would occur in the Nellcor N-100 oximeter without EKG capability, bypassing the inquiry into the presence of an R wave at 616.

If there is EKG synchronization, but no R wave has occurred, then the system exits at 617 and the pulse is not processed. If there is EKG synchronization and a R wave has occurred, then the microprocessor processes the pulse as described below. The LED intensity is evaluated to see if adjustment is necessary at 618. The reset system gain, based on the minimum LED intensity required for adequate signal strength, is checked to see it adjustment is required. The optical pulse historic period, amplitude, and ratio. The system then inquires whether the EKG apparatus is operating period between an R wave and the following optical pulse for the most recent four prior pulses is computed to give the TIME WINDOW at 622. Then the pulse waveform is analyzed to see if it is a dicrotic notch rather than a real optical pulse at 623. The downward slope of a dicrotic notch or other artifact can be misinterpreted as an optical pulse, but typically the pulse amplitude is less than half the amplitude of an actual pulse. If the pulse is determined to be a notch or artifact at 624, then the system exits at 625 and the next pulse presented will be processed. If not determined to be a notch, then it is analyzed to determine if it is a pulse at 626.

Assuming the EKG is synchronized, then the system determines if two criteria are met. The first is whether the time delay falls within the above-computed TIME WINDOW. If it does not, then the microprocessor rejects the pulse. The second criteria tested is whether or not the ratio is within acceptable limits. Only if the pulse satisfies bot criteria, is the pulse accepted and a saturation calculation made.

If the EKG is not synchronized then the comparison must provide any two of three factors, (1) pulse period, (2) amplitude, and (3) ratio, as favorable for the pulse to pass as an accepted pulse at 627. E.g., pulse and period, period and amplitude, pulse and amplitude, or all three. If the pulse is accepted, then the oxygenation saturation is calculated at 628.

After the system is turned on (POWER UP) on after a TIME OUT alarm (a ten second period with no valid optical pulse found) a series of consistant pulses must be found to generate an optical pulse history before the oxygenation saturation will be sent to the display. Thus, if there is no optical pulse synchronization at 629, there will be no saturation display generated at 630. All optical pulses, those accepted and those not accepted, excluding pulses rejected as artifacts, enter the calculation routine section at 631-643. If the EKG is not synchronized then a pulse to pulse period and either an amplitude or a ratio must exist for the optical heart rate (OHR) calculation to be made at 632. If either the EKG or the optical pulse is synchronized, then the HR calculation made at 632 will be displayed at 634. If there is no synchronization, then the OHR is not displayed. At 635-643, the system is evaluating the status for pulse evaluation, i.e., whether signals should continue to be processed after a TIME WINDOW has been opened. If there was EKG synchronization and a good pulse was found, or the TIME WINDOW period has expired then TIME WINDOW is closed until opened by the detection of the next R wave.

In the preferred embodiment, the blood constituent measured is the oxygen saturation of the blood of a patient. The calculation of the oxygen saturation is made based on the ratio of the pulse seen by the red light compared to the pulse seen by the infrared light in accordance with the following equation:

$$\text{Saturation} = 100\% \times \frac{BR2 - R(BR1)}{R(BO1 - BR1) + BR2 - BO2}$$

wherein

BO1 is the extinction coefficient for oxygenated hemoglobin at light wavelength 1 (Infrared)
BO2 is the extinction coefficient for oxygenated hemoglobin at light wavelength 2 (red)
BR1 is the extinction coefficient for reduced hemoglobin at light wavelength 1
BR2 is the extinction coefficient for reduced hemoglobin at light wavelength 2
light wavelength 1 is infrared light
light wavelength 2 is red light
and R is the ratio of the optical density of wavelength 2 to wavelength 1 and is calculated as:

$$R = \frac{\ln[I_{max2}/I_{min2}]}{\ln[I_{max1}/I_{min1}]}$$

wherein
$I_{max2}$ is the maximum light transmitted at light wavelength 2
$I_{min2}$ is the minimum light transmitted at light wavelength 2
$I_{max1}$ is the maximum light transmitted at light wavelength 1
$I_{min1}$ is the minimum light transmitted at light wavelength 1

The various extinction coefficients are determinable by empirical study and are set forth in the software appendix. For convenience of calculation, the natural log of the ratios may be calculated by use of the Taylor expansion series for the natural log.

In an alternate embodiment, the microprocessor program can be adapted to utilize the relationship between the detected R wave DRW pulses and optical pulses without the need for first determining a pulse history. In this embodiment, microprocessor 16 searches status input latch 9G, and when detected R wave DRW is a logical 1, analyzes the optical signals that follow a detected R wave DRW pulse, regardless of the frequency of R wave pulses. By comparing the optical signals following a number of R wave pulses, microprocessor 16 correlates the detection of a pulse indicative of an optical pulse to the period of time by which such a detected pulse follows a detected R wave DRW pulse.

Referring to FIGS. 2a and 2b, the EKG front end printed circuit board schematic shows a respiratory monitor portion which may be used in conjunction with the EKG enhanced oximeter. The respiratory monitor is designed for use with a pressure sensitive transducer for detecting respiration or chest wall movement by measurement of pressure change. The sensor may be, for example, pneumatic-type sensor such as a Grasby Dynamics pressure capsule sensor, or a liquid mercury filled tube of siliconlike rubber secured across the patient's chest acting as a variable resistor. For a pneumatic type sensor, however it is designed, the small pressure change generated during respiratory chest movement is transmitted to a pressure transducer, for example, a Sensym model LX0503A bridge pressure transducer, for conversion to a voltage signal. The bridge output signal, or other voltage signal, is connected to differential amplifier 1A having a gain factor preferably over 100 nominally. The output of amplifier 1A is AC coupled to reject frequencies below about 0.07 Hz, and then buffered by amplifier 1B. The signal is then passed to low pass filter stages 1B and 1C which have a nominal cut off frequency of about 5 Hz. The output of the lowpass filters is further amplified and AC coupled to first buffer amplifier 1D. At that point the signal goes to second amplifier 1D for producing respiratory voltage $V_{resp}$, an analog waveform of the chest wall movement. The signal output from first amplifier 1D is also passed to threshold detector 1E which compares the amplitude of the respiratory waveform to a reference threshold voltage, which may be fixed, or adjusted by the microprocessor. When the amplitude of the respiratory waveform is greater than the referenced threshold, the output of the detector is driven to +5 volts. That +5 volts is inverted by invertor 2A to create digital pulse RSPTRG, corresponding to a respiratory breath. RSPTRG is then coupled to the system electronics of the oximeter at status latch 9G-11.

The respiratory activity is useful to monitor because, for example, many infants and small children have breathing problems and during their sleep have lapses in their breath. Monitoring chest wall breathing can check for such lapses or stoppage of breathing. In the preferred embodiment, the microprocessor creates a respiration history and establishes a regular pattern of breathing. Afterwords, if no breath is detected for a period of time, e.g., 15 seconds, then an alarm may be activated. Monitoring respiratory activity in conjunction with EKG enhanced oximetry can determine, when patient's blood flow characteristics drop during sleep, whether the reason for that drop was because of abnormal breathing, cessation of breathing, or some other cause.

```
;NELLCOR OXIMETER, PRODUCTION VERSION (8085)
;
; THIS VERSION OF THE OXIMETER PROGRAM INCORPORATES SUBSTANTIAL REVISIONS
; TO THE PULSE WAVE DECODING ALGORITHMS
;
; THIS VERSION IS ANNOTATED, FOR INCORPORATION INTO THE PRODUCTION      ///
; VERSION, BY THE APPLICATION OF SLASHES AT THE END OF EACH LINE        ///
; THAT IS HERE SOLELY FOR THE INTERFACE.                                ///
;
;COPYRIGHT (C) 1983, 1984, 1985 NELLCOR INCORPORATED
;
; THIS IS AN ORIGINAL, UNPUBLISHED WORK AND IS PROPRIETARY TO NELLCOR, INC.,
; AND MAY NOT BE DIVULGED OR COPIED IN ANY FORM WHATSOEVER WITHOUT
; EXPRESS PERMISSION FROM NELLCOR, INC.
;
```

| | 005E | | VERSN | EQU | 94 | |
|---|---|---|---|---|---|---|
| | | | NAME | RESPOX | | |

```
;RECENT EDIT HISTORY:
;        30 MAR            DEG    ADD MODE 9, CHG LVSTRG & CONF CHK WITH TW
;         4 MAR            DEG    MODIFY DEFAULT EKG GAIN SETTING
;        18 FEB            DEG    ADD 'TIME WINDOW', SILENT MODE
;        27 JAN            DEG    REDO LED SERVO,ADD GAIN SWITCH, FIX CALCHK
;        26 JAN '85        DEG    ADD AVG RATIO, LOG (MAX/MIN) & ANALOG OUTS-5,6
;        26 OCT            DEG    ALLOW UNFILTERED DATA TO INTERFACE - MODE 6
;        24 OCT            DEG    FIX SOME ALARM INTERFACE BUGS
;        23 OCT            DEG    ADD RESPIRATORY MONITOR - MODE 5
;         6 OCT            DEG    ADD CONFIDENCE CHECKING TO R-WAVE
;         5 OCT            DEG    TRIGGER MUNCH ON R WAVE - IF AVAILABLE
;         3 OCT            DEG    FIX SOME ALARM BUGS
;         2 OCT            DEG    INTEGRATE ALARMS FOR EKG
;         1 OCT            DEG    BEGIN INTEGRATING ECG INFO FOR LEVEL3
;        27 SEPT           DEG    ADD ECG R-WAVE DETECT - MANUAL ECG GN CNTRL
;         9 AUGUST         DEG    MAKE LED SERVO LINEAR - USE VLED DIRECTLY
;        28 JUNE, 1984     DEG    USE 2732A,CHG CHKNCH,CNFLIMS,TWKLED- 4X GAIN
;        18 APR            JEC    FIX MUNCH BUG (MAXIDX) - 5.3
;        27 FEB            JEC    ADD SYNDLY, FIX MATH BUGS, LEVEL 5.0
;        26 FEB            JEC    ADD NEW CALIBRATION
;        24 FEB            JEC    DISPLAY D.P. IN MODE 4
;         1 SEP '83        EMR    FIRST PROD. VERSION W/INTERFACE, VERSION = 4.0
;        11 AUG            JEC    'NEW' LIMITS, PROBE ADDED
;        10 AUG '83        JEC    FIX CORRECTION, NEW FILTER, VERSION = 3.4
;        13 JULY 83        JEC    ADD BUTTON ESCAPE TO ERRDSP, VERSION = 3.3
;        18 MARCH, 1982    JEC    STARTED
;
```

|      | 0000 |       | ASEG   |     |      |                                          |
|------|------|-------|--------|-----|------|------------------------------------------|

```
; DEFINITIONS...HARDWARE FIRST
; OUTPUT REGISTER DEFS...
```

| | 0000 | | DACL | EQU | 00H | ;DAC VALUE, LOWER 8 BITS |
|---|---|---|---|---|---|---|
| | 0001 | | DACH | EQU | 01H | ;DITTO, HIGH 4 BITS (0-3) |
| | 0002 | | MUXSEL | EQU | 02H | ;INPUT MULTIPLEXER SELECT CODES |
| | 000F | | V1PRM | EQU | 0FH | ;IR CHANNEL, OFFSET |
| | 001F | | V2PRM | EQU | 1FH | ;RED CHANNEL, OFFSET |
| | 002F | | V1MX | EQU | 2FH | ;DITTO, WITHOUT OFFSETS |
| | 003F | | V2MX | EQU | 3FH | |
| | 004F | | OFWHX | EQU | 4FH | ;FRONT-END OVERFLOW SENSE |
| | 005F | | VCALHX | EQU | 5FH | ;CALIBRATION RESISTOR |
| | 006F | | VTMPHX | EQU | 6FH | ;THERMISTOR |
| | 007F | | VREFHX | EQU | 7FH | ;CALIBRATION REFERENCE |
| | 008F | | VBMX | EQU | 8FH | ;BATTERY VOLTAGE |
| | 009F | | IDSPMX | EQU | 9FH | ;DISPLAY CURRENT |
| | 00AF | | DEKGHX | EQU | 0AFH | ;ECG WAVEFORM |
| | 00BF | | FEKGHX | EQU | 0BFH | ;BANDPASS FILTERED ECG |
| | 000E | | SHLED1 | EQU | 0EH | ;SAMPLE/HOLD FOR LED1 |
| | 000D | | SHLED2 | EQU | 0DH | ;DITTO, LED2 |
| | 000B | | SHBEEP | EQU | 0BH | ;BEEP PITCH |
| | 0007 | | SHVOL | EQU | 07H | ;BEEPER VOLUME |
| | 0003 | EKGPOL | EQU | | 03H | ;SELECT EKG POLARITY |
| | 0004 | DSPSEL | EQU | | 04H | ;DISPLAY SELECT BITS |
| | 0005 | DSPDIG | EQU | | 05H | ;DISPLAY DIGIT (UNCODED, ALSO RESETS INTERRUPT) |
| | 0006 | CHGEKG | EQU | | 06H | ;SELECT EKG GAIN FOR AGC AMP |
| | 0007 | RSTRWV | EQU | | 07H | ;RESET RWAVE FLIPFLOP |
| | 0077 | | SEG0 | EQU | 77H | ;SEGMENT CODE DEFS |
| | 0024 | | SEG1 | EQU | 24H | |
| | 005D | | SEG2 | EQU | 5DH | |
| | 006D | | SEG3 | EQU | 6DH | |
| | 002E | | SEG4 | EQU. | 2EH | |
| | 006B | | SEG5 | EQU | 6BH | |
| | 007B | | SEG6 | EQU | 7BH | |
| | 0025 | | SEG7 | EQU | 25H | |
| | 007F | | SEG8 | EQU | 7FH | |
| | 002F | | SEG9 | EQU | 2FH | |
| | 005B | | SEGE | EQU | 5BH | |
| | 0018 | | SEGR | EQU | 18H | |
| | 001B | | SEGF | EQU | 1BH | |
| | 0001 | | ALICOD | EQU | 1 | ;ALARM INHIBIT |
| | 0008 | | SLOCOD | EQU | 8 | ;SAT LOW ALARM |
| | 0010 | | SHICOD | EQU | 16 | ;SAT HIGH ALARM |
| | 0002 | | RLOCOD | EQU | 2 | ;RATE LOW ALARM |

```
 48         0004                                    RHICOD   EQU      4            ;RATE HIGH ALARM
 49         0020                                    SYNCOD   EQU      32           ;NO-SYNC ALARM
 50         0080                                    BATCOD   EQU      128          ;BATTERY ALARM
 51         0007                                    FD1MSK   EQU      000111B      ;BLINK MASKS
 52         0038                                    FD2MSK   EQU      111000B
 53
 54                         ; INPUTS:
 55         0004                                    BUTREG   EQU      04H          ;BUTTON INPUT REGISTER (BIT 7 = DAC COMP.)
 56                                                                                ; BITS 0 = CONTROL DIRECTION, BIT 1 = STROBE
 57                                                                                ; BITS 2-6 = BUTTONS
  1         0000                                    STSREG   EQU      00H          ;STATUS: BIT7 = COMPARATOR, BITS 0-5 = JUMPERS
  2         0001                                    DIDJPR   EQU      1            ;ENABLE DIDDLE MODE
  3         0002                                    DRTJPR   EQU      2            ;DISABLE ROM TEST JUMPER
  4
  5                         ; OTHER DEFS...
  6         F8F8                                    BATLM1   EQU      0F8F8H       ;BLINK LIMIT
  7         FB50                                    BATLM2   EQU      0FB50H       ;BAT IN USE LIMIT
  8
  9         006E                                    ALMPCH   EQU      110          ;ALARM PITCH
 10
 11                         ; COMMUNICATION STUFF...
 12
 13         0001                        SRCBIT      EQU      1                     ;SEARCH BIT MASK                      ///
 14         0008                        BATBIT      EQU      8                     ;BATTERY IN USE BIT MASK              ///
 15         0002                        OXIATT      EQU      2                     ;OXIMETER ATTACHED BIT MASK           ///
 16         0004                        AUDENB      EQU      4                     ;AUDIO ALARM ENABLED BIT MASK         ///
 17         0004                        SATBIT      EQU      4                     ;SATURATION ALARM BIT MASK            ///
 18         0002                        LRTBIT      EQU      2                     ;LOW RATE ALARM BIT MASK              ///
 19         0001                        HRTBIT      EQU      1                     ;HIGH RATE BIT MASK                   ///
 20
 21         0040                        MARK        EQU      40H                   ;MARK CONDITION (INVERTS AT OPTO-CPLR) ///
 22         00C0                        SPACE       EQU      0C0H                  ;SPACE CONDITION (INVERTS AT OPTO-CPLR) ///
 23
  1                         ;START-UP CODE....
  2                         ; (FILLED FROM ORG 0 FOR THE SILLY PROM PROGRAMMER)
  3                         ;
  4
  5         0000                                    ORG      0
  6
  7  0000   F3                                      DI
  8  0001   31       7400                           LXI      SP,STCK               ;LOAD STACK POINTER
  9  0004   C3       0040                           JMP      START
 10
 11                         ;COPYRIGHT NOTICE IN ROM...
 12
 13
 14  0007   43       4F                             DB       'COPYRIGHT 1983 NELLCOR INC.'
     0009   50       59
     000B   52       49
     000D   47       48
     000F   54       20
     0011   31       39
     0013   38       33
     0015   20       4E
     0017   45       4C
     0019   4C       43
     001B   4F       52
     001D   20       49
     001F   4E       43
     0021   2E
 15
 16         0012                                    REPT     34H-$
 17                                                 RST      0
 18                                                 ENDR
 19
 20                         ;INTERRUPT VECTORS...
 21                         ;
 22                         ;DISPLAY (4*60HZ) = RST6.5, RESET BY 'DSPDIG' OUTPUT
 23                         ;
 24  0034   C3       1913                           JMP      DSPINT
 25
 26         0005                                    REPT     3CH-$
 27                                                 RST      0
 28                                                 ENDR
 29
 30                         ;CLOCK (2400 BAUD) INTERRUPT = RST7.5, EDGE TRIGGERED.
 31                         ;
 32  003C   C3       18B0                           JMP      CLKINT
 33
 34         0001                                    REPT     40H-$
 35                                                 RST      0
 36                                                 ENDR
  1
  2
  3                         ;CHECK RAM AND LEAVE CLEARED...
  4                         ;
  5  0040   CD       00B3   START:      CALL        HRESET                         ;RESET HARDWARE
  6  0043   CD       00DE               CALL        ROMTST                         ;CHECK ROM CHECKSUMS
  7  0046   CD       00FB               CALL        RAMTST                         ;CHECK RAM
  8  0049   CD       01A6               CALL        LEDTST                         ;CHECK LED'S
  9  004C   CD       022A               CALL        INIT                           ;INITIALIZE VARIABLES
 10  004F   CD       0242               CALL        INIDSP                         ;INITIALIZE DISPLAY
 11  0052   CD       1BFC               CALL        COMBEG                         ;INITIALIZE COMMUNICATIONS    ///
 12                                     ;
 13  0055   3E       19                 MVI         A,19H                          ;RESET 7.5 LATCH + MASK OFF 5.5
```

```
14 0057  30                    SIM                           ;
15 0058  FB                    EI                            ;GO FOR IT....
16                   ;IDLE LOOP....CHECK FOR DATA IN BUFFER, PROCESS IF NOT EMPTY
17                   ;CHECK FOR UP/DOWN KNOB STROBES, THEN CHECK FOR BUTTON CODES.
18                   ;        NOTE- BATCHK HAS BEEN DISABLED, TEMPORARILY
19
20
21 0059  CD  081A    LOOP:  CALL   RSPLV3       ;CHECK FOR RESPIRATORY ACTIVITY
22 005C  CD  0F38           CALL   HUNCH        ;GO CRUNCH SOME RAW DATA...
23 005F  CD  110D           CALL   BLIP         ;RUN THE METER
24 0062  CD  0266           CALL   LEVEL3       ;COMPUTE...
25 0065  CD  072B           CALL   LVL3JR       ;CHECK R-WAVE, COMPUTE IF OK
26 0068  CD  14CE           CALL   BUTTON       ;CHECK FOR BUTTON INPUTS
27 006B  CD  16FF           CALL   KNOB         ;CHECK CONTROL KNOB INPUT
28 006E  CD  17A1           CALL   CLOCK        ;CHECK FOR QUARTER-SECOND ACTION
29 0071  CD  15E7           CALL   RFSHOP       ;REFRESH OPEN PARAMETER
30 0074  CD  1C11           CALL   COMIDL       ;DO IDLE LOOP COMMUNICATIONS CHECKS    ///
31 0077  CD  0141           CALL   ROMIDL       ;DO IDLE-TIME DIAGNOSTICS
32 007A  CD  0176           CALL   RAMIDL       ;
33 007D  CD  13F9           CALL   BLKOUT       ;CHECK/IMPLEMENT SILENT RUNNING MODE
34 0080  C3  0059           JMP    LOOP         ;
35
1                    ;CHECK SUPPLY VOLTS, LIGHT WARNING IF GOING...
2                    ;
3
4 0083  0E  80       BATCHK: MVI   C,BATCOD    ;LAMP CODE
5 0085  2A  7158             LHLD  VBAT        ;GET VOLTS
6 0088  EB                   XCHG
7 0089  21  F8F8             LXI   H,BATLM1    ;UPPER LIMIT OF BATTERY OP.
8 008C  19                   DAD   D
9 008D  DA  00A7             JC    1$          ;IS OK, PLUG IS IN THE WALL.
10 0090  21  FB50            LXI   H,BATLM2
11 0093  19                  DAD   D
12 0094  DA  009B            JC    2$          ;IS SORT OF OK, BUT TURN ON THE LIGHT
13 0097  CD  1484            CALL  BNKLIT      ;BLINK IT, WE'RE RUNNING OUT...
14 009A  C9                  RET
15 009B  CD  146C    2$:     CALL  SETLIT
16 009E  3A  727C            LDA   COSTA       ;                                      ///
17 00A1  F6  08              ORI   BATBIT      ;                                      ///
18 00A3  32  727C            STA   COSTA       ;SET BATTERY IN USE FLAG BIT           ///
19 00A6  C9                  RET
20 00A7  CD  1475    1$:     CALL  CLRLIT      ;CLEAR BATTERY IN USE BIT              ///
21 00AA  3A  727C            LDA   COSTA       ;                                      ///
22 00AD  E6  F7              ANI   NOT BATBIT  ;                                      ///
23 00AF  32  727C            STA   COSTA       ;
24 00B2  C9                  RET

1                    ;RESET HARDWARE AND FLASH THE PRETTY LIGHTS...
2                    ;
3
4 00B3  3E  FF       HRESET: MVI   A,0FFH      ;SET ANALOG VALUES TO FULL-SCALE
5 00B5  D3  00               OUT   DACL
6 00B7  D3  01               OUT   DACH
7 00B9  AF                   XRA   A
8 00BA  D3  02               OUT   MUXSEL      ;SELECT ALL CHANNELS
9 00BC  11  4000             LXI   D,4000H
10 00BF  06  00       1$:    MVI   B,0
11 00C1  78       2$:        MOV   A,B
12 00C2  04                  INR   B
13 00C3  FE  09              CPI   9
14 00C5  CA  00BF            JZ    1$
15 00C8  D3  04              OUT   DSPSEL      ;SELECT DIGIT
16 00CA  3E  FF              MVI   A,0FFH
17 00CC  D3  05              OUT   DSPDIG      ;LIGHT ALL SEGMENTS
18 00CE  1D                  DCR   E
19 00CF  C2  00C1            JNZ   2$
20 00D2  15                  DCR   D
21 00D3  C2  00C1            JNZ   2$
22 00D6  AF                  XRA   A
23 00D7  D3  00              OUT   DACL
24 00D9  D3  01              OUT   DACH
25 00DB  D3  05              OUT   DSPDIG
26 00DD  C9                  RET
27
28                   ;ROM CHECK TEST.....ADD UP ALL THE BYTES AND CALL ERROR IF IT ISN'T RIGHT...
29
30 00DE  21  0000    ROMTST: LXI   H,0
31 00E1  11  20FF            LXI   D,20FFH     ;2 ROMS - 2732A'S
32 00E4  AF                  XRA   A
33 00E5  86       1$:        ADD   M
34 00E6  23                  INX   H
35 00E7  1D                  DCR   E
36 00E8  C2  00E5            JNZ   1$
37 00EB  15                  DCR   D
38 00EC  C2  00E5            JNZ   1$
39 00EF  77                  MOV   M,A         ;STORE SUM IF EMULATING IN RAM
40 00F0  BE                  CMP   M
41 00F1  C8                  RZ                ;IS OK
42 00F2  3E  02              MVI   A,2         ;ROM ERROR= ERROR 2
43 00F4  32  72AE            STA   DIGERR      ;STORE DIAGNOSTIC ERROR                ///
44 00F7  CD  01F0            CALL  ERRDSP
45 00FA  C9                  RET
1                    ;TEST RAM MEMORY ON START-UP...WRITE ALL ZERO'S, ONE'S AND THE ADDRESS IN EACH BYTE.
2                    ;
3
4 00FB  E3       RAMTST: XTHL                  ;SAVE RETURN IN D,E
5 00FC  EB               XCHG
```

```
  6 00FD   21   7000            LXI    H,RAMORG
  7 0100   01   0400            LXI    B,RAMLEN
  8 0103   3E   00       1$:    MVI    A,0
  9 0105   77                   MOV    M,A            ;TEST FOR ZERO
 10 0106   BE                   CMP    M
 11 0107   C2   0133            JNZ    10$
 12 010A   3E   FF              MVI    A,0FFH
 13 010C   77                   MOV    M,A            ;AND ALL 1'S
 14 010D   BE                   CMP    M
 15 010E   C2   0133            JNZ    10$
 16 0111   7D                   MOV    A,L
 17 0112   84                   ADD    H
 18 0113   77                   MOV    M,A            ;STORE LOW + HIGH ADDRESS
 19 0114   23                   INX    H
 20 0115   0B                   DCX    B
 21 0116   78                   MOV    A,B
 22 0117   B1                   ORA    C
 23 0118   C2   0103            JNZ    1$             ;LOOP UNTIL END OF RAM
 24 011B   21   7000            LXI    H,RAMORG       ;RESET POINTER TO BEGINNING
 25 011E   01   0400            LXI    B,RAMLEN
 26 0121   7D            2$:    MOV    A,L
 27 0122   84                   ADD    H
 28 0123   BE                   CMP    M              ;CHECK STORED ADDRESS
 29 0124   C2   0133            JNZ    10$
 30 0127   36   00              MVI    M,0            ;CLEAR M
 31 0129   23                   INX    H
 32 012A   0B                   DCX    B
 33 012B   78                   MOV    A,B
 34 012C   B1                   ORA    C
 35 012D   C2   0121            JNZ    2$
 36 0130   C3   013E            JMP    11$
 37 0133   3E   01       10$:   MVI    A,1            ;ERROR CODE
 38 0135   32   72AE            STA    DIGERR         ;STORE DIAGNOSTIC ERROR
 39 0138   CD   01F0            CALL   ERRDSP
 40 013B   C3   00FB            JMP    RAMTST         ;NO EXIT
 41 013E   EB            11$:   XCHG
 42 013F   E3                   XTHL
 43 0140   C9                   RET

1                      ;IDLE-TIME ROM TEST...
  2                      ;ADD UP A BYTE AT A TIME, CHECK THE CHECKSUM IF AT THE END.
  3                      ;
  4
  5 0141   2A   7174     ROMIDL: LHLD  ROMIDX         ;GET INDEX TO NEXT BYTE TO BE TESTED
  6 0144   3A   7176            LDA    ROMSUM         ;PARTIAL SUM
  7 0147   86                   ADD    M
  8 0148   32   7176            STA    ROMSUM
  9 014B   23                   INX    H
 10 014C   7D                   MOV    A,L
 11 014D   FE   FF              CPI    0FFH
 12 014F   C2   0167            JNZ    1$             ;NOT THE END
 13 0152   7C                   MOV    A,H
 14 0153   FE   1F              CPI    1FH
 15 0155   C2   0167            JNZ    1$
 16 0158   3A   7176            LDA    ROMSUM
 17 015B   77                   MOV    M,A            ;STORE IF EMULATING
 18 015C   BE                   CMP    M              ;CHECK THE CHECKSUM
 19 015D   C2   016B            JNZ    10$            ;NOT OK
 20 0160   AF                   XRA    A
 21 0161   32   7176            STA    ROMSUM         ;RESET SUM
 22 0164   21   0000            LXI    H,0
 23 0167   22   7174     1$:    SHLD   ROMIDX
 24 016A   C9                   RET
 25 016B   3E   02       10$:   MVI    A,2            ;ERROR CODE
 26 016D   32   72AE            STA    DIGERR
 27 0170   CD   01F0            CALL   ERRDSP
 28 0173   C3   0000            JMP    0
 29                      ;
 30                      ;IDLE-TIME RAM TEST...DISABLE INTERRUPT AND TEST A BYTE...
 31                      ;
 32 0176   2A   7172     RAMIDL: LHLD  RAMIDX
 33 0179   F3                   DI
 34 017A   7E                   MOV    A,H            ;GET CURRENT BYTE CONTENTS
 35 017B   2F                   CMA
 36 017C   77                   MOV    M,A            ;COMPLIMENT IT AND RESTORE IT
 37 017D   BE                   CMP    M              ;CHECK IT
 38 017E   C2   019B            JNZ    10$            ;FAILED
 39 0181   2F                   CMA
 40 0182   77                   MOV    M,A            ;RESTORE
 41 0183   BE                   CMP    M              ;CHECK
 42 0184   C2   019B            JNZ    10$
 43 0187   FB                   EI
 44 0188   23                   INX    H
 45 0189   7D                   MOV    A,L
 46 018A   B7                   ORA    A
 47 018B   C2   0197            JNZ    1$             ;CHECK FOR END OF RAM
 48 018E   7C                   MOV    A,H
 49 018F   FE   74              CPI    HIGH(RAMORG+RAMLEN)
 50 0191   C2   0197            JNZ    1$
 51 0194   21   7000            LXI    H,RAMORG
 52 0197   22   7172     1$:    SHLD   RAMIDX
 53 019A   C9                   RET
 54 019B   3E   01       10$:   MVI    A,1
 55 019D   32   72AE            STA    DIGERR
 56 01A0   CD   01F0            CALL   ERRDSP
 57 01A3   C3   0000            JMP    0
```

```
                    ;TEST LED'S ON INITIALIZATION...LIGHT ONE SEGMENT AT A TIME, CHECK CURRENT
                    ; AGAINST HIGH/LOW BOUNDS.

5 01A6  3E  9F     LEDTST: MVI   A,IDSPMX        ;SELECT DISPLAY CURRENT FOR MUX
 6 01A8  D3  02             OUT   MUXSEL
 7 01AA  01  0001           LXI   B,01H           ;B = DIGIT SELECT CODE, C = SEGMENT BIT
 8 01AD  78         1$:     MOV   A,B
 9 01AE  D3  04             OUT   DSPSEL          ;SELECT DIGIT
10 01B0  79                 MOV   A,C
11 01B1  D3  05             OUT   DSPDIG
12 01B3  AF                 XRA   A
13 01B4  3C         5$:     INR   A               ;DELAY FOR COSMETICS AND SETTLING
14 01B5  C2  01B4           JNZ   5$
15 01B8  C5                 PUSH  B
16 01B9  CD  1E5E           CALL  ADCVT           ;DIGITIZE LED CURRENT
17 01BC  C1                 POP   B
18 01BD  21  FFC0           LXI   H,0FFC0H        ;- LOWER LIMIT
19 01C0  19                 DAD   D
20 01C1  D2  01E7           JNC   10$             ;TOO LOW
21 01C4  21  FF00           LXI   H,0FF00H        ;UPPER LIMIT
22 01C7  19                 DAD   D
23 01C8  DA  01E7           JC    10$             ;TOO HIGH (SHORTED)
24 01CB  79         2$:     MOV   A,C
25 01CC  07                 RLC                   ;INCREMENT SEGMENT BIT
26 01CD  4F                 MOV   C,A
27 01CE  D2  01D8           JNC   3$              ;KEEP TRUCKIN'
28 01D1  04                 INR   B               ;NEXT DIGIT
29 01D2  78                 MOV   A,B
30 01D3  FE  09             CPI   9
31 01D5  CA  01EF           JZ    11$             ;ALL DONE
32 01D8  78         3$:     MOV   A,B             ;CHECK FOR UNUSED LAMPS...
33 01D9  FE  08             CPI   8
34 01DB  C2  01AD           JNZ   1$              ;NOT LAMPS, LOOP...
35 01DE  79                 MOV   A,C
36 01DF  E6  50             ANI   64+16           ;CHECK FOR UNUSED LAMPS...
37 01E1  C2  01CB           JNZ   2$              ;HIT ONE
38 01E4  C3  01AD           JMP   1$
39 01E7  3E  03     10$:    MVI   A,3             ;BAD LAMP = ERROR 3
40 01E9  32  72AE           STA   DIGERR          ;STORE FOR POSSIBLE SENDING
41 01EC  CD  01F0           CALL  ERRDSP
42 01EF  C9         11$:    RET

;ERROR DISPLAY...CALLED WITH ERROR CODE IN AC.

4 01F0  F3         ERRDSP: DI
 5 01F1  01  7122           LXI   B,DSPFD2
 6 01F4  CD  13A9           CALL  DSPCVT
 7 01F7  21  711C           LXI   H,DSPFD1
 8 01FA  36  18             MVI   M,SEGR
 9 01FC  23                 INX   H
10 01FD  23                 INX   H
11 01FE  36  18             MVI   M,SEGR
12 0200  23                 INX   H
13 0201  23                 INX   H
14 0202  36  5B             MVI   M,SEGE
15 0204  21  711C   1$:     LXI   H,DIGBUF
16 0207  06  00             MVI   B,0
17 0209  3E  FF     2$:     MVI   A,0FFH
18 020B  D3  04             OUT   DSPSEL          ;BLANK DISPLAY WHILE WE CHANGE DIGITS
19 020D  7E                 MOV   A,M
20 020E  D3  05             OUT   DSPDIG
21 0210  78                 MOV   A,B
22 0211  D3  04             OUT   DSPSEL
23 0213  0D         3$:     DCR   C
24 0214  C2  0213           JNZ   3$
25 0217  23                 INX   H
26 0218  23                 INX   H
27 0219  04                 INR   B
28 021A  78                 MOV   A,B
29 021B  FE  09             CPI   9
30 021D  C2  0209           JNZ   2$
31 0220  DB  04             IN    BUTREG          ;CHECK FOR BUTTON ESCAPE
32 0222  E6  3C             ANI   3CH
33 0224  FE  38             CPI   38H
34 0226  C2  0204           JNZ   1$
35 0229  C9                 RET

;INITIALIZE PARAMETERS FROM INILST...

4 022A  21  1F33   INIT:   LXI   H,INILST
 5 022D  4E         5$:     MOV   C,M
 6 022E  23                 INX   H
 7 022F  46                 MOV   B,M
 8 0230  23                 INX   H
 9 0231  78                 MOV   A,B
10 0232  B1                 ORA   C
11 0233  CA  0241           JZ    6$              ;ZERO ADDRESS TERMINATES
12 0236  7E         7$:     MOV   A,M
13 0237  23                 INX   H
14 0238  B7                 ORA   A               ;ZERO BYTE TERMINATES
15 0239  CA  022D           JZ    5$
16 023C  02                 STAX  B
```

```
17 023D   03                          INX      B
18 023E   C3      0236                JMP      7$              ;LOOP FOR NEXT BYTE
19 0241   C9              6$:         RET
20
21                        ;INITIALIZE DISPLAY
22                        ;
23 0242   3E      00      INIDSP:     MVI      A,0             ;INITIALIZE EKG FLAG AND POLARITY
24 0244   D3      07                  OUT      RSTRWV
25 0246   D3      03                  OUT      EKGPOL
26 0248   01      711C                LXI      B,DSPFD1        ;UPPER DISPLAY
27 024B   AF                          XRA      A
28 024C   CD      13A9                CALL     DSPCVT          ;A ZERO...
29 024F   01      7122                LXI      B,DSPFD2
30 0252   AF                          XRA      A
31 0253   CD      13A9                CALL     DSPCVT          ;LOWER DISPLAY ALSO
32 0256   0E      20                  MVI      C,SYNCOD        ;SET NO-SYNC LIGHT
33 0258   CD      1484                CALL     BNKLIT
34 025B   3A      70F1                LDA      ALIFLG          ;SET ALARM INHIBIT LIGHT IF ALARM INHIBITED
35 025E   B7                          ORA      A
36 025F   C8                          RZ
37 0260   0E      01                  MVI      C,ALICOD
38 0262   CD      1484                CALL     FSTLIT
39 0265   C9                          RET

1                        ;LEVEL 3 ROUTINES...
 2                        ; CALLED ONCE PER ALLEGED PULSE, THESE ROUTINES TRY TO SORT REAL PULSES
 3                        ; FROM ARTIFACT.
 4                        ;
 5                        ;
 6
 7 0266   CD      0E4E    LEVEL3:     CALL     CALCHK          ;CHECK FOR CAL REISTOR
 8 0269   D8                          RC                       ;LEAVE IF NONE
 9 026A   3A      709E                LDA      DATFLG          ;CHECK DATA READY FLAG
10 026D   B7                          ORA      A
11 026E   C8                          RZ                       ;NOT SET, BAG IT.
12 026F   CD      044C                CALL     XFRPLS          ;STORE PULSE PARAMETERS IN CURLST
13 0272   CD      0E0C                CALL     TWKLED          ;RE-SET THE LED DRIVES
14 0275   CD      049E                CALL     HSTCMP          ;COMPUTE HISTORY PARAMETERS
15 0278   CD      061C                CALL     SETLIM          ;SET LIMITS FOR VARIATION AND DIFF
16 027B   3A      7014                LDA      SYNFLG
17 027E   B7                          ORA      A
18 027F   CA      0310                JZ       SYNCOK          ;SYNC'ED
19
20                        ;NOT YET SYNC'ED...DECREMENT SYNC COUNTER TO 1 AND WAIT FOR VARIATION TO DROP.
21                        ;
22 0282   3A      703C    1$:         LDA      AMPAVG          ;CHECK FOR MINIMUM AMPLITUDE
23 0285   FE      08                  CPI      8
24 0287   DA      02FE                JC       4$              ;TOO SMALL
25 028A   3A      700A                LDA      LED1            ;SHOULD WE GO TO LO GAIN?
26 028D   FE      A0                  CPI      160
27 028F   D2      02BB                JNC      10$             ;>160, DON'T SWITCH GAINS
28 0292   3A      700D                LDA      LED2            ;DITTO FOR RED
29 0295   FE      A0                  CPI      160
30 0297   D2      02BB                JNC      10$
31 029A   3A      7012                LDA      GNSEL           ;ARE WE IN HI GAIN?
32 029D   B7                          ORA      A
33 029E   CA      02BB                JZ       10$             ;NO, DO NOTHING
34 02A1   3A      700A                LDA      LED1            ;SINCE SWITCHING GAINS, COMPENSATE BY
35 02A4   C6      40                  ADI      64              ;ADDING 64 TO LED1 AND LED2
36 02A6   32      700A                STA      LED1
37 02A9   3A      700D                LDA      LED2
38 02AC   C6      40                  ADI      64
39 02AE   32      700D                STA      LED2
40 02B1   32      7013                STA      LGFLAG
41 02B4   AF                          XRA      A
42 02B5   32      7012                STA      GNSEL
43 02B8   C3      02FE                JMP      4$
44 02BB   3A      7014    10$:        LDA      SYNFLG          ;LED'S OK, GET SYNC CODE AGAIN
45 02BE   3D                          DCR      A               ;CHECK FOR FLAG=1
46 02BF   C2      02FB                JNZ      3$              ;NOT, STORE PULSE AND COUNT
47 02C2   CD      058A                CALL     VARCHK          ;CHECK FOR EXCESSIVE VARIATION
48 02C5   D2      02D1                JNC      2$              ;VARIATION IS GOOD, GO FOR IT...
49 02C8   CD      06B6                CALL     CHKNCH          ;LOOK OUT FOR SMALL PULSES
50 02CB   DA      0308                JC       5$              ;IS NOTCH, IGNORE IT
51 02CE   C3      02FE                JMP      4$              ;NOT-A-NOTCH; VARIATION STILL NG, STORE IT
52 02D1   AF              2$:         XRA      A
53 02D2   32      7014                STA      SYNFLG          ;SYNC'ED
54 02D5   32      70F6                STA      ALMDLY          ;NO OBSOLETE DELAYED ALARMS ALLOWED
55 02D8   0E      20                  MVI      C,SYNCOD
56 02DA   CD      1475                CALL     CLRLIT
57 02DD   3E      FF                  MVI      A,255
 1 02DF   32      7005                STA      FSATN           ;TURN FILTERS WAY DOWN
 2 02E2   3A      7104                LDA      SN2DLY          ;CHECK FOR EKG SYNC
 3 02E5   B7                          ORA      A
 4 02E6   CA      02EE                JZ       7$              ;IS SYNCED, DONT CHANGE FILTER FOR HR
 5 02E9   3E      FF                  MVI      A,255           ;NOT SYNCED ,TURN HR FILTER DOWN
 6 02EB   32      7006                STA      FRATN
 7 02EE   3E      05      7$:         MVI      A,5
 8 02F0   32      70B4                STA      SYNDLY
 9 02F3   3E      08                  MVI      A,8
10 02F5   32      714A                STA      SATTHR
11 02F8   C3      0310                JMP      SYNCOK          ;GO PROCESS PULSE
12 02FB   32      7014    3$:         STA      SYNFLG          ;STORE SYNC FLAG
13 02FE   CD      0668    4$:         CALL     HSTUPD          ;UPDATE HISTORY
14 0301   AF                          XRA      A
15 0302   32      70B6                STA      NCHFLG          ;WASN'T A NOTCH, RESET FLAG
16 0305   32      70B3                STA      PERCTR
```

```
17 0308   3E    03            5$:   MVI    A,3
18 030A   32    70B5                STA    BPCTR           ;RESET BAD-PULSE COUNTER
19 030D   C3    03FF                JMP    PLSRET          ;DONE HERE

;SYNC'ED...CHECK PULSE AGAINST HISTORY, PROCESS IT IF IT MATCHES.
                                    ;  IF NOT, DECREMENT BAD PULSE COUNTER AND IGNORE THE FIRST FEW BAD PULSES.
                                    ;  IF BAD PULSE COUNTER RUNS OUT THEN STORE IT ANYWAY.
                                    ;
25 0310   CD    05D3          SYNCOK: CALL  DIFCHK          ;CHECK DIFFERENCE CODES
26 0313   FE    02                  CPI    2               ;0 OR 1 IS OK
27 0315   F2    03CC                JP     PLSERR          ;NO GOOD
28 0318   CD    06B6                CALL   CHKNCH          ;MAY BE A NOTCH
29 031B   DA    03CC                JC     PLSERR          ;OH WELL, IT IS...
30 031E   3E    03            PLSOK: MVI   A,3
31 0320   32    70B5                STA    BPCTR           ;RESET BAD PULSE COUNTER
32 0323   0E    20                  MVI    C,SYNCOD        ;RESET SYNC LIGHT
33 0325   CD    1475                CALL   CLRLIT
34 0328   21    70B4                LXI    H,SYNDLY        ;DID WE JUST START?
35 032B   35                        DCR    M
36 032C   F2    0333                JP     2$              ;YES, LEAVE THE FILTER TURNED DOWN
37 032F   34                        INR    M
38 0330   CD    0A41                CALL   FILSET          ;SET FILTER COEFICIENTS
39 0333   3A    7016          2$:   LDA    CURDIF          ;GET DIFF CODES
40 0336   E6    04                  ANI    4               ;DONT UPDATE SAT IF NOT ZERO
41 0338   CA    034A                JZ     1$              ;RATIO NO GOOD-
42 033B   3A    7104          3$:   LDA    SN2DLY          ;IF EKG IS SYNCED - CHECK TIME WINDOW
43 033E   B7                        ORA    A
44 033F   C2    037E                JNZ    5$
45 0342   3A    7016                LDA    CURDIF
46 0345   E6    08                  ANI    8               ; 8 = TIME WINDOW
47 0347   C2    037E                JNZ    5$              ; BOTH NOT OK , DON'T COMPUTE SAT
48 034A   AF            1$:         XRA    A
49 034B   32    7001                STA    SAT
50 034E   3A    7141                LDA    IFLG
51 0351   B7                        ORA    A
52 0352   CA    036B                JZ     11$
53 0355   11    FFFF                LXI    D,-(SAT-RAMORG)
54 0358   2A    713F                LHLD   ICELL
55 035B   19                        DAD    D
56 035C   7D                        MOV    A,L
57 035D   B4                        ORA    H
 1 035E   C2    036B                JNZ    11$
 2 0361   2A    70A9                LHLD   RATRAT
 3 0364   CD    08A0                CALL   XSAT
 4 0367   7C                        MOV    A,H
 5 0368   32    7001                STA    SAT
 6 036B   CD    0947          11$:  CALL   FILRAT          ;FILTER RATIOS
 7 036E   CD    0889                CALL   COMSAT          ;COMPUTE SATURATION
 8 0371   DA    037E                JC     5$
 9 0374   3E    0A                  MVI    A,10
10 0376   32    714A                STA    SATTMR          ;RESET SAT TIME-OUT COUNTER
11 0379   3E    08                  MVI    A,8
12 037B   32    710C                STA    SATCLK          ;RESET SAT ANALOG OUT TIMEOUT
13 037E   3A    7104          5$:   LDA    SN2DLY          ;IF ECG NOT SYNCED, THEN CHECK HR HERE
14 0381   B7                        ORA    A
15 0382   C2    0388                JNZ    8$
16 0385   C3    0398                JMP    6$
17 0388   3A    7016          8$:   LDA    CURDIF          ;CHECK PERIOD DIFF
18 038B   E6    01                  ANI    1
19 038D   C2    0398                JNZ    6$              ;NO COMPUTE IF NON-ZERO
20 0390   CD    06E2          10$:  CALL   COMRAT          ;CALC RATE FROM THE PULSE
21 0393   3E    08                  MVI    A,8             ;RESET HR ANALOG_OUT TIMEOUT
22 0395   32    710B                STA    RATCLK
23 0398   AF            6$:         XRA    A
24 0399   32    712E                STA    DSPBKF          ;CLEAR BLANK DISPLAY FLAG
25 039C   21    714A                LXI    H,SATTMR        ;CHECK SAT TIME-OUT
26 039F   7E                        MOV    A,M
27 03A0   3D                        DCR    A
28 03A1   FA    03A8                JM     7$              ;ALREADY ZERO
29 03A4   77                        MOV    M,A
30 03A5   CC    0BB9                CZ     SATTMO          ;ZERO THE SAT
31 03A8   3A    70B4          7$:   LDA    SYNDLY          ;SEND TO DISPLAY AFTER 2 GOOD BEATS
32 03AB   FE    03                  CPI    3
33 03AD   F2    03B9                JP     12$
34 03B0   CD    0A8F                CALL   DSPSR           ;DISPLAY SAT AND RATE...
35 03B3   CD    0C37                CALL   ALMCHK          ;AND CHECK ALARMS..
36 03B6   CD    0404                CALL   SNDMON          ;SEND GOOD NUMBERS TO INTERFACE
37 03B9   3E    28            12$:  MVI    A,40            ;10 SECONDS WORTH OF TIME-OUT
38 03BB   32    7149                STA    PLSTMR
39 03BE   AF                        XRA    A
40 03BF   32    70B3                STA    PERCTR          ;RESET PERIOD COUNTER ... GOOD PULSES ONLY.
41 03C2   CD    066B                CALL   HSTUPD          ;UPDATE HISTORY
42 03C5   AF                        XRA    A
43 03C6   32    70B6                STA    NCHFLG
44 03C9   C3    03FF                JMP    PLSRET

;BAD PULSE...CHECK BAD PULSE COUNTER FIRST.
                                    ;
48 03CC   AF            PLSERR:     XRA    A               ;RESET TIME WINDOW TIMER
49 03CD   32    710A                STA    WINFLG
50 03D0   3A    70B5                LDA    BPCTR
51 03D3   3D                        DCR    A
52 03D4   FA    03DD                JM     2$              ;OUT OF COUPONS, STORE IT
53 03D7   32    70B5                STA    BPCTR           ;STORE COUNT
54 03DA   C3    03F1                JMP    5$
```

```
55 03DD  CD  0668   2$:     CALL  HSTUPD    ;UPDATE HISTORY
56 03E0  0E  20             MVI   C,SYNCOD
57 03E2  CD  146C           CALL  SETLIT    ;SET SYNC LIGHT (STEADY)
 1 03E5  21  0000           LXI   H,0       ;RESET ANALOG OUTPUTS
 2 03E8  22  7169           SHLD  SATOUT
 3 03EB  22  716B           SHLD  RATOUT
 4 03EE  C3  03FB           JMP   6$        ;RESET PERIOD COUNTER
 5 03F1  21  70B3   5$:     LXI   H,PERCTR
 6 03F4  3A  7028           LDA   PERAVG
 7 03F7  96             SUB   M
 8 03F8  F2  03FF           JP    PLSRET    ;CURRENT PERIOD LESS THAN HISTORY
 9 03FB  AF             6$:     XRA   A
10 03FC  32  70B3           STA   PERCTR    ;RESET LONG PERIOD COUNTS
11 03FF  AF             PLSRET: XRA   A        ;RESET DATA FLAG
12 0400  32  709E           STA   DATFLG
13 0403  C9             RET
14
15                           ; NOW SEND THE RATE AND SATURATION TO THE INTERFACE BUFFER
16
17 0404  3A  7002   SNDMON: LDA   FSAT      ;GET SATURATION                    ///
18 0407  CD  1D3B           CALL  SPLIT     ;SPLIT INTO TWO NIBBLES            ///
19 040A  7A             MOV   A,D       ;SAT MSB'S                         ///
20 040B  F6  20             ORI   20H       ;MONITOR FUNCTION CODE             ///
21 040D  CD  1D22           CALL  TOBUFR    ;PUT INTO BUFFER                   ///
22 0410  7B             MOV   A,E       ;SAT LSB'S                         ///
23 0411  CD  1D22           CALL  TOBUFR    ;                                  ///
24 0414  3A  7170   DECDON: LDA   FMODE
25 0417  D6  03             SUI   3
26 0419  CA  041F           JZ    1$
27 041C  3A  7004           LDA   FRATE     ;RATE                              ///
28 041F  CD  1D3B   1$:     CALL  SPLIT     ;INTO TWO NIBBLES                  ///
29 0422  7A             MOV   A,D       ;UPPER NIBBLE                      ///
30 0423  CD  1D22           CALL  TOBUFR    ;                                  ///
31 0426  3A  7170           LDA   FMODE     ;IF IN MODE 4, SEND DECIMAL PART   ///
32 0429  FE  04             CPI   4         ;                                  ///
33 042B  CA  043D           JZ    SNDDEC    ;                                  ///
34 042E  3A  7007           LDA   TSTMOD    ;IN TEST MODE ?                    ///
35 0431  E6  01             ANI   1         ;BIT 0 INDICATES IT                ///
36 0433  C2  043D           JNZ   SNDDEC    ;YES, DO RATE LSB'S AND SAT DECIMAL ///
37 0436  7B             MOV   A,E       ;NO, THEN PUT END OF TRANSMIT ON   ///
38 0437  F6  70             ORI   70H       ;                                  ///
39 0439  CD  1D22           CALL  TOBUFR    ;AND SEND IT                       ///
40 043C  C9             RET                   ;                                  ///
41 043D  7B             SNDDEC: MOV   A,E       ;SEND RATE LSB'S FIRST             ///
42 043E  CD  1D22           CALL  TOBUFR    ;                                  ///
43 0441  3A  70BD           LDA   FSATDP    ;THEN GET DECIMAL PART             ///
44 0444  E6  0F             ANI   0FH       ;STRIP ANY FUNNY STUFF             ///
45 0446  F6  70             ORI   70H       ;PUT IN END OF TRANSMIT CHARACTER  ///
46 0448  CD  1D22           CALL  TOBUFR    ;AND PUT IT INTO THE BUFFER        ///
47 044B  C9             RET                   ;                                  ///
48
 1                           ;LOAD CURRENT DATA LIST FROM MUNCH'S DATA...
 2                           ;  COMPUTE SMALL-A =LOG( MAX1/MIN1), SMALL-B = DITTO AS THEY GO BY...
 3                           ;
 4
 5 044C  3A  70B3   XFRPLS: LDA   PERCTR    ;GET PERIOD EITHER FROM EKG OR PULSE
 6 044F  32  7026           STA   PERIOD
 7 0452  3A  7104           LDA   SN2DLY    ;TRANSFER TIME WINDOW IF EKG IS USED
 8 0455  B7             ORA   A
 9 0456  C2  045F           JNZ   1$
10 0459  3A  7109           LDA   WINTHR
11 045C  32  7062           STA   PLSDLY
12 045F  2A  709F   1$:     LHLD  MAX1      ;GET MAX1 AS BIG-A
13 0462  EB             XCHG
14 0463  2A  70A1           LHLD  MIN1
15 0466  CD  0505           CALL  LOG       ;COMPUTE LOG (MAX1/MIN1)
16 0469  22  70AB           SHLD  ARAT
17 046C  3E  04             MVI   A,4       ;SCALE FOR HISTORY BUFFER
18 046E  CD  1A71           CALL  SHFTHL
19 0471  D2  0476           JNC   2$
20 0474  3E  FF             MVI   A,0FFH
21 0476  7C             2$:     MOV   A,H
22 0477  32  703A           STA   CURAMP
23 047A  2A  70A3           LHLD  MAX2
24 047D  EB             XCHG
25 047E  2A  70A5           LHLD  MIN2
26 0481  CD  0505           CALL  LOG       ;COMPUTE LOG(MAX2/MIN2)
27 0484  22  70AD           SHLD  BRAT
28 0487  EB             XCHG
29 0488  2A  70AB           LHLD  ARAT
30 048B  3E  02             MVI   A,2
31 048D  CD  1A71           CALL  SHFTHL    ;B RATIO *2
32 0490  44             MOV   B,H
33 0491  4D             MOV   C,L
34 0492  CD  12F6           CALL  DIV16
35 0495  EB             XCHG
36 0496  22  70A9           SHLD  RATRAT
37 0499  7C             MOV   A,H
38 049A  32  704E           STA   CURRAT
39 049D  C9             RET

1                           ;COMPUTE HISTORY PARAMETERS...
 2                           ;COMPUTE MEANS OF HISTORICAL VALUES FOR EACH ROW, THEN COMPUTE VARIATION
 3                           ;  AND CONVERT TO RELATIVE DIFFERENCE CODE (1/16'S).
 4                           ;  THEN COMPARE CURRENT VALUE TO HISTORICAL MEANS AND SET DIFF CODE.
 5                           ;
 6
```

```
  7 049E   3A   7104   HSTCMP: LDA   SN2DLY         ;COMPUTE TIME WINDOW IF EKG IS SYNCED
  8 04A1   B7                  ORA   A
  9 04A2   C2   04AD           JNZ   HSTCP1
 10 04A5   0E   04             MVI   C,4            ;IS SYNCED, ADD TIME WINDOW
 11 04A7   21   7026           LXI   H,HSTBUF
 12 04AA   C3   04B2           JMP   HSTCP2
 13 04AD   0E   03     HSTCP1: MVI   C,3            ;COUNTER
 14 04AF   21   7026           LXI   H,HSTBUF       ;POINT TO BEGINNING OF FIRST ROW
 15 04B2   C5          HSTCP2: PUSH  B              ;SAVE COUNT
 16 04B3   23                  INX   H              ;POINT TO MEAN
 17 04B4   23                  INX   H
 18 04B5   E5                  PUSH  H              ;SAVE MEAN POINTER
 19 04B6   23                  INX   H              ;POINT TO HISTORY DATA
 20 04B7   23                  INX   H
 21 04B8   CD   053D           CALL  HSTAVG         ;COMPUTE MEAN
 22 04BB   E1                  POP   H
 23 04BC   77                  MOV   M,A            ;STORE IT
 24 04BD   E5                  PUSH  H
 25 04BE   23                  INX   H              ;POINT TO DATA AGAIN
 26 04BF   23                  INX   H
 27 04C0   CD   0567           CALL  HSTVAR         ;COMPUTE VARIATION
 28 04C3   E1                  POP   H
 29 04C4   4E                  MOV   C,M            ;GET MEAN
 30 04C5   CD   04F5           CALL  DIFF           ;COMPUTE DIFF CODE (BETWEEN A & C)
 31 04C8   23                  INX   H
 32 04C9   77                  MOV   M,A            ;STORE IT
 33 04CA   2B                  DCX   H              ;POINT TO MEAN AGAIN
 34 04CB   4E                  MOV   C,M            ;GET IT
 35 04CC   2B                  DCX   H
 36 04CD   2B                  DCX   H              ;POINT TO CURRENT
 37 04CE   79                  MOV   A,C            ;GET MEAN VALUE
 38 04CF   96                  SUB   M              ;MINUS CURRENT = DIFF
 39 04D0   D2   04D6           JNC   2$             ;CHECK FOR NEGATIVE DIFF
 40 04D3   4E                  MOV   C,M            ;CURRENT IS BIGGER, GET IT
 41 04D4   2F                  CMA
 42 04D5   3C                  INR   A
 43 04D6   CD   04F5   2$:     CALL  DIFF           ;COMPUTE DIFF CODE
 44 04D9   23                  INX   H
 45 04DA   77                  MOV   M,A            ;STORE IT
 46 04DB   11   0013           LXI   D,HSTINC-1     ;INCREMENT TO NEXT ROW
 47 04DE   19                  DAD   D
 48 04DF   C1                  POP   B              ;COUNTER
 49 04E0   0D                  DCR   C
 50 04E1   C2   04B2           JNZ   HSTCP2
 51 04E4   C9                  RET
 52                    ;
 53                    ; CALL ONLY THE EKG HISTORY ROW FROM LVL3JR
 54                    ;
 55 04E5   0E   01     HSTEKG: MVI   C,1
 56 04E7   21   7076           LXI   H,EKGHBF       ;EKG HISTORY BUFFER
 57 04EA   C3   04B2           JMP   HSTCP2
  1                    ;
  2                    ; CALL ONLY THE RESPIRATORY HISTORY ROW FROM RSPLV3
  3                    ;
  4
  5 04ED   0E   01     HSTRSP: MVI   C,1
  6 04EF   21   708A           LXI   H,RSPHBF
  7 04F2   C3   04B2           JMP   HSTCP2
  8                    ;
  9
 10                    ;COMPUTE DIFF CODE BETWEEN A & C REG'S:
 11 04F5   5F          DIFF:   MOV   E,A
 12 04F6   06   00             MVI   B,0
 13 04F8   16   00             MVI   D,0
 14 04FA   CD   12F6           CALL  DIV16
 15 04FD   7A                  MOV   A,D
 16 04FE   1F                  RAR
 17 04FF   1F                  RAR
 18 0500   1F                  RAR
 19 0501   1F                  RAR
 20 0502   E6   0F             ANI   0FH
 21 0504   C9                  RET
 22
 23                    ;
 24                    ;COMPUTE LOG (A/B) (FOR B<A<2*B) BY TAYLOR EXPANSION
 25                    ;USES 3-TERM EXPANSION:
 26                    ;    LOG (A/B)= (A/B-1) - (A/B-1)^2/2 + (A/B-1)^3/3
 27                    ;CALLED WITH A (MAX) IN D,E AND B (MIN) IN H,L
 28                    ;RETURNS CARRY SET IF A IS NOT BETWEEN B & 2*B
 29                    ;
 30 0505   E5          LOG:    PUSH  H              ;SAVE B
 31 0506   CD   1348           CALL  NEGHL          ;-B
 32 0509   19                  DAD   D              ;A-B
 33 050A   EB                  XCHG                 ;TO D,E AS NUMERATOR
 34 050B   C1                  POP   B              ;B TO DENOMINATOR
 35 050C   D2   0538           JNC   10$            ;ERROR, A<B
 36 050F   CD   12F6           CALL  DIV16          ;FORM (A-B)/B=A/B-1
 37 0512   DA   0538           JC    10$            ;ERROR, A>2*B
 38 0515   D5                  PUSH  D              ;SAVE TERM 1
 39 0516   42                  MOV   B,D            ;COPY TO B,C
 40 0517   4B                  MOV   C,E
 41 0518   CD   1232           CALL  MPY32          ;(A/B-1)^2
 42 051B   AF                  XRA   A
 43 051C   78                  MOV   A,B            ;DIVIDE RESULT BY 2
 44 051D   1F                  RAR
 45 051E   67                  MOV   H,A
```

```
46 051F  79              MOV   A,C
47 0520  1F              RAR
48 0521  6F              MOV   L,A         ;H,L=(A/B-1)^2/2
49 0522  EB              XCHG              ;TERM 2 TO D,E
50 0523  C1              POP   B           ;TERM 1 TO B,C
51 0524  C5              PUSH  B
52 0525  D5              PUSH  D           ;SAVE TERM 2 (W/ + SIGN)
53 0526  CD   1232       CALL  MPY32       ;(A/B-1)*(A/B-1)^2/2
54 0529  11   AAAB       LXI   D,43691     ;.66667
55 052C  CD   1232       CALL  MPY32       ;B,C=(A/B-1)^3/3
56 052F  E1              POP   H           ;2ND TERM
57 0530  CD   1348       CALL  NEGHL       ;-2ND TERM
 1 0533  09              DAD   B           ;SUBTRACT FROM 3RD
 2 0534  D1              POP   D
 3 0535  19              DAD   D           ;ADD 1ST TERM
 4 0536  AF              XRA   A           ;CLEAR CARRY
 5 0537  C9              RET
 6 0538  37         10$: STC               ;ERROR RETURN
 7 0539  21   0000       LXI   H,0
 8 053C  C9              RET

;RETURN MEAN OF ONE ROW OF HISTORY BUFFER...
; CALLED WITH H,L = POINTER TO HISTORY DATA, RETURNS MEAN IN A.
; CHECKS HSTLEN POINTS, IGNORES ZERO'S, RETURNS (IN B) # POINTS SUMMED.
;
 6 053D  06   00    HSTAVG: MVI B,0        ;DATA COUNT
 7 053F  3A   7017      LDA   HSTLEN       ;HIST LENGTH
 8 0542  B7              ORA   A
 9 0543  C8              RZ
10 0544  4F              MOV   C,A         ;COUNTER
11 0545  11   0000       LXI   D,0         ;CLEAR SUM
12 0548  7E         1$:  MOV   A,M         ;GET NEXT POINT
13 0549  B7              ORA   A
14 054A  CA   0554       JZ    2$          ;SKIP ZERO'S
15 054D  83              ADD   E
16 054E  5F              MOV   E,A
17 054F  7A              MOV   A,D
18 0550  CE   00         ACI   0
19 0552  57              MOV   D,A
20 0553  04              INR   B
21 0554  23         2$:  INX   H           ;INC POINTER
22 0555  0D              DCR   C
23 0556  C2   0548       JNZ   1$
24 0559  78              MOV   A,B
25 055A  B7              ORA   A
26 055B  C8              RZ                ;NO DATA, NO DIVIDE
27 055C  C5              PUSH  B           ;SAVE COUNT
28 055D  CD   12F6       CALL  DIV16
29 0560  21   0080       LXI   H,80H
30 0563  19              DAD   D           ;ROUND
31 0564  7C              MOV   A,H
32 0565  C1              POP   B
33 0566  C9              RET

;COMPUTE VARIATION OF ONE ROW OF HISTORY...CALLED THE SAME AS HSTMN.
;
 4 0567  3A   7017  HSTVAR: LDA HSTLEN
 5 056A  B7              ORA   A
 6 056B  C8              RZ
 7 056C  4F              MOV   C,A
 8 056D  06   00         MVI   B,0         ;C=COUNTER, B=DATA BYTES
 9 056F  11   00FF       LXI   D,0FFH      ;CLEAR MIN (E) & MAX (D)
10 0572  7E         1$:  MOV   A,M         ;GET NEXT DATA BYTE
11 0573  B7              ORA   A
12 0574  CA   0582       JZ    10$         ;ZERO, IGNORE IT
13 0577  04              INR   B
14 0578  BA              CMP   D           ;COMPARE WITH MAX
15 0579  DA   057D       JC    2$          ;NOT HIGHER
16 057C  57              MOV   D,A
17 057D  BB         2$:  CMP   E           ;COMPARE WITH MIN
18 057E  D2   0582       JNC   10$
19 0581  5F              MOV   E,A
20 0582  23         10$: INX   H           ;INC POINTER
21 0583  0D              DCR   C
22 0584  C2   0572       JNZ   1$
23 0587  7A              MOV   A,D         ;MAX
24 0588  93              SUB   E           ;-MIN
25 0589  C9              RET

;CHECK VARIATION...
;CHECK EACH ROW OF HISTORY TABLE AGAINST ITS LIMITS.
; THEN CHECK NUMBER OF ROWS OUT OF LIMIT.
; SETS 'CURVAR' WITH FAILURE BITS: 1 = PERIOD, 2 = AMPLITUDE, 4 = RATIO.
;       8 = TIME WINDOW, 16 = EKG , 32 = RESP
;
 8 058A  0E   00    VARCHK: MVI C,0        ;CLEAR FLAGS
 9 058C  06   01         MVI   B,1         ;FIRST FLAG BIT
10 058E  21   7018       LXI   H,VARLIM    ;POINT TO VARIATION LIMIT
11 0591  E5              PUSH  H
12 0592  21   7029       LXI   H,PERVAR    ;POINT TO FIRST VARIATION
13 0595  E3         1$:  XTHL              ;GET LIMIT POINTER
14 0596  7E              MOV   A,M         ;GET LIMIT
15 0597  23              INX   H
16 0598  E3              XTHL
```

```
17 0599  96              SUB   M            ;MINUS VARIATION
18 059A  D2   05A0       JNC   2$           ;OK
19 059D  79              MOV   A,C
20 059E  B0              ORA   B
21 059F  4F              MOV   C,A          ;COUNT FAILURE
22 05A0  11   0014  2$:  LXI   D,HSTINC
23 05A3  19              DAD   D            ;BUMP VAR POINTER
24 05A4  78              MOV   A,B          ;INCREMENT FLAG BIT
25 05A5  07              RLC
26 05A6  47              MOV   B,A
27 05A7  FE   40         CPI   64
28 05A9  C2   0595       JNZ   1$
29 05AC  E1              POP   H
30 05AD  79              MOV   A,C
31 05AE  32   7015       STA   CURVAR       ;SAVE FLAGS
32 05B1  F5              PUSH  PSW
33 05B2  3A   7104       LDA   SN2DLY       ;IF EKG IS SYNCED, LEAVE TIME WINDOW BIT
34 05B5  B7              ORA   A
35 05B6  C2   05BF       JNZ   4$           ;IF NOT, MASK IT OFF AND USE PER, AMP, RATIO
36 05B9  F1              POP   PSW
37 05BA  E6   0E         ANI   14           ;AMPLITUDE, TIME WINDOW, AND RATIO
38 05BC  C3   05C2       JMP   7$
39 05BF  F1         4$:  POP   PSW          ;RESTORE FLAGS
40 05C0  E6   07         ANI   7            ;LVL3JR CHECKS EKG
41 05C2  0E   00    7$:  MVI   C,0          ;CLEAR COUNT
42 05C4  B7         5$:  ORA   A
43 05C5  1F              RAR                ;NEXT FLAG TO CARRY
44 05C6  D2   05CA       JNC   6$           ;NOT SET
45 05C9  0C              INR   C
46 05CA  B7         6$:  ORA   A            ;CHECK FOR NO MORE BITS
47 05CB  C2   05C4       JNZ   5$           ;LOOP (WITH CLEAR CARRY)
48 05CE  79              MOV   A,C
49 05CF  B7              ORA   A            ;RETURN COUNT IN AC
50 05D0  C8              RZ
51 05D1  37              STC
52 05D2  C9              RET
```

```
;CHECK DIFFERENCE CODES...
; RETURNS NUMBER OF FAILURES IN A, WITH CARRY SET IF NON-ZERO, AND
; SETS 'CURDIF' WITH FLAGS FOR FAILURES: 1 = PERIOD, 2 = AMPLITUDE, 4 = RATIO
; 8 = TIME WINDOW, 16 = EKG, 32 = RESP
;
 7 05D3  0E   00    DIFCHK: MVI  C,0         ;CLEAR COUNT
 8 05D5  06   01            MVI  B,1         ;FIRST FLAG BIT
 9 05D7  21   701E          LXI  H,DIFLIM    ;POINT TO DIFF LIMIT
10 05DA  E5                 PUSH H
11 05DB  21   7027          LXI  H,PERDIF    ;POINT TO FIRST DIFF CODE
12 05DE  E3         1$:     XTHL             ;GET LIMIT POINTER
13 05DF  7E                 MOV  A,M         ;GET LIMIT
14 05E0  23                 INX  H
15 05E1  E3                 XTHL
16 05E2  96                 SUB  M           ;MINUS DIFF CODE
17 05E3  D2   05E9          JNC  2$          ;OK
18 05E6  79                 MOV  A,C         ;UPDATE FAILURE CODE
19 05E7  B0                 ORA  B
20 05E8  4F                 MOV  C,A
21 05E9  11   0014  2$:     LXI  D,HSTINC
22 05EC  19                 DAD  D           ;BUMP DIFF POINTER
23 05ED  78                 MOV  A,B         ;SHIFT FAILURE CODE BIT
24 05EE  07                 RLC
25 05EF  47                 MOV  B,A
26 05F0  FE   40            CPI  64          ;DONE?
27 05F2  C2   05DE          JNZ  1$
28 05F5  E1                 POP  H
29 05F6  79                 MOV  A,C
30 05F7  32   7016          STA  CURDIF
31 05FA  F5                 PUSH PSW
32 05FB  3A   7104          LDA  SN2DLY      ; CHECK FOR EKG SYNC
33 05FE  B7                 ORA  A
34 05FF  C2   0608          JNZ  4$
35 0602  F1                 POP  PSW
36 0603  E6   0E            ANI  14          ;AMPLITUDE, TIME WINDOW AND RATIO
37 0605  C3   060B          JMP  7$
38 0608  F1         4$:     POP  PSW         ;MASK OFF EKG BIT SO LEVEL3 DOESN'T USE IT
39 0609  E6   07            ANI  7
40 060B  0E   00    7$:     MVI  C,0
41 060D  B7         5$:     ORA  A           ;CLC
42 060E  1F                 RAR
43 060F  D2   0613          JNC  6$
44 0612  0C                 INR  C
45 0613  B7         6$:     ORA  A
46 0614  C2   060D          JNZ  5$
47 0617  79                 MOV  A,C
48 0618  B7                 ORA  A
49 0619  C8                 RZ
50 061A  37                 STC
51 061B  C9                 RET
```

```
;SET LIMITS FOR VARIATION AND DIFF PER AMPLITUDE
;
4 061C  3A   7007   SETLIM: LDA  TSTMOD     ;DON'T DO THIS IF TEST MODE =128
5 061F  17                  RAL
6 0620  D8                  RC
7 0621  21   0641           LXI  H,LIMTBO
8 0624  3A   703C           LDA  AMPAVG
```

```
  9 0627   BE            1$:    CMP     M
 10 0628   D2    0632           JNC     5$
 11 062B   11    0007           LXI     D,7
 12 062E   19                   DAD     D
 13 062F   C3    0627           JMP     1$              ;TRY NEXT ENTRY
 14 0632   23            5$:    INX     H               ;MOVE TO LIMITS
 15 0633   11    7018           LXI     D,VARLIM        ;POINT D,E TO DESTINATION TABLE
 16 0636   0E    0C             MVI     C,12
 17 0638   7E            2$:    MOV     A,M
 18 0639   12                   STAX    D
 19 063A   13                   INX     D
 20 063B   23                   INX     H
 21 063C   0D                   DCR     C
 22 063D   C2    0638           JNZ     2$
 23 0640   C9                   RET
 24
 25                             ;LIMITS:    AMPL, VAR..., DIFF...
 26 0641   1E    06     LIMTBO: DB       30, 6, 8, 8, 4, 7, 6, 4, 7, 7, 4, 6, 7
    0643   08    08
    0645   04    07
    0647   06    04
    0649   07    07
    064B   04    06
    064D   07
 27 064E   0F    06             DB       15, 6, 10, 10, 4, 7, 6, 4, 8, 8, 4, 6, 7
    0650   0A    0A
    0652   04    07
    0654   06    04
    0656   08    08
    0658   04    06
    065A   07
 28 065B   00    06             DB       0, 6, 12, 10, 5, 7, 6, 5, 10, 10, 5, 6, 7
    065D   0C    0A
    065F   05    07
    0661   06    05
    0663   0A    0A
    0665   05    06
    0667   07

1                             ;STORE CURRENT DATA AS HISTORY...
  2                             ;  LOOKS AT HSTLEN FOR BUFFER SIZE
  3                             ;
  4
  5 0668   3A    7104   HSTUPD: LDA     SN2DLY          ;IF EKG SYNCED, ADD TIME WINDOW
  6 066B   B7                   ORA     A
  7 066C   C2    0677           JNZ     HSTUP1
  8 066F   0E    04             MVI     C,4
  9 0671   21    7026           LXI     H,HSTBUF
 10 0674   C3    067C           JMP     HSTUP2
 11 0677   0E    03     HSTUP1: MVI     C,3             ;ROW COUNTER
 12 0679   21    7026           LXI     H,HSTBUF        ;POINTER
 13 067C   46            HSTUP2: MOV    B,M             ;GET DATA
 14 067D   C5                   PUSH    B
 15 067E   11    0004           LXI     D,4             ;MOVE POINTER TO FIRST DATA POINT
 16 0681   19                   DAD     D
 17 0682   3A    7017           LDA     HSTLEN          ;GET HISTORY LENGTH
 18 0685   3D                   DCR     A
 19 0686   FA    06A4           JM      11$
 20 0689   CA    0699           JZ      10$
 21 068C   4F                   MOV     C,A
 22 068D   06    00             MVI     B,0
 23 068F   09                   DAD     B               ;POINT TO LAST DATA POINT
 24 0690   2B            2$:    DCX     H
 25 0691   7E                   MOV     A,M
 26 0692   23                   INX     H
 27 0693   77                   MOV     M,A             ;SHUFFLE DATA
 28 0694   2B                   DCX     H               ;BACK UP POINTER
 29 0695   0D                   DCR     C               ;CHECK COUNT
 30 0696   C2    0690           JNZ     2$
 31 0699   C1            10$:   POP     B               ;GET DATA
 32 069A   70                   MOV     M,B
 33 069B   11    0010           LXI     D,HSTINC-4
 34 069E   19                   DAD     D
 35 069F   0D                   DCR     C               ;DECREMENT ROW COUNT
 36 06A0   C2    067C           JNZ     HSTUP2
 37 06A3   C9                   RET
 38 06A4   C1            11$:   POP     B
 39 06A5   C9                   RET
 40                             ;
 41                             ;UPDATE HISTORY FOR EKG
 42                             ;
 43 06A6   0E    01     EKGHUP: MVI     C,1
 44 06A8   21    7076           LXI     H,EKGHBF
 45 06AB   C3    067C           JMP     HSTUP2
 46                             ;
 47                             ; UPDATE HISTORY FOR RESPIRATIONS
 48                             ;
 49 06AE   0E    01     RSPHUP: MVI     C,1
 50 06B0   21    708A           LXI     H,RSPHBF
 51 06B3   C3    067C           JMP     HSTUP2

1                             ;CHECK FOR A DICROTIC NOTCH....
  2                             ;IF AMPLITUDE OF CURRENT PULSE < LAST PULSE /2 AND FLAG NOT SET,
  3                             ; THEN RETURN CARRY SET.
  4                             ;
  5
  6 06B6   AF            CHKNCH: XRA    A                ;CLEAR CARRY
  7 06B7   3A    703E           LDA     AMPHST           ;GET MOST RECENT AMPLITUDE
```

```
   8 06BA    1F                     RAR                     ;/2
   9 06BB    6F                     MOV     L,A
  10 06BC    3A   703A              LDA     CURAMP          ;CURRENT
  11 06BF    BD                     CMP     L
  12 06C0    DA   06D7              JC      1$              ;IS OK
  13 06C3    3A   7014              LDA     SYNFLG          ; CHECK IF SYNCED
  14 06C6    B7                     ORA     A
  15 06C7    C2   06E1              JNZ     2$              ;IF SYNCED, CHECK FOR PERIOD /2
  16 06CA    AF                     XRA     A
  17 06CB    3A   702A              LDA     PERHST
  18 06CE    1F                     RAR
  19 06CF    6F                     MOV     L,A
  20 06D0    3A   7026              LDA     PERIOD
  21 06D3    BD                     CMP     L
  22 06D4    D2   06E1              JNC     2$              ; NO NOTCHES HERE
  23 06D7    21   70B6      1$:     LXI     H,NCHFLG        ;CHECK FOR CONSECUTIVE NOTCHES
  24 06DA    7E                     MOV     A,M
  25 06DB    B7                     ORA     A
  26 06DC    C2   06E1              JNZ     2$              ;CAN'T HAVE CONSECUTIVE NOTCHES
  27 06DF    34                     INR     M
  28 06E0    37                     STC
  29 06E1    C9         2$:         RET
   1
   2                                ;COMPUTE PULSE RATE...
   3                                ;
   4 06E2    3A   7026   COMRAT: LDA PERIOD                 ;CHECK FOR ZERO PERIOD
   5 06E5    B7          COMRT3: ORA A                      ;ENTER HERE FOR EKG HR
   6 06E6    CA   06F8              JZ      1$
   7 06E9    47                     MOV     B,A             ;B,C = PERIOD * 256
   8 06EA    0E   00                MVI     C,0
   9 06EC    11   0D95              LXI     D,3477          ;60 SECONDS/MIN * 57 SAMPLES/SEC, FUDGED.
  10 06EF    CD   12F6              CALL    DIV16           ;3600/PERIOD
  11 06F2    3E   00                MVI     A,0
  12 06F4    DA   06F8              JC      1$              ;CHECK FOR OVERFLOW
  13 06F7    7A                     MOV     A,D
  14 06F8    32   7003      1$:     STA     RATE
  15 06FB    CD   09CA              CALL    FILPLS          ;FILTER IT
  16 06FE    3A   7004              LDA     FRATE           ;SCALE 0-1V = 0-250 BPM
  17 0701    CD   1276              CALL    SCL250
  18 0704    22   716B              SHLD    RATOUT          ;CALL IT RATOUT
  19 0707    C9                     RET
  20                                ;
  21                                ; ENTER COMRAT WITH EKG R-R PERIOD
  22                                ;
  23 0708    3A   7076   COMRT2: LDA RRPER
  24 070B    C3   06E5              JMP     COMRT3
  25
  26                                ;
  27                                ;COMPUTE RESPIRATORY RATE FROM RESPIRATORY PERIOD
  28                                ;
  29 070E    3A   708A   COMRSP: LDA RSPPER
  30 0711    B7                     ORA     A
  31 0712    CA   0724              JZ      1$
  32 0715    47                     MOV     B,A
  33 0716    0E   00                MVI     C,0
  34 0718    11   0366              LXI     D,870           ;60 SEC/MIN * 14SAMPLES/SEC - FUDGED
  35 071B    CD   12F6              CALL    DIV16
  36 071E    3E   00                MVI     A,0
  37 0720    DA   0724              JC      1$
  38 0723    7A                     MOV     A,D
  39 0724    32   7113      1$:     STA     RESP
  40 0727    CD   0A1A              CALL    FILRSP
  41 072A    C9                     RET
  42                                ;
  43                                ;
  44                                ;COMPUTE HEART RATE FROM ECG R WAVE
  45                                ;THIS ROUTINE FIGURES OUT WHETHER EKG AND OR OXIMETER
  46                                ;ARE SYNCED. IF EKG ONLY, THEN DO CONFIDENCE CHECKING ON
  47                                ;PERIOD AND DISPLAY AND ALARM CHECK FOR THE HEART RATE
  48                                ;IF OXIMETER IS SYNCED, THEN DETERMIN HR BY THE R-WAVE PERIOD
  49                                ;IF THE CONFIDENCE IS GOOD.
  50                                ;
  51                                ;BEGIN CHECKING R WAVE
  52                                ;
  53 072B    CD   07F9   LVL3JR: CALL LDSCHK                ;CHECK FOR LEADS OFF
  54 072E    D8                     RC                      ;CARRY SET IF LEADS OFF DETECTED
  55 072F    3A   7100              LDA     EKGFLG          ;IS THE EKG FLAG SET?
  56 0732    B7                     ORA     A
  57 0733    C8                     RZ                      ;NOT THIS TIME
   1 0734    3A   70FF              LDA     EKGPER          ;R-WAVE PERIOD COUNT
   2 0737    32   7076              STA     RRPER           ;STORE AS R-R PERIOD
   3 073A    CD   04E5              CALL    HSTEKG          ;COMPUT EKG HISTORY PARAMS
   4 073D    21   7104              LXI     H,SN2DLY        ;5 PULSE DELAY FOR EKG SYNC
   5 0740    7E                     MOV     A,M
   6 0741    3D                     DCR     A
   7 0742    FA   0749              JM      1$
   8 0745    77                     MOV     M,A
   9 0746    C3   07BF              JMP     7$              ;NOT TIMED DOWN - CHECK R-WAVE VARIATION
  10 0749    3E   00        1$:     MVI     A,0             ;WE'RE SYNCED
  11 074B    32   7106              STA     EKGSNC          ;EKG HAS BEEN USED
  12 074E    CD   05D3              CALL    DIFCHK          ;CHECK DIFFERENCE CODES
  13 0751    3A   7016              LDA     CURDIF          ;CHECK ONLY THE PERIOD HERE
  14 0754    E6   10                ANI     16              ;MASK FOR EKG BIT
  15 0756    C2   079B              JNZ     4$              ;FAILED PERIOD, DON'T CALC HR THIS TIME
  16 0759    3E   14                MVI     A,20            ;PERIOD IS GOOD, RESET EKG TIMEOUT
  17 075B    32   70F8              STA     EKGTMR          ;5 SEC TIMEOUT
```

```
18 075E  CD   07E3           CALL  SETTRG     ;SET WINDOW AND FLAG TO TRIGGER MUNCH
19 0761  3E   03             MVI   A,3
20 0763  32   7107           STA   BADEKG     ;BAD EKG TICKET BOOK
21 0766  3A   7014           LDA   SYNFLG     ;CHECK FOR OXIMETER SYNC
22 0769  B7                  ORA   A
23 076A  C2   0777           JNZ   19$        ;NOT
24 076D  3A   70B4           LDA   SYNDLY     ;HAVE 5 PULSES BEEN PROCESSED?
25 0770  B7                  ORA   A
26 0771  CA   0777           JZ    19$        ;YES, DON'T CHANGE FILTER CONSTS
27 0774  C3   077A           JMP   20$        ;NOT YET, SO DON'T DIDDLE FILTER CONSTS FOR IT
28 0777  CD   0A41   19$:    CALL  FILSET     ;SET FILTER CONSTANTS
29 077A  CD   0708   20$:    CALL  COMRT2     ;CALCULATE HR
30 077D  CD   0A8F           CALL  DSPSR      ;SEND TO DISPLAY
31 0780  3A   7014           LDA   SYNFLG     ;CHECK OXIMETER SYNC FOR ALARM CHECKING
32 0783  B7                  ORA   A
33 0784  CA   0795           JZ    5$         ;IS SYNCED, CHECK ALL ALARMS
34 0787  3A   70C9           LDA   ALMFLG     ;NOT SYNCED, MASK OFF HR ALARM ONLY
35 078A  E6   01             ANI   1          ;PRESERVES ALARM DISPLAY FOR OXIMETER NOSYNC
36 078C  32   70C9           STA   ALMFLG
37 078F  CD   0CA0           CALL  ALMCKB     ;RATE AND EKG ALARM CHECKS
38 0792  C3   07A8           JMP   10$        ;GO UPDATE HISTORY
39 0795  CD   0C37   5$:     CALL  ALMCHK     ;FULL ALARM CHECK
40 0798  C3   07A8           JMP   10$
41 079B  3A   7107   4$:     LDA   BADEKG     ;SEE IF WE CAN IGNORE THIS ONE
42 079E  3D                  DCR   A
43 079F  FA   07A8           JM    10$        ;OUT OF TICKETS, STORE IT
44 07A2  32   7107           STA   BADEKG     ;IGNORE THIS ONE
45 07A5  C3   07B7           JMP   12$        ;EXIT HERE
46 07A8  CD   06A6   10$:    CALL  EKGHUP     ;UPDATE HISTORY FOR EKG
47 07AB  AF                  XRA   A          ;RESET TIME WINDOW AND ENABLE
48 07AC  32   7109           STA   WINTMR
49 07AF  32   710A           STA   WINFLG
50 07B2  3E   08             MVI   A,8        ;RESET HR ANALOG OUT TIMEOUT
51 07B4  32   710B           STA   RATCLK
52 07B7  AF            12$:  XRA   A
53 07B8  32   7100           STA   EKGFLG     ;RESET EKG FLAG
54 07BB  32   70FF           STA   EKGPER     ;RESET EKG PERIOD
55 07BE  C9                  RET
56 07BF  CD   058A   7$:     CALL  VARCHK     ;NOT QUITE SYNCED, CHECK PRESYNC VARIATION
57 07C2  3A   7015           LDA   CURVAR     ;CHECK PERIOD ONLY
 1 07C5  E6   10             ANI   16
 2 07C7  CA   07CE           JZ    8$         ;IS OK
 3 07CA  21   7104           LXI   H,SN2DLY   ;NOT OK, BUMP BACK EKG DELAY COUNTER
 4 07CD  34                  INR   H
 5 07CE  3E   14     8$:     MVI   A,20       ;RESET EKG TIMEOUT COUNTER
 6 07D0  32   70F8           STA   EKGTMR
 7 07D3  3E   03             MVI   A,3
 8 07D5  32   7107           STA   BADEKG     ;ONLY USE TICKETS WHEN SYNCED
 9 07D8  3E   FF             MVI   A,255      ;SET HR FILTER LOW AND CALC BASELINE HR
10 07DA  32   7006           STA   FRATN
11 07DD  CD   0708           CALL  COMRT2     ;CALCULATE, BUT DON'T DISPLAY.....YET
12 07E0  C3   07A8           JMP   10$
13
14                          ;
15                          ; RESET MUNCH ON THE R-WAVE.
16                          ;
17 07E3  21   7108   SETTRG: LXI   H,DATTRG   ;SYNCHRONIZE DATBUF TO R-WAVE
18 07E6  7E                  MOV   A,M
19 07E7  E6   FF             ANI   BUFMSK
20 07E9  32   7179           STA   DTOIDX     ;CAUSE MUNCH TO START HERE
21 07EC  21   70CB           LXI   H,MCHMOD   ;INITIALIZE MUNCH PARAMETERS
22 07EF  1E   0B             MVI   E,11
23 07F1  36   00     1$:     MVI   M,0
24 07F3  23                  INX   H
25 07F4  1D                  DCR   E
26 07F5  C2   07F1           JNZ   1$
27 07F8  C9                  RET
28
29                          ;
30                          ;CHECK FOR A LEADS OFF CONDITION
31                          ; THIS IS SENSED BY A WINDOW COMPARATOR (-4V => +4V)
32                          ;IF LEADS OFF DETECTED, SET CARRY
33                          ;
34 07F9  3A   7106   LDSCHK: LDA   EKGSNC
35 07FC  B7                  ORA   A
36 07FD  C0                  RNZ              ;DON'T CHECK IF EKG IS NOT BEING USED
37 07FE  3A   70CA           LDA   STATUS     ;GET COMPARATOR BIT
38 0801  E6   08             ANI   8
39 0803  CA   080B           JZ    1$         ;LEADS OFF IF LOW
40 0806  AF                  XRA   A          ;CLEAR FLAG AND CARRY BIT
41 0807  32   710D           STA   LDSFLG
42 080A  C9                  RET
43 080B  3A   710D   1$:     LDA   LDSFLG     ;ONLY DO THIS ONCE PER EVENT
44 080E  B7                  ORA   A
45 080F  C0                  RNZ
46 0810  3E   01             MVI   A,1
47 0812  32   70F8           STA   EKGTMR     ;FORCE A TIMEOUT
48 0815  32   710D           STA   LDSFLG
49 0818  37                  STC
50 0819  C9                  RET
51
52                          ;
53                          ; COMPUTE RESPIRATORY RATE
54                          ; CHECK RESPIRATORY PERIOD
55                          ; THE RESPIRATORY RATE IS DISPLAYED IN MODE 5
56                          ; THERE IS A 15 SEC APNEA TIMEOUT ONCE THE RESP IS SYNCED
57                          ;
```

```
  1 081A  3A          RSPLV3: LDA   RSPFLG      ;CHECK FLAG
  2 081D  B7                  ORA   A
  3 081E  C8                  RZ                ;NO NEW RESP
  4 081F  3A   710E           LDA   RSPCNT      ;TRANSFER COUNT TO PERIOD
  5 0822  32   708A           STA   RSPPER
  6 0825  CD   04ED           CALL  HSTRSP      ;COMPUTE RESP HISTORY PARAMS
  7 0828  21   7112           LXI   H,SN3DLY    ;HAVE TWO RESPS BEEN PROCESSED?
  8 082B  7E                  MOV   A,M
  9 082C  3D                  DCR   A
 10 082D  FA   0834           JM    1$          ;YES, RESP IS SYNCED
 11 0830  77                  MOV   M,A
 12 0831  C3   0879           JMP   7$          ;NO, NOT YET
 13 0834  AF           1$:    XRA   A
 14 0835  32   7111           STA   RSPSNC      ;RESP MONITOR HAS BEEN USED
 15 0838  3E   3C             MVI   A,60        ;RESET APNEA TIMEOUT
 16 083A  32   710F           STA   RSPTMR
 17 083D  3E   80             MVI   A,128
 18 083F  32   7115           STA   FRSPN       ;RESP FILTER CONSTANT
 19 0842  3A   70C9           LDA   ALMFLG      ;RESET RESP ALARM BIT
 20 0845  E6   07             ANI   7
 21 0847  32   70C9           STA   ALMFLG
 22 084A  3A   7014           LDA   SYNFLG      ;TURN OFF AUDIO ALARM IF OXIM/EKG NOT SYNCED
 23 084D  B7                  ORA   A
 24 084E  CA   085B           JZ    5$
 25 0851  3A   7106           LDA   EKGSNC
 26 0854  B7                  ORA   A
 27 0855  CA   085B           JZ    5$
 28 0858  CD   0D49           CALL  ALMCKC      ;NEITHER SYNCED, TURN OFF RESP ALARM
 29 085B  3A   7170    5$:    LDA   FMODE       ;CHECK FOR MODE 5
 30 085E  FE   05             CPI   5
 31 0860  C2   0868           JNZ   11$
 32 0863  0E   38             MVI   C,FD2MSK    ;UNBLINK DISPLAY IF MODE 5 IS ACTIVE
 33 0865  CD   1464           CALL  DSPUBK
 34 0868  CD   070E    11$:   CALL  COMRSP      ;CALC RESP RATE
 35 086B  CD   0A8F           CALL  DSPSR       ;SEND TO DISPLAY
 36 086E  CD   06AE    4$:    CALL  RSPHUP      ;UPDATE HISTORY
 37 0871  AF                  XRA   A
 38 0872  32   7110           STA   RSPFLG      ;RESET FLAG
 39 0875  32   710E           STA   RSPCNT      ;RESET COUNT
 40 0878  C9                  RET
 41 0879  3E   3C      7$:    MVI   A,60        ;DON'T TIMEOUT UNTIL SYNCED
 42 087B  32   710F           STA   RSPTMR
 43 087E  3E   FF             MVI   A,255       ;TURN DOWN FILTER COEFFICIENT
 44 0880  32   7115           STA   FRSPN
 45 0883  CD   070E           CALL  COMRSP
 46 0886  C3   086E           JMP   4$
 47                    ;
 48                    ;
 49                    ;
 50                    ;COMPUTE OXYGEN SATURATION
 51                    ;COMPUTE SAT=100*(BR2-R*BR1)/(R*(BO1-BR1)+(BR2-BO2))
 52                    ;  TYPICAL VALUES ARE R= .4 TO 2.2 (RATRAT=R/4)
 53                    ;                  BO1=41.4, BR1=115.2, BO2=20.0, BR2=228.6
 54                    ;  SO THE COMPUTATION IS IMPLEMENTED AS
 55                    ;     SAT=200*(BR2/2-2*RATRAT*BR1)/(-4*RATRAT*(BR1-BO1)+(BR2-BO2))
 56                    ;
 57 0889  2A   70AF    COMSAT: LHLD  FRATIO
  1 088C  CD   08A0           CALL  XSAT
  2 088F  D8                  RC
  3 0890  22   70B7           SHLD  SATX
  4 0893  CD   0974           CALL  FILSAT
  5 0896  3A   7002           LDA   FSAT        ;SCALE 0-1V = 0-100% SAO2
  6 0899  CD   125F           CALL  SCL100
  7 089C  22   7169           SHLD  SATOUT
  8 089F  C9                  RET
  9
 10 08A0  22   70B1    XSAT:  SHLD  XRATIO
 11 08A3  3A   7008           LDA   CALOK       ;CHECK CAL FLAG
 12 08A6  B7                  ORA   A
 13 08A7  CA   0928           JZ    20$         ;NO SAT IF NOT SET
 14 08AA  AF                  XRA   A
 15 08AB  32   70B7           STA   SATX        ;RESET FLAG
 16 08AE  2A   70E3           LHLD  BO2
 17 08B1  EB                  XCHG
 18 08B2  2A   70E5           LHLD  BR2
 19 08B5  CD   1340           CALL  NEGDE
 20 08B8  19                  DAD   D           ;H,L = BR2-BO2
 21 08B9  E5                  PUSH  H           ;SAVE IT
 22 08BA  2A   70DF           LHLD  BO1
 23 08BD  EB                  XCHG
 24 08BE  2A   70E1           LHLD  BR1
 25 08C1  CD   1340           CALL  NEGDE
 26 08C4  19                  DAD   D           ;H,L = BR1-BO1
 27 08C5  DA   08D0           JC    1$          ;BR1 > BO1, OK
 28 08C8  CD   1348           CALL  NEGHL       ;BR1 < BO1, FIX IT
 29 08CB  3E   01             MVI   A,1         ;FLAG IT
 30 08CD  32   70B7           STA   SATX
 31 08D0  4D           1$:    MOV   C,L         ;TO B,C
 32 08D1  44                  MOV   B,H
 33 08D2  2A   70B1           LHLD  XRATIO      ;R/4
 34 08D5  EB                  XCHG
 35 08D6  CD   1232           CALL  MPY32       ;B,CDE = (R/4)*(BR1-BO1)
 36 08D9  3E   02             MVI   A,2
 37 08DB  CD   092D           CALL  SHBCDE      ;MULTIPLY BY 4
 38 08DE  D1                  POP   D
 39 08DF  DA   0929           JC    11$         ;ERROR IF OVERFLOWED
```

```
40 08E2  60              MOV    H,B
41 08E3  69              MOV    L,C
42 08E4  3A   70B7       LDA    SATX
43 08E7  B7              ORA    A
44 08E8  C2   08EE       JNZ    2$
45 08EB  CD   1348       CALL   NEGHL           ;NEGATE IT, H,L = R*(B01-BR1)
46 08EE  19         2$:  DAD    D               ;H,L = R*(B01-BR1)+(BR2-B02)
47 08EF  E5              PUSH   H               ;SAVE DENOMINATOR
48 08F0  2A   70E1       LHLD   BR1
49 08F3  EB              XCHG
50 08F4  2A   70B1       LHLD   XRATIO
51 08F7  44              MOV    B,H
52 08F8  4D              MOV    C,L
53 08F9  CD   1232       CALL   MPY32           ;B,CDE = (R/4)*BR1
54 08FC  3E   01         MVI    A,1
55 08FE  CD   092D       CALL   SHBCDE          ;B,CDE = (R*BR1)/2
56 0901  2A   70E5       LHLD   BR2
57 0904  3E   FF         MVI    A,-1
 1 0906  CD   1A71       CALL   SHFTHL
 2 0909  59              MOV    E,C
 3 090A  50              MOV    D,B
 4 090B  CD   1340       CALL   NEGDE
 5 090E  19              DAD    D               ;H,L = BR2/2-(R*BR1)/2
 6 090F  EB              XCHG
 7 0910  C1              POP    B
 8 0911  D2   0929       JNC    11$
 9 0914  CD   12F6       CALL   DIV16           ;DO THE DIVIDE
10 0917  DA   0928       JC     20$             ;OVERFLOW MEANS BAD BOOGIE
11 091A  01   C800       LXI    B,200*256       ;200.00
12 091D  CD   1232       CALL   MPY32           ;B,CDE = SAT
13 0920  60              MOV    H,B
14 0921  69              MOV    L,C
15 0922  7C              MOV    A,H
16 0923  B7              ORA    A               ;CHECK FOR BAD SAT'S
17 0924  FA   0928       JM     20$
18 0927  C9              RET
19 0928  37         20$: STC
20 0929  21   0000  11$: LXI    H,0
21 092C  C9              RET
22
23                       ;SHIFT B,C,D,E LEFT BY (A) BITS
24                       ;
25 092D  B7         SHBCDE: ORA A
26 092E  C8              RZ
27 092F  F5              PUSH   PSW
28 0930  7B              MOV    A,E
29 0931  17              RAL
30 0932  5F              MOV    E,A
31 0933  7A              MOV    A,D
32 0934  17              RAL
33 0935  57              MOV    D,A
34 0936  79              MOV    A,C
35 0937  17              RAL
36 0938  4F              MOV    C,A
37 0939  78              MOV    A,B
38 093A  17              RAL
39 093B  47              MOV    B,A
40 093C  DA   0944       JC     2$
41 093F  F1              POP    PSW
42 0940  3D              DCR    A
43 0941  C3   092D       JMP    SHBCDE
44 0944  F1         2$:  POP    PSW
45 0945  37              STC
46 0946  C9              RET
47
48                       ;
49                       ;FILTER RATIO...
50                       ;COMPUTE FRATIO=RATRAT*(N/256) + FRATIO*(256-N)/256
51                       ;WHERE N IS FSATN, THE SAT FILTER CONSTANT
52                       ;
53 0947  2A   70A9  FILRAT: LHLD RATRAT         ;GET RATIO B/A
54 094A  3A   7007       LDA    TSTMOD          ;CHECK  TEST FLAGS
55 094D  E6   02         ANI    2               ;NO FILTER BIT
56 094F  C2   0970       JNZ    1$              ;BYPASS THE FILTER
57 0952  3A   7170       LDA    FMODE           ;DITTO FOR MODE 6
 1 0955  FE   06         CPI    6
 2 0957  CA   0970       JZ     1$
 3 095A  EB              XCHG                   ;RATIO TO D,E
 4 095B  3A   7005       LDA    FSATN
 5 095E  CD   09BA       CALL   FILMPY          ;DO RATRAT*(N/256)
 6 0961  E5              PUSH   H               ;SAVE THE DATA
 7 0962  2A   70AF       LHLD   FRATIO
 8 0965  EB              XCHG
 9 0966  3A   7005       LDA    FSATN           ;GET    256-N
10 0969  2F              CMA
11 096A  3C              INR    A
12 096B  CD   09BA       CALL   FILMPY          ;DO FRATIO *(256-N)/256
13 096E  D1              POP    D
14 096F  19              DAD    D
15 0970  22   70AF  1$:  SHLD   FRATIO
16 0973  C9              RET
```

```
;SAT FILTER...
;COMPUTE FSAT=INT(FSAT/2 + FSATX/2)
;  WHERE  FSATX= SATX*(N/256) + FSATX*(256-N)/256
;  N IS THE FILTER CONSTANT (SET ELSEWHERE) THAT NORMALLY RANGES FROM 1 TO 64
;  FSAT IS THE INTEGER DISPLAYED SAT
;  FSATX IS THE 16-BIT (INT.FCT) ACCUMULATOR
;  SATX IS THE 16-BIT COMPUTED SAT.
;
0974  2A  70B7   FILSAT: LHLD  SATX          ;GET DATA
0977  3A  7170           LDA   FMODE         ;CHECK FOR MODE 4 (XX.X)
097A  FE  04              CPI   4
097C  CA  09A2            JZ    2$           ;IT IS, SKIP ROUNDING
097F  3A  70B4            LDA   SYNDLY       ;CHECK FOR START-UP
0982  B7                  ORA   A
0983  C2  09A2            JNZ   2$           ;IT IS, SKIP THIS STEP
0986  3A  7007            LDA   TSTMOD       ;CHECK FOR TEST MODE
0989  E6  03              ANI   3            ;NO-FILTER OR XX.X MODE
098B  C2  09AE            JNZ   3$           ;SKIP ROUNDING AND 100 CHECK
098E  3A  7170            LDA   FMODE        ;DITTO FOR MODE 6
0991  FE  06              CPI   6
0993  CA  09AE            JZ    3$
0996  3A  7002            LDA   FSAT         ;OLD DISPLAYED SAT
0999  57                  MOV   D,A
099A  1E  00              MVI   E,0
099C  19                  DAD   D
099D  3E  FF              MVI   A,-1
099F  CD  1A71            CALL  SHFTHL       ;DIVIDE BY 2
09A2  EB       2$:        XCHG               ;NEW 16-BIT SAT TO D,E
09A3  21  9C00            LXI   H,-100*256
09A6  19                  DAD   D
09A7  EB                  XCHG
09A8  D2  09AE            JNC   3$           ;LESS THAN 100, IS OK
09AB  21  6400            LXI   H,100*256    ;100.0
09AE  22  70B9   3$:      SHLD  FSATX        ;STORE IT AT LAST
09B1  11  0080            LXI   D,80H        ;ROUND SUM
09B4  19                  DAD   D
09B5  7C                  MOV   A,H
09B6  32  7002            STA   FSAT
09B9  C9                  RET
;
;MULTIPLY (A)/256 BY (D,E) AND LEAVE ROUNDED RESULT IN H,L
;
09BA  4F       FILMPY: MOV   C,A            ;TO B,C AS N/256
09BB  06  00              MVI   B,0
09BD  CD  1232            CALL  MPY32        ;MULTIPLY INTO BC,DE
09C0  21  0080            LXI   H,80H        ;ROUND UP FRACT TO 8 BITS
09C3  19                  DAD   D
09C4  6C                  MOV   L,H
09C5  79                  MOV   A,C
09C6  CE  00              ACI   0
09C8  67                  MOV   H,A          ;SATX*N/256 IN H,L
09C9  C9                  RET

;FILTER RATE....SAME AS ABOVE
                 ;
09CA  3A  7003  FILPLS: LDA   RATE
09CD  57               MOV   D,A
09CE  1E  00           MVI   E,0            ;DATA TO D,E
09D0  3A  7170         LDA   FMODE
09D3  FE  06           CPI   6              ;NO FILTERING IF MODE 6
09D5  C2  09DD         JNZ   4$
09D8  3E  FF           MVI   A,255
09DA  32  7006         STA   FRATN
09DD  3A  7006  4$:    LDA   FRATN          ;GET N
09E0  CD  09BA         CALL  FILMPY         ;MULTIPLY DATA BY N/256
09E3  E5              PUSH   H              ;SAVE IT
09E4  2A  70BE         LHLD  FRATX          ;GET OLD DATA
09E7  EB              XCHG
09E8  3A  7006         LDA   FRATN
09EB  2F              CMA
09EC  3C              INR    A
09ED  CD  09BA         CALL  FILMPY         ;OLD DATA * (256-N)/256
09F0  D1              POP    D              ;NEW DATA
09F1  19              DAD    D
09F2  22  70BE         SHLD   FRATX         ;SAVE NEW OLD DATA
09F5  3A  7170         LDA    FMODE
09F8  FE  06           CPI    6
09FA  CA  0A11         JZ     1$            ;SKIP NEXT STAGE IF MODE 6
09FD  3A  70B4         LDA    SYNDLY        ;CHECK OR START-UP
0A00  B7              ORA    A
0A01  C2  0A11         JNZ    1$            ;SKIP SECOND STAGE
0A04  3A  7004         LDA    FRATE         ;OLD DISPLAY
0A07  57              MOV    D,A
0A08  1E  00           MVI    E,0
0A0A  19              DAD    D
0A0B  7C              MOV    A,H
0A0C  1F              RAR
0A0D  67              MOV    H,A
0A0E  7D              MOV    A,L
0A0F  1F              RAR
0A10  6F              MOV    L,A
0A11  11  0080  1$:    LXI    D,80H
0A14  19              DAD    D
0A15  7C              MOV    A,H
0A16  32  7004         STA    FRATE
0A19  C9              RET
```

```
                    ; FILTER RESP...SAME AS ABOVE
                    ;
0A1A   3A   7113    FILRSP: LDA    RESP
0A1D   57                   MOV    D,A
0A1E   1E   00              MVI    E,0
0A20   3A   7115            LDA    FRSPN
0A23   CD   09BA            CALL   FILMPY
0A26   E5                   PUSH   H
0A27   2A   7116            LHLD   FRSPX
0A2A   EB                   XCHG
0A2B   3A   7115            LDA    FRSPN
0A2E   2F                   CMA
0A2F   3C                   INR    A
0A30   CD   09BA            CALL   FILMPY
0A33   D1                   POP    D
0A34   19                   DAD    D
0A35   22   7116            SHLD   FRSPX
0A38   11   0080            LXI    D,80H
0A3B   19                   DAD    D
0A3C   7C                   MOV    A,H
0A3D   32   7114            STA    FRSP
0A40   C9                   RET
                    ;
                    ;
                    ;SET FILTER CONSTANTS...
                    ;
0A41   3A   7007    FILSET: LDA    TSTMOD          ;DON'T RESET FILTERS IF TEST MODE = 128
0A44   17                   RAL
0A45   D8                   RC
0A46   3A   7170            LDA    FMODE
0A49   5F                   MOV    E,A
0A4A   16   00              MVI    D,0
0A4C   21   0A85            LXI    H,FILTBL-1
0A4F   19                   DAD    D
0A50   4E                   MOV    C,M             ;GET FILTER INDEX
0A51   41                   MOV    B,C
0A52   3A   7028            LDA    PERAVG          ;CHECK AVERAGE PERIOD
0A55   FE   23              CPI    35              ;CHECK FOR RATE > 100
0A57   D2   0A5E            JNC    1$              ;LESS
0A5A   AF                   XRA    A
0A5B   79                   MOV    A,C             ;GREATER THAN 100 BEATS, UP THE FILTER
0A5C   1F                   RAR
0A5D   4F                   MOV    C,A
0A5E   3A   7014    1$:     LDA    SYNFLG          ;IF NOT PULSE SYNCED, SKIP THIS
0A61   B7                   ORA    A
0A62   C2   0A7D            JNZ    4$
0A65   3A   703C            LDA    AMPAVG          ;CHECK AMPLITUDE
0A68   FE   1E              CPI    30              ;SMALL PULSE?
0A6A   D2   0A75            JNC    2$              ;NO
0A6D   AF                   XRA    A               ;CLEAR CARRY
0A6E   79                   MOV    A,C
0A6F   1F                   RAR
0A70   4F                   MOV    C,A
0A71   AF                   XRA    A
0A72   78                   MOV    A,B
0A73   1F                   RAR
0A74   47                   MOV    B,A
0A75   3A   7005    2$:     LDA    FSATN
0A78   81                   ADD    C
0A79   1F                   RAR
0A7A   32   7005            STA    FSATN
0A7D   3A   7006    4$:     LDA    FRATN
0A80   80                   ADD    B
0A81   1F                   RAR
0A82   32   7006            STA    FRATN
0A85   C9                   RET

0A86   20       FILTBL: DB   32       ;MODE 1
0A87   80               DB   128
0A88   10               DB   16
0A89   10               DB   16       ;DECIMAL MODE
0A8A   20               DB   32       ;RESP RATE INSTEAD OF HR
0A8B   80               DB   128      ;UNFILTERED MODE
0A8C   20               DB   32       ;ZERO ON ANALOG OUTPUTS
0A8D   20               DB   32       ;1/2 SCALE ON ANALOG OUTPUT
0A8E   20               DB   32       ;FULL SCALE ON ANALOG OUTS

;DISPLAY RATE AND SATURATION
                    ; WITH, OF COURSE, DUE CONCERN FOR ANYTHING ELSE GOING ON...
                    ;
0A8F   3A   712F    DSPSR:  LDA    DSPOK           ;IF SET, THEN WE'RE IN SILENT MODE
0A92   B7                   ORA    A
0A93   C0                   RNZ                    ;WE ARE, SO LONG
0A94   3A   713A            LDA    OPNFLG          ;SKIP ALL OF THIS IF A PARAMETER IS OPEN
0A97   B7                   ORA    A
0A98   C0                   RNZ
0A99   3A   712E            LDA    DSPBKF
0A9C   B7                   ORA    A
0A9D   C2   0AF4            JNZ    2$              ;BLANK DISPLAY
0AA0   11   0100            LXI    D,0100H         ;FIELD 1, XX.X FORAMT
0AA3   3A   7170            LDA    FMODE           ;CHECK FOR MODE 4
```

```
16 0AA6  FE    04                CPI    4              ;IT IS, USE XX.X FORMAT
17 0AA8  CA    0AB5              JZ     1$             ;CHECK FOR TEST MODE BIT 0
18 0AAB  3A    7007              LDA    TSTMOD
19 0AAE  E6    01                ANI    1
20 0AB0  C2    0AB5              JNZ    1$             ;IT IS, USE XX.X
21 0AB3  16    00                MVI    D,0            ;OTHERWISE INTEGERS
22 0AB5  2A    70B9       1$:    LHLD   FSATX          ;16-BIT SAT
23 0AB8  44                      MOV    B,H            ;TO B,C
24 0AB9  4D                      MOV    C,L
25 0ABA  CD    1356              CALL   DECDSP
26 0ABD  3A    7170              LDA    FMODE          ;DON'T DISPLAY RATE IN MODE 3
27 0AC0  FE    03                CPI    3
28 0AC2  CA    0B09              JZ     5$             ;DISPLAY RESP IN MODE 5
29 0AC5  FE    05                CPI    5
30 0AC7  C2    0AD0              JNZ    7$
31 0ACA  3A    7114              LDA    FRSP
32 0ACD  C3    0AE5              JMP    6$
33 0AD0  3A    7014       7$:    LDA    SYNFLG         ;SEE IF CALLED BY BUTCLS
34 0AD3  B7                      ORA    A
35 0AD4  CA    0AE2              JZ     10$            ;IF SYNCED, DISPLAY FRATE
36 0AD7  3A    7104              LDA    SN2DLY         ;IF EKG NOT SYNCED AND PULSE NOT SYNCED
37 0ADA  B7                      ORA    A
38 0ADB  CA    0AE2              JZ     10$            ;THEN INSURE THAT 0 IS DISPLAYED
39 0ADE  AF                      XRA    A
40 0ADF  C3    0AE5              JMP    6$
41 0AE2  3A    7004       10$:   LDA    FRATE
42 0AE5  01    7122       6$:    LXI    B,DSPFD2       ;RATE IN LOWER DISPLAY
43 0AE8  CD    13A9              CALL   DSPCVT
44 0AEB  3A    727C              LDA    COSTA          ;SET OXISENSOR ATTACHED BIT
45 0AEE  F6    02                ORI    OXIATT         ;
46 0AF0  32    727C              STA    COSTA          ;
47 0AF3  C9                      RET
48 0AF4  01    711C       2$:    LXI    B,DSPFD1       ;BLANK DISPLAY
49 0AF7  CD    1452              CALL   DSPBLK
50 0AFA  3A    7170       3$:    LDA    FMODE          ;CHECK FOR MODE 3 ONCE MORE FOR EKG ONLY
51 0AFD  FE    03                CPI    3
52 0AFF  CA    0B09              JZ     5$
53 0B02  3A    70F8              LDA    EKGTHR
54 0B05  B7                      ORA    A
55 0B06  C2    0B18              JNZ    4$             ;DON'T BLANK HR UNLESS TIMED OUT ALSO
56 0B09  3A    7170       5$:    LDA    FMODE          ;DONT BLANK DIPLAY IF RESP IS ON
57 0B0C  FE    05                CPI    5              ;AND UPDATE THE DISPLAY
 1 0B0E  CA    0B22              JZ     8$
 2 0B11  01    7122              LXI    B,DSPFD2
 3 0B14  CD    1452              CALL   DSPBLK
 4 0B17  C9                      RET
 5 0B18  01    7122       4$:    LXI    B,DSPFD2       ;REFRESH HR DISPLAY FOR EKG
 6 0B1B  3A    7004              LDA    FRATE
 7 0B1E  CD    13A9              CALL   DSPCVT
 8 0B21  C9                      RET
 9 0B22  3A    7114       8$:    LDA    FRSP
10 0B25  01    7122              LXI    B,DSPFD2
11 0B28  CD    13A9              CALL   DSPCVT
12 0B2B  C9                      RET
 1                               ;PULSE TIME-OUT...RAISE AN ALARM, NO PULSE FOUND.
 2                               ; CALLED BY CLOCK WHEN PLSTHR GOES TO ZERO, DISPLAYS ZERO RATE AND SETS ALARM.
 3                               ;
 4
 5 0B2C  3A    7014       PLSTMO: LDA   SYNFLG         ;CHECK FOR NOT SYNC'ED
 6 0B2F  B7                      ORA    A
 7 0B30  C2    0BB3              JNZ    5$
 8 0B33  AF                      XRA    A              ;ZERO RATE AND SAT
 9 0B34  32    7002              STA    FSAT
10 0B37  21    0000              LXI    H,0            ;ZERO SAT OUTPUT
11 0B3A  22    7169              SHLD   SATOUT
12 0B3D  3A    7104              LDA    SN2DLY         ;ZERO RATE IF EKG TIMED OUT TOO
13 0B40  B7                      ORA    A
14 0B41  CA    0B4E              JZ     1$
15 0B44  AF                      XRA    A
16 0B45  32    7004              STA    FRATE
17 0B48  21    0000              LXI    H,0
18 0B4B  22    716B              SHLD   RATOUT
19 0B4E  21    0000       1$:    LXI    H,0
20 0B51  22    70B9              SHLD   FSATX
21 0B54  3A    712F              LDA    DSPOK          ;IF SILENT MODE, FORGET THIS STUFF
22 0B57  B7                      ORA    A
23 0B58  C2    0B7E              JNZ    3$
24 0B5B  CD    0C37              CALL   ALMCHK         ;CALL ALARM CHECKER
25 0B5E  0E    20                MVI    C,SYNCOD       ;NO-SYNC LITE
26 0B60  CD    1484              CALL   BNKLIT
27 0B63  0E    08                MVI    C,SLOCOD       ;CLR RATE,SAT LED
28 0B65  CD    1475              CALL   CLRLIT
29 0B68  0E    10                MVI    C,SHICOD
30 0B6A  CD    1475              CALL   CLRLIT
31 0B6D  3A    70F8              LDA    EKGTHR
32 0B70  B7                      ORA    A              ;DON'T RESET RATE ALARMS UNLESS EKG TIMED OUT
33 0B71  C2    0B7E              JNZ    3$
34 0B74  0E    04                MVI    C,RHICOD
35 0B76  CD    1475              CALL   CLRLIT
36 0B79  0E    02                MVI    C,RLOCOD
37 0B7B  CD    1475              CALL   CLRLIT
38 0B7E  3E    04         3$:    MVI    A,4            ;RESET SYNC CODE
39 0B80  32    7014              STA    SYNFLG
40 0B83  3E    04                MVI    A,4            ;AND HISTOR LENGTH
41 0B85  32    7017              STA    HSTLEN
42 0B88  3A    700C              LDA    LIITHR         ;CHECK LED'S FOR SERVO'ING
```

```
43 0B8B  47              MOV   B,A
44 0B8C  3A   700F       LDA   L2ITHR
45 0B8F  B0              ORA   B
46 0B90  3E   00         MVI   A,0
47 0B92  CA   0B9F       JZ    2$              ;NOT, SHOW ZERO'S
48 0B95  3A   727C       LDA   COSTA           ;CLEAR OXISENSOR ATTACHED BIT    ///
49 0B98  E6   FD         ANI   NOT_OXIATT                                       ///
50 0B9A  32   727C       STA   COSTA                                            ///
51 0B9D  3E   01         MVI   A,1             ;BLANK DISPLAY
52 0B9F  32   712E  2$:  STA   DSPBKF
53 0BA2  CD   0404       CALL  SNDMON          ;AND LET THE INTERFACE KNOW      ///
54 0BA5  CD   0A8F       CALL  DSPSR           ;DISPLAY ZERO'S OR BLANK'S
55 0BA8  3A   70F2       LDA   ALICTR
56 0BAB  B7              ORA   A               ;CHECK FOR ALARM INHIBITED
57 0BAC  C8              RZ                    ;IS NOT
 1 0BAD  3E   01         MVI   A,1
 2 0BAF  32   70F6       STA   ALMDLY          ;SET UP DELAYED ALARM
 3 0BB2  C9              RET
 4 0BB3  3E   04    5$:  MVI   A,4
 5 0BB5  32   7014       STA   SYNFLG
 6 0BB8  C9              RET
 7                       ;
 8                       ;SAT UPDATE TIME-OUT...SET IT TO ZERO
 9                       ;
10 0BB9  AF         SATTMO: XRA  A
11 0BBA  32   7002       STA   FSAT
12 0BBD  21   0000       LXI   H,0
13 0BC0  22   7169       SHLD  SATOUT
14 0BC3  22   70B9       SHLD  FSATX
15 0BC6  3E   FF         MVI   A,255
16 0BC8  32   7005       STA   FSATN           ;TURN DOWN FILTER FOR QUICK RETURN
17 0BCB  C9              RET
18                       ;
19                       ;EKG TIMED OUT - ZERO RATE IF NOT SYNCED
20                       ;
21 0BCC  AF         EKGTMO: XRA  A
22 0BCD  32   70FF       STA   EKGPER          ;RESET EKG PERIOD
23 0BD0  32   7100       STA   EKGFLG          ;RESET FLAG
24 0BD3  3A   7106       LDA   EKGSNC          ;CHECK FOR EKG SYNC
25 0BD6  B7              ORA   A
26 0BD7  C0              RNZ
27 0BD8  3E   05         MVI   A,5             ;RESET EKG SYNC DELAY
28 0BDA  32   7104       STA   SN2DLY
29 0BDD  3A   7014       LDA   SYNFLG
30 0BE0  B7              ORA   A
31 0BE1  C8              RZ
32 0BE2  AF              XRA   A
33 0BE3  32   7004       STA   FRATE
34 0BE6  21   0000       LXI   H,0
35 0BE9  22   716B       SHLD  RATOUT          ;ZERO RATE ANALOG OUTPUT
36 0BEC  CD   0A8F       CALL  DSPSR
37 0BEF  3A   70C9       LDA   ALMFLG
38 0BF2  E6   01         ANI   1
39 0BF4  32   70C9       STA   ALMFLG
40 0BF7  CD   0CA0       CALL  ALMCKB
41 0BFA  0E   04         MVI   C,RHICOD
42 0BFC  CD   1475       CALL  CLRLIT
43 0BFF  0E   02         MVI   C,RLOCOD
44 0C01  CD   1475       CALL  CLRLIT
45 0C04  3A   70F2       LDA   ALICTR
46 0C07  B7              ORA   A
47 0C08  C8              RZ
48 0C09  3E   01         MVI   A,1
49 0C0B  32   70F6       STA   ALMDLY
50 0C0E  C9              RET
51                       ;
52                       ;RESP TIMED OUT - SET ALARM
53                       ;
54 0C0F  AF         RSPTMO: XRA  A
55 0C10  32   710E       STA   RSPCNT
56 0C13  32   7114       STA   FRSP            ;ZERO COUNT, FLAG, AND RESP
57 0C16  32   7110       STA   RSPFLG
 1 0C19  3E   02         MVI   A,2
 2 0C1B  32   7112       STA   SN3DLY
 3 0C1E  CD   0A8F       CALL  DSPSR           ;ZERO RESP DISPLAY
 4 0C21  3A   70C9       LDA   ALMFLG
 5 0C24  E6   07         ANI   7               ;PRESERVE OTHER ALARM STATUSES
 6 0C26  32   70C9       STA   ALMFLG
 7 0C29  CD   0D49       CALL  ALMCKC          ;SET RESP ALARM
 8 0C2C  3A   70F2       LDA   ALICTR          ;CHECK FOR DELAYED ALARMS
 9 0C2F  B7              ORA   A
10 0C30  C8              RZ
11 0C31  3E   01         MVI   A,1
12 0C33  32   70F6       STA   ALMDLY
13 0C36  C9              RET
14                       ;
 1                       ;
 2                       ;CHECK ALARM VALUES, OUTPUT TO BEEPER...
 3                       ;  A NICE LITTLE BEEP FOR A NORMAL PULSE, A LOUD RAUCUS NOISE FOR ALARM
 4                       ;
 5 0C37  AF         ALMCHK: XRA  A             ;CLEAR ALARM FLAG
 6 0C38  32   70C9       STA   ALMFLG
 7 0C3B  3A   712F       LDA   DSPOK           ;NO ALARMS IN SILENT MODE
 8 0C3E  B7              ORA   A
 9 0C3F  C0              RNZ
10                       ;
```

```
                        ;CHECK LOW SAT, SET LIGHT AND STATUS BIT AND RESET HI SAT ALARM IF SO.
                        ;
 0C40  21  70C2    13$:  LXI   H,SATLL      ;POINT H,L TO LIMITS
 0C43  3A  7002          LDA   FSAT         ;FILTERED SATURATION
 0C46  BE               CMP   M            ;CHECK SAT-LIMIT
 0C47  D2  0C5F          JNC   1$           ;NO ALARM
 0C4A  0E  08            MVI   C,SLOCOD
 0C4C  CD  1484          CALL  BNKLIT       ;TURN ON ALARM LIGHT
 0C4F  0E  10            MVI   C,SHICOD     ;TURN OFF HIGH ALARM
 0C51  CD  1475          CALL  CLRLIT
 0C54  3A  727D          LDA   CPSTA        ;SET ALARM BIT FOR SATURATION        ///
 0C57  F6  04            ORI   SATBIT       ;                                    ///
 0C59  32  727D          STA   CPSTA        ;                                    ///
 0C5C  C3  0C79          JMP   2$

;CHECK HIGH SAT, SET LIGHT AND BIT AND RESET LOW SAT ALARM IF SO.
                        ;
 0C5F  23          1$:   INX   H
 0C60  BE                CMP   M
 0C61  CA  0C89          JZ    3$
 0C64  DA  0C89          JC    3$           ;NO ALARM
 0C67  0E  10            MVI   C,SHICOD     ;TURN ON LIGHT
 0C69  CD  1484          CALL  BNKLIT
 0C6C  0E  08            MVI   C,SLOCOD     ;TURN OFF LOW SAT
 0C6E  CD  1475          CALL  CLRLIT
 0C71  3A  727D          LDA   CPSTA
 0C74  E6  FB            ANI   NOT SATBIT
 0C76  32  727D          STA   CPSTA

;SAT ALARM (HI OR LOW), BLINK FIELD AND SET ALARM FLAG
                        ;
 0C79  0E  07      2$:   MVI   C,FD1MSK
 0C7B  CD  145D          CALL  DSPBNK        ;BLINK THE DIGITS
 0C7E  3A  70C9          LDA   ALMFLG
 0C81  F6  01            ORI   1
 0C83  32  70C9          STA   ALMFLG        ;SET FLAG FOR BEEPER, ETC.
 0C86  C3  0CA0          JMP   4$

;NO SAT ALARM, RESET LIGHTS AND BLINKS.
                        ;
 0C89  0E  07      3$:   MVI   C,FD1MSK      ;NO ALARM, CLEAR BLINKING
 0C8B  CD  1464          CALL  DSPUBK
 0C8E  0E  08            MVI   C,SLOCOD     ;CLEAR LIGHT
 0C90  CD  1475          CALL  CLRLIT
 0C93  0E  10            MVI   C,SHICOD
 0C95  CD  1475          CALL  CLRLIT
 0C98  3A  727D          LDA   CPSTA         ;CLEAR SATURATION ALARM              ///
 0C9B  E6  FB            ANI   NOT SATBIT    ;                                    ///
 0C9D  32  727D          STA   CPSTA         ;                                    ///

;CHECK RATE ALARM, BUT FIRST MAKE SURE IT'S NOT MODE 3.
                        ;
                        4$:
 0CA0  3A  712F   ALMCKB: LDA  DSPOK         ;EXIT IF WE'RE IN SILENT MODE
 0CA3  B7                ORA   A
 0CA4  C0                RNZ
 0CA5  3A  7170          LDA   FMODE         ;DONT CHECK RATE IN MODE 3
 0CA8  FE  03            CPI   3
 0CAA  CA  0D37          JZ    17$
 0CAD  3A  7106          LDA   EKGSNC        ;CHECK FOR EKG SYNC
 0CB0  B7                ORA   A
 0CB1  C2  0CD0          JNZ   15$
 0CB4  3A  7104          LDA   SN2DLY        ;IF TIMED OUT ALSO, THEN ALARM CHECK
 0CB7  B7                ORA   A
 0CB8  CA  0CD0          JZ    15$
 0CBB  0E  80            MVI   C,BATCOD
 0CBD  CD  1484          CALL  BNKLIT        ;SET UP ALARM HERE FOR EKG TIMEOUT
 0CC0  0E  38            MVI   C,FD2MSK      ;IF SYNCED, RATE ALARMS WILL ALSO BE CHECKED
 0CC2  CD  145D          CALL  DSPBNK
 0CC5  3A  70C9          LDA   ALMFLG
 0CC8  F6  04            ORI   4             ;4 = LOST EKG SYNC
 0CCA  32  70C9          STA   ALMFLG
 0CCD  C3  0CD5          JMP   14$
 0CD0  0E  80      15$:  MVI   C,BATCOD
 0CD2  CD  1475          CALL  CLRLIT

;CHECK LOW RATE
                        ;
 0CD5  21  70C6   14$:   LXI   H,RATLL       ;POINT TO RATE LIMITS
 0CD8  3A  7004          LDA   FRATE         ;CHECK RATE
 0CDB  BE                CMP   M             ;LOWER LIM
 0CDC  D2  0CF6          JNC   5$            ;NOT BELOW LOWER LIMIT...
 0CDF  3A  727D          LDA   CPSTA         ;SET LOW RATE ALARM BIT             ///
 0CE2  F6  02            ORI   LRTBIT        ;                                   ///
 0CE4  E6  FE            ANI   NOT HRTBIT
 0CE6  32  727D          STA   CPSTA         ;                                   ///
 0CE9  0E  02            MVI   C,RLOCOD
 0CEB  CD  1484          CALL  BNKLIT
 0CEE  0E  04            MVI   C,RHICOD
 0CF0  CD  1475          CALL  CLRLIT
 0CF3  C3  0D12          JMP   6$

;CHECK HIGH RATE
                        ;
 0CF6  23         5$:    INX   H
 0CF7  BE                CMP   M             ;UPPER LIMIT
```

```
 50 OCF8   CA    0D2A            JZ     7$            ;OK IF EQUAL
 51 0CFB   DA    0D2A            JC     7$            ;OR LESS
 52 0CFE   0E    04              MVI    C,RHICOD      ;SET HI RATE ALARM LITE
 53 0D00   CD    1484            CALL   BNKLIT
 54 0D03   3A    727D            LDA    CPSTA         ;SET HIGH RATE ALARM BIT            ///
 55 0D06   F6    01              ORI    HRTBIT        ;                                   ///
 56 0D08   E6    FD              ANI    NOT LRTBIT    ;CLEAR LOW RATE BIT                 ///
 57 0D0A   32    727D            STA    CPSTA         ;IN PATIENT STATUS BYTE             ///
  1 0D0D   0E    02              MVI    C,RLOCOD
  2 0D0F   CD    1475            CALL   CLRLIT
  3
  4                              ;RATE ALARM, BLINK THE FIELD AND SET FLAG
  5                              ;
  6 0D12   3A    7170     6$:    LDA    FMODE         ;DONT BLINK IF IN MODE 5
  7 0D15   FE    05              CPI    5
  8 0D17   CA    0D1F            JZ     19$
  9 0D1A   0E    38              MVI    C,FD2MSK      ;RATE ALARM, BLINK FIELD 2
 10 0D1C   CD    145D            CALL   DSPBNK
 11 0D1F   3A    70C9     19$:   LDA    ALMFLG        ;SET FLAG BIT
 12 0D22   F6    02              ORI    2
 13 0D24   32    70C9            STA    ALMFLG
 14 0D27   C3    0D49            JMP    8$
 15
 16                              ;NO RATE ALARM, RESET LIGHTS AND BLINKS
 17                              ;
 18 0D2A   3A    7170     7$:    LDA    FMODE         ;DON'T CLEAR BLINK IF IN MODE 5
 19 0D2D   FE    05              CPI    5
 20 0D2F   CA    0D37            JZ     17$
 21 0D32   0E    38              MVI    C,FD2MSK      ;NO ALARM, CLEAR BLINK
 22 0D34   CD    1464            CALL   DSPUBK
 23 0D37   3A    727D     17$:   LDA    CPSTA         ;CLEAR HIGH RATE BIT               ///
 24 0D3A   E6    FC              ANI    NOT (HRTBIT OR LRTBIT) ;                         ///
 25 0D3C   32    727D            STA    CPSTA         ;AND LOW RATE BIT                  ///
 26 0D3F   0E    02              MVI    C,RLOCOD
 27 0D41   CD    1475            CALL   CLRLIT        ;AND CLEAR LIGHT
 28 0D44   0E    04              MVI    C,RHICOD
 29 0D46   CD    1475            CALL   CLRLIT
 30
 31                              ;CHECK FOR AUDIO ALARM...ENTER HERE ALSO FROM CLOCK FOR A DELAYED ALARM...
 32                              ;ENTER HERE ALSO IF RESP TIMED OUT
 33                              ;
 34 0D49                  8$:
 35 0D49   3A    712F     ALMCKC: LDA   DSPOK
 36 0D4C   B7                    ORA    A
 37 0D4D   C0                    RNZ
 38 0D4E   3A    7111            LDA    RSPSNC        ;SEE IF RESP IS SYNCED
 39 0D51   B7                    ORA    A
 40 0D52   C2    0D71            JNZ    8$
 41 0D55   3A    710F            LDA    RSPTMR
 42 0D58   B7                    ORA    A
 43 0D59   C2    0D71            JNZ    8$
 44 0D5C   3A    70C9            LDA    ALMFLG
 45 0D5F   F6    08              ORI    8             ;8=RESP ALARM BIT
 46 0D61   32    70C9            STA    ALMFLG
 47 0D64   3A    7170            LDA    FMODE         ;BLINK DISPLAY IF IN MODE 5
 48 0D67   FE    05              CPI    5
 49 0D69   C2    0D71            JNZ    8$
 50 0D6C   0E    38              MVI    C,FD2MSK
 51 0D6E   CD    145D            CALL   DSPBNK
 52 0D71   3A    70C9     8$:    LDA    ALMFLG
 53 0D74   E6    01              ANI    1             ;CHECK FOR A SAT ALARM
 54 0D76   CA    0D7E            JZ     ALMCK2
 55 0D79   0E    07              MVI    C,FD1MSK      ;IF SO, SET FIELD 1 BLINKING
 56 0D7B   CD    145D            CALL   DSPBNK
 57 0D7E   3A    70C9     ALMCK2: LDA   ALMFLG
  1 0D81   B7                    ORA    A
  2 0D82   CA    0DC4            JZ     10$           ;NO ALARMS...
  3 0D85   3A    70F1            LDA    ALIFLG        ;CHECK FOR ALARM INHIBIT
  4 0D88   B7                    ORA    A
  5 0D89   C2    0DC4            JNZ    11$           ;NOT ZERO, STILL INHIBITED...
  6 0D8C   3A    7014            LDA    SYNFLG        ;MAKE SURE WE ALARM ONLY ONCE PER PULSE
  7 0D8F   B7                    ORA    A
  8 0D90   C2    0DB5            JNZ    9$            ;NOT PULSE SYNCED, SEE IF EKG SYNCED
  9 0D93   3A    7100            LDA    EKGFLG
 10 0D96   B7                    ORA    A             ;IF SET THEN ENABLE ALARM
 11 0D97   C2    0D9F            JNZ    16$
 12 0D9A   3A    70F8            LDA    EKGTMR        ;IF NOT TIMED OUT, THEN WE ALREADY SET ALARM
 13 0D9D   B7                    ORA    A
 14 0D9E   C0                    RNZ
 15 0D9F   3A    70EF     16$:   LDA    ALMVOL        ;GET VOLUME CODE
 16 0DA2   5F                    MOV    E,A
 17 0DA3   0E    6E              MVI    C,ALMPCH      ;GET ALARM PITCH
 18 0DA5   06    FE              MVI    B,254
 19 0DA7   3A    7170            LDA    FMODE
 20 0DAA   FE    03              CPI    3             ;CHECK FOR MODE 3 AGAIN
 21 0DAC   C2    0DB1            JNZ    18$           ;NOT
 22 0DAF   06    FF              MVI    B,255         ;STEADY ALARM
 23 0DB1   CD    148E     18$:   CALL   BEEP
 24 0DB4   C9                    RET
 25 0DB5   3A    7100     9$:    LDA    EKGFLG
 26 0DB8   B7                    ORA    A
 27 0DB9   C2    0D9F            JNZ    16$           ;NOT PULSE SYNCED, BUT EKG IS
 28 0DBC   3A    70F8            LDA    EKGTMR
 29 0DBF   B7                    ORA    A             ;IF TIMED OUT, THEN CALLED BY EKGTMO
 30 0DC0   CA    0D9F            JZ     16$
```

```
31 0DC3    C9                          RET
32                          ;
33                          ;NO ALARM....MAKE A BEEP
34                          ;
35 0DC4                 10$:
36 0DC4    1E   00      11$:   MVI    E,0
37 0DC6    01   0000           LXI    B,0             ;TO SHUT UP ALARM IF NO BEEP
38 0DC9    3A   70F7           LDA    ALCFLG          ;GET ALARM-CHECKING FLAG
39 0DCC    B7                  ORA    A
40 0DCD    C2   0E08           JNZ    19$             ;NO BEEP IF SET
41 0DD0    3A   7170           LDA    FMODE           ;NO BEEP IN MODE 3
42 0DD3    FE   03             CPI    3
43 0DD5    CA   0E08           JZ     19$
44 0DD8    3A   7014           LDA    SYNFLG          ;NO BEEP IF NOT SYNC'ED
45 0DDB    B7                  ORA    A
46 0DDC    C2   0DF9           JNZ    12$
47 0DDF    3A   7100           LDA    EKGFLG          ;IF EKGFLG SET, THEN BEEP
48 0DE2    B7                  ORA    A
49 0DE3    C2   0DEB           JNZ    20$             ; IF EKG NOT TIMED OUT - MUST HAVE BEEPED
50 0DE6    3A   7104           LDA    SN2DLY
51 0DE9    B7                  ORA    A
52 0DEA    C8                  RZ
53 0DEB    3A   70EC    20$:   LDA    BEEVOL
54 0DEE    5F                  MOV    E,A
55 0DEF    3A   7002           LDA    FSAT            ;COMPUTE PITCH FROM SAT
56 0DF2    4F                  MOV    C,A
57 0DF3    06   05             MVI    B,5
 1 0DF5    CD   148E           CALL   BEEP
 2 0DF8    C9                  RET
 3 0DF9    3A   7100    12$:   LDA    EKGFLG          ;NOT SYNCED, BUT CHECK FOR EKG
 4 0DFC    B7                  ORA    A
 5 0DFD    CA   0E08           JZ     19$             ;BEEP, BUT FUDGE A TONE
 6 0E00    3A   70EC           LDA    BEEVOL
 7 0E03    5F                  MOV    E,A
 8 0E04    0E   64             MVI    C,100
 9 0E06    06   05             MVI    B,5
10 0E08    CD   148E    19$:   CALL   BEEP
11 0E0B    C9                  RET
12
13
 1
 2                          ;TWEAK LED LEVELS....
 3                          ; IF MAX1 > 87% THEN LED1 = LED1 - DELTL1, AND IF
 4                          ;    MIN1 < 12% THEN LED1 = LED1 + DELTL1, REPEAT FOR LED2
 5                          ;
 6 0E0C    3A   7011    TWKLED: LDA   INHLED          ;CHECK INHIBIT FLAG
 7 0E0F    B7                  ORA    A
 8 0E10    C0                  RNZ                    ;SET
 9 0E11    3A   7007           LDA    TSTMOD
10 0E14    E6   08             ANI    8
11 0E16    C0                  RNZ
12 0E17    21   700A           LXI    H,LED1
13 0E1A    3A   70A0           LDA    MAX1+1          ;GET HI 4 BITS OF MAX
14 0E1D    FE   F8             CPI    0F8H            ;>7/8 FS?
15 0E1F    DA   0E26           JC     2$              ;NO, IS OK
16 0E22    35                  DCR    M               ;YES, DECREMENT LED BRIGHTNESS
17 0E23    C3   0E2F           JMP    3$
18 0E26    3A   70A2    2$:    LDA    MIN1+1          ;GET HI BYTE OF MIN
19 0E29    FE   C8             CPI    0C8H            ;LESS THAN 1/8?
20 0E2B    D2   0E32           JNC    5$              ;NO, IS OK...
21 0E2E    34                  INR    M               ;INCREMENT LED
22 0E2F    CD   1DF6    3$:    CALL   LD1SET
23 0E32    21   700D    5$:    LXI    H,LED2
24 0E35    3A   70A4           LDA    MAX2+1
25 0E38    FE   F8             CPI    0F8H
26 0E3A    DA   0E41           JC     6$
27 0E3D    35                  DCR    M
28 0E3E    C3   0E4A           JMP    7$
29 0E41    3A   70A6    6$:    LDA    MIN2+1
30 0E44    FE   C8             CPI    0C8H
31 0E46    D2   0E4D           JNC    10$
32 0E49    34                  INR    M
33 0E4A    CD   1E05    7$:    CALL   LD2SET
34 0E4D    C9           10$:   RET
 1                          ;CHECK CALIBRATION...LOOK AT RESISTOR VOLTAGE, SET COUNT-DOWN FLAG IF NO RESISTOR.
 2                          ; IF RESISTOR IS THERE, CHECK FLAG, DECREMENT IF NON-ZERO. IF IT GOES ZERO,
 3                          ; DIVIDE REISTOR BY REFERNCE AND USE AS INDEX INTO CAL TABLE.
 4
 5
 6 0E4E    2A   7152    CALCHK: LHLD  VCAL            ;GET CAL RESISTOR
 7 0E51    EB                  XCHG                   ;INTO D,E (FOR LATER DIVIDE)
 8 0E52    21   FFE0           LXI    H,-32           ;THESHHOLD
 9 0E55    19                  DAD    D
10 0E56    DA   0E67           JC     2$              ;NEAR-ZERO MEANS NO RESISTOR
11 0E59    3E   FF      1$:    MVI    A,255           ;SET COUNT-DOWN FLAG
12 0E5B    32   70E7           STA    CALFLG
13 0E5E    AF                  XRA    A
14 0E5F    32   7009           STA    CALIDX
15 0E62    32   7008           STA    CALOK
16 0E65    37                  STC
17 0E66    C9                  RET
18 0E67    3A   70E7    2$:    LDA    CALFLG          ;CHECK FLAG
19 0E6A    3D                  DCR    A
20 0E6B    32   70E7           STA    CALFLG
21 0E6E    CA   0E73           JZ     5$              ;JUST BECAME ZERO, GO COMPUTE CAL
22 0E71    B7                  ORA    A               ;CLEAR CARRY
```

```
23 0E72   C9                           RET
24                              ;
25                              ; COMPUTE RESISTANCE FROM DAC VALUES FOR RESISTOR AND REFERENCE.
26                              ;
27 0E73   2A    7156      5$:   LHLD   VREF
28 0E76   3E    00              MVI    A,0         ;SUBTRACT REF FROM FULL SCALE (4096)
29 0E78   95                    SUB    L
30 0E79   4F                    MOV    C,A
31 0E7A   3E    10              MVI    A,10H
32 0E7C   9C                    SBB    H
33 0E7D   47                    MOV    B,A
34 0E7E   11    018D            LXI    D,256+141   ;10-VREF IN B,C
35 0E81   CD    1232            CALL   MPY32       ;1.54 IN D,E
36 0E84   41                    MOV    B,C         ;1.54(10-VREF) IN BCD,E
37 0E85   4A                    MOV    C,D         ;
38 0E86   2A    7152            LHLD   VCAL
39 0E89   3E    00              MVI    A,0
40 0E8B   95                    SUB    L
41 0E8C   5F                    MOV    E,A
42 0E8D   3E    10              MVI    A,10H
43 0E8F   9C                    SBB    H           ;10V - VCAL IN D,E
44 0E90   57                    MOV    D,A
45 0E91   CD    12F6            CALL   DIV16       ;DIVIDE BY REFERENCE TO MAKE RESISTANCE CODE
46 0E94   21    FF6A            LXI    H,-150      ;ADD OFFSET TO CORRECT CIRCUIT ERROR
47 0E97   19                    DAD    D
48 0E98   DA    0E9E            JC     4$
49 0E9B   21    0000            LXI    H,0
50 0E9E   EB              4$:   XCHG               ;RESISTOR NOW IN D,E
51                              ;
52                              ;CHECK FOR STABILITY, SET FLAG IF SO.
53                              ;
54 0E9F   2A    70E8            LHLD   CALRES      ;GET OLD VALUE
55 0EA2   CD    1348            CALL   NEGHL
56 0EA5   19                    DAD    D           ;COMPUTE DIFF
57 0EA6   DA    0EAC            JC     6$
 1 0EA9   CD    1348            CALL   NEGHL       ;NEGATIVE DIFF
 2 0EAC   01    FA24      6$:   LXI    B,-1500     ;STABILITY THRESHHOLD + 3 INDICES
 3 0EAF   09                    DAD    B
 4 0EB0   3E    00              MVI    A,0
 5 0EB2   DA    0EB6            JC     7$          ;NOT STABLE
 6 0EB5   3C                    INR    A           ;STABLE, SET OK FLAG
 7 0EB6   32    7008      7$:   STA    CALOK       ;SET OK FLAG
 8 0EB9   EB                    XCHG
 9 0EBA   22    70E8            SHLD   CALRES      ;SAVE FOR REFERENCE
10                              ;
11                              ; CONVERT RESISTANCE CODE TO INDEX BY LOOKING IT UP IN CALTBL.
12                              ;
13 0EBD   3A    7007            LDA    TSTMOD
14 0EC0   E6    04              ANI    4
15 0EC2   C2    0EE7            JNZ    9$
16 0EC5   AF                    XRA    A           ;NEGATE RESISTANCE CODE
17 0EC6   95                    SUB    L
18 0EC7   4F                    MOV    C,A         ;AND MOVE TO B,C
19 0EC8   3E    00              MVI    A,0
20 0ECA   9C                    SBB    H
21 0ECB   47                    MOV    B,A
22 0ECC   21    1EA5            LXI    H,CALTBL    ;POINT TO TABLE
23 0ECF   5E              8$:   MOV    E,M
24 0ED0   23                    INX    H
25 0ED1   56                    MOV    D,M         ;GET TABLE FRACTION
26 0ED2   23                    INX    H
27 0ED3   7A                    MOV    A,D         ;CHECK FOR ZERO
28 0ED4   B3                    ORA    E
29 0ED5   CA    0F36            JZ     20$         ;ERROR, FOUND THE END.
30 0ED8   EB                    XCHG               ;MOVE TABLE FRACT TO H,L
31 0ED9   09                    DAD    B           ;- RESISTOR
32 0EDA   EB                    XCHG
33 0EDB   D2    0ECF            JNC    8$          ;NOT FOUND
34 0EDE   11    E159            LXI    D,-(CALTBL+2)
35 0EE1   19                    DAD    D           ;SUBTRACT TABLE BASE ADDRESS
36 0EE2   7D                    MOV    A,L
37 0EE3   0F                    RRC
38 0EE4   32    7009            STA    CALIDX      ;SAVE INDEX
39 0EE7                   9$:
40                              ;
41                              ;CONVERT CALIBRATION INDEX INTO INDICES FOR RED AND IR BETA'S...
42                              ; IR INDEX IS INTEGER PART OF CALIDX DIVIDED BY 21 (THE NUMBER OF RED STEPS),
43                              ; AND THE RED INDEX IS CALIDX MOD 21, SUBTRACTED FROM 20 (IE INVERTED) IF IR INDEX IS ODD.
44                              ; (SO THAT AN ERROR OF 1 IN CALIDX IS JUST AN ERROR OF 1, NOT 20.)
45                              ;
46 0EE7   3A    7009            LDA    CALIDX
47 0EEA   01    0000            LXI    B,0
48 0EED   3D                    DCR    A           ;DECREMENT INDEX, CHECK FOR ZERO
49 0EEE   FA    0EFE            JM     14$         ;IS ZERO, USE BETA ZERO CODE ZERO.
50 0EF1   4F                    MOV    C,A         ;SAVE CALIDX
51 0EF2   C6    40              ADI    64          ;OFFSET CODE
52 0EF4   32    7009            STA    CALIDX
53 0EF7   3E    14              MVI    A,20
54 0EF9   91                    SUB    C
55 0EFA   4F                    MOV    C,A
56 0EFB   06    01        13$:  MVI    B,1
57 0EFD   0C                    INR    C
 1                              ;
 2                              ;LOOK UP CONSTANTS FOR SAT CALCULATION...B,C = IR & RED INDICES, RESP.
 3                              ;
 4 0EFE   C5              14$:  PUSH   B
```

```
 5 0EFF   79                    MOV    A,C
 6 0F00   07                    RLC                  ;INDEX * 4
 7 0F01   07                    RLC
 8 0F02   4F                    MOV    C,A
 9 0F03   06   00               MVI    B,0
10 0F05   21   1EDB             LXI    H,BBTBL
11 0F08   09                    DAD    B              ;POINTER TO RED BETAS
12 0F09   5E                    MOV    E,M
13 0F0A   23                    INX    H
14 0F0B   56                    MOV    D,M
15 0F0C   23                    INX    H
16 0F0D   EB                    XCHG
17 0F0E   22   70E3             SHLD   BO2
18 0F11   EB                    XCHG
19 0F12   5E                    MOV    E,M
20 0F13   23                    INX    H
21 0F14   56                    MOV    D,M
22 0F15   EB                    XCHG
23 0F16   22   70E5             SHLD   BR2
24 0F19   C1                    POP    B
25 0F1A   78                    MOV    A,B
26 0F1B   07                    RLC
27 0F1C   07                    RLC
28 0F1D   4F                    MOV    C,A
29 0F1E   06   00               MVI    B,0
30 0F20   21   1ED3             LXI    H,BATBL
31 0F23   09                    DAD    B
32 0F24   5E                    MOV    E,M
33 0F25   23                    INX    H
34 0F26   56                    MOV    D,M
35 0F27   23                    INX    H
36 0F28   EB                    XCHG
37 0F29   22   70DF             SHLD   BO1
38 0F2C   EB                    XCHG
39 0F2D   5E                    MOV    E,M
40 0F2E   23                    INX    H
41 0F2F   56                    MOV    D,M
42 0F30   EB                    XCHG
43 0F31   22   70E1             SHLD   BR1
44 0F34   AF                    XRA    A
45 0F35   C9                    RET
46 0F36   37         20$:       STC
47 0F37   C9                    RET
```

```
;DATA PROCESSING ROUTINES...
; MONITOR CH. 1 INPUT, LOOKING FOR BASELINE (MAXIMA), SLOPES AND MINIMA.
; IF A LIKELY PULSE IS FOUND GET THE CORRESPONDING CH. 2 VALUES AND CALL THE
; LEVEL 3 CHECKING AND COMPUTATION ROUTINES...
;
;THE OPERATING MODE IS DEFINED BY MCHMOD: MODE 0 IS THE INITIAL MODE, LOOKING
;FOR A SIGNAL MAXIMUM; MODE 1 IS LOOKING FOR A MAX SLOPE; AND MODE 2 IS LOOKING
;FOR A MINIMUM.
```

```
11 0F3B   21   7178    MUNCH:   LXI    H,DATIDX       ;POINT TO DATA (IN) INDEX
12 0F3B   7E                    MOV    A,M            ;GET IT (POINTS TO NEXT FREE BYTE)
13 0F3C   23                    INX    H              ;POINT TO BUFFER INDEX (DTOIDX)
14 0F3D   BE                    CMP    M              ;SAME??
15 0F3E   C8                    RZ                    ;YES, WE'RE CAUGHT UP.
16 0F3F   5E         3$:        MOV    E,M            ;GET IT
17 0F40   16   00               MVI    D,0
18 0F42   23                    INX    H              ;ADJUST POINTER TO BUFFER ORIGIN
19 0F43   19                    DAD    D              ;POINT INTO BUFFER
20 0F44   4E                    MOV    C,M            ;GET DATA WORD INTO B,C
21 0F45   23                    INX    H
22 0F46   46                    MOV    B,M
23 0F47   23                    INX    H              ;(LEAVE POINTER AT CH.2 WORD)
24 0F48   78                    MOV    A,B
25 0F49   B1                    ORA    C
26 0F4A   CA   10D4             JZ     MCHER9         ;ZERO DATA MEANS ERROR ?
```

```
;CHECK FOR MODE 0 (LOOKING FOR MAX)
;
30 0F4D   3A   70CB             LDA    MCHMOD         ;GET MODE
31 0F50   B7                    ORA    A
32 0F51   C2   0FB3             JNZ    MCH1           ;NOT MODE ZERO, GO CHECK FOR 1

;LOOK FOR MAX....IF DATA>MAX THEN STORE DATA AS MAX;
;IF DATA < (MAX-NOISE) THEN GO TO MODE 1
;
37 0F54   2A   70CC             LHLD   PLSMX1         ;GET MAX
38 0F57   CD   10D9             CALL   BCGTHL         ;DATA > MAX?
39 0F5A   DA   0F6B             JC     1$             ;NO, NOT A NEW MAX
40 0F5D   69                    MOV    L,C
41 0F5E   60                    MOV    H,B
42 0F5F   22   70CC             SHLD   PLSMX1         ;STORE DATA AS NEW MAX
43 0F62   3A   7179             LDA    DTOIDX
44 0F65   32   70D6             STA    MAXIDX         ;SAVE POINTER
45 0F68   C3   10BD             JMP    MCHRET
46 0F6B   3A   70D8    1$:      LDA    NOISE          ;GET NOISE, NEGATE IT
47 0F6E   2F                    CMA
48 0F6F   3C                    INR    A
49 0F70   5F                    MOV    E,A            ;TO D,E
50 0F71   16   FF               MVI    D,0FFH
51 0F73   19                    DAD    D              ;MAX-NOISE
52 0F74   CD   10D9             CALL   BCGTHL         ;DATA > (MAX-NOISE)?
53 0F77   D2   10BD             JNC    MCHRET         ;YES, NOT READY FOR MODE 1 YET
54 0F7A   21   70CB             LXI    H,MCHMOD       ;INCREMENT THE MODE
```

```
55 0F7D   34              INR   H
56 0F7E   3A   70D6       LDA   MAXIDX        ;NOW INTEGRATE 2 POINTS BACKWARDS
57 0F81   47              MOV   B,A
 1 0F82   3E   02         MVI   A,2
 2 0F84   11   0000       LXI   D,0
 3 0F87   CD   10E0       CALL  ISUM
 4 0F8A   DA   10D4       JC    MCHER9
 5 0F8D   EB              XCHG
 6 0F8E   3E   01         MVI   A,1
 7 0F90   CD   1A71       CALL  SHFTHL        ;SCALE UP TO DATA*4
 8 0F93   22   70CC       SHLD  PLSMX1
 9 0F96   3A   70D6       LDA   MAXIDX
10 0F99   C6   02         ADI   2
11 0F9B   47              MOV   B,A
12 0F9C   3E   02         MVI   A,2
13 0F9E   11   0000       LXI   D,0
14 0FA1   CD   10E0       CALL  ISUM
15 0FA4   DA   10D4       JC    MCHER9
16 0FA7   EB              XCHG
17 0FA8   3E   01         MVI   A,1
18 0FAA   CD   1A71       CALL  SHFTHL
19 0FAD   22   70D2       SHLD  PLSMX2
20 0FB0   C3   10BD       JMP   MCHRET
 1
 2                        ;CHECK FOR MODE 1 (LOOKING FOR SLOPE)
 3                        ;
 4 0FB3   3D              MCH1: DCR   A
 5 0FB4   C2   1014       JNZ   MCH2          ;NOT 1, CHECK FOR 2...
 6                        ;
 7                        ;FIND MAX SLOPE, INTEGRATING BACKWARDS 2*SPLEN POINTS
 8                        ;
 9 0FB7   11   0000       LXI   D,0           ;CLEAR SUM ACCUMULATOR (C,D,E)
10 0FBA   0E   00         MVI   C,0
11 0FBC   3A   7179       LDA   DTOIDX        ;CURRENT DATA INDEX, CHANNEL A
12 0FBF   47              MOV   B,A
13 0FC0   3A   70D7       LDA   SPLEN         ;SPAN
14 0FC3   CD   10E0       CALL  ISUM          ;SUM LAST (SPLEN) POINTS
15 0FC6   DA   10D4       JC    MCHER9        ;ERROR IF A ZERO ENCOUNTERED
16 0FC9   CD   134E       CALL  NEGCDE        ;NEGATE SUM
17 0FCC   3A   70D7       LDA   SPLEN         ;RESET COUNT (POINTER KEEPS GOING BACKWARDS)
18 0FCF   CD   10E0       CALL  ISUM          ;SUM SECOND HALF
19 0FD2   DA   10D4       JC    MCHER9        ;ERROR IF A ZERO ENCOUNTERED
20 0FD5   79              MOV   A,C           ;CHECK FOR OVERFLOW
21 0FD6   B7              ORA   A
22 0FD7   F2   0FE0       JP    6$            ;NEG?
23 0FDA   0E   00         MVI   C,0           ;YES, ZERO SLOPE
24 0FDC   11   0000       LXI   D,0
25 0FDF   AF              XRA   A
26 0FE0   CA   0FE6  6$:  JZ    7$            ;OVERFLOW?
27 0FE3   11   FFFF       LXI   D,0FFFFH      ;SET TO MAX
28 0FE6   2A   70D0  7$:  LHLD  PLSSLP        ;GET OLD MAX SLOPE
29 0FE9   42              MOV   B,D           ;TO B,C
30 0FEA   4B              MOV   C,E
31 0FEB   CD   10D9       CALL  BCGTHL        ;NEW SLOPE > OLD SLOPE?
32 0FEE   DA   0FF8       JC    15$           ;NOPE, MUST BE OVER THE TOP...
33 0FF1   EB        8$:   XCHG
34 0FF2   22   70D0       SHLD  PLSSLP        ;STORE NEW MAX
35 0FF5   C3   10BD       JMP   MCHRET
36 0FF8   21   70CB  15$: LXI   H,MCHMOD
37 0FFB   34              INR   H             ;OVER THE TOP, GO TO MODE 2
38 0FFC   3A   70D7       LDA   SPLEN         ;BACK UP POINTER TO MID-SLOPE
39 0FFF   57              MOV   D,A
40 1000   07              RLC
41 1001   07              RLC
42 1002   5F              MOV   E,A
43 1003   21   7179       LXI   H,DTOIDX
44 1006   7E              MOV   A,M
45 1007   93              SUB   E
46 1008   E6   FF         ANI   BUFMSK
47 100A   77              MOV   M,A
48 100B   21   70B3       LXI   H,PERCTR      ;FUDGE COUNTER FOR THE BACK-UP
49 100E   7E              MOV   A,M
50 100F   92              SUB   D
51 1010   77              MOV   M,A
52 1011   C3   10BD       JMP   MCHRET
 1
 2                        ;IF MODE 2 LOOK FOR MIN...
 3                        ;
 4 1014   3D        MCH2: DCR   A
 5 1015   C2   10BD       JNZ   MCHRET
 6                        ;
 7                        ;IF DATA > MIN THEN SET MODE=3
 8                        ;IF DATA < MIN THEN STORE AS NEW MIN
 9                        ;
10 1018   2A   70CE       LHLD  PLSMN1        ;GET OLD MIN
11 101B   7D              MOV   A,L           ;CHECK FOR ZERO
12 101C   B4              ORA   H
13 101D   CA   1026       JZ    1$            ;IT IS, STORE DATA
14 1020   CD   10D9       CALL  BCGTHL        ;DATA LARGER?
15 1023   D2   102E       JNC   MCH3          ;YES, PAST MIN.
16 1026   60        1$:   MOV   H,B           ;STORE NEW MIN
17 1027   69              MOV   L,C
18 1028   22   70CE       SHLD  PLSMN1
19 102B   C3   10BD       JMP   MCHRET
20                        ;
21 102E   3A   7179  MCH3: LDA  DTOIDX
```

```
22 1031   47              MOV    B,A
23 1032   3E    02        MVI    A,2
24 1034   11    0000      LXI    D,0
25 1037   CD    10E0      CALL   ISUM              ;SUM LAST 2 POINTS AS MIN
26 103A   DA    10D4      JC     MCHER9
27 103D   EB              XCHG
28 103E   3E    01        MVI    A,1
29 1040   CD    1A71      CALL   SHFTHL
30 1043   22    70CE      SHLD   PLSMN1
31 1046   3A    7179      LDA    DTOIDX
32 1049   C6    02        ADI    2
33 104B   47              MOV    B,A
34 104C   3E    02        MVI    A,2
35 104E   11    0000      LXI    D,0
36 1051   CD    10E0      CALL   ISUM
37 1054   DA    10D4      JC     MCHER9
38 1057   EB              XCHG
39 1058   3E    01        MVI    A,1
40 105A   CD    1A71      CALL   SHFTHL
41 105D   22    70D4      SHLD   PLSMN2
```

;DATA IS READY FOR COMPUTE ROUTINES...STORE MIN/MAX AND INDEX, SET FLAG
                     ;
```
 4 1060   2A    70D0      LHLD   PLSSLP            ;GET INTEGRATED SLOPE
 5 1063   EB              XCHG
 6 1064   2A    70D9      LHLD   PLSTHD            ;GET THRESHHOLD
 7 1067   AF              XRA    A                 ;NEGATE THRESHHOLD
 8 1068   95              SUB    L
 9 1069   6F              MOV    L,A
10 106A   3E    00        MVI    A,0
11 106C   9C              SBB    H
12 106D   67              MOV    H,A
13 106E   3E    01        MVI    A,1               ;ERROR CODE
14 1070   19              DAD    D                 ;SLOPE - THRESHHOLD
15 1071   D2    10AE      JNC    MCHERR            ;TOO SMALL
16 1074   21    709E      LXI    H,DATFLG          ;CHECK FOR FLAG ALREADY SET...
17 1077   7E              MOV    A,M
18 1078   B7              ORA    A
19 1079   3E    0A        MVI    A,10              ;ERROR 10 IF SO
20 107B   C2    10AE      JNZ    MCHERR            ;ALREADY SET, SKIP THIS...ERROR 10...
21 107E   34              INR    M                 ;SET FLAG
22 107F   2A    70CC      LHLD   PLSMX1
23 1082   22    709F      SHLD   MAX1              ;STORE DATA
24 1085   2A    70CE      LHLD   PLSMN1
25 1088   22    70A1      SHLD   MIN1
26 108B   2A    70D0      LHLD   PLSSLP
27 108E   22    70A7      SHLD   MXSLOP
28 1091   2A    70D2      LHLD   PLSMX2
29 1094   22    70A3      SHLD   MAX2
30 1097   2A    70D4      LHLD   PLSMN2
31 109A   22    70A5      SHLD.  MIN2
32 109D   2A    709F      LHLD   MAX1              ;STORE MAX FOR BLIP...
33 10A0   3E    FE        MVI    A,-2
34 10A2   CD    1A71      CALL   SHFTHL
35 10A5   22    70DC      SHLD   OLDMAX
36 10A8   3E    01        MVI    A,1               ;STOP TIME WINDOW TIMER
37 10AA   32    710A      STA    WINFLG
38 10AD   AF         4$:  XRA    A                 ;NO ERROR, CODE = 0
```

;ERROR...STORE ERROR CODE, RESET PARAMETERS AND START OVER...SIGH...
                     ;
```
 4 10AE   32    70DB  MCHERR: STA  ERRCOD
 5 10B1   21    70CB      LXI    H,MCHMOD          ;POINT TO PARAMETERS, SET COUNTER AND CLEAR
 6 10B4   1E    0B        MVI    E,11
 7 10B6   36    00    1$: MVI    M,0
 8 10B8   23              INX    H
 9 10B9   1D              DCR    E
10 10BA   C2    10B6      JNZ    1$
11 10BD   3A    70B3  MCHRET: LDA  PERCTR          ;INCREMENT LEVEL 3'S PERIOD COUNTER
12 10C0   3C              INR    A
13 10C1   CA    10C7      JZ     1$
14 10C4   32    70B3      STA    PERCTR
15 10C7   21    7179  1$: LXI    H,DTOIDX          ;INCREMENT INDEX
16 10CA   7E              MOV    A,M
17 10CB   C6    04        ADI    4
18 10CD   E6    FF        ANI    BUFMSK
19 10CF   77              MOV    M,A
20 10D0   CD    110D      CALL   BLIP              ;OUTPUT TO METER
21 10D3   C9              RET
22 10D4   3E    09    MCHER9: MVI  A,9
23 10D6   C3    10AE      JMP    MCHERR
```

;
                     ;COMPARE BC, TO H,L AND RETURN CARRY IF BC NOT GREATER
                     ;
```
27 10D9   78        BCGTHL: MOV  A,B
28 10DA   BC              CMP    H
29 10DB   D8              RC
30 10DC   C0              RNZ
31 10DD   79              MOV    A,C
32 10DE   BD              CMP    L
33 10DF   C9              RET
```

;SUM (A) POINTS BACKWARDS FROM INDEX IN B, RETURN (24 BITS) IN C,D,E
                     ;RETURN CARRY SET IF A ZERO IS ENCOUNTERED (INDICATING OVERFLOW OR LED'S CHANGING)
                     ;
```
 5 10E0                ISUM:
```

```
  6 10E0  F5              1$:   PUSH  PSW              ;SAVE COUNT
  7 10E1  21    717A            LXI   H,DATBUF         ;GENERATE POINTER
  8 10E4  7D                    MOV   A,L
  9 10E5  80                    ADD   B                ;BASE ADDRESS + INDEX
 10 10E6  6F                    MOV   L,A
 11 10E7  7C                    MOV   A,H
 12 10E8  CE    00              ACI   0
 13 10EA  67                    MOV   H,A
 14 10EB  7E                    MOV   A,H
 15 10EC  23                    INX   H
 16 10ED  B6                    ORA   H                ;CHECK FOR ZERO DATA
 17 10EE  CA    110A            JZ    10$
 18 10F1  2B                    DCX   H
 19 10F2  7B                    MOV   A,E              ;ADD DATA TO SUM
 20 10F3  86                    ADD   H
 21 10F4  5F                    MOV   E,A
 22 10F5  23                    INX   H
 23 10F6  7A                    MOV   A,D
 24 10F7  8E                    ADC   H
 25 10F8  57                    MOV   D,A
 26 10F9  79                    MOV   A,C
 27 10FA  CE    00              ACI   0
 28 10FC  4F                    MOV   C,A
 29 10FD  78                    MOV   A,B              ;DECREMENT INDEX
 30 10FE  D6    04              SUI   4
 31 1100  E6    FF              ANI   BUFMSK
 32 1102  47                    MOV   B,A
 33 1103  F1                    POP   PSW              ;GET COUNT BACK
 34 1104  B7                    ORA   A                ;CLEAR CARRY
 35 1105  3D                    DCR   A
 36 1106  C2    10E0            JNZ   1$               ;LOOP
 37 1109  C9                    RET
 38 110A  F1              10$:  POP   PSW
 39 110B  37                    STC
 40 110C  C9                    RET

;COMPUTE OUTPUT FOR ANALOG 'METER' DISPLAY...
                          ;   COMPARE DATA (IN B,C) MINUS 'OLDMAX' WITH LIST
                          ;   OF THRESHOLDS (BLPTHT) FOR EACH LIGHT.
                          ;   TABLE IS TWO BYTES PER LIGHT (8 TOTAL), IF DATA > N'TH ENTRY THEN
                          ;   LIGHT.N'TH LED. (REMEMBER THAT THE DATA GOES DOWN FROM MAX, DISPLAYED AS A
                          ;   RISING BLIP).
                          ;
  9 110D  3A    70DE      BLIP: LDA   BLPIDX           ;GET DATA
 10 1110  5F                    MOV   E,A
 11 1111  16    00              MVI   D,0
 12 1113  3A    7178            LDA   DATIDX
 13 1116  BB                    CMP   E
 14 1117  C8                    RZ
 15 1118  21    717A            LXI   H,DATBUF
 16 111B  19                    DAD   D
 17 111C  4E                    MOV   C,H
 18 111D  23                    INX   H
 19 111E  46                    MOV   B,H
 20 111F  C5                    PUSH  B                ;SAVE DATA FOR BARGRAPH     ///
 21 1120  60                    MOV   H,B
 22 1121  69                    MOV   L,C              ;TO H,L
 23 1122  3E    04              MVI   A,4
 24 1124  CD    1A71            CALL  SHFTHL           ;MOVE 8 BITS TO H
 25 1127  7C                    MOV   A,H
 26 1128  CD    1D3B            CALL  SPLIT            ;MAKE INTO TWO NIBBLES (HUH ?)  ///
 27 112B  7A                    MOV   A,D                                              ///
 28 112C  F6    10              ORI   10H              ;PUT IN IDENTIFIER             ///
 29 112E  EA    1133            JPE   STIK1                                           ///
 30 1131  F6    80              ORI   80H              ;SET PARITY IF NEEDED         ///
 31 1133  32    7281      STIK1: STA  PLS1             ;STORE FIRST GUY              ///
 32 1136  7B                    MOV   A,E              ;GET LOWER NIBBLE             ///
 33 1137  F6    70              ORI   70H              ;PUT IN END OF MESSAGE IDENTIFIER ///
 34 1139  EA    113E            JPE   STIK2                                           ///
 35 113C  F6    80              ORI   80H              ;MAKE SURE PARITY IS OK       ///
 36 113E  32    7282      STIK2: STA  PLS2             ;STORE SECOND GUY             ///
 37 1141  3E    02              MVI   A,2                                             ///
 38 1143  32    72A8            STA   CPLSFL           ;SET FLAG TO SEND THEM        ///
 39 1146  C1                    POP   B                ;RESTORE DATA WORD            ///

;CHECK FOR LED DRIVE-LEVEL DISPLAY (IF NOT YET SYNC'ED)
                          ;OTHERWISE COMPUTE BAR-GRAPH FROM PULSE AMPLITUDE 44 1147  3A    7014            LDA   SYNFLG
 45 114A  FE    03              CPI   3
 46 114C  F2    11D0            JP    BLIP2            ;NO SYNC, SHOW LED DRIVE'S
 47 114F  3A    713A            LDA   OPNFLG           ;CHECK FOR MODE DISPLAY
 48 1152  B7                    ORA   A
 49 1153  CA    1162            JZ    1$               ;NOPE
 50 1156  11    8E90            LXI   D,-FMODE
 51 1159  2A    7138            LHLD  OPNPRM
 52 115C  19                    DAD   D
 53 115D  7C                    MOV   A,H
 54 115E  B5                    ORA   L
 55 115F  CA    11D0            JZ    BLIP2

;COMPUTE PULSE AMPLITUDE DISPLAY 2 1162  78              1$:   MOV   A,B
  3 1163  B1                    ORA   C
  4 1164  CA    119B            JZ    11$              ;ZERO DATA, NO BLIP
```

```
   5 1167  2A  70DC         LHLD  OLDMAX      ;GET LAST MAX VALUE
   6 116A  AF                XRA  A           ;NEGATE IT
   7 116B  95                SUB  L
   8 116C  6F                MOV  L,A
   9 116D  3E  00            MVI  A,0
  10 116F  9C                SBB  H
  11 1170  67                MOV  H,A
  12 1171  09                DAD  B           ;DATA - MAX = DELTA (NEGATIVE SINCE DATA < MAX)
  13 1172  3E  00            MVI  A,0
  14 1174  DA  119B          JC   11$         ;DATA IS GREATER, NO DISPLAY
  15 1177  44       2$:      MOV  B,H         ;DELTA TO B,C
  16 1178  4D                MOV  C,L
  17 1179  11  11B0          LXI  D,BLPTHT    ;TABLE POINTER IN D,E
  18 117C  21  0000          LXI  H,0         ;START WITH NO LIGHTS
  19 117F  E5                PUSH H
  20 1180  EB       5$:      XCHG
  21 1181  5E                MOV  E,M         ;GET TABLE ENTRY
  22 1182  23                INX  H
  23 1183  56                MOV  D,M
  24 1184  23                INX  H
  25 1185  EB                XCHG
  26 1186  09                DAD  B           ;TABLE - DELTA
  27 1187  DA  1197          JC   10$         ;TABLE LARGER, ALL DONE
  28 118A  37                STC              ;SET CARRY (THIS MAY BE REDUNDANT??)
  29 118B  E3                XTHL             ;GET LIGHTS FROM TOP OF STACK
  30 118C  7D                MOV  A,L
  31 118D  17                RAL              ;SHIFT IN ANOTHER
  32 118E  6F                MOV  L,A
  33 118F  7C                MOV  A,H
  34 1190  17                RAL
  35 1191  67                MOV  H,A
  36 1192  E3                XTHL             ;PUT THEM BACK
  37 1193  B7                ORA  A           ;CHECK FOR ALL-FULL
  38 1194  F2  1180          JP   5$          ;IS NOT, KEEP GOING
  39 1197  E1       10$:     POP  H           ;GET LIGHTS
  40 1198  C3  119E          JMP  12$
  41 119B  21  0001 11$:     LXI  H,1         ;NO LIGHTS
  42 119E  7D       12$:     MOV  A,L
  43 119F  32  7128          STA  DSPMTL      ;STORE THEM FOR DISPLAY
  44 11A2  7C                MOV  A,H
  45 11A3  32  712A          STA  DSPMTH
  46 11A6  21  70DE          LXI  H,BLPIDX
  47 11A9  7E                MOV  A,M
  48 11AA  C6  04            ADI  4
  49 11AC  E6  FF            ANI  BUFMSK
  50 11AE  77                MOV  M,A
  51 11AF  C9                RET
  52
  53                       ;THRESHOLD TABLE...LOG SCALE BASED ON 1.302, 16 STEPS FROM .10% TO 4%
  54                       ;
  55 11B0  0000     BLPTHT:  DW   0
  56 11B2  0010              DW   16          ;0.10%
  57 11B4  0015              DW   21
   1 11B6  001C              DW   28
   2 11B8  0024              DW   36
   3 11BA  002F              DW   47
   4 11BC  003D              DW   61
   5 11BE  0050              DW   80
   6 11C0  006A              DW   106
   7 11C2  0089              DW   137
   8 11C4  00B0              DW   176
   9 11C6  00E5              DW   229
  10 11C8  0129              DW   297
  11 11CA  0183              DW   387
  12 11CC  01F7              DW   503
  13 11CE  028F              DW   655         ;4.00%
  14
  15                       ;DISPLAY LED DRIVE LEVEL GRAPHICALLY
  16
  17
  18 11D0  21  0001 BLIP2:   LXI  H,1
  19 11D3  11  0000          LXI  D,0
  20 11D6  3A  7008          LDA  CALOK
  21 11D9  B7                ORA  A
  22 11DA  CA  11EA          JZ   1$
  23 11DD  3A  700A          LDA  LED1
  24 11E0  CD  11F5          CALL XBLIP2
  25 11E3  EB                XCHG
  26 11E4  3A  700D          LDA  LED2
  27 11E7  CD  11F5          CALL XBLIP2
  28 11EA  7C       1$:      MOV  A,H
  29 11EB  B2                ORA  D
  30 11EC  32  712A          STA  DSPMTH
  31 11EF  7D                MOV  A,L
  32 11F0  B3                ORA  E
  33 11F1  32  7128          STA  DSPMTL
  34 11F4  C9                RET
  35
  36 11F5  21  0001 XBLIP2:  LXI  H,1
  37 11F8  D6  40            SUI  64
  38 11FA  D8                RC
  39 11FB  4F       1$:      MOV  C,A
  40 11FC  7D                MOV  A,L
  41 11FD  17                RAL
  42 11FE  6F                MOV  L,A
  43 11FF  7C                MOV  A,H
  44 1200  17                RAL
```

```
45 1201   67                      MOV    H,A
46 1202   79                      MOV    A,C
47 1203   D6   0D                 SUI    13
48 1205   D2   11FB               JNC    1$
49 1208   C9                      RET
 1
 2                        ;ARITHMETIC UTILITIES.....
 3                        ;
 4                        ;INTEGER MULTILY ROUTINE:
 5                        ; MULTIPLY B+C BY D+E, PRODUCT RETURNED IN D+E. (MULTIPLIER LOST)
 6                        ; EACH REGISTER PAIR IS TREATED AS AN UNSIGNED INTEGER, ALTHOUGH D.F.'S CAN BE
                          ASSUMED.
 7                        ; A CARRY IS RETURNED IF THE PRODUCT OVERFLOWS..
 8                        ; H,L SAVED
 9                        ;
10 1209   C5              MPY16:  PUSH   B
11 120A   E5                      PUSH   H
12 120B   21   0000               LXI    H,0             ;PARTIAL PRODUCT
13                        ;
14                        ; SHIFT MULTIPLIER RIGHT ONE BIT, ADD MULTIPLICAND TO PRODUCT IF LOW
15                        ; M'ER BIT WAS SET. QUIT WHEN THERE ARE NO MORE MULT'ER BITS.
16                        ;
17 120E   B7              1$:     ORA    A               ;CLEAR CARRY
18 120F   7A                      MOV    A,D             ;SHIFT MULTIPLIER DOWN
19 1210   1F                      RAR
20 1211   57                      MOV    D,A
21 1212   7B                      MOV    A,E
22 1213   1F                      RAR
23 1214   5F                      MOV    E,A
24 1215   D2   121C               JNC    2$              ;LOW BIT WAS NOT SET
25 1218   09                      DAD    B               ;ADD MULT'AND TO PRODUCT
26 1219   DA   122E               JC     11$             ;OVERFLOW ERROR
27 121C   7B              2$:     MOV    A,E             ;CHECK FOR NO MORE MULTIPLIER BITS
28 121D   B2                      ORA    D
29 121E   CA   122E               JZ     10$             ;DONE IF SO (CARRY CLEAR)
30                        ;
31                        ;SHIFT MULTIPLICAND UP ONE BIT...WATCH FOR OVERFLOW
32                        ;
33 1221   B7                      ORA    A               ;CLC
34 1222   79                      MOV    A,C
35 1223   17                      RAL
36 1224   4F                      MOV    C,A
37 1225   78                      MOV    A,B
38 1226   17                      RAL
39 1227   47                      MOV    B,A
40 1228   DA   122E               JC     11$             ;SHIFTED A BIT OUT...ERROR
41 122B   C3   120E               JMP    1$              ;DO IT AGAIN
42 122E                   11$:                           ;OVERFLOW ERROR...CARRY ALREADY SET
43 122E   EB              10$:    XCHG                   ;MOVE PRODUCT TO D+E
44 122F   E1                      POP    H
45 1230   C1                      POP    B               ;RESTORE MULT'AND
46 1231   C9                      RET
 1
 2                        ;32-BIT MULTIPLY...
 3                        ;AS ABOVE, EXCEPT MULTIPLIES B,C BY D,E TO FORM A 32-BIT PRODUCT IN B,C,D,E.
 4                        ;
 5 1232   21   0000       MPY32:  LXI    H,0             ;CLEAR HI PARTIAL PRODUCT
 6 1235   E5                      PUSH   H               ;AND LOW PARTIAL
 7 1236   3E   10                 MVI    A,16            ;COUNTER (ALWAYS MULTIPLY ALL 16 BITS)
 8 1238   32   70C0       1$:     STA    XMPY            ;SAVE COUNTER
 9 123B   B7                      ORA    A               ;CLEAR CARRY
10 123C   7A                      MOV    A,D             ;SHIFT MULTIPLIER DOWN
11 123D   1F                      RAR
12 123E   57                      MOV    D,A
13 123F   7B                      MOV    A,E
14 1240   1F                      RAR
15 1241   5F                      MOV    E,A
16 1242   D2   1246               JNC    2$              ;NEXT BIT ZERO, NO ADD
17 1245   09                      DAD    B               ;ADD MULTIPLICAND TO PRODUCT
18 1246   7C              2$:     MOV    A,H             ;SHIFT PRODUCT DOWN (INCLUDING CARRY)
19 1247   1F                      RAR
20 1248   67                      MOV    H,A
21 1249   7D                      MOV    A,L
22 124A   1F                      RAR
23 124B   6F                      MOV    L,A
24 124C   E3                      XTHL                   ;ALL 32 BITS
25 124D   7C                      MOV    A,H
26 124E   1F                      RAR
27 124F   67                      MOV    H,A
28 1250   7D                      MOV    A,L
29 1251   1F                      RAR
30 1252   6F                      MOV    L,A
31 1253   E3                      XTHL
32 1254   3A   70C0               LDA    XMPY
33 1257   3D                      DCR    A
34 1258   C2   1238               JNZ    1$              ;LOOP 16 BITS WORTH
35 125B   44                      MOV    B,H             ;HIGH PRODUCT
36 125C   4D                      MOV    C,L
37 125D   D1                      POP    D               ;LOW HALF
38 125E   C9                      RET
 1
 2                        ; ENTER WITH VALUE TO BE SCALED IN REGISTER A
 3                        ; OUTPUT WILL BE IN HL REGISTER PAIR
 4
 5
 6 125F   D5              SCL100: PUSH   D
```

```
  7 1260  C5                      PUSH  B
  8 1261  F5                      PUSH  PSW
  9
 10 1262  11    0FFF              LXI   D,4095
 11 1265  CD    12E4              CALL  MULT
 12 1268  5F                      MOV   E,A
 13 1269  16    00                MVI   D,0
 14 126B  01    03E8              LXI   B,1000          ;0-100 % SAO2 = 0-1V
 15 126E  CD    12C3              CALL  DIVRND
 16 1271  EB                      XCHG
 17 1272  F1                      POP   PSW
 18 1273  C1                      POP   B
 19 1274  D1                      POP   D
 20 1275  C9                      RET
 21
 22 1276  D5          SCL250:     PUSH  D
 23 1277  C5                      PUSH  B
 24 1278  F5                      PUSH  PSW
 25 1279  11    0FFF              LXI   D,4095
 26 127C  CD    12E4              CALL  MULT
 27 127F  5F                      MOV   E,A
 28 1280  16    00                MVI   D,0
 29 1282  01    09C4              LXI   B,2500          ;0-250 BPM = 0-1V
 30 1285  CD    12C3              CALL  DIVRND
 31 1288  EB                      XCHG
 32 1289  F1                      POP   PSW
 33 128A  C1                      POP   B
 34 128B  D1                      POP   D
 35 128C  C9                      RET
 36
 37
 38                  ;        MULTIPLICATION AND DIVISION
 39
 40                  ; 'DIV' IS A 32 BY 16 BIT DIVISION ROUTINE
 41                  ; INPUT DIVIDEND IN DEHL AND DIVISOR IN BC
 42                  ; OUTPUT QUOTIENT IN DE, REMAINDER IN HL, AND DIVISOR IN BC.
 43
 44                  ; 'DMULT' IS A 16 BY 16 BIT MULTIPLICATION ROUTINE.
 45                  ; INPUT MULTIPLICAND IN DE AND MULTIPLIER IN BC.
 46                  ; OUTPUT PRODUCT IN DEHL.
 47
 48                  ; MULT IS AN 8 BY 16 BIT MULTIPLICATION
 49                  ; INPUT MULTIPLICAND IN DE AND MULTIPLIER IN A
 50                  ; OUTPUT PRODUCT IN AHL
 51
 52 128D  EB          DIV:        XCHG                  ;SWAP HI AND LO WORDS
 53 128E  3E    11                MVI   A,17            ;INITIALIZE LOOP COUNTER
 54 1290  F5                      PUSH  PSW
 55 1291  AF                      XRA   A               ;SAVE ON STACK AND CLEAR A AND CARRY
 56
 57 1292  F5          DLOOP:      PUSH  PSW
  1 1293  7D                      MOV   A,L             ;SAVE CARRY BYTE ON STACK
  2 1294  91                      SUB   C               ;HL-BC 16 BIT SUBTRACT
  3 1295  6F                      MOV   L,A
  4 1296  7C                      MOV   A,H
  5 1297  98                      SBB   B
  6 1298  67                      MOV   H,A
  7 1299  E3                      XTHL                  ;RESTORE CARRY BYTE
  8 129A  7C                      MOV   A,H
  9 129B  DE    00                SBI   0               ;COMPLETE SUBTRACTION
 10 129D  E1                      POP   H               ;RESTORE REMAINDER TO HL
 11
 12 129E  D2    12A2              JNC   TEST            ;IF BORROW OCCURRED
 13 12A1  09                      DAD   B               ;ADD DIVISOR BACK, HL:BC
 14
 15 12A2  3F          TEST:       CMC                   ;COMPLEMENT BORROW BIT
 16 12A3  7B                      MOV   A,E             ;32 BIT LEFT SHIFT W/CARRY
 17 12A4  17                      RAL
 18 12A5  5F                      MOV   E,A
 19 12A6  7A                      MOV   A,D
 20 12A7  17                      RAL
 21 12A8  57                      MOV   D,A
 22 12A9  E3                      XTHL                  ;GET LOOP COUNTER OFF STACK
 23 12AA  25                      DCR   H               ;DECREMENT IT
 24 12AB  E3                      XTHL                  ;PUT IT BACK
 25 12AC  CA    12B9              JZ    EXIT            ;AND EXIT WHEN DONE
 26 12AF  7D                      MOV   A,L
 27 12B0  17                      RAL
 28 12B1  6F                      MOV   L,A
 29 12B2  7C                      MOV   A,H
 30 12B3  17                      RAL
 31 12B4  67                      MOV   H,A
 32 12B5  9F                      SBB   A               ;A=CARRY FROM SHIFT
 33 12B6  C3    1292              JMP   DLOOP           ;AND GO ON AROUND AGAIN
 34 12B9  F1          EXIT:       POP   PSW             ;RESTORE STACK
 35 12BA  C9                      RET
 36
 37 12BB  29          RNDOFF:     DAD   H               ;IF REM > .5 * DIVISOR
 38 12BC  CD    1348              CALL  NEGHL           ;HL=-2*REM
 39 12BF  09                      DAD   B               ;>DIVISOR ?
 40 12C0  D8                      RC                    ;NO, THEN QUOTIENT IS OK
 41 12C1  13                      INX   D               ;YES, THEN BUMP QUOTIENT
 42 12C2  C9                      RET
 43
 44 12C3  CD    128D  DIVRND:     CALL  DIV             ;FOR DOING WITH ROUNDING
 45 12C6  CD    12BB              CALL  RNDOFF          ;MUST CALL IN SEQUENCE
 46 12C9  C9                      RET
```

```
 47
 48
 49 12CA   79              DMULT:  MOV     A,C             ;MULTIPLIER LO BYTE IN A
 50 12CB   C5                      PUSH    B               ;SAVE MULTIPLIER
 51 12CC   CD   12E4                CALL   MULT            ;AHL=MPCD*LO(MPLR)
 52 12CF   E3                      XTHL                    ;SWAP MPLR AND PP1 LO BYTES
 53 12D0   F5                      PUSH    PSW             ;SAVE PP1 HI BYTE
 54 12D1   7C                      MOV     A,H             ;MPLR HI BYTE IN A
 55 12D2   CD   12E4                CALL   MULT            ;AHL=MPCD * HI(MPLR)
 56 12D5   58                      MOV     E,B             ;E=B=0
 57 12D6   C1                      POP     B               ;PP1 HI BYTE IN B
  1 12D7   55                      MOV     D,L
  2 12D8   4C                      MOV     C,H             ;PF2 LO BYTES IN C,D
  3 12D9   E1                      POP     H               ;PP1 LO BYTES IN HL
  4 12DA   19                      DAD     D               ;HL=LO(PP2) + PP1 LO BYTES
  5 12DB   57                      MOV     D,A             ;PF2 HI BYTE IN D
  6 12DC   78                      MOV     A,B             ;ADD PP1 HI BYTE + CARRY
  7 12DD   89                      ADC     C               ;TO PF2 MID BYTE
  8 12DE   5F                      MOV     E,A             ;RESULT TO E
  9 12DF   7A                      MOV     A,D             ;PP2 HI BYTE IN A
 10 12E0   CE   00                  ACI    0               ;ADD CARRY FROM MID BYTE
 11 12E2   57                      MOV     D,A             ;RESULT NOW IN DEHL
 12 12E3   C9                      RET
 13
 14 12E4   21   0000       MULT:   LXI     H,0             ;INITIALIZE PARTIAL PRODUCT
 15 12E7   06   08                  MVI    B,8             ;INITIALIZE LOOP COUNTER
 16
 17 12E9   29              MLOOP:  DAD     H               ;SHIFT PP LEFT ONE
 18 12EA   17                      RAL                     ;SHIFT MPLR LEFT ONE
 19 12EB   D2   12F1                JNC    DEC             ;IF MSB OF MPLR=1,
 20 12EE   19                      DAD     D               ;ADD MPCD TO PP
 21 12EF   CE   00                  ACI    0               ;INCLUDING CARRY TO A
 22 12F1   05              DEC:    DCR     B               ;LAST BIT DONE ?
 23 12F2   C2   12E9                JNZ    MLOOP           ;NO, KEEP GOING
 24 12F5   C9                      RET
 25
 26
 27
 28
  1
  2
  3                                ;16-BIT DIVIDE ROUTINE....
  4                                ; DIVIDE 16-BIT INTEGER IN D,E BY ANOTHER IN B,C, FORMING A 16-BIT FRACTION
  5                                ; STORED INTO D,E....ON THE CONDITION THAT D,E < B,C, RETURN CARRY OTHERWISE
  6                                ; H,L SAVED.
  7
  8 12F6   E5              DIV16:  PUSH    H
  9 12F7   AF                      XRA     A               ;FIRST DIVIDE DIVISOR BY 2
 10 12F8   78                      MOV     A,B             ; (ON THE ASSUMPTION THAT IT IS BIGGER)
 11 12F9   1F                      RAR
 12 12FA   47                      MOV     B,A
 13 12FB   79                      MOV     A,C
 14 12FC   1F                      RAR
 15 12FD   4F                      MOV     C,A
 16 12FE   AF                      XRA     A               ;NOW MAKE THE DIVISOR NEGATIVE
 17 12FF   91                      SUB     C
 18 1300   4F                      MOV     C,A
 19 1301   3E   00                  MVI    A,0
 20 1303   98                      SBB     B
 21 1304   47                      MOV     B,A
 22 1305   EB                      XCHG                    ;DIVIDEND TO H,L
 23 1306   11   0001                LXI    D,1             ;CLEAR PARTIAL PRODUCT, SET CHASE (17TH) BIT
 24 1309   E5              1$:     PUSH    H               ;SAVE DIVIDEND IN CASE SUBTRACT FAILS
 25 130A   09                      DAD     B               ;SUBTRACT DIVISOR FROM D'END
 26 130B   DA   1312                JC     2$              ;OK, WAS LESS
 27 130E   E1                      POP     H               ;WAS TOO BIG, RESTORE DIVIDEND
 28 130F   C3   1314                JMP    3$
 29 1312   33              2$:     INX     SP              ;DUMP UNUSED DIVIDEND
 30 1313   33                      INX     SP
 31 1314   7B              3$:     MOV     A,E             ;SHIFT NEW BIT INTO QUOTIENT
 32 1315   17                      RAL
 33 1316   5F                      MOV     E,A
 34 1317   7A                      MOV     A,D
 35 1318   17                      RAL
 36 1319   57                      MOV     D,A
 37 131A   DA   132B                JC     10$             ;CHASE BIT POPPED OUT
 38 131D   7D                      MOV     A,L             ;SHIFT REMAINING DIVIDEND UP...SHOULD NOT
                                                            OVERFLOW IF DE < BC
 39 131E   17                      RAL
 40 131F   6F                      MOV     L,A
 41 1320   7C                      MOV     A,H
 42 1321   17                      RAL
 43 1322   67                      MOV     H,A
 44 1323   D2   1309                JNC    1$              ;NO OVERFLOW
 45 1326   11   FFFF                LXI    D,0FFFFH        ;OVERFLOW VALUE
 46 1329   E1                      POP     H
 47 132A   C9                      RET                     ;RETURN CARRY SET
 48 132B   B7              10$:    ORA     A               ;CLEAR CARRY
 49 132C   E1                      POP     H
 50 132D   C9                      RET
  1
  2                                ;INTEGER ROUTINE...CONVERT D,E FROM INT.FRACT TO INT.000
  3
  4 132E   EB              INTDE:  XCHG
  5 132F   CD   1334                CALL   INTHL
  6 1332   EB                      XCHG
```

```
  3                            ; CALLED WITH B,C = DISPLAY BUFFER POINTER ('DSPFD1' OR 'DSPFD2').
  4                            ; USES E = L.Z. FLAG, B,C = DISPLAY POINTER, C = DIGIT COUNTER, D = REMAINDER
  5                            ;
  6  13A9  21    0004   DSPCVT: LXI   H,4
  7  13AC  09                   DAD   B                   ;MOVE POINTER TO M.S.DIGIT
  8  13AD  E5                   PUSH  H                   ;SAVE IT FOR THE DURATION
  9  13AE  21    13F6           LXI   H,DECTBL            ;SET POINTER TO DECIMAL FACTOR TABLE
 10  13B1  C3    13B5           JMP   DSPCV2
 11  13B4  C5            XDSPCV: PUSH  B                   ;SAVE DISPLAY POINTER
 12  13B5  1E    00     DSPCV2: MVI   E,0                 ;RESET LEADING ZERO FLAG
 13  13B7  57                   MOV   D,A
 14  13B8  7A            1$:    MOV   A,D                 ;LOOP FOR NEXT DIGIT - GET REMAINING NUMBER
 15  13B9  01    0000           LXI   B,0                 ;CLEAR DIGIT COUNTER
 16  13BC  96            3$:    SUB   M                   ;SUBTRACT FACTOR
 17  13BD  DA    13C4           JC    4$                  ;DIDN'T FIT
 18  13C0  0C                   INR   C                   ;BUMP DIGIT
 19  13C1  C3    13BC           JMP   3$                  ;UNTIL IT UNDERFLOWS
 20  13C4  86            4$:    ADD   M                   ;RESTORE LAST SUBTRACTION
 21  13C5  57                   MOV   D,A                 ;SAVE REMAINDER
 22  13C6  79                   MOV   A,C                 ;DIGIT COUNT
 23  13C7  B3                   ORA   E                   ;CHECK FOR ZERO DIGIT AND LEADING ZERO FLAG=0
 24  13C8  CA    13CD           JZ    6$                  ;IS, OUTPUT A ZERO (= BLANK)
 25  13CB  1C                   INR   E                   ;NOT ZERO, SET FLAG FOR TRAILING ZEROS
 26  13CC  0C            5$:    INR   C                   ;OFFSET DIGIT CODE BY 1 (LOOP HERE FOR LAST
                                                          ; DIGIT)
 27  13CD  E3            6$:    XTHL                      ;TRADE FACTOR POINTER FOR BUFFER POINTER
 28  13CE  E5                   PUSH  H                   ;SAVE BUFFER POINTER
 29  13CF  21    13EB           LXI   H,SEGTBL            ;POINTER TO 7-SEG CODE TABLE
 30  13D2  09                   DAD   B                   ;PLUS DIGIT COUNTER (OH, YOU CLEVER DEVIL!)
 31  13D3  7E                   MOV   A,M                 ;GET CODE
 32  13D4  E1                   POP   H                   ;RESTORE FACTOR POINTER
 33  13D5  77                   MOV   M,A                 ;STORE DIGIT CODE
 34  13D6  2B                   DCX   H                   ;BUMP IT
 35  13D7  2B                   DCX   H                   ;TWICE
 36  13D8  E3                   XTHL                      ;RESTORE FACTOR POINTER
 37  13D9  AF                   XRA   A
 38  13DA  BE                   CMP   M                   ;CHECK FOR ZERO FACTOR
 39  13DB  CA    13E9           JZ    10$                 ;IT WAS, MUST BE THE LAST TIME THROUGH
 40  13DE  23                   INX   H                   ;POINT TO NEXT FACTOR
 41  13DF  BE                   CMP   M                   ;IS THAT ZERO?
 42  13E0  C2    13B8           JNZ   1$                  ;NO, LOOP NORMALLY
 43  13E3  06    00             MVI   B,0                 ;SHORT-CIRCUIT THE LAST LOOP
 44  13E5  4A                   MOV   C,D                 ;REMAINDER BECOMES DIGIT
 45  13E6  C3    13CC           JMP   5$
 46  13E9  C1            10$:   POP   B                   ;DUMP BUFFER POINTER
 47  13EA  C9                   RET
 48                            ;
 49                            ;TABLE OF 7-SEGMENT CODES, STARTING WITH A BLANK FOR LEADING ZEROS (MORE
                                ; CLEVERNESS!!)
 50                            ;
 51  13EB  00    77     SEGTBL: DB    0, SEG0, SEG1, SEG2, SEG3, SEG4, SEG5, SEG6, SEG7, SEG8, SEG9
     13ED  24    5D
     13EF  6D    2E
     13F1  6B    7D
     13F3  25    7F
     13F5  2F
 52
  1  13F6  64    0A     DECTBL: DB    100, 10, 0          ;IT SURE IS A BIG ROUTINE FOR A TWO-ENTRY
     13F8  00                                             ; TABLE!!!!
  2
  3                            ;
  4                            ;
  5                            ; CHECK IF SWITCH IS SET FOR SILENT RUNNING. IF SO, DISABLE ALL
  6                            ; ALARMS AND DISPLAYS, EXCEPT FOR BLIP. ALSO DISABLE BUTTONS AND
  7                            ; KNOB. OUTPUT SAT AND RATE UNFILTERED
  8                            ;
  9  13F9  DB    00     BLKOUT: IN    STSREG              ;GET STATUS
 10  13FB  E6    06             ANI   6                   ;MASK FOR SWITCH SETTING
 11  13FD  CA    1419           JZ    3$                  ;SILENT RUNNING
 12  1400  3A    712F           LDA   DSPOK               ;IF ZERO, WE'VE ALREADY DONE THIS STUFF
 13  1403  B7                   ORA   A
 14  1404  C8                   RZ
 15  1405  AF                   XRA   A                   ;NOT ZERO, RESTORE FMODE AND CLEAR FLAG
 16  1406  32    712F           STA   DSPOK
 17  1409  3A    7130           LDA   MODESV              ;GET PRIOR FMODE
 18  140C  32    7170           STA   FMODE               ;RESTORE IT
 19  140F  21    70F4           LXI   H,ALIPER
 20  1412  CD    16C7           CALL  ALICHK              ;CHECK FOR DELAYED ALARMS THAT WERE QUASHED
 21  1415  CD    0ABF           CALL  DSPSR               ;RESTORE DISPLAY
 22  1418  C9                   RET
 23  1419  3A    712F   3$:     LDA   DSPOK               ;FORGET ALL THIS IF WE ALREADY DID IT
 24  141C  B7                   ORA   A
 25  141D  C2    1451           JNZ   7$
 26  1420  3E    01             MVI   A,1                 ;BLANK ALL THE ALARM, STATUS LIGHTS
 27  1422  4F            4$:    MOV   C,A
 28  1423  F5                   PUSH  PSW
 29  1424  CD    1475           CALL  CLRLIT
 30  1427  F1                   POP   PSW
 31  1428  17                   RAL
 32  1429  D2    1422           JNC   4$
 33  142C  01    711C   5$:     LXI   B,DSPFD1            ;BLANK THE DISPLAYS
 34  142F  CD    1452           CALL  DSPBLK
 35  1432  01    7122           LXI   B,DSPFD2
 36  1435  CD    1452           CALL  DSPBLK
 37  1438  01    0000           LXI   B,0                 ;SHUT THE BEEPER UP
 38  143B  1E    00             MVI   E,0
 39  143D  CD    148E           CALL  BEEP
```

```
  7 1333   C9                        RET
  8                          ;
  9                          ;SAME FOR H,L
 10                          ;
 11 1334   D5           INTHL: PUSH   D
 12 1335   11    0080          LXI    D,80H
 13 1338   19                  DAD    D
 14 1339   D1                  POP    D
 15 133A   2E    00            MVI    L,0
 16 133C   D0                  RNC
 17 133D   26    FF            MVI    H,0FFH
 18 133F   C9                  RET
 19
 20                          ;NEGATE D,E
 21                          ;
 22 1340   AF           NEGDE: XRA    A
 23 1341   93                  SUB    E
 24 1342   5F                  MOV    E,A
 25 1343   3E    00            MVI    A,0
 26 1345   9A                  SBB    D
 27 1346   57                  MOV    D,A
 28 1347   C9                  RET
 29                          ;
 30                          ;NEGATE H,L
 31                          ;
 32 1348   EB           NEGHL: XCHG
 33 1349   CD    1340          CALL   NEGDE
 34 134C   EB                  XCHG              ;ANOTHER TOUGHIE
 35 134D   C9                  RET
 36                          ;
 37                          ;NEGATE C,D AND E TOGETHER
 38                          ;
 39 134E   CD    1340   NEGCDE: CALL  NEGDE
 40 1351   3E    00            MVI    A,0
 41 1353   99                  SBB    C
 42 1354   4F                  MOV    C,A
 43 1355   C9                  RET
 44
  1
  2
  3                          ;DISPLAY SERVICE ROUTINES....
  4                          ;
  5                          ;DISPLAY B,C AS 'XXX' (ROUNDED) IF D = 0, OR
  6                          ;            AS 'XX.X' IF D = 1 AND B,C < 99.9
  7                          ; E = FIELD CODE (0 = DSPFD1, 1 = DSPFD2)
  8                          ;CALLS XDSPCVT FOR INTEGER PART WITH B,C = DISPLAY POINTER, A=DATA AND
  9                          ;  H,L = DECIMAL TABLE POINTER SET APPROPRIATLY.
 10 1356   21    9C01   DECDSP: LXI   H,-25599           ;-99.9
 11 1359   09                  DAD    B                  ;CHECK FOR OVERFLOW
 12 135A   D2    135F          JNC    1$                 ;OK
 13 135D   16    00            MVI    D,0                ;NO DECIMAL FRACTION
 14 135F   7A           1$:    MOV    A,D                ;CHECK FOR FRACTION
 15 1360   B7                  ORA    A
 16 1361   C2    136B          JNZ    2$                 ;YUP
 17 1364   21    0080          LXI    H,80H              ;ROUND TO INTEGER
 18 1367   09                  DAD    B
 19 1368   44                  MOV    B,H
 20 1369   0E    00            MVI    C,0
 21 136B   21    7120   2$:    LXI    H,DSPFD1+4         ;SET FIELD POINTER
 22 136E   7B                  MOV    A,E
 23 136F   B3                  ORA    E
 24 1370   CA    1376          JZ     3$
 25 1373   21    7126          LXI    H,DSPFD2+4
 26 1376   59           3$:    MOV    E,C                ;SAVE FRACTIONAL DATA
 27 1377   D5                  PUSH   D                  ;ALONG WITH FLAG
 28 1378   E5                  PUSH   H                  ;SAVE DISPLAY POINTER
 29 1379   21    13F6          LXI    H,DECTBL           ;DECIMAL CONVERT TABLE
 30 137C   7A                  MOV    A,D
 31 137D   B7                  ORA    A
 32 137E   CA    1382          JZ     4$
 33 1381   23                  INX    H                  ;DOING FRACTION, START WITH 10'S DIGIT
 34 1382   78           4$:    MOV    A,B                ;GET INTEGER DATA TO A
 35 1383   C1                  POP    B                  ;DISPLAY POINTER TO B,C
 36 1384   CD    13B4          CALL   XDSPCV             ;CONVERT INTEGER
 37 1387   D1                  POP    D                  ;D = FRACTION FLAG, E = FRACTION
 38 1388   7A                  MOV    A,D
 39 1389   B7                  ORA    A
 40 138A   CA    13A8          JZ     10$                ;NO FRACTION
 41 138D   21    13EB          LXI    H,SEGTBL           ;POINT TO SEGMENT TABLE
 42 1390   7B                  MOV    A,E                ;GET DATA
 43 1391   1E    FF            MVI    E,-1
 44 1393   23           5$:    INX    H                  ;BUMP DIGIT POINTER
 45 1394   1C                  INR    E
 46 1395   D6    1A            SUI    26                 ;0.1, ABOUT
 47 1397   D2    1393          JNC    5$
 48 139A   7E                  MOV    A,M                ;SEGMENT CODE
 49 139B   02                  STAX   B                  ;TO DISPLAY BUFFER
 50 139C   21    0002          LXI    H,2
 51 139F   09                  DAD    B                  ;BACK UP TO PREVIOUS DIGIT
 52 13A0   7E                  MOV    A,M
 53 13A1   F6    80            ORI    80H                ;SET D.P.
 54 13A3   77                  MOV    M,A
 55 13A4   7B                  MOV    A,E
 56 13A5   32    70BD          STA    FSATDP             ;SAVE DECIMAL FRACTION DIGIT
 57 13A8   C9           10$:   RET
  1
  2                          ; CONVERT A INTO DECIMAL 7-SEGMENT CHARACTERS AND STORE IN DISPLAY BUFFER.
```

```
40 1440   21   7170         LXI    H,FMODE          ;SAVE OLD FMODE
41 1443   7E                MOV    A,M
42 1444   32   7130         STA    MODESV
43 1447   3E   06           MVI    A,6
44 1449   32   7170         STA    FMODE            ;UNFILTER SAT AND RATE
45 144C   3E   01           MVI    A,1              ;DISABLE FURTHER DISPLAY STUFF
46 144E   32   712F         STA    DSPOK
47 1451   C9         7$:    RET

1                          ;BLANK A DISPLAY FIELD...
 2                          ; CALLED WITH B,C = POINTER TO FIELD
 3
 4
 5 1452   1E   03    DSPBLK: MVI   E,3
 6 1454   AF         1$:    XRA    A
 7 1455   02                STAX   B                ;STORE A ZERO
 8 1456   03                INX    B
 9 1457   03                INX    B
10 1458   1D                DCR    E
11 1459   C2   1454         JNZ    1$
12 145C   C9                RET

13                          ;
14                          ;BLINK A DISPLAY FIELD...CALLED WITH C = FIELD MASK
15                          ;
16 145D   21   7118  DSPBNK: LXI   H,DIGBNK
17 1460   79                MOV    A,C
18 1461   B6                ORA    M
19 1462   77                MOV    M,A
20 1463   C9                RET

21                          ;
22                          ;UN-BLINK A FIELD...CALLED WITH C = MASK
23                          ;
24 1464   21   7118  DSPUBK: LXI   H,DIGBNK
25 1467   79                MOV    A,C
26 1468   2F                CMA
27 1469   A6                ANA    M
28 146A   77                MOV    M,A
29 146B   C9                RET

30                          ;
31                          ;SET/CLEAR ANNUNCIATOR LIGHTS...REG C = LITE BIT
32                          ;
33 146C   21   712C  SETLIT: LXI   H,DSPLMP         ;FIRST LED BYTE
34 146F   7E                MOV    A,M
35 1470   B1                ORA    C
36 1471   77                MOV    M,A
37 1472   C3   147C         JMP    CLRLT2           ;CLEAR BLINK BITS 38
39                          ;CLEAR LIGHT AND BLINK BITS...
40
41 1475   21   712C  CLRLIT: LXI   H,DSPLMP
42 1478   79                MOV    A,C
43 1479   2F                CMA
44 147A   A6                ANA    M
45 147B   77                MOV    M,A
46 147C   79         CLRLT2: MOV   A,C
47 147D   2F                CMA
48 147E   21   7119         LXI    H,INDBNK
49 1481   A6                ANA    M                ;CLEAR IT
50 1482   77                MOV    M,A
51 1483   C9                RET 52
53                          ;SET LITE BLINKING ONCE PER SECOND...
54
55 1484              FSTLIT:                        ;DISABLED FOR NOW
56 1484   CD   146C  BNKLIT: CALL  SETLIT           ;TURN IT ON...
57 1487   21   7119         LXI    H,INDBNK         ;POINT TO BLINK FLAGS
 1 148A   79                MOV    A,C
 2 148B   B6                ORA    M                ;SET BLINK BIT
 3 148C   77                MOV    M,A
 4 148D   C9                RET

1                          ;MAKE A BEEP....CALLED WITH B = DURATION (1/60'S SEC, MINUS FOR CONTINUOUS) AND
 2                          ; C = PITCH (0 TO 100 LOW TO HIGH), E = VOLUME...
 3                          ; (FOR NEGATIVE DURATION, SET NO TONE FOR THAT DURATION AND THEN START TONE
 4                          CONTINUOUSLY)
 5                          ;
 6 148E   78         BEEP:  MOV    A,B
 7 148F   B7                ORA    A                ;CHECK FOR MINUS DURATION
 8 1490   F2   1495         JP     1$
 9 1493   2F                CMA                     ;MAKE IT PLUS
10 1494   3C                INR    A
11 1495   32   70EA  1$:    STA    BEECNT           ;BEEP COUNTER
12 1498   16   08           MVI    D,08H            ;CHASE BIT TO SHIFT VOLUME UP 5 BITS
13 149A   AF                XRA    A
14 149B   7B         2$:    MOV    A,E
15 149C   17                RAL
16 149D   5F                MOV    E,A
17 149E   7A                MOV    A,D
18 149F   17                RAL
19 14A0   57                MOV    D,A
20 14A1   D2   149B         JNC    2$
21 14A4   21   0190         LXI    H,400            ;1 VOLT OFFSET
22 14A7   19                DAD    D
23 14A8   11   0000         LXI    D,0              ;POST-BEEP VOLTAGE (= OFF)
24 14AB   78                MOV    A,B              ;GET DURATION AGAIN
25 14AC   B7                ORA    A
26 14AD   F2   14B1         JP     4$               ;PLUS, BEEP FIRST THEN QUIET
```

```
27 14B0  EB             XCHG                    ;VICE-VERSA FOR MINUS
28 14B1  22   7165  4$: SHLD    VVOL            ;VOLUME VOLTAGE
29 14B4  EB             XCHG
30 14B5  22   7167      SHLD    VVOLSV          ;SAVE THE POST-BEEP VOLTAGE
31 14B8  1E   04        MVI     E,4
32 14BA  AF             XRA     A
33 14BB  47             MOV     B,A
34 14BC  79         3$: MOV     A,C             ;SHIFT PITCH CODE UP SIMILARY
35 14BD  17             RAL
36 14BE  4F             MOV     C,A
37 14BF  78             MOV     A,B
38 14C0  17             RAL
39 14C1  47             MOV     B,A
40 14C2  1D             DCR     E
41 14C3  C2   14BC      JNZ     3$
42 14C6  21   04B0      LXI     H,1200
43 14C9  09             DAD     D
44 14CA  22   7163      SHLD    VBEEP           ;STORE PITCH VOLTAGE (2-9V)
45 14CD  C9             RET

1                     ;BUTTON SERVICE ROUTINE....
 2                     ; WHEN A BUTTON (OR COMBINATION) IS PRESSED IT GETS LOOKED UP IN THE FIRST HALF
 3                     ; OF THE BUTTON TABLE, BUTTBL, WHICH SPECIFIES THAT A PARAMETER IS TO BE
 4                     ; 'OPENED' OR A DISPATCH JUMP TAKEN (VIA A 'CALL'). AN OPEN PARAMETER
 5                     ; IS DISPLAYED AND CAN BE INCREMENTED OR DECREMENTED BY SUBSEQUENCE KNOB STROBES.
 6                     ; THE PARAMETER REMAINS OPEN AS LONG AS THE BUTTON IS HELD, AND, OPTIONALLY FOR
 7                     ; A TWO-SECOND PERIOD FOLLOWING RELEASE.
 8                     ;
 9
10 14CE  3A   712F  BUTTON: LDA  DSPOK          ;IF SILENT MODE, NO BUTTON
11 14D1  B7             ORA     A
12 14D2  C0             RNZ
13 14D3  21   7135      LXI     H,BUTFLG        ;POINT TO BUTTON FLAG
14 14D6  7E             MOV     A,M
15 14D7  3D             DCR     A               ;DECREMENT IT
16 14D8  F8             RM                      ;WAS ZERO
17 14D9  77             MOV     M,A             ;UPDATE COUNT
18 14DA  2B             DCX     H               ;POINT TO NEW BUTTON CODE
19 14DB  7E             MOV     A,M             ;CHECK BUTTON-UP'S FIRST ... GET NEW CODE
20 14DC  32   7137      STA     NEWBUT          ;SAVE IT TO AVOID A RACE
21 14DF  5F             MOV     E,A             ;SAVE IN 'E' FOR 3$
22 14E0  2F             CMA                     ;1 = BUTTON UP
23 14E1  57             MOV     D,A
24 14E2  3A   7136      LDA     OLDBUT          ;1 = BUTTON USED TO BE DOWN
25 14E5  A2             ANA     D               ;1 = UP NOW, WAS DOWN..
26 14E6  CA   14F5      JZ      2$              ;NONE...GO CHECK NEW BUTTON-DOWNS
27 14E9  0E   30        MVI     C,30H           ;BIT MASK FOR BUTTON FLAGS
28 14EB  3A   7136      LDA     OLDBUT          ;USE OLD BUTTON CODE
29 14EE  C3   1501      JMP     3$
30 14F1  3A   7137  1$: LDA     NEWBUT          ;GET NEW BUTTON CODE
31 14F4  5F             MOV     E,A
32 14F5  0E   C0    2$: MVI     C,0C0H          ;MASK BITS FOR BUTTON-DOWN
33 14F7  3A   7136      LDA     OLDBUT          ;GET OLD ONE
34 14FA  2F             CMA                     ;1 = BIT NOT PREVIOUSLY SET
35 14FB  A3             ANA     E               ;COMPARE W/NEW BUTTON CODE
36 14FC  7B             MOV     A,E             ;UPDATE OLD CODE
37 14FD  32   7136      STA     OLDBUT
38 1500  C8             RZ                      ;NO NEW BUTTON-DOWN, RETURN
39 1501  5F         3$: MOV     E,A             ;BUTTON CODE
40 1502  16   00        MVI     D,0
41 1504  21   175A      LXI     H,BUTTBL        ;GENERATE POINTER TO BUTTON TABLE
42 1507  19             DAD     D
43 1508  7E             MOV     A,M             ;GET CODE (INDEX INTO PRMTBL)
44 1509  B7             ORA     A
45 150A  CA   14F1      JZ      1$              ;IGNORE THIS ONE
46 150D  17             RAL                     ;*3 BYTES/ENTRY
47 150E  86             ADD     H
48 150F  5F             MOV     E,A
49 1510  21   177A      LXI     H,PRMTBL
50 1513  19             DAD     D               ;POINT INTO PARAM. TABLE
51 1514  E5             PUSH    H
52 1515  79             MOV     A,C             ;SAVE MASK
53 1516  23             INX     H               ;GET ADDRESS
54 1517  5E             MOV     E,M
55 1518  23             INX     H
56 1519  56             MOV     D,M
57 151A  23             INX     H               ;GET LIMITS
 1 151B  EB             XCHG                    ;POINTER TO H,L TO GET LIMITS
 2 151C  2B             DCX     H
 3 151D  4E             MOV     C,M             ;GET LOWER LIMIT (PRECEEDING BYTE)
 4 151E  23             INX     H
 5 151F  23             INX     H
 6 1520  46             MOV     B,M             ;GET UPPER LIMIT (FOLLOWING BYTE)
 7 1521  2B             DCX     H
 8 1522  EB             XCHG
 9 1523  E1             POP     H               ;POINT BACK TO FLAGS
10 1524  A6             ANA     M               ;GET FLAGS, MASKED BY A
11 1525  07             RLC
12 1526  DA   1538      JC      7$              ;BIT 7 = DISPATCH
13 1529  07             RLC
14 152A  DA   1540      JC      6$              ;BIT 6
15 152D  07             RLC
16 152E  DA   1545      JC      5$
17 1531  07             RLC
18 1532  DA   154C      JC      4$
19 1535  C3   14F1      JMP     1$              ;NOTHING TO DO...
20 1538  EB         7$: XCHG                    ;DISPATCH ADDR TO H,L
```

```
21 1539  1A              LDAX   D         ;GET FLAGS IN A
22 153A  11     153F     LXI    D,10$     ;RETURN ADDR
23 153D  D5              PUSH   D         ;ONTO STACK
24 153E  E9              PCHL             ;CALL...
25 153F  C9       10$:   RET
26 1540  7E       6$:    MOV    A,M       ;GET FLAGS
27 1541  CD     1552     CALL   BUTOPN    ;OPEN A PARAM...
28 1544  C9              RET
29 1545  7E       5$:    MOV    A,M       ;GET FLAGS
30 1546  CD     15B7     CALL   BUTCLS    ;REGULAR CLOSE
31 1549  C3     14F1     JMP    1$        ;CHECK FOR OPEN
32 154C  CD     15E0  4$: CALL  BUTCTO    ;CLOSE AFTER TIME-OUT
33 154F  C3     14F1     JMP    1$

;OPEN AND CLOSE ROUTINES....
         ;   A = FLAGS, B = UPPER LIMIT, C = LOWER LIMIT, D,E = PARAMETER ADDRESS
         ;
 5 1552  21     7138  BUTOPN: LXI  H,OPNPRM
 6 1555  73              MOV    M,E       ;STORE POINTER TO OPEN PARAMETER
 7 1556  23              INX    H
 8 1557  72              MOV    M,D
 9 1558  23              INX    H
10 1559  23              INX    H
11 155A  71              MOV    M,C       ;LOWER LIMIT
12 155B  23              INX    H
13 155C  70              MOV    M,B       ;UPPER LIMIT
14 155D  23              INX    H
15 155E  36     00       MVI    M,0       ;RESET TIMER
16 1560  1F              RAR              ;CHECK ALARM INHIBIT FLAG
17 1561  D2     158C     JNC    3$        ;NOT SET
18 1564  F5              PUSH   PSW
19 1565  21     70F1     LXI    H,ALIFLG  ;POINT TO FLAG
20 1568  7E              MOV    A,M
21 1569  B7              ORA    A         ;SET ALREADY?
22 156A  C2     1581     JNZ    1$        ;YES, RESET IT (TURN OFF INHIBIT)
23 156D  34              INR    M         ;NO, SET IT
24 156E  01     0000     LXI    B,0
25 1571  1E     00       MVI    E,0
26 1573  CD     148E     CALL   BEEP      ;SHUT UP BEEPER
27 1576  3A     727C     LDA    COSTA     ;CLEAR AUDIO ENABLED BIT      ///
28 1579  E6     FB       ANI    NOT AUDENB ;                            ///
29 157B  32     727C     STA    COSTA     ;                             ///
30 157E  C3     158B     JMP    2$
31 1581  36     00   1$: MVI    M,0       ;CLEAR TIMER
32 1583  3A     727C     LDA    COSTA     ;SET AUDIO ALARM ENABLED BIT  ///
33 1586  F6     04       ORI    AUDENB    ;                             ///
34 1588  32     727C     STA    COSTA     ;                             ///
35 158B  F1          2$: POP    PSW
36 158C  1F          3$: RAR              ;CHECK SOUND-ALARM BIT
37 158D  D2     15A2     JNC    5$        ;NOPE
         ;
         ;SOUND ALARM (TO SET VOLUME, ETC.)
         ;
41 1590  F5              PUSH   PSW
42 1591  0E     6E       MVI    C,ALMPCH
43 1593  06     FF       MVI    B,255
44 1595  3A     70EF     LDA    ALMVOL
45 1598  5F              MOV    E,A
46 1599  CD     148E     CALL   BEEP
47 159C  3E     01       MVI    A,1
48 159E  32     70F7     STA    ALCFLG    ;SET ALARM-CHECKING FLAG
49 15A1  F1              POP    PSW
50 15A2  1F          5$: RAR              ;CHECK DISPLAY BIT
51 15A3  DA     15B6     JC     7$        ;SET, INHIBIT DISPLAY

;DISPLAY PARAMETER...
         ;
 4 15A6  1F              RAR              ;SET FIELD BIT TO CARRY
 5 15A7  3E     01       MVI    A,1
 6 15A9  32     713A     STA    OPNFLG    ;SET OPEN FLAG
 7 15AC  D2     15B0     JNC    6$        ;CHECK ALTERNATE (LOWER) FIELD BIT
 8 15AF  3C              INR    A
 9 15B0  32     7142  6$: STA   PRMFLD    ;SAVE FLAG (1=FIELD1, 2 =FIELD2)
10 15B3  CD     161E     CALL   DSPOPN    ;DISPLAY OPEN PARAM
11 15B6  C9          7$: RET

;CLOSE OPEN PARAMETER...
         ;
15 15B7  E6     02   BUTCLS: ANI 2        ;CHECK BEEPER FLAG
16 15B9  CA     15C3     JZ     2$        ;NOT SET
17 15BC  06     00       MVI    B,0
18 15BE  1E     00       MVI    E,0
19 15C0  CD     148E     CALL   BEEP      ;RESET BEEPER
20 15C3  AF          2$: XRA    A
21 15C4  32     713A     STA    OPNFLG
22 15C7  32     713D     STA    OPNTMR    ;RESET OPEN PARAMETER FLAG AND TIMER
23 15CA  32     7141     STA    IFLG      ;RESET INDIRECT FLAG
24 15CD  32     70F7     STA    ALCFLG    ;AND ALARM-CHECKING FLAG
25 15D0  21     70EC     LXI    H,BEEVOL  ;SET UP VOLUME FOR DEFAULT CHANGES
26 15D3  22     713B     SHLD   OPNPRM
27 15D6  21     6400     LXI    H,6400H   ;LIMITS
28 15D9  22     713B     SHLD   OPNLL
29 15DC  CD     0A8F     CALL   DSPSR     ;RESTORE DISPLAY
30 15DF  C9              RET

;SET TIMER TO CLOSE IN 3 SECONDS...IF NO ACTIVITY...
```

```
 33                       ;
 34 15E0  3A  713E  BUTCTO: LDA   OPNDLY      ;NOMINAL DELAY
 35 15E3  32  713D          STA   OPNTMR
 36 15E6  C9              RET
 37                       ;
 38                       ;RE-DISPLAY OPEN PARAMETER, CALLED BY MONITOR TO KEEP DISPLAY UP TO DATE.
 39                       ;
 40 15E7  3A  712F  RFSHOP: LDA   DSPOK       ;DON'T DO THIS IF IN SILENT MODE
 41 15EA  B7            ORA   A
 42 15EB  C0            RNZ
 43 15EC  CD  161E          CALL  DSPOPN      ;DISPLAY OPEN PARAM'S...
 44 15EF  3A  70F7          LDA   ALCFLG      ;CHECK FOR ALARM-CHECKING
 45 15F2  B7            ORA   A
 46 15F3  C8            RZ                ;NOPE
 47 15F4  0E  6E            MVI   C,ALMPCH    ;RE-START ALARM
 48 15F6  06  64            MVI   B,100       ;AN ARBITRARY POSITIVE COUNT
 49 15F8  3A  70EF          LDA   ALMVOL
 50 15FB  5F            MOV   E,A
 51 15FC  CD  148E          CALL  BEEP
 52 15FF  C9            RET
  1                       ;SPECIAL ROUTINE (CALLED VIA DISPATCH) TO OPEN A CELL INDIRECTLY...
  2                       ;   ASSUMES 'ICELL' HAS BEEN SET, AND SHOWS IT IN THE LOWER FIELD
  3                       ;   AND OPENS RAMORG+(ICELL).
  4                       ;
  5                       ;
  6 1600  DB  00    INDRCT: IN    STSREG
  7 1602  E6  01            ANI   DIDJPR
  8 1604  C0            RNZ               ;CHECK FOR JUMPER FIRST...
  9 1605  3E  02            MVI   A,2         ;SET IFLG = 2 FOR CHANGING CONTENTS
 10 1607  32  7141          STA   IFLG
 11 160A  C3  1612          JMP   ILOOK2      ;OPEN CELL, DISPLAY CONTENTS
 12                       ;
 13                       ;DISPATCH ROUTINE TO OPEN INDIRECT ADDRESS, AND CAUSE CONTENTS TO BE DISPLAYED.
 14                       ;
 15 160D  3E  01    ILOOK:  MVI   A,1         ;SET INDIRECT FLAG =1 (CHANGING ADDRESS)
 16 160F  32  7141          STA   IFLG
 17 1612  11  713F  ILOOK2: LXI   D,ICELL
 18 1615  01  FF00          LXI   B,0FF00H    ;NO LIMITS
 19 1618  3E  00            MVI   A,0
 20 161A  CD  1552          CALL  BUTOPN      ;OPEN AND DISPLAY ADDRESS & CONTENTS
 21 161D  C9            RET
 22                       ;
 23                       ;OPEN CELL DISPLAY....DISPLAY (OPNPRM) IN FIELD 1 (TOP), AND IF IFLG NONZERO THEN
 24                       ;   DISPLAY ((OPNPRM)) ON LOWER DISPLAY.
 25                       ;
 26 161E  3A  713A  DSPOPN: LDA   OPNFLG
 27 1621  B7            ORA   A
 28 1622  CA  1679          JZ    4$          ;IF NOT OPEN, REBLINK DISPLAYS, IF APPROPRIATE
 29 1625  0E  3F            MVI   C,FD1MSK+FD2MSK
 30 1627  CD  1464          CALL  DSPUBK      ;TURN OFF BLINKING
 31 162A  01  711C          LXI   B,DSPFD1
 32 162D  3A  7142          LDA   PRMFLD
 33 1630  3D            DCR   A           ;CHECK FOR FIELD 1/2
 34 1631  CA  1637          JZ    1$
 35 1634  01  7122          LXI   B,DSPFD2
 36 1637  2A  7138  1$:     LHLD  OPNPRM
 37 163A  C5            PUSH  B
 38 163B  CD  16C7          CALL  ALICHK      ;CHECK FOR ALARM PERIOD OPEN
 39 163E  C1            POP   B
 40 163F  DA  164D          JC    5$          ;IS NOT (PERIOD RETURNED IN A)
 41 1642  FE  79            CPI   121         ;CHECK FOR >120
 42 1644  C2  164D          JNZ   5$
 43 1647  CD  16BB          CALL  OFFDSP
 44 164A  C3  1668          JMP   2$
 45 164D  7E    5$:     MOV   A,M
 46 164E  E5            PUSH  H
 47 164F  CD  13A9          CALL  DSPCVT      ;DISPLAY AS FIELD 1
 48 1652  E1            POP   H
 49 1653  3A  7141          LDA   IFLG
 50 1656  B7            ORA   A
 51 1657  CA  1668          JZ    2$          ;NOT INDIRECT
 52 165A  11  7000          LXI   D,RAMORG    ;LOOK UP (RAMORG+(OPNPRM))
 53 165D  5E            MOV   E,H         ;CONTENTS OF OPEN PARAM (NOMINALLY CONTENTS OF ICELL)
 54 165E  1A            LDAX  D           ;GET IT
 55 165F  01  7122          LXI   B,DSPFD2
 56 1662  CD  13A9          CALL  DSPCVT
 57 1665  C3  1678          JMP   10$
  1 1668  01  7122  2$:     LXI   B,DSPFD2
  2 166B  3A  7142          LDA   PRMFLD
  3 166E  3D            DCR   A
  4 166F  CA  1675          JZ    3$
  5 1672  01  711C          LXI   B,DSPFD1
  6 1675  CD  1452  3$:     CALL  DSPBLK
  7 1678  C9    10$:    RET
  8 1679  3A  70C9  4$:     LDA   ALMFLG      ;SEE IF ALARM BITS ARE SET
  9 167C  B7            ORA   A
 10 167D  C8            RZ
 11 167E  1F            RAR               ;TEST SAT ALARM BIT
 12 167F  D2  1689          JNC   6$
 13 1682  F5            PUSH  PSW         ;SAVE THE FLAG
 14 1683  0E  07            MVI   C,FD1MSK    ;REBLINK IT
 15 1685  CD  145D          CALL  DSPBNK
 16 1688  F1            POP   PSW
 17 1689  1F    6$:     RAR               ;TEST HR BIT
```

```
 18 168A    D2               JNC    8$
 19 168D    3A  7170         LDA    FMODE      ;REBLANK HR DISPLAY IF IN MODE 3
 20 1690    FE  05           CPI    5
 21 1692    CA  16A7         JZ     8$
 22 1695    FE  03           CPI    3          ;DON'T BLINK/BLANK IF IN MODE 5
 23 1697    C2  16A1         JNZ    7$
 24 169A    01  7122         LXI    B,DSPFD2   ;BLANK IT
 25 169D    CD  1452         CALL   DSPBLK
 26 16A0    C9               RET
 27 16A1    0E  38       7$: MVI    C,FD2MSK
 28 16A3    CD  145D         CALL   DSPBNK
 29 16A6    C9               RET
 30 16A7    3A  70C9     8$: LDA    ALMFLG     ;GET IT BACK
 31 16AA    1F               RAR
 32 16AB    1F               RAR               ;AND GET THE RESP ALARM BIT
 33 16AC    1F               RAR
 34 16AD    1F               RAR               ;TEST FOR RESP ALARM BIT
 35 16AE    D0               RNC
 36 16AF    3A  7170         LDA    FMODE
 37 16B2    FE  05           CPI    5
 38 16B4    C0               RNZ               ;ONLY REBLINK IF MODE 5
 39 16B5    0E  38           MVI    C,FD2MSK
 40 16B7    CD  145D         CALL   DSPBNK
 41 16BA    C9               RET
 42
 43                          ;DISPLAY 'OFF' IN THE FIELD POINTED TO BY H,L
 44                          ;
 45 16BB    3E  1B       OFFDSP: MVI A,SEGF
 46 16BD    02               STAX   D
 47 16BE    03               INX    B
 48 16BF    03               INX    B
 49 16C0    02               STAX   B
 50 16C1    03               INX    B
 51 16C2    03               INX    B
 52 16C3    3E  77           MVI    A,SEG0
 53 16C5    02               STAX   B
 54 16C6    C9               RET
 55
 56                          ;CHECK ALARM INHIBIT ACTION...TRY TO KEEP LIGHTS UP WITH KNOB...
 57                          ;
  1 16C7    EB           ALICHK: XCHG           ;MOVE OPNPRM TO D,E
  2 16C8    21  8F0C         LXI    H,-ALIPER
  3 16CB    19               DAD    D
  4 16CC    EB               XCHG
  5 16CD    7A               MOV    A,D
  6 16CE    B3               ORA    E
  7 16CF    37               STC
  8 16D0    C0               RNZ               ;NOT LOOKING AT PERIOD
  9 16D1    E5               PUSH   H          ;SAVE POINTER
 10 16D2    0E  01           MVI    C,ALICOD   ;TO SET LIGHT
 11 16D4    3A  70F1         LDA    ALIFLG     ;CHECK FOR ALARM OFF
 12 16D7    B7               ORA    A
 13 16D8    CA  16F4         JZ     10$        ;NOT OFF, PERIOD DOESN'T MATTER
 14 16DB    7E               MOV    A,M        ;GET PERIOD
 15 16DC    FE  79           CPI    121
 16 16DE    CA  16EE         JZ     5$         ;PERIOD IS 121, PERMANENTLY OFF,
 17 16E1    32  70F2         STA    ALICTR     ;SET TIMER TO PERIOD
 18 16E4    AF               XRA    A
 19 16E5    32  70F6         STA    ALMDLY     ;CLEAR ANY PENDING DELAYED ALARMS
 20 16E8    CD  146C         CALL   SETLIT     ;TURN LIGHT ON STEADILY
 21 16EB    C3  16FB         JMP    12$
 22 16EE    CD  1484     5$: CALL   BNKLIT     ;OFF FOREVER, BLINK THE LIGHT
 23 16F1    C3  16F7         JMP    11$
 24 16F4    CD  1475    10$: CALL   CLRLIT     ;NOT OFF, TURN OFF THE LIGHT
 25 16F7    AF          11$: XRA    A
 26 16F8    32  70F2         STA    ALICTR     ;CLEAR TIMER
 27 16FB    E1          12$: POP    H
 28 16FC    7E               MOV    A,M        ;GET PERIOD AGAIN
 29 16FD    B7               ORA    A          ;CLEAR CARRY
 30 16FE    C9               RET
  1
  2                          ; CHECK FOR KNOB ACTION....
  3                          ;
  4 16FF    3A  712F     KNOB: LDA   DSPOK      ;NO KNOB IN SILENT MODE
  5 1702    B7               ORA    A
  6 1703    C0               RNZ
  7 1704    11  7132         LXI    D,KNBCTR   ;POINT TO KNOB COUNT
  8 1707    1A               LDAX   D          ;GET IT
  9 1708    B7               ORA    A          ;CHECK FOR ZERO
 10 1709    C8               RZ
 11 170A    F5               PUSH   PSW
 12 170B    2A  7138         LHLD   OPNPRM     ;POINT TO PARAM
 13 170E    3A  7141         LDA    IFLG
 14 1711    FE  02           CPI    2          ;CHECK FOR INDIRECT DIDDLE-CONTENTS MODE
 15 1713    C2  171B         JNZ    1$         ;IS NOT
 16 1716    7E               MOV    A,M        ;GET CONTENTS
 17 1717    21  7000         LXI    H,RAMORG
 18 171A    6F               MOV    L,A
 19 171B    F1           1$: POP    PSW
 20 171C    B7               ORA    A
 21 171D    FA  1739         JM     3$         ;DOWN COUNT
 22 1720    3D               DCR    A          ;DECREMENT COUNT
 23 1721    12               STAX   D
 24 1722    3A  713C         LDA    OPNUL      ;GET UPPER LIMIT
 25 1725    BE               CMP    H
 26 1726    CA  1736         JZ     2$         ;AT LIMIT
```

```
27 1729  34                     INR   M                ;MAKE SURE THE ALARM IS DISABLED IF WE
28 172A  BE                     CMP   M                ;HAVE JUST SET ALM DELAY TO OFF
29 172B  C2   1736              JNZ   2$
30 172E  FE   79                CPI   121              ;CHANGING ALM?
31 1730  C2   1736              JNZ   2$
32 1733  32   70F1              STA   ALIFLG           ;LIGHT THE LED AND DISABLE ALM
33 1736  C3   1743        2$:   JMP   5$               ;GO DISPLAY
34 1739  3C                3$:  INR   A                ;DECREMENT COUNT
35 173A  12                     STAX  D
36 173B  3A   713B              LDA   OPNLL            ;LOWER LIMIT
37 173E  BE                     CMP   M
38 173F  CA   1743              JZ    4$               ;AT LIMIT
39 1742  35                     DCR   M                ;DECREMENT PARAM
40 1743                    4$:
41 1743  3A   713A        5$:   LDA   OPNFLG           ;EXIT HERE IF WE ARE TWEAKING VOLUME BY DEFAULT
42 1746  B7                     ORA   A
43 1747  CA   1759              JZ    6$
44 174A  CD   161E              CALL  DSPOPN           ;RE-DISPLAY PARAMETER
45 174D  21   713D              LXI   H,OPNTMR         ;RESET TIMER IF RUNNING
46 1750  7E                     MOV   A,M
47 1751  B7                     ORA   A
48 1752  CA   1759              JZ    6$
49 1755  3A   713E              LDA   OPNDLY
50 1758  77                     MOV   M,A
51 1759                    6$:
52 1759  C9                10$: RET

;BUTTON TABLES...
; THE FIRST IS A TRANSLATION TABLE FROM HARDWARE BUTTON CODES (0-31)
; TO TOKENS THAT INDEX THE PARAMETER TABLE...
; THE PARAMETER TABLE IS 5 BYTES PER ACTIVE BUTTON CODE:
;     BYTE 0 = FLAGS....  BIT 7 = DISPATCH CALL ON BUTTON DOWN
;                         BIT 6 = OPEN PARAM ON BUTTON DOWN
;                         BIT 5 = CLOSE PARAM ON BUTTON UP (NO TIME-OUT)
;                         BIT 4 = CLOSE PARAM AFTER TIME-OUT
;                         BIT 3 = ALTERNATE FIELD DISPLAY (FIELD 2)
;                         BIT 2 = INHIBIT PARAMETER DISPLAY
;                         BIT 1 = SOUND ALARM
;                         BIT 0 = INHIBIT ALARM
;     BYTE 1,2 = PARAMETER/DISPATCH ADDRESS
;     LOWER/UPPER LIMITS ARE THE BYTES PRECEEDING AND FOLLOWING A PARAMTER BYTE.

17 175A  00           BUTTBL: DB  0    ;0
18 175B  04                   DB  4    ;1    BOTTOM BUTTON
19 175C  03                   DB  3    ;2
20 175D  0A                   DB  10   ;3
21 175E  02                   DB  2    ;4
22 175F  08                   DB  8    ;5
23 1760  09                   DB  9    ;6
24 1761  00                   DB  0    ;7
25 1762  01                   DB  1    ;8
26 1763  07                   DB  7    ;9
27 1764  0B                   DB  11   ;10
28 1765  00                   DB  0    ;11
29 1766  06                   DB  6    ;12
30 1767  00                   DB  0    ;13
31 1768  00                   DB  0    ;14
32 1769  00                   DB  0    ;15
33 176A  05                   DB  5    ;16
34 176B  00                   DB  0    ;17
35 176C  00                   DB  0    ;18
36 176D  00                   DB  0    ;19
37 176E  00                   DB  0    ;20
38 176F  00                   DB  0    ;21
39 1770  00                   DB  0    ;22
40 1771  00                   DB  0    ;23
41 1772  00                   DB  0    ;24
42 1773  00                   DB  0    ;25
43 1774  00                   DB  0    ;26
44 1775  00                   DB  0    ;27
45 1776  00                   DB  0    ;28
46 1777  00                   DB  0    ;29
47 1778  00                   DB  0    ;30
48 1779  00                   DB  0    ;31

50 177A  00   00     PRMTBL: DB  0,0,0            ;ZERO UNUSED
   177C  00

52 177D  50                  DB  50H              ;1 = SAT LIMIT
53 177E  70C2                DW  SATLL 55 1780  58                  DB  58H              ;2 = RATE UPPER LIMIT
56 1781  70C7                DW  RATUL 2 1783  58                  DB  58H              ;3 = RATE LOWER LIMIT
 3 1784  70C6                DW  RATLL 5 1786  61                  DB  61H              ;4 = INHIBIT ALARM
 6 1787  70F4                DW  ALIPER 8 1789  50                  DB  50H              ;5 = SAT UPPER LIMIT
 9 178A  70C3                DW  SATUL 11 178C  60                  DB  60H              ;6 = SET EKG POLARITY - LOSAT/HIRATE BUTS
12 178D  70FA                DW  POLEKG
```

```
14 178F   A0              DB     0A0H           ;7 = INDIRECT DIDDLE-ADDRESS DISPATCH
15 1790   160D            DW     ILOOK
16
17 1792   A0              DB     0A0H           ;8 = INDIRECT DIDDLE-CONTENTS DISPATCH
18 1793   1600            DW     INDRCT
19
20 1795   60              DB     60H            ;9 = FILTER MODE
21 1796   7170            DW     FMODE
22
23 1798   60              DB     60H            ;10 = ALARM INHIBIT PERIOD
24 1799   70F4            DW     ALIPER
25
26 179B   60              DB     60H            ;11 = DIDDLE EKG GAIN - LOSAT/LORATE BUTS
27 179C   70FD            DW     GNEKG
28
29 179E   00              DB     0
30 179F   0000            DW     0
31
 1
 2                               ;CLOCK SERVICE ROUTINE.....CALLED EVERY QUARTER-SECOND BY MONITOR.
 3                               ;MAINTAIN TIME REGISTERS, MARK MINUTES ON VEXT'S.
 4                               ;
 5 17A1   21   7145  CLOCK: LXI   H,QSCFLG      ;POINT TO QUARTER-SECOND FLAG
 6 17A4   7E              MOV   A,M
 7 17A5   3D              DCR   A             ;DECREMENT SAME
 8 17A6   F8              RM                  ;WAS ALREADY ZERO, RETURN
 9 17A7   77              MOV   M,A
10 17A8   2B              DCX   H             ;POINT TO COUNTER (MSCTR)
11 17A9   3E   8E         MVI   A,142         ;FUDGE FOR 6MHZ CRYSTAL ******
12 17AB   86              ADD   M
13 17AC   77              MOV   M,A
14 17AD   23              INX   H
15 17AE   D2   17B2       JNC   1$            ;OVERFLOWED THE COUNTER?
16 17B1   34              INR   M             ;YES, SET ANOTHER COUNT
17 17B2   23        1$:   INX   H             ;POINT TO QUARTER-SEC COUNTER
18 17B3   34              INR   M             ;BUMP IT, CHECK FOR END OF MINUTE
19 17B4   7E              MOV   A,M
20 17B5   FE   F0         CPI   240
21 17B7   C2   17C8       JNZ   5$            ;NOT YET
22 17BA   36   00         MVI   M,0
23 17BC   23              INX   H
24 17BD   34              INR   M             ;BUMP MINUTES AND CHECK FOR AN HOUR
25 17BE   7E              MOV   A,M
26 17BF   FE   3C         CPI   60
27 17C1   C2   17C8       JNZ   5$
28 17C4   36   00         MVI   M,0
29 17C6   23              INX   H
30 17C7   34              INR   M             ;BUMP HOURS
31 17C8   21   713D  5$:  LXI   H,OPNTMR      ;POINT TO TIMER FOR BUTTON CODE
32 17CB   7E              MOV   A,M
33 17CC   3D              DCR   A             ;A SPECULATIVE DECREMENT
34 17CD   FA   17D7       JM    14$           ;WAS ZERO, FORGET IT
35 17D0   77              MOV   M,A           ;NOT ZERO, STORE DECREMENTED VALUE
36 17D1   C2   17D7       JNZ   14$           ;NOT YET ZERO
37 17D4   CD   15B7       CALL  BUTCLS        ;TIMED OUT, CLOSE THE BUT...(A = 0)
38 17D7   21   7149 14$:  LXI   H,PLSTMR      ;CHECK PULSE TIME-OUT
39 17DA   7E              MOV   A,M
40 17DB   3D              DCR   A
41 17DC   FA   17E6       JM    17$           ;NO SET, IGNORE
42 17DF   77              MOV   M,A
43 17E0   C2   17E6       JNZ   17$
44 17E3   CD   0B2C       CALL  FLSTMO
45 17E6   21   70F8 17$:  LXI   H,EKGTMR      ;DECREMENT EKG TIMEOUT COUNTER
46 17E9   7E              MOV   A,M
47 17EA   3D              DCR   A
48 17EB   FA   17F5       JM    3$
49 17EE   77              MOV   M,A
50 17EF   C2   17F5       JNZ   3$
51 17F2   CD   0BCC       CALL  EKGTMO        ;EKG TIMED OUT - CLEAR RATE AND SET ALARM
52 17F5   21   710F 3$:   LXI   H,RSPTMR      ;DECREMENT RESP TIMEOUT COUNTER
53 17F8   7E              MOV   A,M
54 17F9   3D              DCR   A
55 17FA   FA   1804       JM    19$
56 17FD   77              MOV   M,A
57 17FE   C2   1804       JNZ   19$
 1 1801   CD   0C0F       CALL  RSPTMO
 2 1804   21   710B 19$:  LXI   H,RATCLK      ;TIME DOWN RATE CLOCK
 3 1807   7E              MOV   A,M
 4 1808   3D              DCR   A
 5 1809   FA   1816       JM    4$            ;TIMED OUT, ZERO RATE OUTPUT
 6 180C   77              MOV   M,A
 7 180D   C2   1816       JNZ   4$
 8 1810   21   0000       LXI   H,0
 9 1813   22   716B       SHLD  RATOUT
10 1816   21   710C 4$:   LXI   H,SATCLK      ;DITTO FOR SAT CLOCK
11 1819   7E              MOV   A,M
12 181A   3D              DCR   A
13 181B   FA   1828       JM    6$
14 181E   77              MOV   M,A
15 181F   C2   1828       JNZ   6$
16 1822   21   0000       LXI   H,0
17 1825   22   7169       SHLD  SATOUT
18 1828   3A   7105 6$:   LDA   HRRFSH        ;RESET EKG GAIN EVERY SEC WHEN EKTMR IS 0
19 182B   3C              INR   A
20 182C   FE   05         CPI   5
21 182E   CA   1834       JZ    20$
```

```
22 1831    32    7105           STA   HRRFSH
23 1834    3A    7146    20$:   LDA   QSCCTR
24 1837    E6    01             ANI   1
25 1839    CC    1881           CZ    BNKON          ;Q-SEC = 0 OR 2...LITES ON.
26
27                       ;CHECK ALARM INHIBIT TIME-OUT, SOUND DELAYED TIME-OUT ALARM IF SET...
28                       ;
29 183C    3A    7146           LDA   QSCCTR
30 183F    2F                   CMA
31 1840    E6    03             ANI   3
32 1842    CC    188F           CZ    BNKOFF         ;Q-SEC = 3, SLOW BLINKERS
33 1845    3A    7146           LDA   QSCCTR         ;CHECK FOR 1-SECOND
34 1848    E6    03             ANI   3
35 184A    C2    1880           JNZ   18$            ;IS NOT
36 184D    3A    70F2           LDA   ALICTR         ;CHECK ALARM-INHIBIT TIME-OUT
37 1850    B7                   ORA   A
38 1851    CA    1880           JZ    18$            ;NOT SET
39 1854    3D                   DCR   A
40 1855    32    70F2           STA   ALICTR
41 1858    C2    1880           JNZ   18$
42 185B    32    70F1           STA   ALIFLG         ;CLEAR INHIBIT FLAG
43 185E    0E    01             MVI   C,ALICOD
44 1860    CD    1475           CALL  CLRLIT         ;CLEAR LIGHT
45 1863    3A    727C           LDA   COSTA
46 1866    F6    04             ORI   AUDENB
47 1868    32    727C           STA   COSTA
48 186B    3A    70F6           LDA   ALMDLY         ;CHECK FOR DELAYED ALARM
49 186E    B7                   ORA   A
50 186F    CA    1880           JZ    18$            ;NOT SET
51 1872    AF                   XRA   A
52 1873    32    70F6           STA   ALMDLY
53 1876    3A    7014           LDA   SYNFLG         ;CHECK FOR SYNC
54 1879    B7                   ORA   A
55 187A    CA    1880           JZ    18$            ;IT IS
56 187D    CD    0D7E           CALL  ALMCK2         ;DELAYED TIME-OUT ALARM IF NOT RE-SYNCED
57 1880    C9             18$:  RET
 1                       ;
 1
 2                       ;SET BLINKING DIGITS AND LIGHTS TO 'ON' STATE
 3                       ;
 4 1881    21    711C    BNKON: LXI   H,DIGBUF
 5 1884    0E    09             MVI   C,9
 6 1886    23             1$:   INX   H
 7 1887    36    FF             MVI   M,0FFH
 8 1889    23                   INX   H
 9 188A    0D                   DCR   C
10 188B    C2    1886           JNZ   1$
11 188E    C9                   RET
12                       ;
13                       ;SET BLINKING DIGITS TO 'OFF' STATE IF THEIR BLINK BIT IS SET...
14                       ;
15 188F    3A    7118    BNKOFF: LDA  DIGBNK
16 1892    5F                   MOV   E,A
17 1893    0E    06             MVI   C,6
18 1895    21    711C           LXI   H,DIGBUF
19 1898    23             1$:   INX   H
20 1899    7B                   MOV   A,E
21 189A    1F                   RAR                  ;CHECK DIGIT BIT...
22 189B    5F                   MOV   E,A
23 189C    D2    18A1           JNC   3$
24 189F    AF                   XRA   A
25 18A0    77                   MOV   M,A
26 18A1    23             3$:   INX   H
27 18A2    0D                   DCR   C
28 18A3    C2    1898           JNZ   1$
29 18A6    3A    7119           LDA   INDBNK         ;CLEAR INDICATOR BITS
30 18A9    2F                   CMA
31 18AA    21    712D           LXI   H,DSPLHF+1
32 18AD    A6                   ANA   M
33 18AE    77                   MOV   M,A
34 18AF    C9                   RET
 1                       ;INTERRUPT HANDLERS...
 2                       ;
 3                       ;CLOCK INTERRUPT.....
 4                       ;THIS IS A SERIAL OUTPUT ROUTINE WITH 6 STATES, DEPENDING ON THE     ///
 5                       ; ADDRESS OF THE SUBROUTINE STORED AT 'SNDMOD' IT WILL PERFORM ONE OF ///
 6                       ; THE FOLLOWING TASKS.                                               ///
 7                       ; 1.  NULMOD  DOES NOTHING BUT RESTORE THE HL REGISTER PAIR          ///
 8                       ; 2.  STARTS  SETS THE SOD LINE TO SPACE FOR CHARACTER START         ///
 9                       ; 3.  SPINR   SETS THE SOD LINE ACCORDING TO CURRENT BIT AND ROTATES ///
10                       ; 4.  STOPBG  SETS THE SOD LINE TO MARK FOR STOP BIT STARTING        ///
11                       ; 5.  ENDSND  SETS THE SOD LINE TO MARK CONDITION FOR TERMINATION    ///
12                       ; 6.  WATMOD  FORCES A MINIMUM TIME BETWEEN CHARACTERS SO RECEIVING  ///
13                       ;             UART CAN BE READY FOR THE NEXT CHARACTER               ///
14                       ;             RESETS SNDMOD BACK TO NULMOD                           ///
15                       ;
16
17 18B0    E5             CLKINT: PUSH H              ;SAVE THE POOR GUY                      ///
18 18B1    2A    72AA           LHLD  SNDMOD         ;GET ADDRESS OF ROUTINE CURRENTLY ACTIV ///
19 18B4    E9                   PCHL                 ;AND GO DO IT                           ///
20
21 18B5    E1             NULMOD: POP  H              ;RESTORE HL PAIR                        ///
22 18B6    FB                   EI                   ;                                       ///
23 18B7    C9                   RET                  ;AND WE'RE DONE                         ///
24
25 18B8    21    18D9    STARTS: LXI  H,SPINR        ;SET MODE TO SPINR FOR NEXT PASS        ///
```

```
26 18BB  22    72AA         SHLD  SNDMOD
27 18BE  F5                 PUSH  PSW
28 18BF  3E    C0           MVI   A,SPACE   ;SET SOD LINE TO SPACE CONDITION
29 18C1  30                 SIM             ;SEND IT
30 18C2  3E    08           MVI   A,8       ;INITIALIZE NUMBER OF BITS
31 18C4  32    72AC         STA   BITCNT
32 18C7  F1                 POP   PSW       ;RESTORE REGGIES
33 18C8  E1                 POP   H
34 18C9  FB                 EI
35 18CA  C9                 RET             ;
36
37 18CB  21    18FC  STOPBG: LXI  H,ENDSND
38 18CE  22    72AA         SHLD  SNDMOD    ;SET MODE TO NULL AT END OF TRANSMISSIO
39 18D1  F5                 PUSH  PSW       ;
40 18D2  3E    40           MVI   A,MARK    ;SET SOD TO MARKING
41 18D4  30                 SIM
42 18D5  F1                 POP   PSW       ;RESTORE
43 18D6  E1                 POP   H         ;
44 18D7  FB                 EI
45 18D8  C9                 RET             ;
46
47 18D9  F5           SPINR: PUSH PSW       ;SAVE HIM
48 18DA  3A    72A9         LDA   CHAR      ;GET THIS DIZZY CHARACTER
49 18DD  0F                 RRC             ;POSITION BIT AT MSB AND ROTATE FOR NEX
50 18DE  32    72A9         STA   CHAR
51 18E1  2F                 CMA             ;INVERT FOR OPTO-COUPLER
52 18E2  F6    40           ORI   40H       ;SET SOD ENABLE BIT
53 18E4  E6    C0           ANI   0C0H      ;STRIP MASK SET STUFF
54 18E6  30                 SIM             ;AND DO IT
55 18E7  21    72AC         LXI   H,BITCNT
56 18EA  35                 DCR   H         ;DECREMENT BIT COUNT
57 18EB  CA    18F2         JZ    MODCHG    ;IF DONE, THEN CHANGE MODE TO STOP BIT
 1 18EE  F1                 POP   PSW       ;IF NOT, THEN RESTORE REGISTERS
 2 18EF  E1                 POP   H         ;
 3 18F0  FB                 EI
 4 18F1  C9                 RET             ;AND WE'RE DONE
 5
 6 18F2  21    18CB  MODCHG: LXI  H,STOPBG
 7 18F5  22    72AA         SHLD  SNDMOD    ;SET MODE TO STOP BIT BEGINNING
 8 18F8  F1                 POP   PSW       ;RESTORE REGISTERS
 9 18F9  E1                 POP   H
10 18FA  FB                 EI
11 18FB  C9                 RET             ;
12
13 18FC  F5           ENDSND: PUSH PSW      ;SAVE THAT HAPPY ACCUMULATOR
14 18FD  3E    40           MVI   A,MARK    ;SET SOD TO MARK CONDITION
15 18FF  30                 SIM
16 1900  21    190A         LXI   H,WATMOD  ;JUST WAIT A BIT 'TIL NEXT
17 1903  22    72AA         SHLD  SNDMOD    ;AND SET TO DO NOTHING NEXT TIME 'ROUND
18 1906  F1                 POP   PSW       ;RESTORE REGGIES
19 1907  E1                 POP   H         ;
20 1908  FB                 EI
21 1909  C9                 RET             ;
22
23 190A  21    18B5  WATMOD: LXI  H,NULMOD  ;SET TO NULL MODE
24 190D  22    72AA         SHLD  SNDMOD    ;
25 1910  E1                 POP   H
26 1911  FB                 EI              ;JUST WAIT HERE A BIT
27 1912  C9                 RET             ;
28
29
 1                          ;
 2                          ;DISPLAY INTERRUPT...OUTPUT DISPLAY SELECT BIT AND DIGIT, OUTPUT
 3                          ; SAMPLE/HOLD VALUE AND SELECT, AND CHECK FOR BUTTON/CONTROL INPUT.
 4                          ; EVERY FOURTH INTERRUPT DO A/D CONVERSION FOR INPUT CHANNELS, ADJUSTING
 5                          ; OFFSET IF REQUIRED...
 6                          ;
 7                          ;
 8 1913  F5           DSPINT: PUSH PSW
 9 1914  C5                 PUSH  B
10 1915  D5                 PUSH  D
11 1916  E5                 PUSH  H         ;SAVE REGISTERS
12 1917  2A    7144         LHLD  MSCTR     ;BUMP CLOCK
13 191A  23                 INX   H
14 191B  22    7144         SHLD  MSCTR
15 191E  3E    0F           MVI   A,0FH
16 1920  D3    04           OUT   DSPSEL    ;DE-SELECT TO BLANK DISPLAY
17 1922  21    711B         LXI   H,DIGIDX  ;POINT TO DIGIT COUNTER
18 1925  7E                 MOV   A,M
19 1926  3C                 INR   A         ;INCREMENT IT
20 1927  FE    09           CPI   9
21 1929  C2    192D         JNZ   1$
22 192C  AF                 XRA   A         ;RESET IT IF IT REACHED MAX
23 192D  77           1$:   MOV   M,A
24 192E  07                 RLC
25 192F  5F                 MOV   E,A
26 1930  16    00           MVI   D,0       ;D,E = DIGIT INDEX *2
27 1932  23                 INX   H         ;POINT TO FIRST BYTE
28 1933  19                 DAD   D         ;POINT TO NEXT DIGIT
29 1934  7E                 MOV   A,M       ;GET DIGIT
30 1935  23                 INX   H
31 1936  A6                 ANA   M         ;MASK WITH MASK BYTE
32 1937  D3    05           OUT   DSPDIG    ;OUTPUT, RESETTING INTERRUPT
33 1939  7B                 MOV   A,E       ;GET INDEX AGAIN
34 193A  0F                 RRC
35 193B  D3    04           OUT   DSPSEL
```

```
 36 193D  3A   7012          LDA   GNSEL      ;LOAD GNMSK WITH CORRECT VALUE
 37 1940  B7                 ORA   A
 38 1941  CA   1946          JZ    4$         ;LO GAIN=0
 39 1944  3E   80            MVI   A,128      ;HI GAIN=128
 40 1946  32   72AF    4$:   STA   GNMSK
 41 1949  3E   0A            MVI   A,0AH
 42 194B  30                 SIM              ;TURN OFF INT 6.5 (OURS)
 43 194C  FB                 EI               ;ALLOW CLOCK INTERRUPTS HERE
  1
  2                ;CHECK BUTTON INPUT REGISTER, STORE IF DIFFERENT...
  3                ;
  4 194D  21   7132          LXI   H,KNBCTR   ;POINT TO KNOB UP/DOWN COUNT
  5 1950  DB   04            IN    BUTREG     ;GET BUTTON/KNOB DATA
  6 1952  4F                 MOV   C,A
  7 1953  E6   03            ANI   3          ;ISOLATE KNOB BITS
                                              ;STEP BIT TO CARRY, DIR TO BIT0
  8 1955  1F                 RAR
  9 1956  D2   1965          JNC   3$
 10 1959  07                 RLC              ;DIR TO BIT 1
 11 195A  3D                 DCR   A          ;MAKE A 1 OR -1
 12 195B  2B                 DCX   H          ;POINT TO OUR FLAG
 13 195C  BE                 CMP   M          ;SET SAME AS OUR UP/DOWN CODE?
 14 195D  C2   1961          JNZ   2$         ;NO, DO IT
 15 1960  AF                 XRA   A          ;CLEAR UP/DOWN CODE (TO SKIP ALTERNATE STEPS)
 16 1961  77         2$:     MOV   M,A        ;STORE CODE OR ZERO
 17 1962  23                 INX   H
 18 1963  86                 ADD   M          ;ADD TO KNOB COUNT
 19 1964  77                 MOV   M,A
 20 1965  23         3$:     INX   H          ;POINT TO BUTTON FILTER
 21 1966  79                 MOV   A,C
 22 1967  A6                 ANA   M          ;MASK DATA WITH LAST INPUT (REQUIRING
                                              ; CONSECUTIVE 1'S)
 23 1968  71                 MOV   M,C        ;STORE NEW DATA
 24 1969  23                 INX   H          ;POINT TO BUTCOD
 25 196A  0F                 RRC
 26 196B  0F                 RRC
 27 196C  2F                 CMA              ;BUTTON DOWN = ZERO, MAKE IT ONE.
 28 196D  E6   1F            ANI   1FH        ;MASK BUTTON CODE
 29 196F  BE                 CMP   M          ;SAME??
 30 1970  CA   1976          JZ    5$         ;YES
 31 1973  77                 MOV   M,A        ;STORE NEW ONE (HOPE OLD ONE PROCESSED)
 32 1974  23                 INX   H
 33 1975  34                 INR   M          ;FLAG IT
 34 1976             5$:
  1
  2                ;DIGITIZE PRIMARY DATA VALUES EVERY 8TH PASS (57HZ, ABOUT)
  3                ;
  4 1976  21   7177   ADCHK: LXI   H,DATCLK
  5 1979  34                 INR   M
  6 197A  7E                 MOV   A,M
  7 197B  E6   07            ANI   7
  8 197D  C2   19F8          JNZ   ADCHK2     ;NOT TIME YET
  9 1980  3E   0F            MVI   A,V1PRM    ;CHANNEL 1 MUX CODE
 10 1982  D3   02            OUT   MUXSEL     ;PRE-SELECT IT
 11 1984  23                 INX   H
 12 1985  7E                 MOV   A,M        ;GET BUFFER INDEX
 13 1986  4F                 MOV   C,A
 14 1987  C6   04            ADI   4          ;4 BYTES PER SAMPLE -
 15 1989  E6   FF            ANI   BUFMSK     ;MASK TO WRAP AT BUFFER END
 16 198B  77                 MOV   M,A
 17 198C  06   00            MVI   B,0
 18 198E  23                 INX   H          ;FIRST BUFFER BYTE
 19 198F  23                 INX   H
 20 1990  09                 DAD   B          ;PLUS INDEX
 21 1991  E5                 PUSH  H          ;SAVE H,L
 22 1992  CD   1AA6          CALL  CHKEKG     ;CHECK FOR VALID R WAVE
 23 1995  CD   1AF6          CALL  CHKWIN     ;BUMP TIME WINDOW TIMER
 24 1998  E1                 POP   H
 25 1999  CD   1E5E          CALL  ADCVT      ;GET DATA INTO D,E
 26 199C  3E   1F            MVI   A,V2PRM    ;PRE-SELECT MUX FOR CH.2
 27 199E  D3   02            OUT   MUXSEL
 28 19A0  E5                 PUSH  H
 29 19A1  CD   1D48          CALL  CKLED1     ;RE-SET LED CURRENT BASED ON DAC DATA
 30 19A4  21   3000          LXI   H,3000H
 31 19A7  19                 DAD   D          ;ADD DATA TO OFFSET
 32 19A8  EB                 XCHG
 33 19A9  E1                 POP   H
 34 19AA  3A   700C          LDA   L1ITMR     ;CHECK LED INHIBIT TIMER
 35 19AD  B7                 ORA   A
 36 19AE  CA   19B4          JZ    1$         ;NOT CHANGING, STORE DATA
 37 19B1  11   0000          LXI   D,0        ;ZERO OUR HARD WORK
 38 19B4  73         1$:     MOV   M,E        ;STORE LOW BYTE
 39 19B5  23                 INX   H
 40 19B6  72                 MOV   M,D        ;STORE DATA + OFFSET
 41 19B7  23                 INX   H
 42 19B8  CD   1E5E          CALL  ADCVT
 43 19BB  E5                 PUSH  H
 44 19BC  CD   1D9F          CALL  CKLED2
 45 19BF  21   3000          LXI   H,3000H
 46 19C2  19                 DAD   D
 47 19C3  EB                 XCHG
 48 19C4  E1                 POP   H
 49 19C5  3A   700F          LDA   L2ITMR
 50 19C8  B7                 ORA   A
 51 19C9  CA   19CF          JZ    2$
 52 19CC  11   0000          LXI   D,0
 53 19CF  73         2$:     MOV   M,E
```

```
54 19D0   23                          INX    H
55 19D1   72                          MOV    M,D

;CHECK THE BEEP COUNTER (57HZ RATE)...
;
 4 19D2   21   70EA                   LXI    H,BEECNT    ;GET BEEPER COUNTER
 5 19D5   7E                          MOV    A,M
 6 19D6   3D                          DCR    A
 7 19D7   FA   19E4                   JM     3$          ;WAS ZERO, BORING
 8 19DA   77                          MOV    M,A         ;UPDATE, CHECK FOR NOW ZERO
 9 19DB   C2   19E4                   JNZ    3$
10 19DE   2A   7167                   LHLD   VVOLSV
11 19E1   22   7165                   SHLD   VVOL        ;RESET VOLUME VOLTAGE
12 19E4   3A   700C         3$:       LDA    L1ITMR      ;DECREMENT LED TIMERS
13 19E7   3D                          DCR    A
14 19E8   FA   19EE                   JM     4$
15 19EB   32   700C                   STA    L1ITMR
16 19EE   3A   700F         4$:       LDA    L2ITMR
17 19F1   3D                          DCR    A
18 19F2   FA   19F8                   JM     5$
19 19F5   32   700F                   STA    L2ITMR
20 19F8                     5$:
;
;DO A/D CONVERSION ON SECONDARY MUX INPUTS EVERY SO OFTEN...
;
24 19F8   3A   7177         ADCHK2:   LDA    DATCLK
25 19FB   3C                          INR    A
26 19FC   E6   07                     ANI    7           ;DON'T CHECK AT THE SAME TIME AS D/A...
27 19FE   C2   1A1F                   JNZ    DSPRET
28 1A01   21   714B                   LXI    H,ADIDX
29 1A04   7E                          MOV    A,M         ;GET INDEX
30 1A05   07                          RLC
31 1A06   5F                          MOV    E,A
32 1A07   16   00                     MVI    D,0
33 1A09   07                          RLC
34 1A0A   07                          RLC
35 1A0B   07                          RLC
36 1A0C   C6   2F                     ADI    V1MX
37 1A0E   D3   02                     OUT    MUXSEL
38 1A10   7E                          MOV    A,M         ;INCREMENT INDEX
39 1A11   3C                          INR    A
40 1A12   E6   07                     ANI    7
41 1A14   77                          MOV    M,A
42 1A15   21   714C                   LXI    H,V1        ;FIRST PARAMATER IN BUFFER
43 1A18   19                          DAD    D           ;PLUS INDEX
44 1A19   CD   1E5E                   CALL   ADCVT
45 1A1C   73                          MOV    M,E
46 1A1D   23                          INX    H
47 1A1E   72                          MOV    M,D         ;STORE DATA

;RETURN...OUTPUT TO NEXT SAMPLE/HOLD
;
 4 1A1F   CD   1B23         DSPRET:   CALL   SETEKG      ;CHECK GAIN,POLARITY SETTING
 5 1A22   3A   7177                   LDA    DATCLK      ;EVERY 32ND PASS, UPDATE RESP COUNTER
 6 1A25   3C                          INR    A
 7 1A26   E6   1F                     ANI    31
 8 1A28   C2   1A2E                   JNZ    3$
 9 1A2B   CD   1A98                   CALL   RSPCTR
10 1A2E   3E   0F           3$:       MVI    A,0FH
11 1A30   D3   02                     OUT    MUXSEL      ;TURN OFF GATES
12 1A32   2A   715D                   LHLD   SHPTR       ;GET POINTER AND INDEX
13 1A35   3A   715C                   LDA    SHIDX
14 1A38   B7                          ORA    A
15 1A39   C2   1A44                   JNZ    1$
16 1A3C   CD   1B66                   CALL   SNDOUT      ;OUTPUT SAO2/HR VOLTAGES
17 1A3F   3E   01                     MVI    A,1         ;RESET IF INDEX IS ZERO
18 1A41   21   715F                   LXI    H,SHBUF
19 1A44   4F           1$:            MOV    C,A         ;SAVE INDEX
20 1A45   5E                          MOV    E,M
21 1A46   23                          INX    H
22 1A47   56                          MOV    D,M         ;GET VALUE
23 1A48   23                          INX    H
24 1A49   22   715D                   SHLD   SHPTR
25 1A4C   3A   72AF                   LDA    GNMSK       ;ADD GAIN SELECT TO DACH
26 1A4F   B2                          ORA    D
27 1A50   F6   70                     ORI    070H        ;MASK OFF MIDDLE 3 BITS (FOR ANALOG OUTPUTS)
28 1A52   D3   01                     OUT    DACH
29 1A54   7B                          MOV    A,E
30 1A55   D3   00                     OUT    DACL
31 1A57   79                          MOV    A,C
32 1A58   2F                          CMA
33 1A59   E6   0F                     ANI    0FH
34 1A5B   D3   02                     OUT    MUXSEL
35 1A5D   79                          MOV    A,C
36 1A5E   17                          RAL
37 1A5F   E6   0F                     ANI    0FH
38 1A61   32   715C                   STA    SHIDX
39 1A64   CD   1CC3                   CALL   COM240      ;CALL 240 HZ. COMMUNICATIONS ROUTINE    ///
40 1A67   F3                          DI                 ;RE-ENABLE OUR INTERRUPT
41 1A68   3E   08                     MVI    A,08H
42 1A6A   30                          SIM                ;******** 8085 ********
43 1A6B   E1                          POP    H
44 1A6C   D1                          POP    D
45 1A6D   C1                          POP    B
46 1A6E   F1                          POP    PSW
47 1A6F   FB                          EI
```

```
 48 1A70   C9                        RET
 49                           ;
 50                           ;SHIFT H,L RIGHT OR LEFT (A) PLACES (RIGHT FOR NEGATIVE)
 51                           ;
 52 1A71   B7            SHFTHL: ORA    A
 53 1A72   C8                        RZ
 54 1A73   C5                        PUSH   B
 55 1A74   4F                        MOV    C,A
 56 1A75   FA   1A85                 JM     2$
 57 1A78   AF            1$:         XRA    A         ;NO CARRY AROUND
  1 1A79   7D                        MOV    A,L
  2 1A7A   17                        RAL
  3 1A7B   6F                        MOV    L,A
  4 1A7C   7C                        MOV    A,H
  5 1A7D   17                        RAL
  6 1A7E   67                        MOV    H,A
  7 1A7F   0D                        DCR    C
  8 1A80   C2   1A78                 JNZ    1$
  9 1A83   C1                        POP    B
 10 1A84   C9                        RET
 11 1A85   AF            2$:         XRA    A
 12 1A86   7C                        MOV    A,H
 13 1A87   1F                        RAR
 14 1A88   67                        MOV    H,A
 15 1A89   7D                        MOV    A,L
 16 1A8A   1F                        RAR
 17 1A8B   6F                        MOV    L,A
 18 1A8C   0C                        INR    C
 19 1A8D   C2   1A85                 JNZ    2$
 20 1A90   C1                        POP    B
 21 1A91   C9                        RET
 22                           ;
 23                           ;SAME EXCEPT SHIFTS D,E INSTEAD OF H,L
 24                           ;
 25 1A92   EB            SHFTDE: XCHG
 26 1A93   CD   1A71                 CALL   SHFTHL
 27 1A96   EB                        XCHG
 28 1A97   C9                        RET
 29                           ;
 30                           ; COUNTER FOR RESP PERIOD - APPROX 14HZ
 31                           ;
 32 1A98   3A   7110       RSPCTR: LDA    RSPFLG
 33 1A9B   B7                        ORA    A
 34 1A9C   C0                        RNZ              ;INSURE WE'RE NOT AHEAD OF OURSELVES
 35 1A9D   3A   710E                 LDA    RSPCNT
 36 1AA0   3C                        INR    A
 37 1AA1   C8                        RZ
 38 1AA2   32   710E                 STA    RSPCNT
 39 1AA5   C9                        RET
 40                           ;
 41                           ;
 42                           ;CHECK FOR A VALID R-WAVE AND RESP WAVE. SET FLAG IF SO.
 43                           ;RETURN IF EKG SETTINGS HAVE BEEN CHANGED RECENTLY
 44                           ;
 45 1AA6   3A   7100       CHKEKG: LDA    EKGFLG     ;EXIT IF WE'RE AHEAD OF LEVEL3
 46 1AA9   B7                        ORA    A
 47 1AAA   C0                        RNZ
 48 1AAB   3A   70FF                 LDA    EKGPER     ;EKG PERIOD COUNTER
 49 1AAE   3C                        INR    A
 50 1AAF   CA   1AB5                 JZ     1$
 51 1AB2   32   70FF                 STA    EKGPER
 52 1AB5   3A   7103       1$:       LDA    DLYEKG     ;DELAY FOR CHANGING PARAMETERS
 53 1AB8   3D                        DCR    A
 54 1AB9   FA   1AC2                 JM     2$         ;IS ZERO, DATA IS VALID
 55 1ABC   32   7103                 STA    DLYEKG
 56 1ABF   C3   1AE7                 JMP    4$         ;NOT VALID, RESET R WAVE FLAG AND EXIT
 57 1AC2   DB   00         2$:       IN     STSREG     ;GET FLAG
  1 1AC4   32   70CA                 STA    STATUS
  2 1AC7   E6   30                   ANI    30H        ;MASK FOR EKG + RESP
  3 1AC9   CA   1AEB                 JZ     7$
  4 1ACC   CD   1B04                 CALL   CHKRSP     ;SEE IF RESP BIT IS SET
  5 1ACF   E6   20                   ANI    20H        ;CHECK EKG BIT
  6 1AD1   CA   1AE7                 JZ     4$
  7 1AD4   3A   70FF                 LDA    EKGPER     ;CHECK IF HR >285 - REJECT
  8 1AD7   FE   0C                   CPI    12
  9 1AD9   DA   1AEC                 JC     8$
 10 1ADC   21   7100                 LXI    H,EKGFLG   ;VALID R WAVE
 11 1ADF   36   01                   MVI    M,1
 12 1AE1   3A   7178                 LDA    DATIDX
 13 1AE4   32   7108                 STA    DATTRG     ;STORE DATBUF POINTER WHEN R-WAVE OCCURRED
 14 1AE7   3E   00         4$:       MVI    A,0        ;RESET THE HARDWARE FLAG
 15 1AE9   D3   07                   OUT    RSTRWV
 16 1AEB   C9         7$:            RET
 17 1AEC   AF         8$:            XRA    A          ;ZERO PARAMS DUE TO REJECTED R WAVE
 18 1AED   32   7100                 STA    EKGFLG
 19 1AF0   32   70FF                 STA    EKGPER
 20 1AF3   D3   07                   OUT    RSTRWV
 21 1AF5   C9                        RET
 22                           ;
 23                           ;
 24                           ;TIME DELAY BETWEEN R-WAVE AND OPTICAL PULSE
 25                           ;
 26 1AF6   3A   710A       CHKWIN: LDA    WINFLG     ;DON'T DO THIS IF FLAG IS SET
 27 1AF9   B7                        ORA    A
 28 1AFA   C0                        RNZ
 29 1AFB   3A   7109                 LDA    WINTMR
```

```
30 1AFE   3C                       INR   A
31 1AFF   C8                       RZ
32 1B00   32    7109               STA   WINTMR
33 1B03   C9                       RET
                                ;
                                ; CHECK FOR THE RESP BIT - SET FLAG IF SO
                                ;
37 1B04   F5              CHKRSP: PUSH  PSW           ;SAVE FOR EKG
38 1B05   E6    10                ANI   10H           ;MASK FOR RESP
39 1B07   CA    1B21              JZ    1$            ;RESP NOT SET
40 1B0A   3A    710E              LDA   RSPCNT
41 1B0D   FE    07                CPI   7             ;NO RESP >120
42 1B0F   DA    1B1A              JC    2$
43 1B12   21    7110              LXI   H,RSPFLG
44 1B15   36    01                MVI   M,1           ;SET FLAG
45 1B17   C3    1B21              JMP   1$
46 1B1A   AF              2$:     XRA   A
47 1B1B   32    7110              STA   RSPFLG
48 1B1E   32    710E              STA   RSPCNT        ;RESET PARAMS
49 1B21   F1              1$:     POP   PSW
50 1B22   C9                      RET
                                ;
                                ;CHECK TO SEE IF EKG PARAMETERS HAVE BEEN CHANGED.
                                ;SET A DELAY IF PARAMETERS ARE TO BE CHANGED
                                ;
55 1B23   CD    1B4D     SETEKG: CALL  CKRFSH
56 1B26   21    70FA             LXI   H,POLEKG
57 1B29   7E                     MOV   A,M
 1 1B2A   21    7101             LXI   H,POLSAV      ;COMPARE NEW WITH OLD
 2 1B2D   BE                     CMP   M
 3 1B2E   CA    1B39             JZ    4$            ;SAME - NO CHANGE
 4 1B31   77                     MOV   M,A
 5 1B32   D3    03               OUT   EKGPOL        ;SEND OUT NEW POLARITY DATA
 6 1B34   3E    06               MVI   A,6
 7 1B36   32    7103             STA   DLYEKG        ;SET DELAY
 8 1B39   21    70FD     4$:     LXI   H,GNEKG
 9 1B3C   7E                     MOV   A,M
10 1B3D   21    7102             LXI   H,GAINSV
11 1B40   BE                     CMP   M
12 1B41   CA    1B4C             JZ    6$            ;DITTO FOR GAIN CHANGES
13 1B44   77                     MOV   M,A
14 1B45   D3    06               OUT   CHGEKG        ;SEND IT OUT
15 1B47   3E    06               MVI   A,6
16 1B49   32    7103             STA   DLYEKG
17 1B4C   C9              6$:    RET
                                ;
                                ;CHECK REFRESH TO EKG - TEMPORARY UNTIL SOFWARE AGC IS IMPLEMENTED
                                ;
21 1B4D   21    7105     CKRFSH: LXI   H,HRRFSH
22 1B50   3A    70FB             LDA   EKGTMR
23 1B53   FE    00               CPI   0
24 1B55   CA    1B59             JZ    1$
25 1B58   C9                     RET
26 1B59   7E              1$:    MOV   A,M
27 1B5A   FE    04               CPI   4
28 1B5C   C2    1B65             JNZ   2$
29 1B5F   36    00               MVI   M,0
30 1B61   21    7102             LXI   H,GAINSV
31 1B64   35                     DCR   M
32 1B65   C9              2$:    RET
                                ;
                                ;SEND OUT HR/SAO2 TO SAMPLE/HOLDS EVERY 4TH PASS
                                ;
37 1B66   3A    7170     SHDOUT: LDA   FMODE         ;IF MODE 7, THEN OUTPUT 0V
38 1B69   FE    07               CPI   7
39 1B6B   C2    1B7A             JNZ   2$
40 1B6E   21    0000             LXI   H,0
41 1B71   22    7169             SHLD  SATOUT
42 1B74   22    716B             SHLD  RATOUT
43 1B77   C3    1B99             JMP   1$
44 1B7A   FE    08       2$:     CPI   8             ;MODE 8, 1/2 SCALE OUTPUTS
45 1B7C   C2    1B8B             JNZ   3$
46 1B7F   21    00CD             LXI   H,205
47 1B82   22    7169             SHLD  SATOUT
48 1B85   22    716B             SHLD  RATOUT
49 1B88   C3    1B99             JMP   1$
50 1B8B   FE    09       3$:     CPI   9             ;MODE 9 , OUTPUT FULL SCALE
51 1B8D   C2    1B99             JNZ   1$
52 1B90   21    019A             LXI   H,410         ;1VOLT
53 1B93   22    7169             SHLD  SATOUT
54 1B96   22    716B             SHLD  RATOUT
55 1B99   21    7169     1$:     LXI   H,SATOUT
56 1B9C   5E                     MOV   E,M
57 1B9D   23                     INX   H
 1 1B9E   56                     MOV   D,M
 2 1B9F   3A    72AF             LDA   GNMSK         ;ADD IN GAIN MASK
 3 1BA2   B2                     ORA   D
 4 1BA3   F6    70               ORI   070H          ;MASK OFF GATE, FOR NOW
 5 1BA5   F5                     PUSH  PSW           ;SAVE IT
 6 1BA6   D3    01               OUT   DACH          ;OUTPUT SAT VOLTAGE
 7 1BA8   7B                     MOV   A,E
 8 1BA9   D3    00               OUT   DACL
 9 1BAB   00                     NOP                 ;ALLOW FOR A LITTLE SETTLING
10 1BAC   00                     NOP
11 1BAD   00                     NOP
```

```
12 1BAE  F1              POP   PSW              ;NOW SELECT GATE
13 1BAF  E6  BF          ANI   0BFH
14 1BB1  D3  01          OUT   DACH             ;LET THE CAPS CHARGE A BIT
15 1BB3  00              NOP
16 1BB4  00              NOP
17 1BB5  00              NOP
18 1BB6  00              NOP
19 1BB7  F6  70          ORI   070H             ;OK, TURN 'EM OFF
20 1BB9  D3  01          OUT   DACH
21 1BBB  23              INX   H                ;SAME FOR RATE OUT
22 1BBC  5E              MOV   E,M
23 1BBD  23              INX   H
24 1BBE  56              MOV   D,M
25 1BBF  3A  72AF        LDA   GNMSK
26 1BC2  B2              ORA   D
27 1BC3  F6  70          ORI   070H
28 1BC5  F5              PUSH  PSW
29 1BC6  D3  01          OUT   DACH
30 1BC8  7B              MOV   A,E
31 1BC9  D3  00          OUT   DACL
32 1BCB  00              NOP
33 1BCC  00              NOP
34 1BCD  00              NOP
35 1BCE  F1              POP   PSW
36 1BCF  E6  DF          ANI   0DFH
37 1BD1  D3  01          OUT   DACH
38 1BD3  00              NOP
39 1BD4  00              NOP
40 1BD5  00              NOP
41 1BD6  00              NOP
42 1BD7  F6  70          ORI   070H
43 1BD9  D3  01          OUT   DACH             ;OUTPUT THRESHOLD FOR R-WAVE COMPARATOR
44 1BDB  23              INX   H
45 1BDC  5E              MOV   E,M
46 1BDD  23              INX   H
47 1BDE  56              MOV   D,M
48 1BDF  3A  72AF        LDA   GNMSK
49 1BE2  B2              ORA   D
50 1BE3  F6  70          ORI   070H
51 1BE5  F5              PUSH  PSW
52 1BE6  D3  01          OUT   DACH
53 1BE8  7B              MOV   A,E
54 1BE9  D3  00          OUT   DACL
55 1BEB  00              NOP
56 1BEC  00              NOP
57 1BED  00              NOP
 1 1BEE  F1              POP   PSW
 2 1BEF  E6  EF          ANI   0EFH
 3 1BF1  D3  01          OUT   DACH
 4 1BF3  00              NOP
 5 1BF4  00              NOP
 6 1BF5  00              NOP
 7 1BF6  00              NOP
 8 1BF7  F6  70          ORI   070H
 9 1BF9  D3  01          OUT   DACH
10 1BFB  C9              RET
11
12
13                       ;
 1                       ;COMMUNICATIONS ROUTINES FOR SERIAL OUTPUT.                       ///
 2                       ; COMBEG      CALLED AT POWER-UP FOR POINTER AND IMAGE INITIALIZATION ///
 3                       ; COMIDL      CALLED FROM IDLE FOR STATUS/LIMIT/MINUTE CHANGE CHECK ///
 4                       ; COM240      CALLED 240 HZ FOR MOVING FROM BUFFER TO OUTPUT      ///
 5                       ;
 6                       ; UTILITY ROUTINES FOR COMMUNICATIONS                             ///
 7                       ; SPLIT       SPLITS A BYTE INTO TWO NIBBLES IN D AND E           ///
 8                       ; TOBUFR      PUTS A CHARACTER INTO THE BUFFER AND UPDATES POINTER ///
 9                       ; BMPBUF      BUFFER POINTER INCREMENT WITH WRAP-AROUND           ///
10
11
12 1BFC  21  7287  COMBEG: LXI  H,COMBUF                                                   ///
13 1BFF  22  7283         SHLD LSTOUT          ;INITIALIZE LAST SENT POINTER              ///
14 1C02  22  7285         SHLD BUFPTR          ;AND BUFFER POINTER                        ///
15 1C05  21  18B5         LXI  H,NULMOD                                                   ///
16 1C08  22  72AA         SHLD SNDMOD          ;SET OUTPUT ROUTINE TO DO NOTHING          ///
17 1C0B  3E  05           MVI  A,5             ;INITIALIZE OXIMETER STATUS IMAGE          ///
18 1C0D  32  727C         STA  COSTA                                                      ///
19 1C10  C9               RET                                                             ///
20 1C11  3A  7014  COMIDL: LDA  SYNFLG                                                    ///
21 1C14  A7               ANA  A                                                          ///
22 1C15  3A  727C         LDA  COSTA                                                      ///
23 1C18  4F               MOV  C,A             ;IF SYNC'D                                 ///
24 1C19  3E  01           MVI  A,SRCBIT        ;CLEAR SEARCH BIT                          ///
25 1C1B  CA  1C23         JZ   STKSER          ;IF NOT, THEN SET IT                       ///
26 1C1E  2F               CMA                                                             ///
27 1C1F  A1               ANA  C                                                          ///
28 1C20  C3  1C24         JMP  STKSR2                                                     ///
29 1C23  B1        STKSER: ORA  C                                                         ///
30 1C24  32  727C  STKSR2: STA  COSTA          ;STORE THE NEW VALUE                       ///
31
32 1C27  21  72AD         LXI  H,OMINS         ;HAS MINUTES COUNTER CHANGED ?             ///
33 1C2A  3A  7147         LDA  MINCTR                                                     ///
34 1C2D  BE               CMP  M                                                          ///
35 1C2E  77               MOV  M,A             ;UPDATE ANYWAY                             ///
36 1C2F  C2  1C65         JNZ  UPDALL          ;YES, UPDATE AND SEND LIMITS AND STATUS    ///
37 1C32  21  727A         LXI  H,OCOSTA                                                   ///
```

```
38 1C35   3A   727C           LDA    COSTA        ;HAS OXIMETER STATUS CHANGED ?        ///
39 1C38   AE                  XRA    M            ;                                     ///
40 1C39   4F                  MOV    C,A          ;                                     ///
41 1C3A   21   727B           LXI    H,OCPSTA                                           ///
42 1C3D   3A   727D           LDA    CPSTA        ;OR ALARM STATUS CHANGED ?            ///
43 1C40   AE                  XRA    M            ;                                     ///
44 1C41   B1                  ORA    C            ;                                     ///
45 1C42   C4   1C6C           CNZ    UPDSTA       ;YES, THEN GO DO STATUS OUTPUT        ///
46
47 1C45   3A   713A   LMCK:   LDA    OPNFLG       ;ARE LIMITS IN FLUX ?                 ///
48 1C48   A7                  ANA    A            ;                                     ///
49 1C49   C0                  RNZ                 ;YES, THEN GO AWAY                    ///
50 1C4A   21   727E           LXI    H,OSATLL     ;NO, THEN CHECK OLD AGAINST NEW       ///
51 1C4D   3A   70C2           LDA    SATLL        ;                                     ///
52 1C50   BE                  CMP    M            ;                                     ///
53 1C51   C2   1C83           JNZ    UPDLIM       ;IF CHANGED, SEND THEM                ///
54 1C54   23                  INX    H            ;                                     ///
55 1C55   3A   70C6           LDA    RATLL        ;                                     ///
56 1C58   BE                  CMP    M            ;                                     ///
57 1C59   C2   1C83           JNZ    UPDLIM       ;                                     ///
 1 1C5C   23                  INX    H            ;                                     ///
 2 1C5D   3A   70C7           LDA    RATUL        ;                                     ///
 3 1C60   BE                  CMP    M            ;                                     ///
 4 1C61   C2   1C83           JNZ    UPDLIM       ;                                     ///
 5 1C64   C9                  RET                 ;IF NO DIFFERENT, THEN GO AWAY        ///
 6
 7 1C65   CD   1C6C   UPDALL: CALL   UPDSTA       ;UPDATE STATUS                        ///
 8 1C68   CD   1C83           CALL   UPDLIM       ;AND LIMITS                           ///
 9 1C6B   C9                  RET                 ;                                     ///
10
11 1C6C   2A   727C   UPDSTA: LHLD   COSTA        ;GET OXIMETER AND ALARM STATUS        ///
12 1C6F   22   727A           SHLD   OCOSTA       ;UPDATE "OLD" IMAGES                  ///
13 1C72   3A   727C           LDA    COSTA        ;GET OXIMETER STATUS                  ///
14 1C75   F6   30             ORI    30H          ;TAG ON THE IDENTIFIER BITS           ///
15 1C77   CD   1D22           CALL   TOBUFR       ;AND PUT IT INTO BUFFER               ///
16 1C7A   3A   727D           LDA    CPSTA        ;GET ALARM STATUS                     ///
17 1C7D   F6   70             ORI    70H          ;TAG ON END OF MESSAGE                ///
18 1C7F   CD   1D22           CALL   TOBUFR       ;PUT INTO BUFFER                      ///
19 1C82   C9                  RET                 ;                                     ///
20
21 1C83   21   727E   UPDLIM: LXI    H,OSATLL     ;FIRST UPDATE OLD LIMITS              ///
22 1C86   3A   70C2           LDA    SATLL        ;                                     ///
23 1C89   77                  MOV    M,A          ;                                     ///
24 1C8A   23                  INX    H            ;                                     ///
25 1C8B   3A   70C6           LDA    RATLL        ;AND RATE LOWER                       ///
26 1C8E   77                  MOV    M,A          ;                                     ///
27 1C8F   23                  INX    H            ;                                     ///
28 1C90   3A   70C7           LDA    RATUL        ;                                     ///
29 1C93   77                  MOV    M,A          ;                                     ///
30 1C94   3A   70C2           LDA    SATLL        ;SATURATION LOWER LIMIT               ///
31 1C97   CD   1D3B           CALL   SPLIT        ;INTO NIBBLES                         ///
32 1C9A   7A                  MOV    A,D          ;UPPER NIBBLE                         ///
33 1C9B   F6   40             ORI    40H          ;SAT LIMIT IDENTIFIER                 ///
34 1C9D   CD   1D22           CALL   TOBUFR       ;PUT IT INTO BUFFER                   ///
35 1CA0   7B                  MOV    A,E          ;AND LOWER NIBBLE                     ///
36 1CA1   CD   1D22           CALL   TOBUFR       ;                                     ///
37 1CA4   3A   70C6           LDA    RATLL        ;RATE LOWER LIMIT                     ///
38 1CA7   CD   1D3B           CALL   SPLIT        ;INTO TWO NIBBLES                     ///
39 1CAA   7A                  MOV    A,D          ;MSB'S                                ///
40 1CAB   CD   1D22           CALL   TOBUFR       ;                                     ///
41 1CAE   7B                  MOV    A,E          ;LSB'S                                ///
42 1CAF   CD   1D22           CALL   TOBUFR       ;                                     ///
43 1CB2   3A   70C7           LDA    RATUL        ;RATE UPPER LIMIT                     ///
44 1CB5   CD   1D3B           CALL   SPLIT        ;INTO NIBBLES                         ///
45 1CB8   7A                  MOV    A,D          ;MSB'S                                ///
46 1CB9   CD   1D22           CALL   TOBUFR       ;                                     ///
47 1CBC   7B                  MOV    A,E          ;LSB'S                                ///
48 1CBD   F6   70             ORI    70H          ;END OF MESSAGE IDENTIFIER            ///
49 1CBF   CD   1D22           CALL   TOBUFR       ;                                     ///
50 1CC2   C9                  RET                 ;                                     ///
51
52 1CC3   11   E74A   COM240: LXI    D,-(NULMOD+1) ;SEE IF CHARACTER IN PROGRESS        ///
53 1CC6   2A   72AA           LHLD   SNDMOD       ;                                     ///
54 1CC9   19                  DAD    D            ;IF SNDMOD > NULMOD THEN BUG OFF      ///
55 1CCA   D8                  RC                  ;                                     ///
56
57 1CCB   3A   72A8           LDA    CPLSFL       ;IS PULSE SAMPLE GOING OUT ?          ///
 1 1CCE   FE   01             CPI    1            ;                                     ///
 2 1CD0   C2   1CDE           JNZ    RDYCHK       ;NO, THEN GO SEE IF ONE IS READY TO   ///
 3 1CD3   3A   7282           LDA    PLS2         ;YES, THEN GET THE SECOND HALF OF IT  ///
 4 1CD6   CD   1D12           CALL   SENDIT       ;AND SEND IT IMMEDIATELY              ///
 5 1CD9   AF                  XRA    A            ;AND CLEAR THE PULSE IN PROGRESS FLAG ///
 6 1CDA   32   72A8           STA    CPLSFL       ;                                     ///
 7 1CDD   C9                  RET                 ;                                     ///
 8
 9 1CDE   FE   02     RDYCHK: CPI    2            ;SAMPLE READY ?                       ///
10 1CE0   C2   1CEE           JNZ    BUFCHK       ;NO, THEN GO CHECK THE BUFFER         ///
11 1CE3   3D                  DCR    A            ;YES, THEN SET PULSE GOING FLAG       ///
12 1CE4   32   72A8           STA    CPLSFL       ;                                     ///
13 1CE7   3A   7281           LDA    PLS1         ;GET TOP HALF OF MESSAGE              ///
14 1CEA   CD   1D12           CALL   SENDIT       ;SEND IT OUT                          ///
15 1CED   C9                  RET                 ;                                     ///
16
17 1CEE   2A   7283   BUFCHK: LHLD   LSTOUT       ;HAS LAST IN BEEN SENT ?              ///
18 1CF1   7D                  MOV    A,L          ;I.E. LSTOUT=BUFPTR ?                 ///
```

```
 19 1CF2  2F                   CMA                        ;                                              ///
 20 1CF3  6F                   MOV     L,A                ;                                              ///
 21 1CF4  7C                   MOV     A,H                ;                                              ///
 22 1CF5  2F                   CMA                        ;                                              ///
 23 1CF6  67                   MOV     H,A                ;                                              ///
 24 1CF7  23                   INX     H                  ;TWO'S COMPLEMENT                              ///
 25 1CF8  EB                   XCHG                       ;                                              ///
 26 1CF9  2A   7285            LHLD    BUFPTR             ;GET BUFFER POINTER                            ///
 27 1CFC  19                   DAD     D                  ;POINTER=LAST ?                                ///
 28 1CFD  7C                   MOV     A,H                ;                                              ///
 29 1CFE  B5                   ORA     L                  ;                                              ///
 30 1CFF  C8                   RZ                         ;YES, THEN WE'RE CAUGHT UP, GO AWAY !          ///
 31                                                                                                      
 32 1D00  2A   7283            LHLD    LSTOUT             ;NO, THEN GET CHARACTER TO GO                  ///
 33 1D03  7E                   MOV     A,M                ;GET CHARACTER                                 ///
 34 1D04  CD   1D12            CALL    SENDIT             ;PUT IT OUT                                    ///
 35 1D07  2A   7283            LHLD    LSTOUT             ;                                              ///
 36 1D0A  CD   1D2D            CALL    BMPBUF             ;BUMP THE POINTER                              ///
 37 1D0D  22   7283            SHLD    LSTOUT             ;FOR NEXT GO AROUND                            ///
 38 1D10  7E                   MOV     A,M                ;GET CHARACTER                                 ///
 39 1D11  C9                   RET                        ;                                              ///
 40                                                                                                      
 41 1D12  A7           SENDIT: ANA     A                  ;MAKE SURE PARITY BIT IS OK                    ///
 42 1D13  EA   1D18            JPE     STKCHR             ;                                              ///
 43 1D16  F6   80               ORI    80H                ;NO, THEN SET IT                               ///
 44 1D18  32   72A9    STKCHR: STA    CHAR                ;SET IT INTO THE CANNON                        ///
 45 1D1B  21   18B8            LXI     H,STARTS           ;AND LIGHT THE FUSE TO SEND THE SERIAL         ///
 46 1D1E  22   72AA            SHLD    SNDMOD             ;                                              ///
 47 1D21  C9                   RET                        ;                                              ///
 48                                                                                                      
 49 1D22  2A   7285    TOBUFR: LHLD    BUFPTR             ;GET BUFFER POINTER                            ///
 50 1D25  77                   MOV     M,A                ;STORE CHARACTER                               ///
 51 1D26  CD   1D2D            CALL    BMPBUF             ;BUMP HL WITH WRAP-AROUND                      ///
 52 1D29  22   7285            SHLD    BUFPTR             ;AND UPDATE BUFFER POINTER                     ///
 53 1D2C  C9                   RET                        ;                                              ///
 54                                                                                                      
 55 1D2D  23           BMPBUF: INX     H                  ;BUMP HL PAIR                                  ///
 56 1D2E  E5                   PUSH    H                  ;SAVE HE                                       ///
 57 1D2F  D5                   PUSH    D                  ;SAVE FROM CALCULATION                         ///
  1 1D30  11   8D59            LXI     D,-BUFTOP          ;SEE IF OVER THE TOP                           ///
  2 1D33  19                   DAD     D                  ;                                              ///
  3 1D34  D1                   POP     D                  ;RESTORE REGGIES                               ///
  4 1D35  E1                   POP     H                  ;                                              ///
  5 1D36  D0                   RNC                        ;IF NOT, THEN HL IS OK AS IS                   ///
  6 1D37  21   7287            LXI     H,COMBUF           ;NO, THEN WRAP-AROUND                          ///
  7 1D3A  C9                   RET                        ;                                              ///
  8                                                                                                      
  9 1D3B  F5           SPLIT:  PUSH    PSW                ;SAVE IT                                       ///
 10 1D3C  E6   0F               ANI    0FH                ;STRIP OFF MSB'S                               ///
 11 1D3E  5F                   MOV     E,A                ;STICK LSB'S INTO E                            ///
 12 1D3F  F1                   POP     PSW                ;RETRIEVE IT                                   ///
 13 1D40  0F                   RRC                        ;                                              ///
 14 1D41  0F                   RRC                        ;                                              ///
 15 1D42  0F                   RRC                        ;                                              ///
 16 1D43  0F                   RRC                        ;                                              ///
 17 1D44  E6   0F               ANI    0FH                ;GET MSB'S AND STRIP LSB'S                     ///
 18 1D46  57                   MOV     D,A                ;AND PUT MSB'S INTO D                          ///
 19 1D47  C9                   RET                        ;                                              ///
 20                                                                                                      
 21                                                                                                      
  1                            ;CHECK LED LEVELS, CALLED BY A/D CONVERSION ROUTINE
  2                            ;    WITH DATA IN D,E...
  3                            ;    DECREASE LED LEVEL IS DATA IS OVERFLOWED, AND INCREASE IT IF UNDERFLOWED.
  4                            ;
  5                                                                                                      
  6 1D48  3A   7011    CKLED1: LDA     INHLED             ;CHECK INHIBIT FLAG
  7 1D4B  FE   02              CPI     2
  8 1D4D  F0                   RP                         ;SET, NO CHECK
  9 1D4E  3A   7007            LDA     TSTMOD
 10 1D51  E6   08              ANI     8
 11 1D53  C0                   RNZ
 12 1D54  21   700C            LXI     H,L1ITMR           ;LED LEVEL CODE
 13 1D57  7E                   MOV     A,M                ;GET TIMER
 14 1D58  B7                   ORA     A
 15 1D59  2B                   DCX     H
 16 1D5A  2B                   DCX     H
 17 1D5B  C0                   RNZ                        ;STILL TIMING FROM LAST TIME, NO CHECK
 18 1D5C  7B                   MOV     A,E
 19 1D5D  B2                   ORA     D                  ;CHECK DATA FOR ZERO
 20 1D5E  C2   1D81            JNZ     2$
 21 1D61  34                   INR     M                  ;INCREMENT
 22 1D62  7E                   MOV     A,M                ;FETCH IT
 23 1D63  B7                   ORA     A                  ;WRAP AROUND TO 64
 24 1D64  C2   1D6C            JNZ     5$
 25 1D67  32   7013            STA     LGFLAG             ;OVERFLOWED, SO ALLOW EITHER GAIN
 26 1D6A  36   40              MVI     M,64
 27 1D6C  3A   7013    5$:     LDA     LGFLAG             ;IF LGFLAG<>64, STAY IN LOW GAIN
 28 1D6F  B7                   ORA     A
 29 1D70  C2   1D9B            JNZ     3$
 30 1D73  7E                   MOV     A,M
 31 1D74  FE   E0              CPI     224                ;COMPARE LED1 TO 224
 32 1D76  DA   1D9B            JC      3$                 ;STILL OK, NO GAIN CHANGE
 33 1D79  3E   01              MVI     A,1                ;RAISE GAIN
 34 1D7B  32   7012            STA     GNSEL
 35 1D7E  C3   1D9B            JMP     3$
 36 1D81  7A           2$:     MOV     A,D
```

```
37 1D82  F6          FO              ORI    0F0H
38 1D84  A3                          ANA    E              ;CHECK FOR ALL 1'S
39 1D85  3C                          INR    A
40 1D86  C2          1D9E            JNZ    4$
41 1D89  35                          DCR    M
42 1D8A  7E                          MOV    A,M            ;FETCH LED CODE
43 1D8B  FE          40              CPI    64             ;WRAP AROUND FROM 64 TO 255
44 1D8D  D2          1D92            JNC    6$
45 1D90  36          FF              MVI    M,255
46 1D92  FE          60       6$:    CPI    96             ;96 IS LOWER LIMIT
47 1D94  D2          1D9B            JNC    3$             ;STILL FINE
48 1D97  AF                          XRA    A              ;CUT GAIN
49 1D98  32          7012            STA    GNSEL
50 1D9B  CD          1DF6     3$:    CALL   LD1SET
51 1D9E  C9                   4$:    RET
52 1D9F  3A          7011   CKLED2:  LDA    INHLED
53 1DA2  FE          02              CPI    2
54 1DA4  F0                          RP
55 1DA5  3A          7007            LDA    TSTMOD
56 1DA8  E6          08              ANI    8
57 1DAA  C0                          RNZ
 1 1DAB  21          700F            LXI    H,L2ITMR
 2 1DAE  7E                          MOV    A,M
 3 1DAF  B7                          ORA    A
 4 1DB0  2B                          DCX    H
 5 1DB1  2B                          DCX    H
 6 1DB2  C0                          RNZ
 7 1DB3  7A                          MOV    A,D
 8 1DB4  B3                          ORA    E
 9 1DB5  C2          1DD8            JNZ    2$
10 1DB8  34                          INR    M
11 1DB9  7E                          MOV    A,M
12 1DBA  B7                          ORA    A
13 1DBB  C2          1DC3            JNZ    5$
14 1DBE  32          7013            STA    LGFLAG
15 1DC1  36          40              MVI    M,64
16 1DC3  3A          7013     5$:    LDA    LGFLAG
17 1DC6  B7                          ORA    A
18 1DC7  C2          1DF2            JNZ    3$
19 1DCA  7E                          MOV    A,M
20 1DCB  FE          E0              CPI    224
21 1DCD  DA          1DF2            JC     3$
22 1DD0  3E          01              MVI    A,1
23 1DD2  32          7012            STA    GNSEL
24 1DD5  C3          1DF2            JMP    3$
25 1DD8  7A                   2$:    MOV    A,D
26 1DD9  F6          F0              ORI    0F0H
27 1DDB  A3                          ANA    E
28 1DDC  3C                          INR    A
29 1DDD  C2          1DF5            JNZ    4$
30 1DE0  35                          DCR    M
31 1DE1  7E                          MOV    A,M
32 1DE2  FE          40              CPI    64
33 1DE4  D2          1DE9            JNC    6$
34 1DE7  36          FF              MVI    M,255
35 1DE9  FE          60       6$:    CPI    96
36 1DEB  D2          1DF2            JNC    3$
37 1DEE  AF                          XRA    A
38 1DEF  32          7012            STA    GNSEL
39 1DF2  CD          1E05     3$:    CALL   LD2SET
40 1DF5  C9                   4$:    RET
 1
 2                                   ;COMPUTE VOLTAGE FROM LED CODE AND OUTPUT...
 3                                   ;   CALLED WHENEVER LED CODE CHANGES, DOES A QUASI-LOG CONVERSION TO VOLTS.
 4                                   ;
 5 1DF6  21          700A   LD1SET:  LXI    H,LED1         ;POINT TO LED CODE
 6 1DF9  7E                          MOV    A,M            ;GET IT
 7 1DFA  23                          INX    H
 8 1DFB  BE                          CMP    M              ;COMPARE TO LAST CODE
 9 1DFC  C8                          RZ                    ;SAME, RETURN
10 1DFD  77                          MOV    M,A
11 1DFE  CD          1E14            CALL   LDXSET         ;NOT THE SAME, UPDATE
12 1E01  22          715F            SHLD   VLED1
13 1E04  C9                          RET
14
15 1E05  21          700D   LD2SET:  LXI    H,LED2
16 1E08  7E                          MOV    A,M
17 1E09  23                          INX    H
18 1E0A  BE                          CMP    M              ;COMPARE TO LAST CODE
19 1E0B  C8                          RZ                    ;SAME, RETURN
20 1E0C  77                          MOV    M,A
21 1E0D  CD          1E14            CALL   LDXSET
22 1E10  22          7161            SHLD   VLED2
23 1E13  C9                          RET
24
25 1E14  D5                 LDXSET:  PUSH   D
26 1E15  4E                          MOV    C,M            ;GET LED CODE
27 1E16  23                          INX    H
28 1E17  3A          7010            LDA    INHPER
29 1E1A  77                          MOV    M,A            ;SET INHIBIT PERIOD
30 1E1B  3A          7014            LDA    SYNFLG         ;CHECK FOR SYNC
31 1E1E  B7                          ORA    A
32 1E1F  CA          1E24            JZ     3$             ;GO FAST IF NOT
33 1E22  36          01              MVI    M,1
34 1E24  21          1E3F     3$:    LXI    H,LEDTBL-3     ;CONVERSION TABLE
35 1E27  23                   1$:    INX    H
```

```
36 1E28    23                      INX    H              ;MOVE TO 1ST TABLE ENTRY
37 1E29    23                      INX    H
38 1E2A    79                      MOV    A,C            ;GET CODE
39 1E2B    96                      SUB    M              ;-FACTOR
40 1E2C    23                      INX    H              ;PUINT TO INCREMENT
41 1E2D    DA   1E27               JC     1$             ;CODE LESS THAN FACTOR, KEEP LOOKING
42 1E30    4E                      MOV    C,M            ;GET INCREMENT
43 1E31    06   00                 MVI    B,0
44 1E33    23                      INX    H
45 1E34    5E                      MOV    E,M
46 1E35    23                      INX    H
47 1E36    56                      MOV    D,M
48 1E37    EB                      XCHG
49 1E38    3D            2$:       DCR    A
50 1E39    FA   1E40               JM     10$
51 1E3C    09                      DAD    B
52 1E3D    C3   1E38               JMP    2$
53 1E40    D1            10$:      POP    D
54 1E41    C9                      RET

;TABLE OF LED CODE VALUES, INCREMENTS AND BASE VOLTAGES
;IF LED CODE>TABLE CODE, THEN MULT. DIFF BY INCREMENT AND ADD TO BASE
;
 1 1E42    E0   40       LEDTBL:   DB     224,64
 2 1E44    0800                    DW     2048
 3 1E46    C0   20                 DB     192,32
 4 1E48    0400                    DW     1024
 5 1E4A    A0   10                 DB     160,16
 6 1E4C    0200                    DW     512
 7 1E4E    80   08                 DB     128,8
 8 1E50    0100                    DW     256
 9 1E52    60   04                 DB     96,4
10 1E54    0080                    DW     128
11 1E56    40   02                 DB     64,2
12 1E58    0040                    DW     64
13 1E5A    00   01                 DB     0,1
14 1E5C    0000                    DW     0

;A/D CONVERSION ROUTINE....
;CALLED WITH MUX SELECTED, RETURNS DATA IN D,E
;H,L PRESERVED
;
 6 1E5E    AF            ADCVT:    XRA    A
 7 1E5F    D3   00                 OUT    DACL           ;CLEAR LOW BYTE
 8 1E61    57                      MOV    D,A
 9 1E62    3A   72AF               LDA    GNMSK
10 1E65    5F                      MOV    E,A            ;GET GAIN SEL INTO E AND ADD TO DACH
11 1E66    06   08                 MVI    B,08H          ;MSB
12 1E68    16   00                 MVI    D,0
13 1E6A    78                      MOV    A,B            ;GET NEXT BIT TO BE CHECKED
14 1E6B    B2            1$:       ORA    D
15 1E6C    B3                      ORA    E
16 1E6D    F6   70                 ORI    070H           ;MASK OFF ANAOLOG OUTPUT
17 1E6F    D3   01                 OUT    DACH           ;TRY IT
18 1E71    4F                      MOV    C,A            ;HIGH BYTE W/NEW BIT (D = HIGH BYTE W/O)
19 1E72    00                      NOP                   ;SETTLING TIME
20 1E73    00                      NOP
21 1E74    00                      NOP
22 1E75    DB   00                 IN     STSREG
23 1E77    17                      RAL                   ;COMP. FLAG TO CARRY
24 1E78    DA   1E7C               JC     2$             ;ONE MEANS DAC IS LOWER
25 1E7B    51                      MOV    D,C
26 1E7C    78            2$:       MOV    A,B
27 1E7D    0F                      RRC
28 1E7E    47                      MOV    B,A            ;SHIFT BIT RIGHT ONE PLACE, CHECK FOR
                                                         ;   FALLING OFF BOTTOM
29 1E7F    D2   1E6B               JNC    1$
;
;NOW DO SAME THING FOR LOW BYTE...LEAVE HIGH BYTE SET
;
33 1E82    7A                      MOV    A,D
34 1E83    B3                      ORA    E
35 1E84    F6   70                 ORI    070H
36 1E86    D3   01                 OUT    DACH           ;LAST HI BYTE VALUE
37 1E88    E6   0F                 ANI    0FH            ;STRIP OFF GAIN STUFF FROM DAC DATA
38 1E8A    57                      MOV    D,A
39 1E8B    0E   80                 MVI    C,80H
40 1E8D    1E   00                 MVI    E,0
41 1E8F    79                      MOV    A,C            ;NEW BIT
42 1E90    B3            3$:       ORA    E              ;PLUS LOW BYTE SO FAR...
43 1E91    D3   00                 OUT    DACL
44 1E93    47                      MOV    B,A            ;SAVE LOW BYTE W/ NEW BIT
45 1E94    00                      NOP
46 1E95    00                      NOP
47 1E96    00                      NOP
48 1E97    DB   00                 IN     STSREG         ;GET COMP. FLAG
49 1E99    17                      RAL
50 1E9A    DA   1E9E               JC     4$
51 1E9D    58                      MOV    E,B            ;UPDATE LOW BYTE
52 1E9E    79            4$:       MOV    A,C            ;NEW BIT
53 1E9F    0F                      RRC
54 1EA0    4F                      MOV    C,A
55 1EA1    D2   1E90               JNC    3$
56 1EA4    C9                      RET
```

```
                        ;CALIBRATION TABLES.....
                        ; FIRST A TABLE OF RESISTOR CODES AND BETA INDICES, TO MAP RESISTANCE INTO AN INDEX
                        ;   INDEX = 65536*1.5*R/(10+R), R IN K-OHMS
                        ;
1EA5   3232             CALTBL: DW      12850           ;1500 OHMS

1EA7   91B6                     DW      37302           ;64
1EA9   93E9                     DW      37865
1EAB   9611                     DW      38417
1EAD   9842                     DW      38978
1EAF   9A79                     DW      39545
1EB1   9CB7                     DW      40119
1EB3   9EFA                     DW      40698
1EB5   A133                     DW      41267
1EB7   A370                     DW      41840
1EB9   A5B2                     DW      42418
1EBB   A7F7                     DW      42999
1EBD   AA40                     DW      43584
1EBF   AC7D                     DW      44157
1EC1   AEBC                     DW      44732
1EC3   B10C                     DW      45324
1EC5   B35D                     DW      45917
1EC7   B5AF                     DW      46511
1EC9   B800                     DW      47104
1ECB   BA44                     DW      47684
1ECD   BC88                     DW      48264
1ECF   BED7                     DW      48855

1ED1   0000                     DW      0

;TABLE OF IR BETA CONSTANTS...
                        ;
1ED3   3C66   2833     BATBL:   DW      15462,  10291   ;NOMINAL ( 302,201 )
1ED7   2966   7333              DW      10598,  29491

;RED BETA CONSTANTS...
                        ;
1EDB   1933   BD9A     BBTBL:   DW      6451,   48538   ;0 = NOMINAL ( 126,948 )
1EDF   129A   BC0D              DW      4762,   48141   ;1 = 670NM
1EE3   129A   C05C              DW      4762,   49244
1EE7   12CD   C4AB              DW      4813,   50347
1EEB   12CD   C8FA              DW      4813,   51450
1EEF   1300   CCC7              DW      4864,   52423
1EF3   1300   D116              DW      4864,   53526
1EF7   1333   D4A2              DW      4915,   54434
1EFB   1333   D7EE              DW      4915,   55278
1EFF   1366   DAF8              DW      4966,   56056
1F03   1366   DDC2              DW      4966,   56770
1F07   139A   E04B              DW      5018,   57419
1F0B   13CD   E293              DW      5069,   58003
1F0F   1400   E4B8              DW      5120,   58552
1F13   1433   E660              DW      5171,   58976
1F17   1466   E7E5              DW      5222,   59365
1F1B   149A   E929              DW      5274,   59689
1F1F   14CD   E9EC              DW      5325,   59884
1F23   1500   EAAF              DW      5376,   60079
1F27   1533   EB30              DW      5427,   60208
1F2B   1566   EBF3              DW      5478,   60403
1F2F   15CD   ECF7              DW      5581,   60663   ;21 = 650NM

;DATA SPACE.....
                        ;
                        ;FIRST, THE INITIALIATION LIST....ADDRESS FOLLOWED BY A BYTE OF
                        ;   DATA, ZERO TERMINATES...
                        ;
1F33   7000             INILST: DW      VERCOD
1F35   5E                       DB      VERSN
1F36   00                       DB      0

1F37   70C1                     DW      SATLLL
1F39   32                       DB      50
1F3A   55                       DB      85              ;SATLL
1F3B   64                       DB      100
1F3C   64                       DB      100
1F3D   28                       DB      40
1F3E   37                       DB      55              ;RATLL
1F3F   8C                       DB      140             ;RATUL
1F40   FA                       DB      250
1F41   00                       DB      0

1F42   716F                     DW      FMODLL
1F44   01                       DB      1               ;FMODE LIMIT
1F45   01                       DB      1
1F46   09                       DB      9
1F47   00                       DB      0

1F48   7014                     DW      SYNFLG
1F4A   04                       DB      4               ;SYNC INHIBIT COUNT
1F4B   00                       DB      0

1F4C   7017                     DW      HSTLEN
1F4E   04    00                 DB      4,0
```

```
34  1F50   7018          DW    VARLIM          ;VARIATION AND DIFF LIMITS
35  1F52   06            DB    6               ;RATE VAR
36  1F53   06            DB    6               ;AMPLITUDE
37  1F54   03            DB    3               ;RATIO
38  1F55   03            DB    3               ;TIME WINDOW
39  1F56   06            DB    6               ;EKG
40  1F57   06            DB    6               ;RESP
41  1F58   04            DB    4
42  1F59   04            DB    4
43  1F5A   02            DB    2
44  1F5B   02            DB    2
45  1F5C   04            DB    4
46  1F5D   06            DB    6
47  1F5E   00            DB    0
48
49  1F5F   70D7          DW    SPLEN           ;SLOPE SPAN
50  1F61   03            DB    3
51  1F62   14            DB    20              ;NOISE GATE
52  1F63   20            DB    32              ;SLOPE THRESHHOLD
53  1F64   00            DB    0
54
55  1F65   70EC          DW    BEEVOL
56  1F67   14            DB    20              ;BEEVOL
57  1F68   64            DB    100
 1  1F69   00            DB    0
 2
 3  1F6A   70FA          DW    POLEKG          ;EKG POLARITY
 4  1F6C   01            DB    1
 5  1F6D   00            DB    0
 6  1F6E   70FB          DW    POLEKG+1
 7  1F70   01            DB    1
 8  1F71   00            DB    0
 9
10  1F72   70F3          DW    ALILL
11  1F74   1E    3C      DB    30, 60, 121, 0
    1F76   79    00
12
13  1F78   713E          DW    OPNDLY
14  1F7A   08            DB    8
15  1F7B   00            DB    0
16
17  1F7C   7138          DW    OPNPRM
18  1F7E   70EC          DW    BEEVOL
19  1F80   00            DB    0
20
21  1F81   713C          DW    OPNUL
22  1F83   64            DB    100
23  1F84   00            DB    0
24
25  1F85   7010          DW    INHPER
26  1F87   06            DB    6
27  1F88   00            DB    0
28
29  1F89   7173          DW    RAMIDX+1
30  1F8B   70            DB    HIGH(RAMOKG)
31  1F8C   00            DB    0
32
33  1F8D   70EF          DW    ALHVOL
34  1F8F   28            DB    40
35  1F90   00            DB    0
36
37  1F91   70FD          DW    GNEKG           ;EKG GAIN
38  1F93   03            DB    3
39  1F94   FF            DB    255
40  1F95   00            DB    0
41
42  1F96   7106          DW    EKGSNC          ;EKG SYNC FLAG- RESET ONCE
43  1F98   01            DB    1               ;IF RESET, THEN EKG WAS USED AT SOME POINT
44  1F99   00            DB    0
45
46  1F9A   7111          DW    RSPSNC          ;SYNC FOR RESP - SAME AS EKG
47  1F9C   01            DB    1
48  1F9D   00            DB    0
49
50  1F9E   7104          DW    SN2DLY          ;EKG SYNC DELAY
51  1FA0   05            DB    5
52  1FA1   00            DB    0
53
54  1FA2   7112          DW    SN3DLY          ;RESP SYNC DELAY
55  1FA4   02            DB    2
56  1FA5   00            DB    0
 1
 2  1FA6   700A          DW    LED1            ;START LED CODES AT 64
 3  1FA8   40            DB    64
 4  1FA9   00            DB    0
 5
 6  1FAA   700D          DW    LED2
 7  1FAC   40            DB    64
 8  1FAD   00            DB    0
 9
10  1FAE   716D          DW    VTH             ;R-WAVE COMPARATOR VOLTAGE = 5.25V
11  1FB0   67            DB    103             ;= 2151 = 5.25V
12  1FB1   08            DB    8
13  1FB2   00            DB    0
14
```

```
15 1FB3  0000              DW    0              ;PATCH SPACE
16 1FB5  00                DB    0
17 1FB6  0000              DW    0
18 1FB8  00                DB    0
19 1FB9  0000              DW    0              ;TERMINATOR
20
21
22                 ;FILL ROM WITH ZERO'S...
23
24       0045              REPT  2000H-$
25                         DB    0
26                         ENDR 1
 2       7000              RAMORG  EQU   7000H    ;ORIGIN...
 3       0400              RAMLEN  EQU   0400H    ;AND LENGTH
 4
 5       7000              ORG     RAMORG
 6
 7                 ;VERSION CODE...FIRST BYTE
 8
 9 7000  00        VERCOD: DB    0
10
11                 ;FILTERED DATA AND PARAMETERS
12
13 7001  00        SAT:    DB    0              ;SATURATION
14 7002  00        FSAT:   DB    0              ;FILTERED SAT.
15 7003  00        RATE:   DB    0              ;PULSE RATE
16 7004  00        FRATE:  DB    0              ;FILTERED RATE
17
18 7005  00        FSATN:  DB    0              ;'N' COUNT FOR SAT FILTER
19 7006  00        FRATN:  DB    0              ;SAME FOR RATE
20
21 7007  00        TSTMOD: DB    0              ;TEST FLAGS: 1=XX.X, 2=NO FILTER, 4=NO CAL, 8=NO LED SET
22
23 7008  00        CALOK:  DB    0              ;1 = CALIBRATION STABLE
24 7009  00        CALIDX: DB    0              ;CALIBRATION INDEX
25
26                 ;LED LEVELS
27
28 700A  00        LED1:   DB    0              ;LED CODE
29 700B  00        LED1SV: DB    0              ;OLD LED CODE
30 700C  00        L1ITMR: DB    0              ;LED CURRENT-CHANGING INHIBIT FLAG
31 700D  00        LED2:   DB    0
32 700E  00        LED2SV: DB    0
33 700F  00        L2ITMR: DB    0
34 7010  00        INHPER: DB    0              ;INHIBIT PERIOD (A CONSTANT)
35 7011  00        INHLED: DB    0              ;SET NON-ZERO TO INHIBIT LED TWEAKING
36 7012  00        GNSEL:  DB    0              ;GAIN SELECT
37 7013  00        LGFLAG: DB    0              ;HI GAIN INHIBIT FLAG
38
39                 ;SOME LEVEL3 STUFF:
40
41 7014  00        SYNFLG: DB    0              ;COUNTED DOWN TO ZERO FOR PULSE SYNC (BY LEVEL3)
42 7015  00        CURVAR: DB    0              ;CURRENT VARIATION FLAGS
43 7016  00        CURDIF: DB    0              ;DIFFERENCE FLAGS
44 7017  00        HSTLEN: DB    0              ;CURRENT HISTORY LENGTH
45 7018  00  00    VARLIM: DB    0,0,0,0,0,0    ;VARIATION LIMITS
   701A  00  00
   701C  00  00
46 701E  00  00    DIFLIM: DB    0,0,0,0,0,0    ;DIFFERENCE LIMITS
   7020  00  00
   7022  00  00
47 7024  00  00            DB    0,0            ;FILL....
48
49                 ;HISTORY BUFFERS.....
50
51 7026            HSTBUF:
52       0014              HSTINC  EQU   20
53       000F              HSTMAX  EQU   HSTINC-5
 1 7026  00        PERIOD: DB    0
 2 7027  00        PERDIF: DB    0
 3 7028  00        PERAVG: DB    0
 4 7029  00        PERVAR: DB    0
 5 702A            PERHST: BLKB  HSTMAX+1
 6
 7 703A  00        CURAMP: DB    0
 8 703B  00        AMPDIF: DB    0
 9 703C  00        AMPAVG: DB    0
10 703D  00        AMPVAR: DB    0
11 703E            AMPHST: BLKB  HSTMAX+1
12
13 704E  00        CURRAT: DB    0
14 704F  00        RATDIF: DB    0
15 7050  00        RATAVG: DB    0
16 7051  00        RATVAR: DB    0
17 7052            RATHST: BLKB  HSTMAX+1
18
19 7062  00        PLSDLY: DB    0
20 7063  00        DLYDIF: DB    0
21 7064  00        DLYAVG: DB    0
22 7065  00        DLYVAR: DB    0
23 7066            DLYHST: BLKB  HSTMAX+1
24
25 7076            EKGHBF:
26 7076  00        RRPER:  DB    0
27 7077  00        RRDIF:  DB    0
```

```
28 7078    00              RRAVG:  DB      0
29 7079    00              RRVAR:  DB      0
30 707A                    RRHST:  BLKB    HSTMAX+1
31
32 708A                    RSPHBF:
33 708A    00              RSPPER: DB      0
34 708B    00              RSPDIF: DB      0
35 708C    00              RSPAVG: DB      0
36 708D    00              RSPVAR: DB      0
37 708E                    RSPHST: BLKB    HSTMAX+1
38
39                         ;DATA PARAMETERS...
40
41 709E    00              DATFLG: DB      0       ;DATA-READY FLAG (SET BY MUNCH)
42 709F    0000            MAX1:   DW      0       ;WAVEFORM MAX - CH.1 (IR)
43 70A1    0000            MIN1:   DW      0
44 70A3    0000            MAX2:   DW      0
45 70A5    0000            MIN2:   DW      0
46 70A7    0000            MXSLOP: DW      0       ;MAX SLOPE, CH.1
47
48 70A9    0000            RATRAT: DW      0
49 70AB    0000            ARAT:   DW      0
50 70AD    0000            BRAT:   DW      0
51 70AF    0000            FRATIO: DW      0
52 70B1    0000            XRATIO: DW      0
53
54 70B3    00              PERCTR: DB      0       ;PERIOD COUNTER, INCREMENTED BY MUNCH, RESET BY LEVEL3
55
56 70B4    00              SYNDLY: DB      0       ;DELAY FOR FILTERING
57 70B5    00              BPCTR:  DB      0       ;BAD PULSE COUNTER
 1 70B6    00              NCHFLG: DB      0       ;NOTCH COUNTER
 2
 3 70B7    0000            SATX:   DW      0
 4 70B9    0000            FSATX:  DW      0
 5 70BB    0000            FSATAC: DW      0
 6 70BD    00              FSATDP: DB      0
 7 70BE    0000            FRATX:  DW      0
 8 70C0    00              XMPY:   DB      0
 9
10
11 70C1    00              SATLLL: DB      0       ;SAT LOWER LIMIT LIMIT
12 70C2    00              SATLL:  DB      0       ;SATURATION ALARM LOWER LIMIT
13 70C3    00              SATUL:  DB      0
14 70C4    00              SATULL: DB      0       ;UPPER LIMIT LIMIT
15 70C5    00              RATLLL: DB      0       ;RATE LOWER LIMIT LIMIT
16 70C6    00              RATLL:  DB      0       ;PULSE RATE LOWER LIMIT
17 70C7    00              RATUL:  DB      0       ;DITTO UPPER LIMIT
18 70C8    00              RATULL: DB      0       ;UPPER LIMIT LIMIT
19 70C9    00              ALMFLG: DB      0       ;ALARM FLAG BITS (SALBIT, RALBIT)
20 70CA    00              STATUS: DB      0       ;STATUS REGISTER FOR LEADS OFF BIT
21
22                         ;PULSE PARAMETERS...
23
24 70CB    00              MCHMOD: DB      0
25 70CC    0000            PLSMX1: DW      0       ;CURRENT MAX - CH. 1
26 70CE    0000            PLSMN1: DW      0       ;CURRENT CH.1 MIN
27 70D0    0000            PLSSLP: DW      0       ;MAX SLOPE - CH.1
28 70D2   -0000            PLSMX2: DW      0       ;CH.2 MAX/MIN
29 70D4    0000            PLSMN2: DW      0
30 70D6    00              MAXIDX: DB      0
31
32 70D7    00              SPLEN:  DB      0       ;SLOPE SPAN (# POINTS, ODD)
33 70D8    00              NOISE:  DB      0       ;NOISE GATE
34 70D9    0000            PLSTHD: DW      0       ;PULSE THRESHHOLD
35 70DB    00              ERRCOD: DB      0       ;ERROR CODE
36 70DC    0000            OLDMAX: DW      0       ;LAST MAX CODE (FOR BLIP)
37 70DE    00              BLPIDX: DB      0       ;DATA BUFFER INDEX FOR BLIP
38
39 70DF    0000            B01:    DW      0       ;BETA CONSTANTS
40 70E1    0000            BR1:    DW      0
41 70E3    0000            B02:    DW      0
42 70E5    0000            BR2:    DW      0
43 70E7    00              CALFLG: DB      0       ;COUNT-DOWN FLAG
44 70E8    0000            CALRES: DW      0       ;RESISTOR CODE (CAL/REF)
45
46                         ;BEEPER PARAMETERS...
47
48 70EA    00              BEECNT: DB      0       ;BEEP TIMER (1/60'S SEC, CONTINUOUS IF MINUS)
49 70EB    00              BEEVLL: DB      0       ;LOWER LIMIT FOR BEEP VOL
50 70EC    00              BEEVOL: DB      0       ;NOMINAL VOLUME (NON-ALARM)
51 70ED    00              BEEVUL: DB      0       ;UPPER LIMIT
52 70EE    00              ALMVLL: DB      0       ;ALARM LOWER LIMIT
53 70EF    00              ALMVOL: DB      0       ;ALARM VOLUME
54 70F0    00              ALMVUL: DB      0       ;ALARM UPPER LIMIT
55 70F1    00              ALIFLG: DB      0       ;ALARM INHIBIT FLAG
56 70F2    00              ALICTR: DB      0       ;ALARM INHIBIT TIMER
57
 1 70F3    00              ALILL:  DB      0       ;LOWER PERIOD LIMIT
 2 70F4    00              ALIPER: DB      0       ;ALARM INHIBIT TIMER PERIOD
 3 70F5    00              ALIUL:  DB      0       ;PERIOD UPPER LIMIT
 4
 5 70F6    00              ALMDLY: DB      0       ;DELAYED TIME-OUT ALARM
 6 70F7    00              ALCFLG: DB      0       ;ALARM-CHECKING FLAG
 7
 8                         ;               EKG STUFF
 9                         ;
```

```
10 70F8   00              EKGTMR: DB    0       ;EKG TIMEOUT COUNTER
11 70F9   00              POLCGL: DB    0       ;LOWER LIMIT FOR POLARIT
12 70FA   00              POLEKG: DB    0       ;POLARITY SETTING
13 70FB   00              POLCGH: DB    0       ;HIGH LIMIT
14 70FC   00              GNEKGL: DB    0       ;DITTO FOR GAIN
15 70FD   00              GNEKG:  DB    0
16 70FE   00              GNEKGH: DB    0
17 70FF   00              EKGPER: DB    0       ;R WAVE PERIOD COUNTER
18 7100   00              EKGFLG: DB    0       ;R WAVE FLAG
19 7101   00              POLSAV: DB    0       ;PRIOR POLARITY SETTING
20 7102   00              GAINSV: DB    0       ;PRIOR GAIN SETTING
21 7103   00              DLYEKG: DB    0       ;DELAY FOR CHANGING DATA
22 7104   00              SN2DLY: DB    0       ;EKG SYNC DELAY
23 7105   00              HRRFSH: DB    0       ;3 SEC TIMER FOR AUC GAIN REFRESH ONLY WHEN NO ECG
24 7106   00              EKGSNC: DB    0       ;EKG SYNC CONDITION FLAG
25 7107   00              BADEKG: DB    0       ; BAD EKG PULSE REJECT TICKETS
26 7108   00              DATTRG: DB    0       ;POINTER TO PULSE DATA TO SYNCRONIZE R-WAVE
27 7109   00              WINTMR: DB    0       ;TIMER FOR R-WAVE TO OPTICAL PULSE DELAY
28 710A   00              WINFLG: DB    0       ;FLAG TO STOP TIMING WHEN A PULSE IS FOUND
29 710B   00              RATCLK: DB    0       ;TIMEOUT COUNTER FOR RATE ANALOG OUTPUT
30 710C   00              SATCLK: DB    0       ;TIMEOUT COUNTER FOR SAT ANALOG OUTPUT
31 710D   00              LDSFLG: DB    0       ;LEADS OFF DETECTION FLAG
32
33         ;
34         ;   RESP STUFF
35         ;
36 710E   00              RSPCNT: DB    0       ;PERIOD COUNTER
37 710F   00              RSPTMR: DB    0       ;TIMEOUT COUNTER
38 7110   00              RSPFLG: DB    0       ;FLAG
39 7111   00              RSPSNC: DB    0       ;SYNC CONDITION FLAG
40 7112   00              SN3DLY: DB    0       ;SYNC DELAY BEFORE DISPLAYING PARAMS
41 7113   00              RESP:   DB    0       ;UNFILTERED RESP RATE
42 7114   00              FRSP:   DB    0       ;FILTERED RATE
43 7115   00              FRSPN:  DB    0       ;FILTER COEFFICIENT
44 7116   0000            FRSPX:  DW    0       ;OLD FILTERED DATA
45
46         ;DISPLAY PARAMETERS...
47
48 7118   00              DIGBNK: DB    0       ;DISPLAY BLINK BITS (1 = BLINK)
49 7119   00              INDBNK: DB    0       ;BLINK BITS FOR INDICATORS
50 711A   00              FSTBNK: DB    0       ;FAST BLINK BITS FOR DITTO
51 711B   00              DIGIDX: DB    0       ;DISPLAY BUFFER INDEX (3 BITS)
52 711C                   DIGBUF:               ;BUFFER...FIRST BYTE = DATA, 2ND = MASK BITS
53 711C   0000            DSPFD1: DW    0       ;UPPER DISPLAY, LSD
54 711E   0000                    DW    0
55 7120   0000                    DW    0
56 7122   0000            DSPFD2: DW    0
57 7124   0000                    DW    0
 1 7126   0000                    DW    0
 2 7128   0000            DSPMTL: DW    0       ;ANALOG METER, LOW BYTE
 3 712A   0000            DSPMTH: DW    0
 4 712C   0000            DSPLMP: DW    0       ;LAMP BITS
 5 712E   00              DSPBKF: DB    0       ;SET NON-ZERO FOR BLANK DISPLAY (BY TIME-OUT)
 6 712F   00              DSPOK:  DB    0       ;FLAG FOR SILENT RUNNING MODE
 7 7130   00              MODESV: DB    0       ;OLD FMODE - USED FOR RETURN FROM SILENT MODE
 8
 9         ;KNOB & BUTTON PARAMETERS...
10
11 7131   00              KNBFLG: DB    0       ;SET TO +/-1 TO SKIP NEXT STEP OF SAME DIRECTION
12 7132   00              KNBCTR: DB    0       ;KNOB UP/DOWN COUNT REQUEST
13 7133   00              BUTFIL: DB    0       ;BOUNCE FILTER
14 7134   00              BUTCOD: DB    0       ;BUTTON CODE (STORED BY INTERRUPT)
15 7135   00              BUTFLG: DB    0       ;BUTTON STORED FLAG ( "" )
16 7136   00              OLDBUT: DB    0       ;PREVIOUS BUTTON CODE
17 7137   00              NEWBUT: DB    0
18
19 7138   0000            OPNPRM: DW    0       ;POINTER TO OPEN PARAMETER
20 713A   00              OPNFLG: DB    0       ;SET NON-ZERO TO INHIBIT NORMAL DISPLAY
21 713B   00              OPNLL:  DB    0       ;LOWER LIMIT FOR ABOVE PARAMETER
22 713C   00              OPNUL:  DB    0       ;UPPER LIMIT
23 713D   00              OPNTMR: DB    0       ;TIMER FOR OPEN PARAM.
24 713E   00              OPNDLY: DB    0       ;NOMINAL TIME FOR ABOVE
25 713F   0000            ICELL:  DW    0       ;INDIRECT PARAMETER
26 7141   00              IFLG:   DB    0       ;1 = DIDDLE ADDRESS, 2 = DIDDLE CONTENTS
27 7142   0000            PRMFLD: DW    0       ;PARAMETER DISPLAY FIELD (DSPFD1 OR DSPFD2)
28
29
30         ;CLOCK STUFF...
31
32 7144   00              MSCTR:  DB    0       ;MILLISECOND COUNTER
33 7145   00              QSCFLG: DB    0       ;QUARTER-SECOND FLAG
34 7146   00              QSCCTR: DB    0       ;QUARTER-SECOND COUNTER
35 7147   00              MINCTR: DB    0       ;MINUTE COUNTER (0 TO 59)
36 7148   00              HRCTR:  DB    0       ;HOUR COUNTER
37 7149   00              PLSTMR: DB    0       ;PULSE TIME-OUT
38 714A   00              SATTMR: DB    0       ;SAT UPDATE TIME-OUT
39
40         ;MISC...
41
42 714B   00              ADIDX:  DB    0       ;A/D CONVERSION INDEX
43 714C   0000            V1:     DW    0       ;NON-OFFSET SIGNAL
44 714E   0000            V2:     DW    0
45 7150   0000            OFWSNS: DW    0       ;OVERFLOW SENSE
46 7152   0000            VCAL:   DW    0       ;CAL RESISTOR VOLTAGE
47 7154   0000            VTMP:   DW    0
48 7156   0000            VREF:   DW    0       ;CAL REFERENCE
49 7158   0000            VBAT:   DW    0       ;BATTERY VOLTAGE...
```

```
50 715A  0000              IDSP:   DW      0
51
52                         ;SAMPLE-HOLD OUTPUT STUFF...
53
54 715C  00                SHIDX:  DB      0       ;INDEX BIT
55 715D  0000              SHPTR:  DW      0       ;POINTER TO NEXT WORD
56 715F                    SHBUF:
57 715F  0000              VLED1:  DW      0       ;LED CONTROL VOLTAGES
 1                         ;STACK...
 2
 3       0040                      STCKLN  EQU     64      ;BYTES
 4
 5       73C0                      ORG     RAMORG+RAMLEN-STCKLN
 6
 7                                 BLKB    STCKLN
 8 7400                    STCK:
 9
10
11
12
13                                 END
 1 7161  0000              VLED2:  DW      0
 2 7163  0000              VBEEP:  DW      0       ;BEEPER CONTROL VOLTAGE
 3 7165  0000              VVOL:   DW      0       ;VOLUME
 4 7167  0000              VVOLSV: DW      0       ;SAVED VOLUME (FOR END OF COUNT)
 5 7169  0000              SATOUT: DW      0       ;ANALOG SAT OUT
 6 716B  0000              RATOUT: DW      0       ;RATE OUT
 7 716D  0000              VTH:    DW      0       ;R-WAVE COMPARATOR OUTPUT
 8
 9                         ;FILTER BUFFERS...
10
11 716F  00                FMODLL: DB      0       ;FILTER MODE LIMIT
12 7170  00                FMODE:  DB      0       ;FILTER MODE (1 = NORMAL, 2 = BETA-BEAT, 3 = SAT ONLY)
13 7171  00                FMODUL: DB      0
14
15 7172  0000              RAMIDX: DW      0
16 7174  0000              ROMIDX: DW      0
17 7176  00                ROMSUM: DB      0
18
19                         ;DATA INPUT BUFFER...
20
21       0100                      BUFLEN  EQU     256     ;64 SAMPLES...(APPROX 1 SEC)
22       00FF                      BUFMSK  EQU     BUFLEN-1
23 7177  00                DATCLK: DB      0       ;TIMER
24 7178  00                DATIDX: DB      0       ;BUFFER INDEX, USED BY INTERRUPT ROUTINE
25 7179  00                DTOIDX: DB      0       ;DATA OUT INDEX (USED BY MUNCH ROUTINE)
26 717A                    DATBUF: BLKB    BUFLEN          ;RING BUFFER, 4 BYTES PER 2-VALUE SAMPLE
27
28                         ; COMMUNICATIONS DATA STORAGE...
29
30 727A  00                OCOSTA: DB      0       ;OLD OXIMETER STATUS                      ///
31 727B  00                OCPSTA: DB      0       ;OLD ALARM (PATIENT) STATUS               ///
32 727C  00                COSTA:  DB      0       ;OXIMETER CURRENT STATUS                  ///
33 727D  00                CPSTA:  DB      0       ;ALARM (PATIENT) CURRENT STATUS           ///
34
35 727E  00                OSATLL: DB      0       ;OLD SATURATION LIMIT                     ///
36 727F  00                ORATLL: DB      0       ;OLD RATE LOWER LIMIT                     ///
37 7280  00                ORATUL: DB      0       ;OLD RATE UPPER LIMIT                     ///
38
39 7281  00                PLS1:   DB      0       ;PULSE SAMPLE FIRST CHARACTER             ///
40 7282  00                PLS2:   DB      0       ;PULSE SAMPLE SECOND CHARACTER            ///
41
42 7283  0000              LSTOUT: DW      0       ;LAST CHARACTER SENT POINTER              ///
43 7285  0000              BUFPTR: DW      0       ;NEXT CHARACTER INTO BUFFER POINTER       ///
44 7287                    COMBUF: BLKB    32      ;COMMUNICATIONS BUFFER                    ///
45 72A7  00                BUFTOP: DB      0       ;TOP OF COMMUNICATIONS BUFFER             ///
46 72A8  00                CPLSFL: DB      0       ;PULSE IN PROGRESS FLAG                   ///
47 72A9  00                CHAR:   DB      0       ;CHARACTER IN TRANSMISSION                ///
48 72AA  0000              SNDMOD: DW      0       ;MODE OF SERIAL OUTPUT ROUTINE            ///
49 72AC  00                BITCNT: DB      0       ;BIT COUNT FOR SERIAL OUTPUT              ///
50
51 72AD  00                OMINS:  DB      0       ;OLD MINUTES STORAGE                      ///
52 72AE  00                DIGERR: DB      0       ;DIAGNOSTIC CODE STORAGE (BUT NOTHING HAPPENS) ///
53
54 72AF  00                GNMSK:  DB      0       ;GAIN MASK FOR DACH DATA
55                         ;
56                         ;
57
A       %0007      ADCHK    1976      ADCHK2   19F8      ADCVT    1E5E      ADIDX    714B
ALCFLG  70F7       ALICHK   16C7      ALICOD=  0001      ALICTR   70F2      ALIFLG   70F1
ALILL   70F3       ALIPER   70F4      ALIUL    70F5      ALMCHK   0C37      ALMCKB   0CA0
ALMCKC  0D49       ALMCK2   0D7E      ALMDLY   70F6      ALMFLG   70C9      ALMPCH=  006E
ALMVLL  70EE       ALMVOL   70EF      ALMVUL   70F0      AMFAVG   703C      AMFDIF   703B
AMPHST  703E       AMPVAR   703D      ARAT     70AB      AUDENB=  0004      B        %0000
BADEKG  7107       BATBIT=  0008      BATBL    1ED3      BATCHK   0083      BATCOD=  0080
BATLM1= F8F8       BATLM2=  FB50      BBTBL    1EDB      BCGTHL   10D9      BEECNT   70EA
BEEP    148E       BEEVLL   70EB      BEEVOL   70EC      BEEVUL   70ED      BITCNT   72AC
BLIP    110D       BLIP2    11D0      BLKOUT   13F9      BLPIDX   70DE      BLPTHT   11B0
BMPBUF  1D2D       BNKLIT   1484      BNKOFF   188F      BNKON    1881      BO1      70DF
BO2     70E3       BPCTR    70B5      BRAT     70AD      BR1      70E1      BR2      70E5
BUFCHK  1CEE       BUFLEN=  0100      BUFMSK=  00FF      BUFPTR   7285      BUFTOP   72A7
BUTCLS  15B7       BUTCOD   7134      BUTCTO   15E0      BUIFIL   7133      BUTFLG   7135
BUTOPN  1552       BUTREG=  0004      BUTTBL   175A      BUTTON   14CE      C        %0001
CALCHK  0E4E       CALFLG   70E7      CALIDX   7009      CALOK    7008      CALRES   70E8
CALTBL  1EA5       CHAR     72A9                         CHGEKG=  0006      CHKEKG   1AA6      CHKNCH   06B6
```

| Symbol | Value | Symbol | Value | Symbol | Value | Symbol | Value | Symbol | Value |
|---|---|---|---|---|---|---|---|---|---|
| CHKRSP | 1B04 | CHKWIN | 1AF6 | CKLED1 | 1D48 | CKLED2 | 1D9F | CKRFSH | 1B4D |
| CLKINT | 18B0 | CLOCK | 17A1 | CLRLIT | 1475 | CLRLT2 | 147C | COMBEG | 1BFC |
| COMBUF | 7287 | COMIDL | 1C11 | COMRAT | 06E2 | COMRSP | 070E | COMRT2 | 0708 |
| COMRT3 | 06E5 | COMSAT | 0889 | COM240 | 1CC3 | COSTA | 727C | CPLSFL | 72A8 |
| CPSTA | 727D | CURAMP | 703A | CURDIF | 7016 | CURRAT | 704E | CURVAR | 7015 |
| D | X0002 | DACH | = 0001 | DACL | = 0000 | DATBUF | 717A | DATCLK | 7177 |
| DATFLG | 709E | DATIDX | 7178 | DATIRG | 7108 | DEC | 12F1 | DECDON | 0414 |
| DECDSP | 1356 | DECTBL | 13F6 | DEKGMX= | 00AF | DIDJFR= | 0001 | DECERR | 05D3 |
| DIFF | 04F5 | DIFLIM | 701E | DIGBNK | 7118 | DIGBUF | 711C | DIGERR | 72AE |
| DIGIDX | 711B | DIV | 128D | DIVRND | 12C3 | DIV16 | 12F6 | DLOOP | 1292 |
| DLYAVG | 7064 | DLYDIF | 7063 | DLYEKG | 7103 | DLYHST | 7066 | DLYVAR | 7065 |
| DMULT | 12CA | DRTJPR= | 0002 | DSPBKF | 712E | DSPBLK | 1452 | DSPBNK | 1450 |
| DSPCVT | 13A9 | DSPCV2 | 13B5 | DSPDIG= | 0005 | DSPFD1 | 711C | DSPFD2 | 7122 |
| DSPINT | 1913 | DSPLMF | 712C | DSPMTH | 712A | DSPMTL | 7128 | DSPOK | 712F |
| DSPOPN | 161E | DSPRET | 1A1F | DSPSEL= | 0004 | DSPSR | 0A8F | DSPUBK | 1464 |
| DTOIDX | 7179 | E | X0003 | EKGFLG | 7100 | EKGHBF | 7076 | EKGHUP | 06A6 |
| EKGPER | 70FF | EKGPOL= | 0003 | EKGSNC | 7106 | EKGTMO | 0BCC | EKGTMR | 70F8 |
| ENDSND | 18FC | ERRCOD | 70DB | ERRDSP | 01F0 | EXIT | 12B9 | FD1MSK= | 0007 |
| FD2MSK= | 0038 | FEKGMX= | 00BF | FILMPY | 09BA | FILPLS | 09CA | FILRAT | 0947 |
| FILRSP | 0A1A | FILSAT | 0974 | FILSET | 0A41 | FILTBL | 0A86 | FMODE | 7170 |
| FMODLL | 716F | FMODUL | 7171 | FRATE | 7004 | FRATIO | 70AF | FRATN | 7006 |
| FRATX | 70BE | FRSP | 7114 | FRSPN | 7115 | FRSPX | 7116 | FSAT | 7002 |
| FSATAC | 70BB | FSATDF | 70BD | FSATN | 7005 | FSATX | 70B9 | FSTBNK | 711A |
| FSTLIT | 1484 | GAINSV | 7102 | GNEKG | 70FD | GNEKGH | 70FE | GNEKGL | 70FC |
| GNMSK | 72AF | GNSEL | 7012 | H | X0004 | HRCTR | 7148 | HRESET | 00B3 |
| HRRFSH | 7105 | HRTBIT= | 0001 | HSTAVG | 053D | HSTBUF | 7026 | HSTCMP | 049E |
| HSTCP1 | 04AD | HSTCP2 | 04B2 | HSTEKG | 04E5 | HSTINC= | 0014 | HSTLEN | 7017 |
| HSTMAX= | 000F | HSTRSP | 04ED | HSTUPD | 0668 | HSTUP1 | 0677 | HSTUP2 | 067C |
| HSTVAR | 0567 | ICELL | 713F | IDSP | 715A | IDSPMX= | 009F | IFLG | 7141 |
| ILOOK | 160D | ILOOK2 | 1612 | INDBNK | 7119 | INDRCT | 1600 | INHLED | 7011 |
| INHPER | 7010 | INILST | 0242 | INIDSP | 1F33 | INIT | 022A | INTDE | 132E |
| INTHL | 1334 | ISUM | 10E0 | KNBCTR | 7132 | KNBFLG | 7131 | KNOB | 16FF |
| L | X0005 | LDSCHK | 07F9 | LDSFLG | 710D | LDXSET | 1E14 | LD1SET | 10F6 |
| LD2SET | 1E05 | LEDTBL | 1E42 | LEDTST | 01A6 | LED1 | 700A | LED1SV | 700B |
| LED2 | 700D | LED2SV | 700E | LEVEL3 | 0266 | LGFLAG | 7013 | LIMTBQ | 0641 |
| LMCK | 1C45 | LOG | 0505 | LOOP | 0059 | LRTBIT= | 0002 | LSTOUT | 7293 |
| LVL3JR | 072B | L1ITMR | 700C | L2ITMR | 700F | M | X0006 | MARK | = 0040 |
| MAXIDX | 70D6 | MAX1 | 709F | MAX2 | 70A3 | MCHERR | 10AE | MCHER9 | 10D4 |
| MCHMOD | 70CB | MCHRET | 10BD | MCH1 | 0FB3 | MCH2 | 1014 | MCH3 | 102E |
| MINCTR | 7147 | MIN1 | 70A1 | MIN2 | 70A5 | MLOOP | 12E9 | MODCHG | 18F2 |
| MODESV | 7130 | MPY16 | 1209 | MPY32 | 1232 | MSCTR | 7144 | MULT | 12E4 |
| MUNCH | 0F38 | MUXSEL= | 0002 | NCHFLG | 70B6 | NEGCDE | 134E | | |
| NEGDE | 1340 | NEGHL | 1348 | NEWBUT | 7137 | NOISE | 70D8 | NULMOD | 1BB5 |
| OCOSTA | 727A | OCPSTA | 727B | OFFDSP | 16BB | OFWMX | = 004F | OFWSNS | 7150 |
| OLDBUT | 7136 | OLDMAX | 70DC | OHINS | 72AD | OPNDLY | 713E | OPNFLG | 713A |
| OPNLL | 713B | OPNPRM | 7138 | OPNTHR | 713D | OPNUL | 713C | ORATLL | 727F |
| ORATUL | 7280 | OSATLL | 727E | OXIATT= | 0002 | PERAVG | 7028 | PERCTR | 70B3 |
| PERDIF | 7027 | PERHST | 702A | PERIOD | 7026 | PERVAR | 7029 | PLSDLY | 7062 |
| PLSERR | 03CC | PLSMN2 | 70CE | PLSMX2 | 70D4 | PLSMX2 | 70CC | PLSMX2 | 70D2 |
| PLSOK | 031E | PLSRET | 03FF | PLSSLP | 70D0 | PLSTHD | 70D9 | PLSTMO | 0B2C |
| PLSTHR | 7149 | PLS1 | 7281 | PLS2 | 7282 | POLCGH | 70FB | POLCGL | 70F9 |
| POLEKG | 70FA | POLSAV | 7101 | PRMFLD | 7142 | PRMTBL | 177A | PSW | X0006 |
| QSCCTR | 7146 | QSCFLG | 7145 | RAMIDL | 0176 | RAMIDX | 7172 | RAMLEN= | 0400 |
| RAMORG= | 7000 | RAMTST | 00FB | RATAVG | 7050 | RATCLK | 710B | RATDIF | 704F |
| RATE | 7003 | RATHST | 7052 | RATLL | 70C6 | RATLLL | 70C5 | RATOUT | 716B |
| RATRAT | 70A9 | RATUL | 70C7 | RATULL | 70C8 | RATVAR | 7051 | RDYCHK | 1CDE |
| RESP | 7113 | RFSHOP | 15E7 | RHICOD= | 0004 | RLOCOD= | 0002 | RNDOFF | 12BB |
| ROMIDL | 0141 | ROMIDX | 7174 | ROMSUM | 7176 | ROMTST | 00BE | RRAVG | 7078 |
| RRDIF | 7077 | RRHST | 707A | RRPER | 7076 | RRVAR | 7079 | RSPAVG | 708C |
| RSPCNT | 710E | RSPCTR | 1A98 | RSPDIF | 708B | RSPFLG | 7110 | RSPHBF | 708A |
| RSPHST | 708E | RSPHUP | 06AE | RSPLV3 | 081A | RSPSER | 708A | RSPSNC | 7111 |
| RSPTMO | 0C0F | RSPTSP | 710F | RSTRWV= | 0007 | | | SAT | 7001 |
| SATBIT= | 0004 | SATCLK | 710C | SATLL | 70C2 | SATLLL | 70C1 | SATOUT | 7169 |
| SATTMO | 0BB9 | SATTMR | 714A | SATUL | 70C3 | SATULL | 70C4 | SATX | 70B7 |
| SCL100 | 125F | SCL250 | 1276 | SEGE | = 005B | SEGF | = 001B | SEGR | = 0018 |
| SEGTBL | 13EB | SEG0 | = 0077 | SEG1 | = 0024 | SEG2 | = 005D | SEG3 | = 006D |
| SEG4 | = 002E | SEG5 | = 006B | SEG6 | = 007B | SEG7 | = 0025 | SEG8 | = 007F |
| SEG9 | = 002F | SENDIT | 1D12 | SETEKG | 1B23 | SETLIM | 061C | SETLIT | 146C |
| SETIRG | 07E3 | SHBCDE | 092D | SHBEEP= | 000B | SHBUF | 715F | SHIFTDE | 1A92 |
| SHFTHL | 1A71 | SHICOD= | 0010 | SHIDX | 715C | SHLED1= | 000E | SHLED2= | 000D |
| SHPTR | 715D | SHVOL | = 0007 | SLOCOD= | 0008 | SNDDEC | 043D | SNDMOD | 72AA |
| SNDMON | 0404 | SNDOUT | 1B66 | SN2DLY | 7104 | SN3DLY | 7112 | SP | X0006 |
| SPACE | = 00C0 | SPINR | 18D9 | SPLEN | 7D07 | SPLIT | 1D3B | SRCBIT= | 0001 |
| START | 0040 | STARTS | 18B8 | STATUS | 70CA | STCK | 7400 | STCKLN= | 0040 |
| STIK1 | 1133 | STIK2 | 113E | STKCHR | 1D18 | STKSER | 1C23 | STKSR2 | 1C24 |
| STOPBG | 18CB | STSREG= | 0020 | SYNCOK | 0310 | SYNCOR | 0310 | SYNDLY | 70B4 |
| SYNFLG | 7014 | TEST | 12A2 | TOBUFR | 1D22 | TSTMOD | 7007 | TWKLED | 0E0C |
| UPDALL | 1C65 | UPDLIM | 1C83 | UPDSTA | 1C6C | VARLIM | 058A | VARLIM | 7018 |
| VBAT | 7158 | VBEEP | 7163 | VBMX | = 008F | VCAL | 7152 | VCALMX= | 005F |
| VERCOD | 7000 | VERSN | = 005E | VLED1 | 715F | VLED2 | 7161 | VREF | 7156 |
| VREFMX= | 007F | VTH | 716D | VTMP | 7154 | VTHFMX= | 006F | VVOL | 7165 |
| VVOLSV | 7167 | V1 | 714C | V1MX | = 002F | V1PRM | = 000F | V2 | 714E |
| V2MX | = 003F | V2PRM | = 001F | WATMOD | 190A | WINFLG | 710A | WINTMR | 7109 |
| XBLIP2 | 11F5 | XDSPCV | 13B4 | XFRPLS | 044C | XMPY | 70C0 | XRATIO | 70B1 |
| XSAT | 08A0 | | | | | | | | |
| @ ABS@ | 7400 | 00 | | | | | | | |

```
MODULE: RESPOX
ERRORS DETECTED: 0

FREE CORE: 118. WORDS
,LP:=RESPOX
```

We claim:

1. An improved method for photoelectrically detecting arterial pulses of a patient comprising:
   detecting the blood flow, which may include arterial pulses and artifacts, at the patient's body tissue using a device that calculates blood constituents from the detected blood flow;
   detecting the occurrence of a selected portion of the patient's EKG waveform as the occurrence of the heartbeat of the patient;
   correlating the occurrence of the heartbeat with the detection of pulses by the blood constituent calculating device; and
   determining whether or not a detected pulse is likely to be a detected arterial pulse by using the determined correlation and a detected heartbeat.

2. The method of claim 1 wherein the selected portion of the patient's EKG waveform is the R wave portion.

3. The method of claim 1 wherein the device that calculates blood constituents is adapted for calculating oxygen saturation of hemoglobin in arterial blood, and the method further comprises measuring oxygen saturation of hemoglobin in arterial blood.

4. Improved apparatus for detecting arterial pulses of a patient comprising:
   means for photoelectrically detecting the flood flow, which may include arterial pulses and artifacts, at the body tissue;
   means for detecting the electrical heart activity of the patient in the form of an EKG waveform;
   circuit means for filtering and processing the EKG waveform to detect a selected component of the EKG waveform, so that the occurrence of that selected component represents the occurrence of a heartbeat;
   means for correlating detected arterial pulses with the occurrence of the heartbeat; and
   means for confirming whether or not a detected pulse is likely to be an arterial pulse, said confirming means being responsive to the detected arterial pulse and a detected heartbeat.

5. The apparatus of claim 4 wherein the selected component of the EKG waveform is the R wave component.

6. A method for calculating the amount of a blood constituent from the blood flow characteristics of a patient comprising:
   detecting an absorption signal corresponding to the absorption of light in the patient's tissue including periodic changes caused by periodic arterial pulses in the blood flow characteristics and changes caused by artifact;
   detecting an EKG signal corresponding to the patient's EKG waveform including a selected portion of the EKG waveform corresponding to the periodic electrical heart activity of the patient;
   correlating the detected absorption and EKG signals;
   processing the absorption signal and the determined correlation to identify the periodic changes in the absorption signal likely to correspond to arterial pulses in the patient's blood flow characteristics; and
   calculating the amount of the blood constituent from the identified periodic changes in the absorption signal.

7. The method of claim 6 wherein correlating the absorption and EKG signals further comprises:
   synchronizing the occurrence of a plurality of changes in the absorption signals;
   synchronizing the occurrences of a plurality of selected portions of the EKG signal; and
   correlating the synchronized portions of the absorption signal with the synchronized portions of the EKG signal.

8. The method of claim 6 wherein calculating thee amount of a blood constituent further comprises calculating the amount of oxygen saturation of hemoglobin in arterial blood.

9. The method of claim 6 wherein the selected portion of the patient's EKG signal further comprises the R wave component.

10. An apparatus for use in calculating the amount of a blood constituent from the blood flow characteristics of a patient comprising:
    means for photoelectrically detecting an absorption signal corresponding to the absorption of light in the patient's tissue including periodic changes caused by periodic arterial pulses in the blood flow characteristics and changes caused by artifacts;
    means for electrically detecting an EKG signal corresponding to the patient's EKG waveform including a selected portion of the EKG waveform corresponding to the periodic electrical heart activity of the patient;
    means for correlating the detected absorption and EKG signals;
    first processing means for processing the absorption signal and the determined correlation to identify the periodic changes in the absorption signal likely to correspond to arterial pulses in the patient's blood flow characteristics; and
    means for calculating the blood constituent from the identified periodic changes in the absorption signal.

11. The apparatus of claim 10 wherein the correlating means further comprises:
    first synchronizing means for synchronizing the occurrence of a plurality of changes in the absorption signal;
    second synchronizing means for synchronizing the occurrence of a plurality of selected portions of the EKG signal; and
    means for correlating the synchronized changes in the absorption signal with the synchronized selected portions of the EKG signal.

12. The apparatus of claim 10 wherein the calculating means is adapted for calculating the amount of oxygen saturation of hemoglobin in arterial blood.

13. The apparatus of claim 10 wherein means for detecting the selected portion of the patient's EKG signal is adapted for detecting the R wave component.

* * * * *